US012667619B2

(12) United States Patent
Li et al.

(10) Patent No.: US 12,667,619 B2
(45) **Date of Patent: *Jun. 30, 2026**

(54) INTEGRIN TARGETING LIGANDS AND USES THEREOF

(71) Applicant: Arrowhead Pharmaceuticals, Inc., Pasadena, CA (US)

(72) Inventors: Zhen Li, Westfield, NJ (US); Jeffrey Carlson, Madison, WI (US); Anthony Nicholas, Oregon, WI (US); Xiaokai Li, Middleton, WI (US); Dongxu Shu, Madison, WI (US); Matthew Fowler-Watters, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 972 days.

This patent is subject to a terminal disclaimer.

(21) Appl. No.: 17/050,042

(22) PCT Filed: Apr. 26, 2019

(86) PCT No.: PCT/US2019/029393

§ 371 (c)(1),
(2) Date: Oct. 23, 2020

(87) PCT Pub. No.: WO2019/210200

PCT Pub. Date: Oct. 31, 2019

(65) Prior Publication Data

US 2021/0093725 A1 Apr. 1, 2021

Related U.S. Application Data

(60) Provisional application No. 62/790,372, filed on Jan. 9, 2019, provisional application No. 62/663,763, filed on Apr. 27, 2018.

(51) Int. Cl.
*A61K 47/54* (2017.01)
*A61K 47/60* (2017.01)
*A61P 35/00* (2006.01)
*C12N 15/113* (2010.01)

(52) U.S. Cl.
CPC ............ *A61K 47/545* (2017.08); *A61K 47/60* (2017.08); *A61P 35/00* (2018.01); *C12N 15/113* (2013.01); *C12N 2310/14* (2013.01)

(58) Field of Classification Search
CPC .................................................... A61K 47/545
See application file for complete search history.

(56) References Cited

U.S. PATENT DOCUMENTS

| | | | |
|---|---|---|---|
| 4,522,811 A | 6/1985 | Eppstein et al. | |
| 6,017,926 A | 1/2000 | Askew et al. | |
| 6,048,861 A | 4/2000 | Askew et al. | |
| 9,132,188 B2 | 9/2015 | Barbas, III | |
| 9,487,556 B2 * | 11/2016 | Cheng | C07K 5/06043 |
| 9,694,089 B2 * | 7/2017 | Rajopadhye | C09B 23/0008 |
| 2003/0129188 A1 | 7/2003 | Barbas et al. | |
| 2004/0224986 A1 | 11/2004 | De Corte et al. | |

FOREIGN PATENT DOCUMENTS

| | | |
|---|---|---|
| WO | 1999031061 A1 | 6/1999 |
| WO | 2006020768 A2 | 2/2006 |
| WO | 2009114776 A2 | 9/2009 |
| WO | 2013110578 A1 | 8/2013 |
| WO | 2014134255 A2 | 9/2014 |
| WO | 2016134223 A2 | 8/2016 |
| WO | 2016154369 A1 | 9/2016 |
| WO | 2016172710 A2 | 10/2016 |
| WO | 2016176532 A1 | 11/2016 |
| WO | 2016196239 A1 | 12/2016 |
| WO | 2019161213 A1 | 8/2019 |
| WO | 2019210200 A1 | 10/2019 |

OTHER PUBLICATIONS

Vhora, Adv Protein Chem Struct Biol. 2015:98:1-55.*
Pezzoli, Journal of Drug Delivery Science and Technology (2017), 37, 115-122.*
Dwivedi, Evergreening: A deceptive device in patent rights, Technology in Society 32.*
Feldman, Understanding 'Evergreening' : Making Minor Modifications Of Existing Medications To Extend Protections, Health Affairs Jun. 2022 41:6, 801-804.*
Dwivedi, Evergreening: A deceptive device in patent rights, Technology in Society 32 (2010) 324-330.*
Battistini, RGD Peptide-Drug Conjugates as Effective Dual Targeting Platforms: Recent Advances, Eur. J. Org. Chem. 2021, 2506-2528.*
Bhatnagar S, Verma KD, Hu Y, Khera E, Priluck A, Smith DE, Thurber GM. Oral Administration and Detection of a Near-Infrared Molecular Imaging Agent in an Orthotopic Mouse Model for Breast Cancer Screening. Mol Pharm. May 7, 2018;15(5):1746-1754. doi: 10.1021/acs.molpharmaceut.7b00994. Epub Apr. 26, 2018. PMID: 29696981; PMCID: PMC5941251.
Hutchinson et al.; "Nonpeptide alphavbeta3 antagonists. 8. In vitro and in vivo evaluation of a potent alphavbeta3 antagonist for the prevention and treatment of osteoporosis"; J. Med. Chem; 46(22):4790-4798; 2003.

(Continued)

*Primary Examiner* — Nizal S Chandrakumar
(74) *Attorney, Agent, or Firm* — Paul Vandervelde; Meibo Chen; Mitchell Porter

(57) ABSTRACT

Compounds having affinity for integrins, the synthesis of these compounds, and the use of these compounds as ligands to facilitate the delivery of cargo molecules to cells expressing integrins are described. The described integrin targeting ligands have serum stability and affinity for αvβ3 integrin and/or αvβ5 integrin, and are suitable for conjugation to cargo molecules, such as such as oligonucleotide-based therapeutic agents (e.g., RNAi agents), to facilitate delivery of the cargo molecules to cells and tissues, such as tumor cells, that express integrin αvβ3, integrin αvβ5, or both integrin αvβ3 and integrin αvβ5. Compositions that include integrin targeting ligands and methods of use are also described.

7 Claims, No Drawings

Specification includes a Sequence Listing.

(56) References Cited

OTHER PUBLICATIONS

Extended European Search Report for corresponding Application No. 19794009 dated Feb. 8, 2002.
Adams, et al. Structure Activity Relationships of αv Integrin Antagonists for Pulmonary Fibrosis by Variation in Aryl Substituents. ACS Med Chem Lett. Sep. 19, 2014; 5(11): 1207-12. doi: 10.1021/ml5002079. PMID: 25408832; PMCID: PMC4233353.
Database Reaxys (Online); Johnson & Johnson Inc.; "Piperidinyl targeting compounds that selectively bind Integrins" XP055976959; Jan. 1, 2004.
Temming, et al.; "RGD-based strategies for selective delivery of therapeutics and imaging agents to the tumour vasculature"; vol. 8, Issue 6, 381-402; (2005).
Brooks, et al., "Integrin αvβ3 Antagonists Promote Tumor Regression by Inducing Apoptosis of Angiogenic Blood Vessels"; 79 Cell 1157-1164 (1994).
Coleman, et al., "Nonpeptide αvβ3 Antagonists. Part 11: Discovery and Preclinical Evaluation of Potent αvβ3 Antagonists for the Prevention and Treatment of Osteoporosis"; J. Med. Chem.; 2004; 47, 4829-4837.
Desgrosellier, JS et al., "Integrins in cancer: biological implications and therapeutic opportunities"; Nat Rev Cancer, 10(1):9-22 (2010).
Horton, MA, "The αvβ3 Integrin 'vitronectin receptor'"; Int. J. Biochem. Cell Biol.; vol. 29, No. 5, pp. 721-725; 1997.
Kapp T. et al.; "A Comprehensive Evaluation of the Activity and Selectivity Profile of Ligands for RGD-binding Integrins"; Nature Scientific Reports; vol. 7; 1-13; 2017.
Ley, et al., "Integrin-based therapeutics: biological basis, clinical use and new drugs"; 15(3) Nat. Rev. Drug Discov.; vol. 15; pp. 173-183 (2016).
Mas-Moruno, et al., "Cilengitide: The First Anti-Angiogenic Small Molecule Drug Candidate. Design, Synthesis and Clinical Evaluation"; Anticancer Agents Med Chem, 10:753-768; 2010.
Ross, et al., "Bone-Induced Expression of Integrin beta-3 Enables Targeted Nanotherapy of Breast Cancer Metastases", Cancer Research; vol. 77(22); pp. 6303-6313; 2017.
International Search Report and Written Opinion for corresponding Application No. PCT/US19/29393 dated Aug. 8, 2019.
Extended European Search Report for corresponding Application No. 24179088.0 dated Jan. 16, 2025.
Wendt JA, Wu H, Stenmark HG, Boys ML, Downs VL, Penning TD, Chen BB, Wang Y, Duffin T, Finn MB, Keene JL, Engleman VW, Freeman SK, Hanneke ML, Shannon KE, Nickols MA, Steininger CN, Westlin M, Klover JA, Westlin W, Nickols GA, Russell MA. Synthesis of 2,5-thiazole butanoic acids as potent and selective alpha(v)beta3 integrin receptor antagonists with improved oral pharmacokinetic properties. Bioorg Med Chem Lett. Feb. 15, 2006;16(4):845-9. doi: 10.1016/j.bmcl.2005.11.017. Epub Nov. 21, 2005. PMID: 16303301.

* cited by examiner

SEQUENCE LISTING

```
<160> NUMBER OF SEQ ID NOS: 6

<210> SEQ ID NO 1
<211> LENGTH: 21
<212> TYPE: RNA
<213> ORGANISM: Homo sapiens
<220> FEATURE:
<223> OTHER INFORMATION: RNAi agent antisense strand modified sequence

<400> SEQUENCE: 1

uuucaugaaa ucguuacguu g                                              21


<210> SEQ ID NO 2
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 2

caacguaacg auuucaugaa a                                              21


<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 3

uuucaugaaa ucguuacguu g                                              21


<210> SEQ ID NO 4
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 4

caacguaacg auuucaugaa a                                              21


<210> SEQ ID NO 5
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 5

uuucaugaaa ucguuacguu g                                              21


<210> SEQ ID NO 6
<211> LENGTH: 21
<212> TYPE: RNA
<213> ORGANISM: Artificial sequence
```

-continued

```
<220> FEATURE:
<223> OTHER INFORMATION: RNAi agent sense strand modified sequence

<400> SEQUENCE: 6

caacguaacg auuucaugaa a                                              21
```

INTEGRIN TARGETING LIGANDS AND USES THEREOF

CROSS REFERENCE TO RELATED APPLICATIONS

This application is a U.S. National Phase Application under 35 U.S.C. § 371 of International Patent Application No. PCT/US19/29393, filed on Apr. 26, 2019 which claims priority to U.S. Provisional Patent Application Nos. 62/663,763, filed on Apr. 27, 2018, and 62/790,372, filed on Jan. 9, 2019, the entirety of which are incorporated by reference herein.

FIELD OF INVENTION

Disclosed herein are compounds that have affinity for integrins, methods of synthesis of such compounds, and the use of such compounds as ligands to deliver cargo molecules in vivo.

BACKGROUND

Integrins are transmembrane glycoproteins that mediate cell-cell and cell-matrix interactions. The integrins alpha-v beta-3 (αvβ3) and alpha-v beta-5 (αvβ5) are members of the integrin superfamily of adhesion molecules and are known for being receptors for the extracellular matrix (ECM) protein vitronectin. (Horton, MA, 29(5) *Int. J. Biochem. Cell Biol.* 721-725 (1997)). Altered expression of certain integrins, including integrin αvβ3 and integrin αvβ5, are believed to contribute to tumor progression, invasiveness, and metastases.

Indeed, overexpression of integrins, including integrins αvβ3 and αvβ5, have been reported in many tumor cells. (Desgrosellier, J S et al., Nat Rev Cancer, 10(1):9-22 (2010)). Antagonists of αvβ3 (and to a lesser extent αvβ5) have been considered for use in a variety of diseases associated with altered integrin function. For example, attempts have been made to develop αvβ3 inhibitors as potential cancer treatments, as the inhibition of the (RV receptor has been shown to inhibit angiogenesis, thereby preventing the formation of new blood vessels which are believed to be necessary for tumor growth. (See, e.g., Brooks et al., 79 *Cell* 1157-1164 (1994); Mas-Moruno et al., Anticancer Agents Med Chem, 10(10):753-768). However, one leading example of an αvβ3 inhibitor, the antagonist Cilengitide, was shown to be non-efficacious in clinical trials aimed at limiting tumor angiogenesis and progression in patients with glioblastoma. (See, e.g., Ley et al., *Integrin-based Therapeutics: Biological Basis, Clinical Use and New Drugs,* 15(3) Nat. Rev. Drug Discov. 173-183 (2016)).

In general, the delivery of cargo molecules in vivo, including therapeutically effective pharmaceutical compounds or active pharmaceutical ingredients, to desired cells and/or tissues, continues to be a general challenge in the development of therapeutically viable drug products. There continues to exist a need for stable and effective targeting compounds that have affinity for and/or are able to selectively bind to specific cells and tissues, which can be utilized or employed as ligands to facilitate the delivery of therapeutic cargo molecules to those specific cells or tissues. Moreover, there exists a specific need for compounds that are capable of selectively targeting integrin alpha-v beta-3 and which are suitable to be conjugated to cargo molecules and deliver the cargo molecules to cells expressing such integrins, such as tumor cells, in vivo. For oligonucleotides and oligonucleotide-based therapeutics in particular (e.g., an oligonucleotide-based compound such as an antisense oligonucleotide or an RNAi agent), there continues to exist a need for ligands that are able to target integrin alpha-v beta-3 and/or integrin alpha-v beta-5 and facilitate the delivery of these oligonucleotide-based compounds to cells expressing such integrins.

SUMMARY

Described herein are compounds that have affinity for certain integrins, including αvβ3 and αvβ5, which can be employed as ligands (referred to herein as "integrin targeting ligands," "αvβ3 integrin targeting ligands," "αvβ3 integrin ligands," or simply "integrin ligands") to selectively direct compounds or other molecules to which they are attached to cells or tissues that express integrin αvβ3 and/or αvβ5. The integrin targeting ligands disclosed herein are stable in serum and have affinity for, and can bind with specificity to, these integrins. The integrin targeting ligands disclosed herein can be conjugated to cargo molecule(s) to facilitate the delivery of the cargo molecule(s) to cells or tissues that express integrin αvβ3 and/or αvβ5.

In another aspect, described herein are methods of delivering a cargo molecule to a tissue and/or cell expressing integrin αvβ3 and/or integrin αvβ5 in vivo, wherein the methods include administering to a subject one or more integrin targeting ligands disclosed herein that has been conjugated to one or more cargo molecules. Further disclosed herein are methods of treatment of a subject having a disease, symptom, or disorder for which the delivery of a therapeutic cargo molecule (e.g., an active pharmaceutical ingredient) to a cell expressing αvβ3 integrin and/or αvβ5 integrin is capable of treating the subject, wherein the methods include administering to a subject one or more integrin targeting ligands disclosed herein that has been conjugated to one or more therapeutic cargo molecules.

Further described herein are methods of inhibiting expression of a target gene in a cell in vitro or in vivo, wherein the methods include administering to the cell an effective amount of a conjugate that includes one or more integrin targeting ligands disclosed herein that have been conjugated to one or more oligonucleotide-based therapeutics, such as an RNAi agent, that are capable of inhibiting expression of a target gene in a cell. In some embodiments, described herein are methods of inhibiting expression of a target gene in a cell of a subject, wherein the subject is administered an effective amount of one or more oligonucleotide-based therapeutics (such as an RNAi agent) that has been conjugated to one or more integrin targeting ligands disclosed herein.

In yet another aspect, described herein are compositions that include the integrin targeting ligands disclosed herein. The compositions described herein can be pharmaceutical compositions or medicaments that include one or more integrin targeting ligands disclosed herein conjugated to one or more therapeutic cargo molecules, such as an RNAi agent or other cargo molecule or therapeutic substance.

In some embodiments, described herein are methods of treatment of a subject having a disease or disorder mediated at least in part by expression of a target gene in a cell that expresses integrin αvβ3, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, drat is conjugated to one or more integrin targeting ligands disclosed herein. In some embodiments, described herein are methods of treatment of a subject having a disease or disorder mediated at least in part by expression of a target gene in a tumor cell, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, conjugated to one or more integrin targeting ligands disclosed herein. In some embodiments, described herein are methods of treatment of a subject having a disease or disorder mediated at least in part by expression of a target gene in a kidney tumor cell, such as a clear cell renal carcinoma tumor cell, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, conjugated to one or more integrin targeting ligands disclosed herein.

In a first aspect, this disclosure provides synthetic integrin targeting ligands.

In some embodiments, an integrin targeting ligand disclosed herein includes the structure of the following formula:

(Formula I)

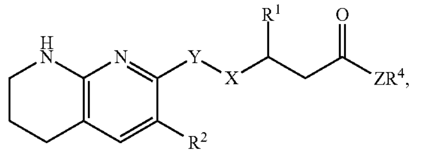

or a pharmaceutically acceptable salt thereof, wherein,

X is $—C(R^3)_2—$, $—NR^3—$,

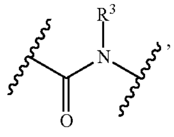, 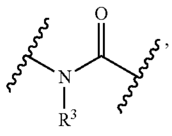, or 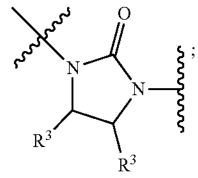;

Y is optionally substituted alkylene;

Z is O, $NR^3$, or S;

n is an integer from 1 to 8;

$R^1$ is optionally substituted aryl, optionally substituted heteroaryl, optionally substituted heterocyclyl, optionally substituted cycloalkyl or $R^1$ comprises a cargo molecule;

$R^2$ is H, optionally substituted alkyl, or $R^2$ comprises a cargo molecule;

each instance of $R^3$ is independently selected from the group consisting of H and optionally substituted alkyl, or $R^3$ comprises a cargo molecule;

$R^4$ is H or optionally substituted alkyl; and wherein at least one of Y, $R^1$, $R^2$, any instance of $R^3$, and $R^4$ comprises a cargo molecule.

Any of the integrin targeting ligands disclosed herein can be linked to a cargo molecule, a reactive group, and/or a protected reactive group. Linking to a reactive group, for example, can be used to facilitate conjugation of the integrin targeting ligand to a cargo molecule. The integrin targeting ligands disclosed herein can increase targeting of a cargo molecule to a cell expressing an integrin, including αvβ3 integrin and/or αvβ5 integrin. A cargo molecule can be, but is not limited to, a pharmaceutically active ingredient or compound, a prodrug, or another substance with known therapeutic benefit. In some embodiments, a cargo molecule can be, but is not limited to, a small molecule, an antibody, an antibody fragment, an immunoglobulin, a monoclonal antibody, a label or marker, a lipid, a natural or modified oligonucleotide, a modified oligonucleotide-based compound (e.g., an antisense oligonucleotide or an RNAi agent), a natural or modified nucleic acid, a peptide, an aptamer, a polymer, a polyamine, a protein, a toxin, a vitamin, a poly ethylene glycol, a hapten, a digoxigenin, a biotin, a radioactive atom or molecule, or a fluorophore. In some embodiments, a cargo molecule includes a pharmaceutically active ingredient or a prodrug. In some embodiments, a cargo molecule is or includes an oligonucleotide-based therapeutic, such as an antisense compound or an RNAi agent. In some embodiments, a cargo molecule is or includes an oligonucleotide-based compound that is a pharmaceutically active ingredient. In some embodiments, a cargo molecule is or includes an RNAi agent that is a pharmaceutically active ingredient.

Described herein is the use of the described αvβ3/5 integrin targeting ligands to target and deliver a cargo molecule to a cell that expresses integrins. The cargo molecule can be delivered to a cell in vitro, in situ, ex vivo, or in vivo.

In another aspect, this disclosure provides compositions that include one or more of the integrin targeting ligands described herein. For example, in some embodiments, compositions comprising one or more integrin targeting ligands disclosed herein include one or more oligonucleotide-based compounds, such as one or more RNAi agents, to be delivered to a cell in vivo. In some embodiments, described herein are compositions for delivering an RNAi agent to a cell in vivo, wherein the RNAi agent is linked to one or more integrin targeting ligands.

Compositions that include one or more integrin targeting ligands are described. In some embodiments, a composition comprises a pharmaceutically acceptable excipient. In some embodiments, a composition that includes one or more integrin targeting ligands comprises one or more other pharmaceutical substances or pharmaceutically active ingredients or compounds. In some embodiments, medicaments that include one or more integrin targeting ligands are described herein.

Compositions that include one or more integrin targeting ligands disclosed herein can be delivered in vivo or in vitro to various cancer cells, including for example, clear cell renal carcinoma tumor cells (e.g., A498), other kidney cancer cells (e.g., ACHN, CAKI-2, 769-P, 786-O), melanoma cells (e.g., A375), glioblastoma cells (e.g., U87MG), pancreatic cancer cells (e.g., (PANC-1), lung cancer cells (e.g., H460, H661, H1573, H2126), colon cancer cells (e.g., HT29, HCT116), liver cancer cells (e.g., Hep2G, Hep3B), breast cancer cells (e.g., MCF7, SK-BR3), prostate cancer cells (e.g., DU 145, PC3, LNCaP, MDA-PCa-2b), oral cancer cells (e.g., KB), tongue cancer cells (e.g., CAL27, SCC9), pharynx cancer cells (e.g., Detroit562), and/or ovarian cancer cells (e.g., OVCAR3, SKOV3, A2780) and/or other patient derived xenografts.

In another aspect, the present disclosure provides methods that include the use of one or more integrin targeting ligands and/or compositions as described herein and, if desired, bringing the disclosed integrin targeting ligands and/or compositions into a form suitable for administration as a pharmaceutical product. In other embodiments, the disclosure provides methods for the manufacture of the ligands and compositions, e.g., medicaments, described herein.

Compositions that include one or more integrin targeting ligands can be administered to subjects in vivo using routes of administration known in the art to be suitable for such administration in view of the cargo molecule sought to be administered, including, for example, subcutaneous, intravenous, intratumoral, inhaled (aerosol or dry powder formulations), intranasal, intraperitoneal, intradermal, transdermal, oral, sublingual, or topical administration. In some embodiments, the compositions that include one or more integrin targeting ligands may be administered for systemic delivery, for example, by intravenous or subcutaneous administration.

In some embodiments, disclosed herein are methods for delivering one or more desired cargo molecule(s) to a clear cell renal carcinoma tumor cell in vivo, wherein the methods include administering to the subject one or more integrin targeting ligands conjugated to one or more cargo molecules.

In some embodiments, disclosed herein are methods of delivering an oligonucleotide-based compound to a tumor cell in vivo, wherein the methods include administering to the subject one or more integrin targeting ligands conjugated to the one or more oligonucleotide-based compounds. In some embodiments, disclosed herein are methods of delivering an RNAi agent to a tumor cell in vivo, wherein the methods include administering to the subject one or more integrin targeting ligands conjugated to the one or more RNAi agents. In some embodiments, disclosed herein are methods of inhibiting the expression of a target gene in a clear cell renal carcinoma tumor cell in vivo, wherein the methods include administering to the subject an RNAi agent conjugated to one or more ligands having affinity for αvβ3 integrin and/or αvβ5 integrin.

Other objects, features, aspects, and advantages of the invention will be apparent from the following detailed description and from the claims.

DETAILED DESCRIPTION

Integrin Targeting Ligands

Described herein are compounds that have affinity for integrins, exhibit serum stability in vivo, and can be used as ligands to facilitate the delivery of cargo molecules to cells and/or tissues that express integrins, such as integrin αvβ3 and/or integrin αvβ5. The integrin targeting ligands can be used to target cells that express integrins in vitro, in situ, ex vivo, and/or in vivo.

In some embodiments, the integrin targeting ligands disclosed herein can be conjugated to one or more cargo molecules to preferentially direct and target the cargo molecules to cells or tissues that express integrins, including integrin αvβ3 and/or integrin αvβ5. In some embodiments, the cargo molecules include or consist of pharmaceutically active compounds. In some embodiments, the cargo molecules include or consist of oligonucleotide-based compounds, such as RNAi agents. In some embodiments, the integrin targeting ligands disclosed herein are conjugated to cargo molecules to direct the cargo molecules to tumor cells in vivo. In some embodiments, the integrin targeting ligands disclosed herein are conjugated to cargo molecules to direct the cargo molecules to clear cell renal carcinoma tumor cells in vivo.

Formula I

In one aspect, the invention provides integrin ligands of the structure:

(Formula I)

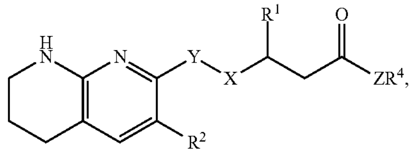

wherein,

X is $-C(R^3)_2-$, $-NR^3-$,

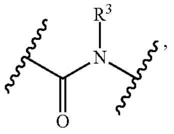, 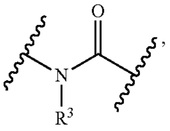, or 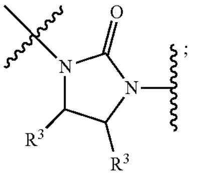;

Y is optionally substituted alkylene;

Z is O, $NR^3$, or S;

n is an integer from 1 to 8;

$R^1$ is optionally substituted aryl, optionally substituted heteroaryl, optionally substituted heterocyclyl, optionally substituted cycloalkyl or $R^1$ comprises a cargo molecule;

$R^2$ is H, optionally substituted alkyl, or $R^2$ comprises a cargo molecule;

each instance of $R^3$ is independently selected from the group consisting of H and optionally substituted alkyl, or $R^3$ comprises a cargo molecule;

$R^4$ is H or optionally substituted alkyl; and wherein at least one of Y, $R^1$, $R^2$, any instance of $R^3$, and $R^4$ comprises a cargo molecule.

In some embodiments of Formula I, $R^1$ is selected from the group consisting of:

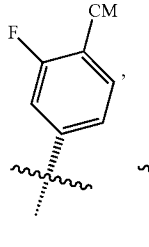, 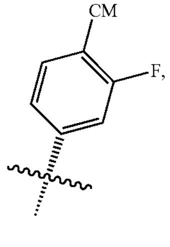 and 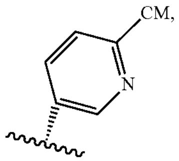

wherein  indicates the point of attachment and CM comprises a cargo molecule.

In some embodiments of Formula I, Y is $C_1$ to $C_6$ alkylene.

Formula II

In some embodiments of Formula I, an integrin targeting ligand disclosed herein includes the structure of the following formula:

(Formula II)

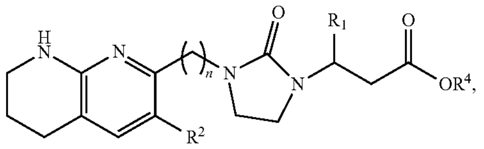

or a pharmaceutically acceptable salt thereof, wherein
- n is an integer from 1 to 8;
- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- $R^4$ is H or optionally substituted alkyl; and wherein at least one of $R^1$ or $R^2$ comprises a cargo molecule.

Formula III

In some embodiments of Formula I, an integrin targeting ligand disclosed herein includes the structure of the following formula:

(Formula III)

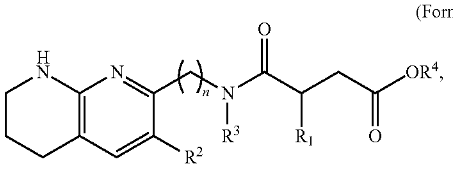

or a pharmaceutically acceptable salt thereof, wherein
- n is an integer from 1 to 8;
- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- $R^3$ is selected from the group consisting of H and optionally substituted alkyl, or $R^3$ comprises a cargo molecule;
- $R^4$ is H or optionally substituted alkyl; and
- wherein at least one of $R^1$, $R^2$ and $R^3$ comprises a cargo molecule.

Formula IV

In some embodiments of Formula I, an integrin targeting ligand disclosed herein includes the structure of the following formula:

(Formula IV)

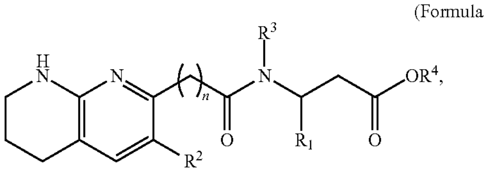

or a pharmaceutically acceptable salt thereof, wherein
- n is an integer from 1 to 8;
- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- $R^3$ is selected from the group consisting of H and optionally substituted alkyl, or $R^3$ comprises a cargo molecule;
- $R^4$ is H or optionally substituted alkyl; and
- wherein at least one of $R^1$, $R^2$ and $R^3$ comprises a cargo molecule.

Formula V

In some embodiments of Formula I, an integrin targeting ligand disclosed herein includes the structure of the following formula:

(Formula V)

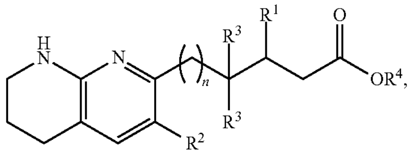

or a pharmaceutically acceptable salt thereof, wherein
- n is an integer from 1 to 8;
- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- each instance of $R^3$ is independently selected from the group consisting of H and optionally substituted alkyl, or $R^3$ comprises a cargo molecule;
- $R^4$ is H or optionally substituted alkyl; and
- wherein at least one of $R^1$, $R^2$ and $R^3$ comprises a cargo molecule.

Formula VI

In some embodiments of Formula I, an integrin targeting ligand disclosed herein includes the structure of the following formula:

(Formula VI)

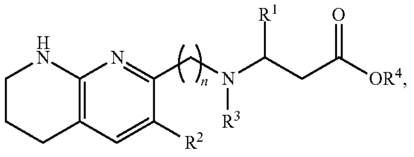

or a pharmaceutically acceptable salt thereof, wherein
- n is an integer from 1 to 8;
- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- each instance of $R^3$ is independently selected from the group consisting of H and optionally substituted alkyl, or $R^3$ comprises a cargo molecule;
- $R^4$ is H or optionally substituted alkyl; and
- wherein at least one of $R^1$, $R^2$ and $R^3$ comprises a cargo molecule.

Formula VII

In some embodiments of Formula I, an integrin targeting ligand disclosed herein includes the structure of the following formula:

(Formula VII)

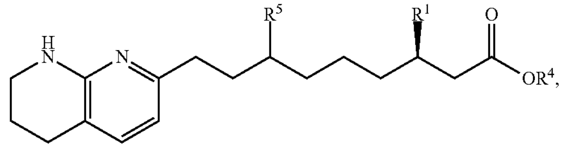

or a pharmaceutically acceptable salt thereof, wherein

- $R^1$ is optionally substituted aryl, optionally substituted heteroaryl, optionally substituted heterocyclyl, optionally substituted cycloalkyl or $R^1$ comprises a cargo molecule;
- $R^2$ is H, optionally substituted alkyl, or $R^2$ comprises a cargo molecule;
- $R^4$ is H or optionally substituted alkyl; and
- wherein at least one of $R^1$, $R^4$ and $R^5$ comprises a cargo molecule.

$R^1$

In embodiments of Formula I, $R^1$ is optionally substituted aryl, optionally substituted heteroaryl, optionally substituted heterocyclyl, optionally substituted cycloalkyl or $R^1$ comprises a cargo molecule. In some embodiments, $R^1$ is selected from the group consisting

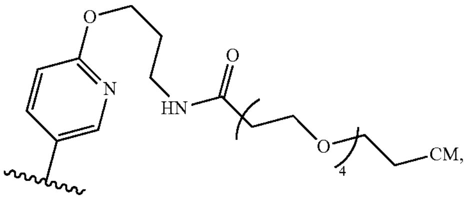

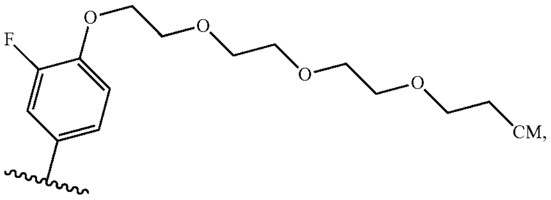

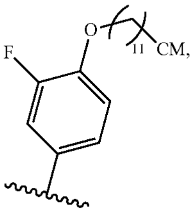

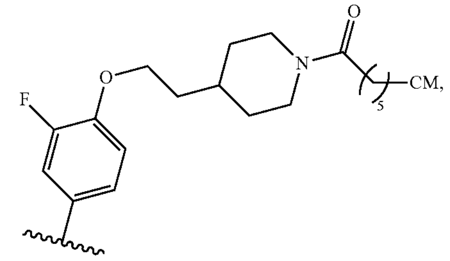

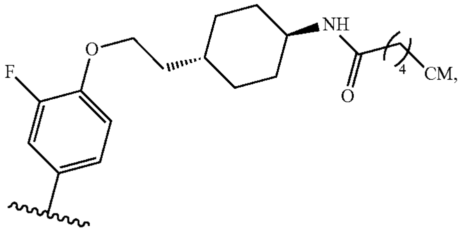

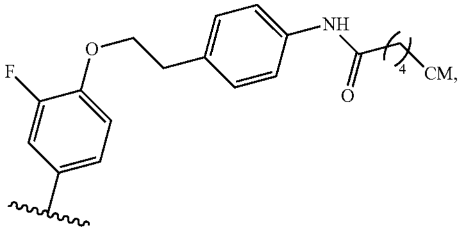

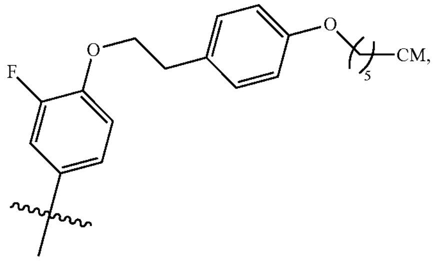

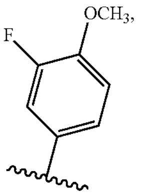

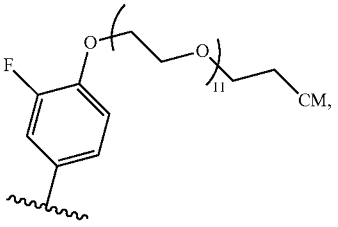

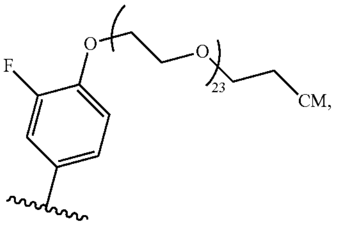

-continued

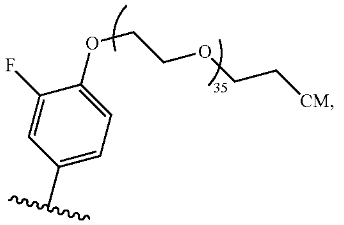

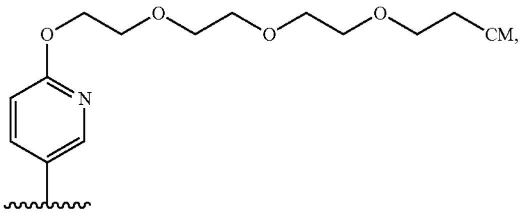

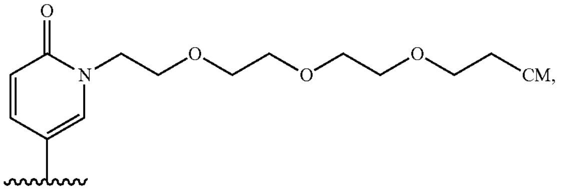

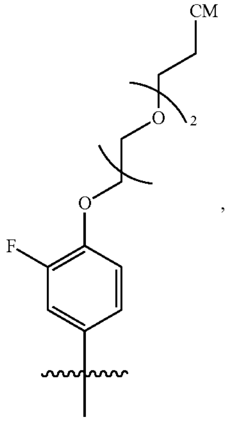

,

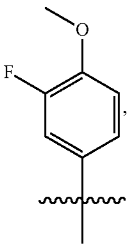

, and

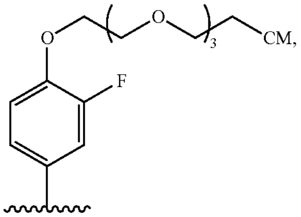

wherein  indicates the point of attachment and CM comprises a cargo molecule.

Integrin Targeting Ligand Precursors

In some embodiments, the invention provides integrin targeting ligand precursors which can be used to attach an integrin targeting ligand to a moiety comprising a cargo molecule. Provided herein are integrin targeting ligand precursors of the formula:

(Formula Ip)

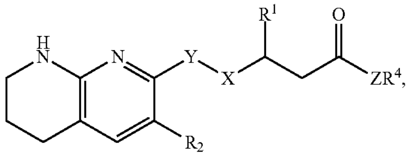

wherein,

X is $-C(R^3)_2-$, $-NR^3-$,

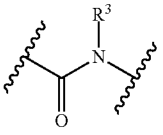

,

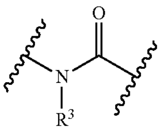

, or

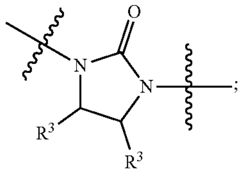

;

Y is optionally substituted alkylene;

Z is O, $NR^3$, or S;

n is an integer from 1 to 8;

$R^1$ is optionally substituted aryl, optionally substituted heteroaryl, optionally substituted heterocyclyl, optionally substituted cycloalkyl or $R^1$ comprises a cargo molecule;

$R^2$ is H, optionally substituted alkyl, or $R^2$ comprises a cargo molecule;

each instance of $R^3$ is independently selected from the group consisting of H and optionally substituted alkyl, or $R^3$ comprises a cargo molecule;

$R^4$ is H or optionally substituted alkyl; and wherein at least one of Y, $R^1$, $R^2$, any instance of $R^3$, and $R^4$ comprises a reactive group.

In some embodiments of compounds of Formula Ip, the reactive group comprises an azide.

Compounds of Formula I

In some embodiments, the integrin targeting ligands disclosed herein have structures that include, consist of, or consist essentially of, any of the structures represented by the following:

(Structure 1a)
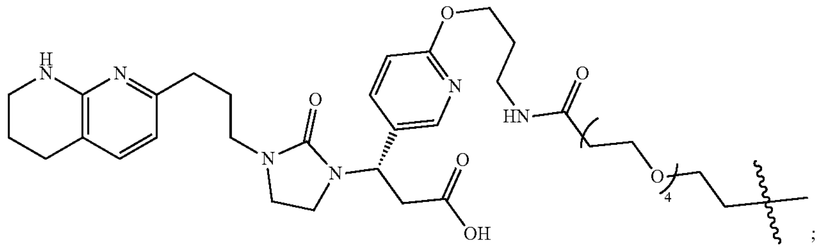
;
(Structure 2a)
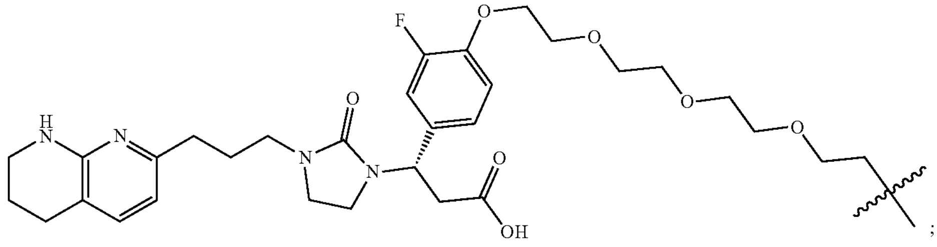
;
(Structure 2.1a)
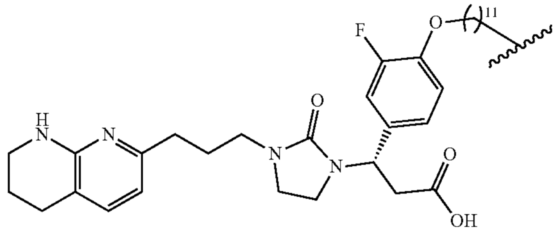
;
(Structure 2.2a)
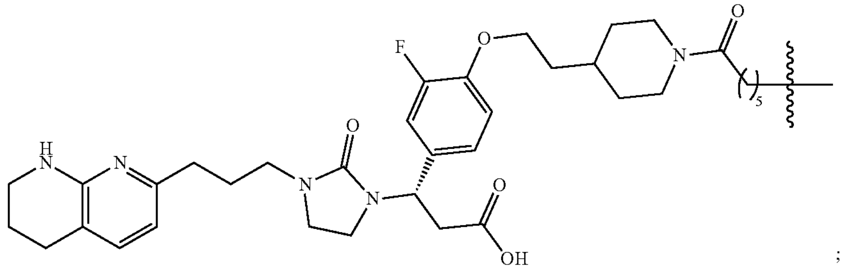
;
(Structure 2.3a)
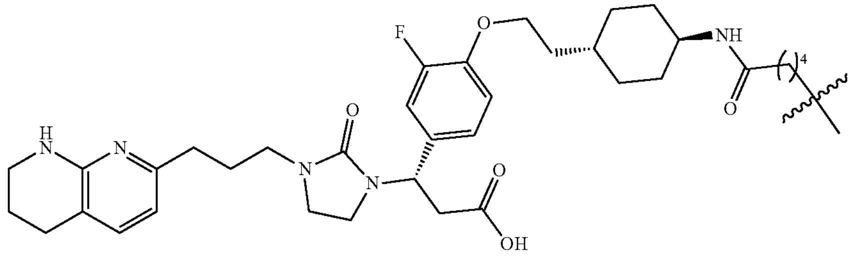
;
(Structure 2.4a)
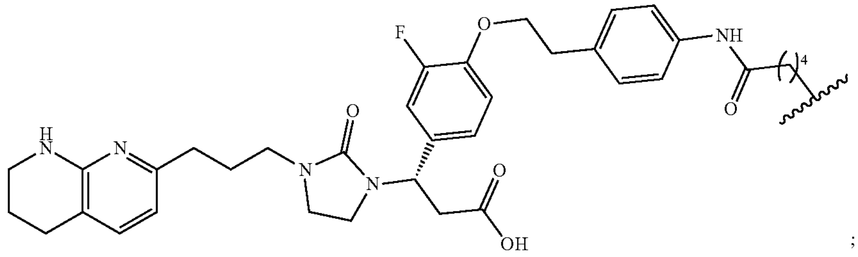
;

-continued
(Structure 2.5a)
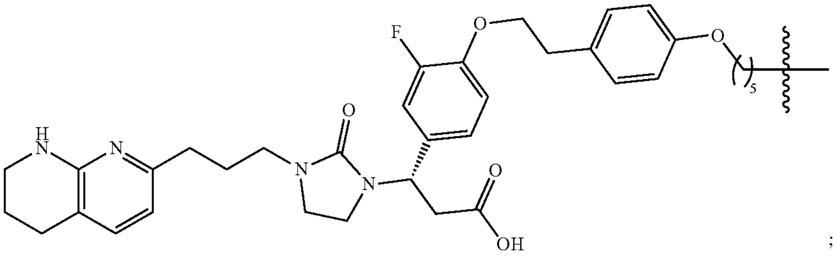
;
(Structure 2.6a)
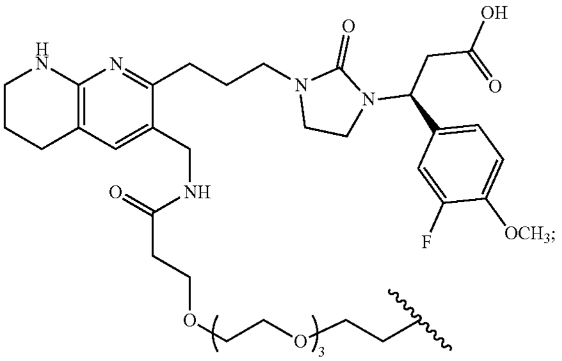
(Structure 2.7a)
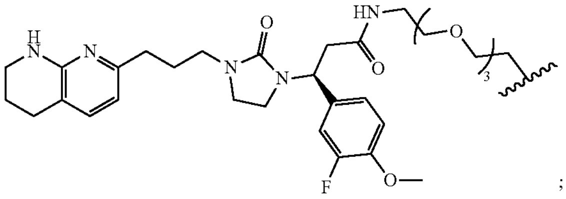
;
(Structure 2.8a)
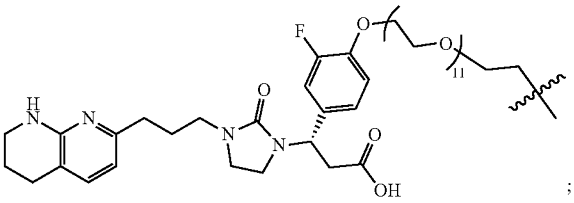
;
(Structure 2.9a)
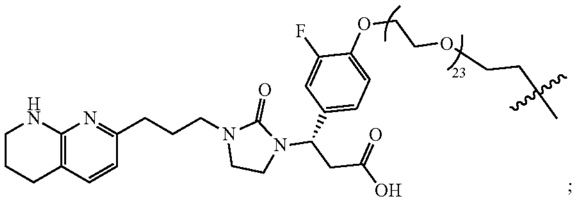
;
(Structure 2.10a)
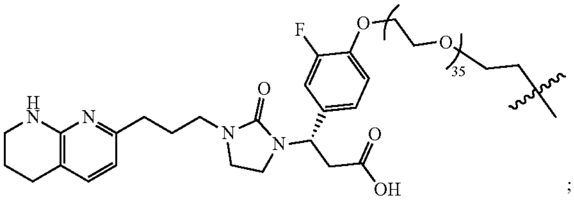
;
(Structure 2.11a)
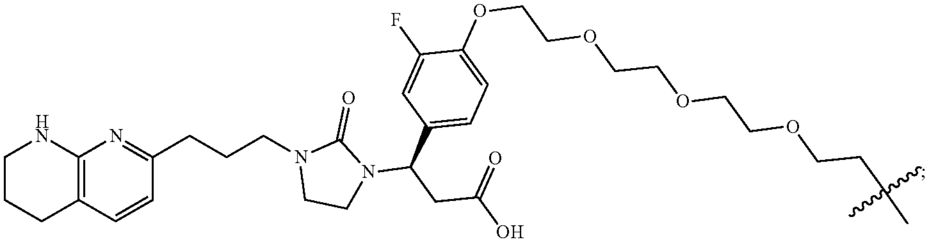
(Structure 28a)
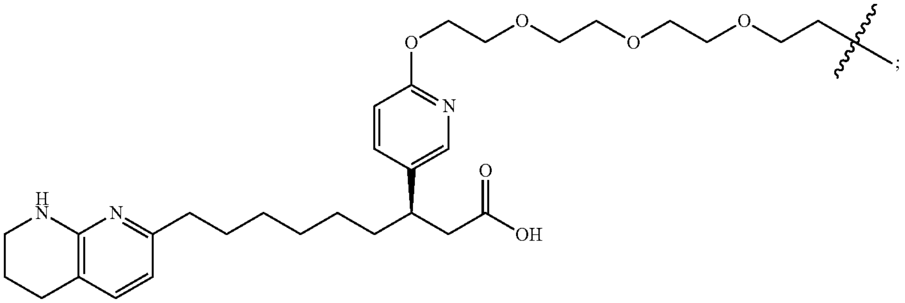

-continued
(Structure 29a)
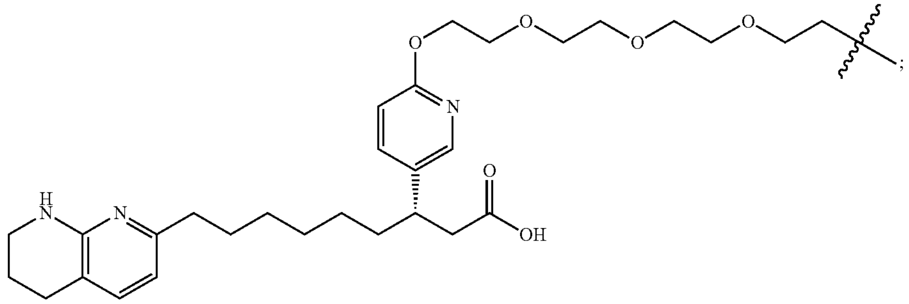
(Structure 30a)
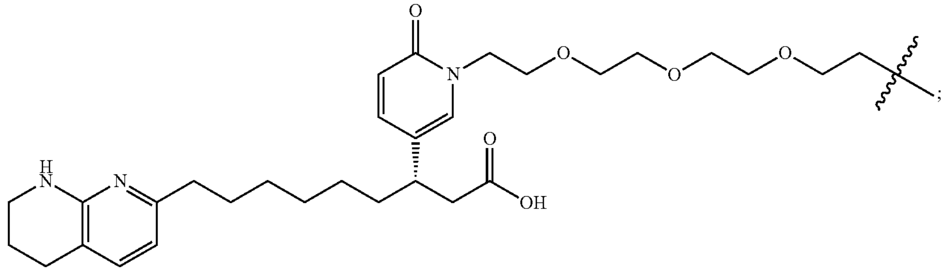
(Structure 31a)
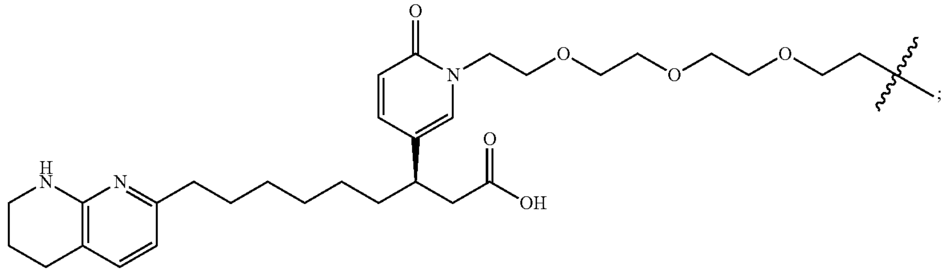
(Structure 32a)
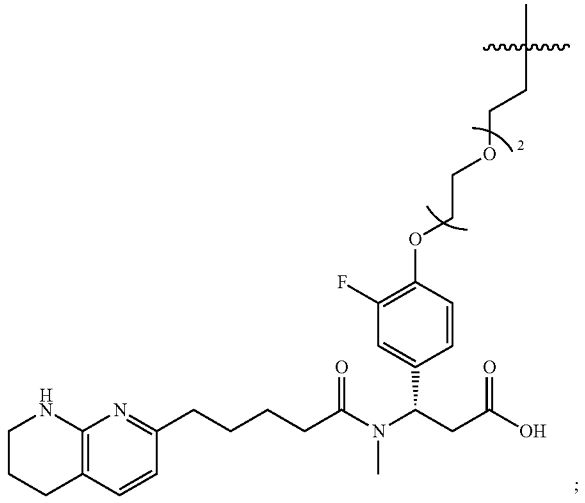
(Structure 33a)
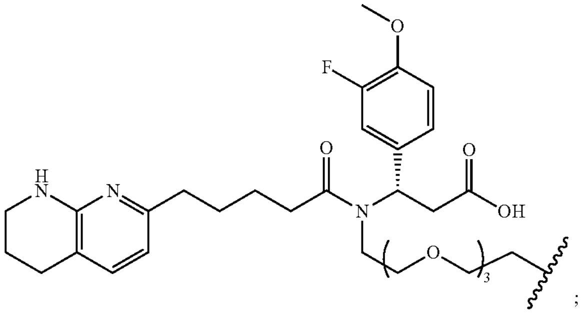

-continued (Structure 34a)

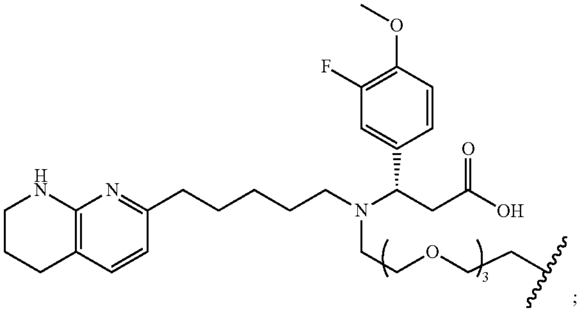

;

(Structure 36a)

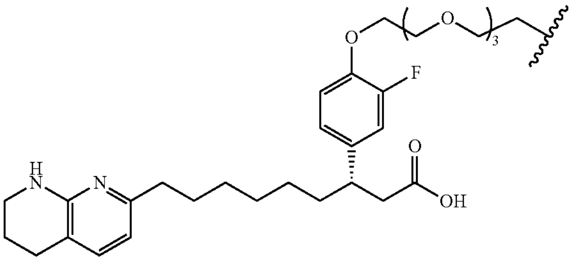

;

(Structure 37a)

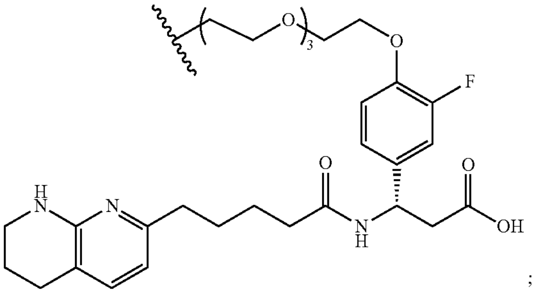

;

(Structure 38a)

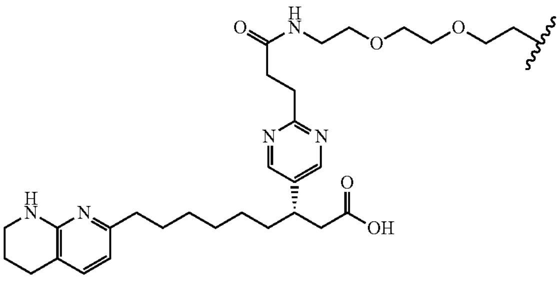

;

(Structure 39a)

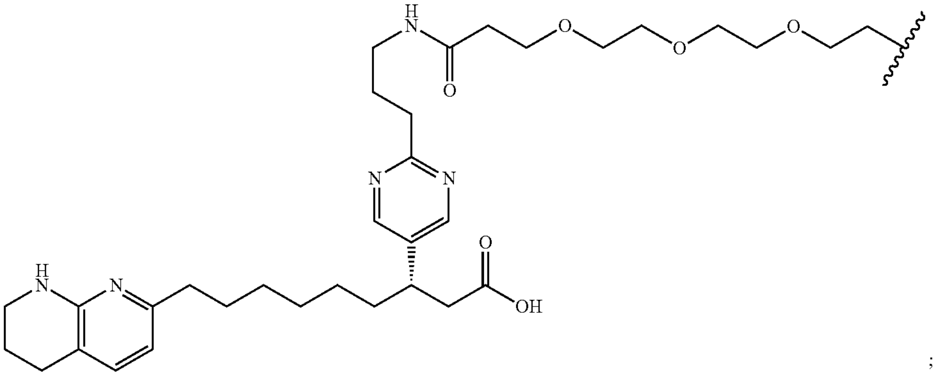

;

(Structure 40a)

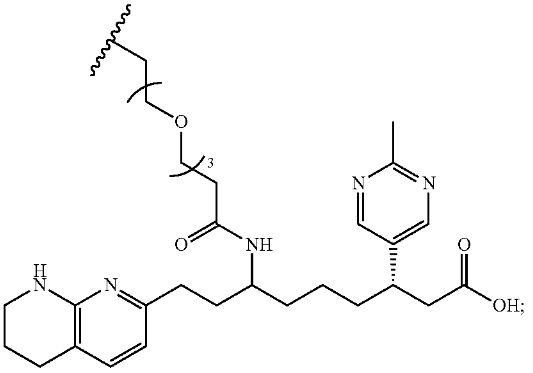

; and (Structure 41a)

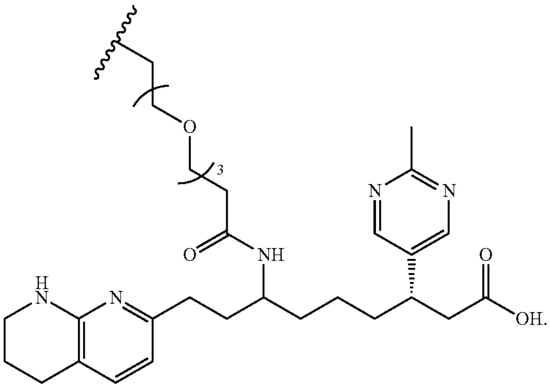

.

In some embodiments, an integrin targeting ligand disclosed herein can be conjugated to one or more (e.g., 2, 3, 4, 5, 6, 7, 8, 9, 10; or 1 to 10, 2 to 10, 1 to 9, 1 to 8, 1 to 7, 1 to 6, 1 to 5, 1 to 4, 1 to 3, 1 to 2, 2 to 10, 3 to 10, 4 to 10, 5 to 10, 2 to 5, 2 to 4, or 3 to 5) cargo molecules (e.g., any of the cargo molecules described herein or known in the art).

In some embodiments, more than one integrin targeting ligand disclosed herein (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30 integrin targeting ligands) can be conjugated to one cargo molecule (e.g., any of the cargo molecules described herein or known in the art).

In some embodiments, the integrin targeting ligands disclosed herein are optionally conjugated to one or more cargo molecules via a linking group, such as, for example, a polyethylene glycol (PEG) group.

In some embodiments, the integrin targeting ligands disclosed herein are optionally conjugated to one or more cargo molecules via a scaffold that includes at least one attachment point for each ligand and at least one attachment point for each cargo molecule. In some embodiments, the integrin targeting ligands comprise, consist of, or consist essentially of, an integrin targeting ligand conjugated to one cargo molecule. In some embodiments, the integrin targeting ligands comprise, consist of, or consist essentially of, an integrin targeting ligand conjugated to more than one cargo molecule.

In some embodiments, the integrin targeting ligand comprises, consists of, or consists essentially of, any of Structure 1a, Structure 2a, Structure 2.1a, Structure 2.2a, Structure 2.3a, Structure 2.4a, Structure 2.5a, Structure 2.6a, Structure 2.8a, Structure 2.9a, Structure 2.10a, Structure 2.11a, Structure 28a, Structure 29a, Structure 30a, Structure 31a, Structure 32a, Structure 33a, Structure 34a, Structure 36a, Structure 37a, Structure 38a, Structure 39a, Structure 40a, and Structure 41a each as disclosed herein.

In some embodiments, an integrin targeting ligand disclosed herein comprises the following structure:

(Structure 1a)

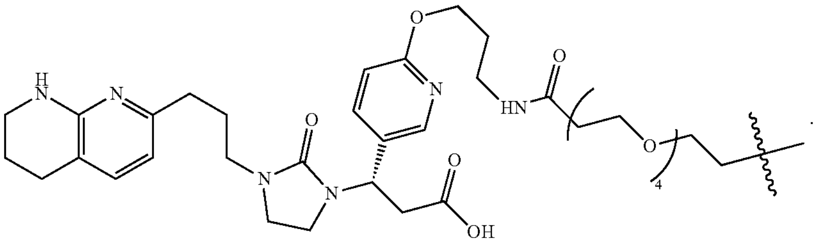

In some embodiments, the integrin targeting ligand of Structure 1a is linked to one or more cargo molecules (e.g., RNAi agent(s)).

In some embodiments, an integrin targeting ligand can be synthesized to include a reactive group, a protected reactive group, or a cargo molecule, and comprises the following structure:

(Structure 1b)

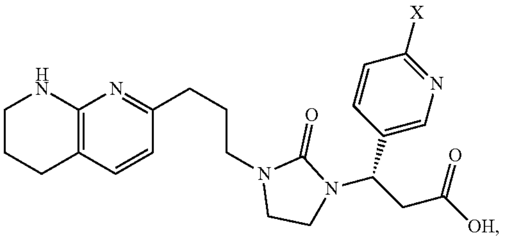

wherein X includes a reactive group, a protected reactive group, or a cargo molecule (e.g., an RNAi agent).

In some embodiments, an integrin targeting ligand precursor can be synthesized to include an azide reactive group, and comprises the following structure:

(Structure 1c)

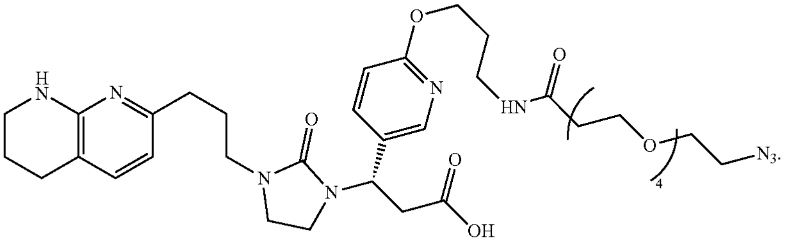

A reactive group (or protected reactive group) can be used to facilitate the conjugation of the integrin targeting ligand to a molecule of interest, e.g., to a cargo molecule (either directly or via one or more scaffolds and/or linkers).

In some embodiments, an integrin targeting ligand disclosed herein comprises the structure:

(Structure 2a)

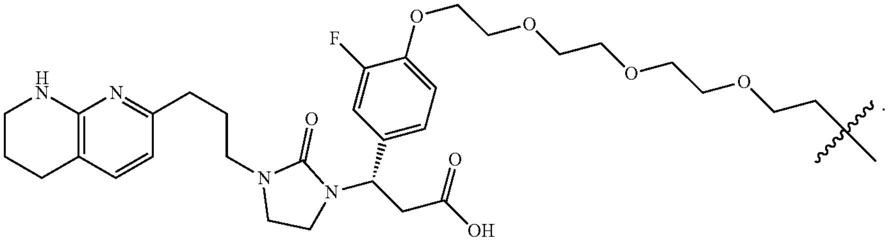

In some embodiments, the integrin targeting ligand of Structure 2a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 2b)

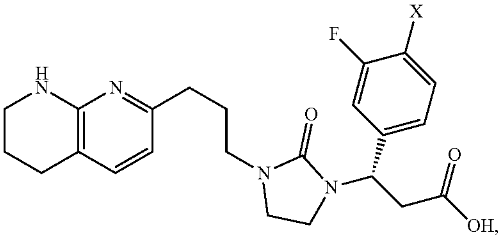

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 2c)

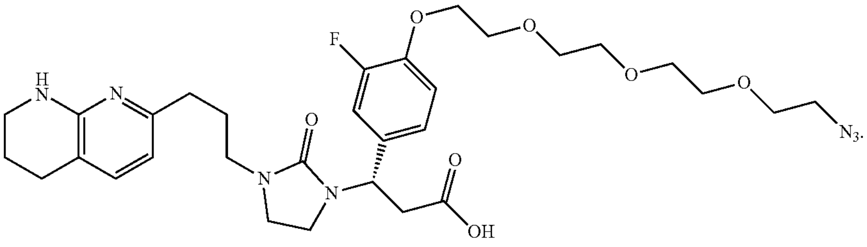

In some embodiments, an integrin targeting ligand disclosed herein comprises the following structure:

(Structure 2.1a)

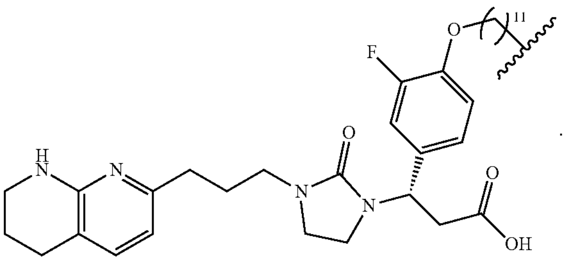

In some embodiments, the integrin targeting ligand of Structure 2.1a is linked to one or more cargo molecules (e.g., RNAi agent(s)).

In some embodiments, the integrin targeting ligand can be synthesized to include an azide reactive group, and comprises the following structure:

(Structure 2.1c)

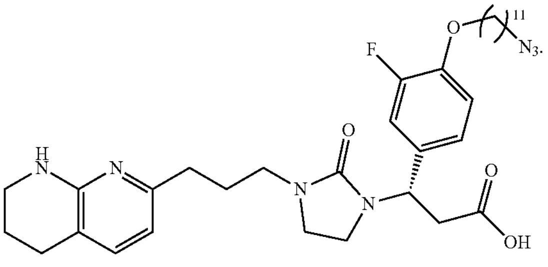

In some embodiments, an integrin targeting ligand disclosed herein comprises the following structure:

(Structure 2.2a)

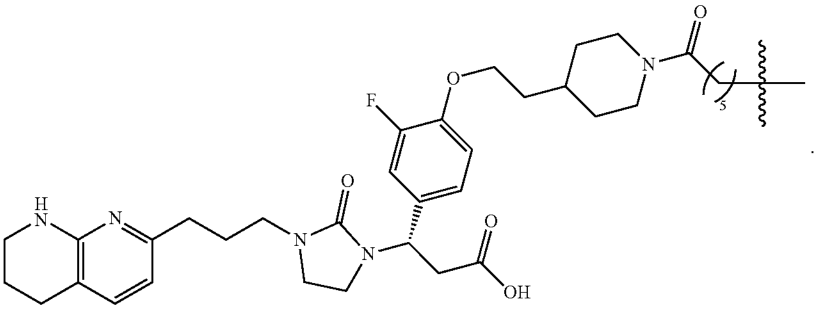

In some embodiments, the integrin targeting ligand of Structure 2.2a is linked to one or more cargo molecules (e.g., RNAi agent(s)).

In some embodiments, the integrin targeting ligand can be synthesized to include an azide reactive group, and comprises the following structure:

(Structure 2.2c)

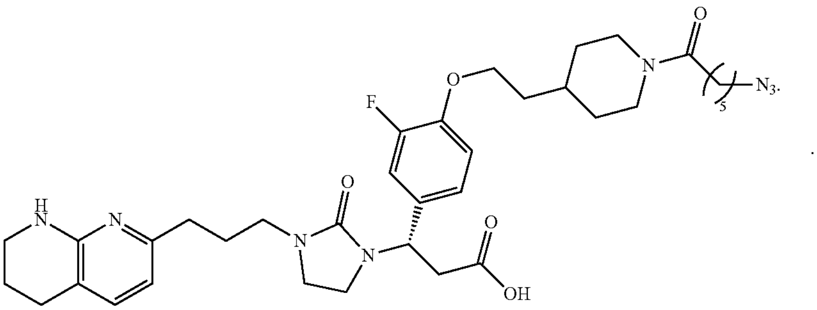

In some embodiments, an integrin targeting ligand disclosed herein comprises the following structure:

(Structure 2.3a)

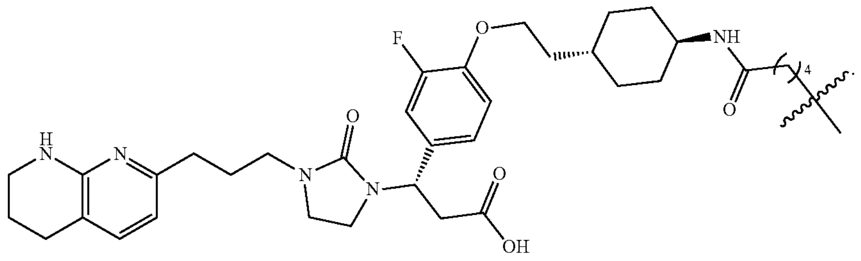

In some embodiments, the integrin targeting ligand of Structure 2.3a is linked to one or more cargo molecules (e.g., RNAi agent(s)).

In some embodiments, the integrin targeting ligand can be synthesized to include an azide reactive group, and comprises the following structure:

(Structure 2.3c)

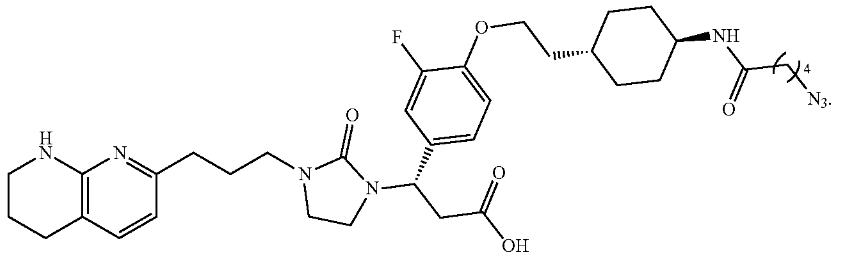

In some embodiments, an integrin targeting ligand disclosed herein comprises the following structure:

(Structure 2.4a)

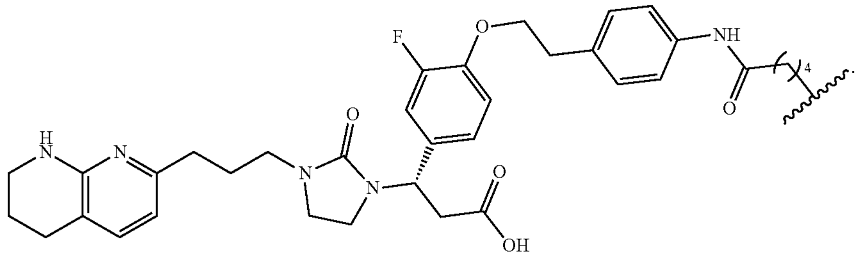

In some embodiments, the integrin targeting ligand of Structure 2.4a is linked to one or more cargo molecules (e.g., RNAi agent(s)).

In some embodiments, the integrin targeting ligand can be synthesized to include an azide reactive group, and comprises the following structure:

(Structure 2.4c)

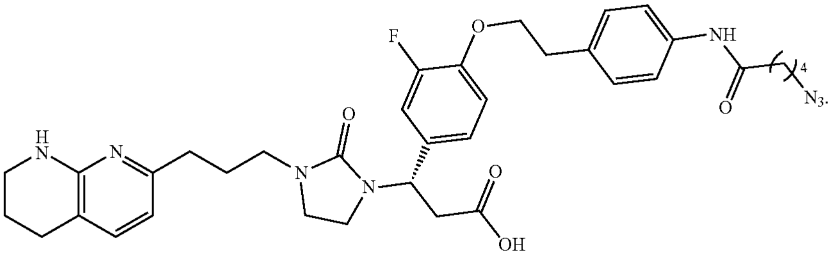

In some embodiments, an integrin targeting ligand disclosed herein comprises the following structure:

(Structure 2.5a)

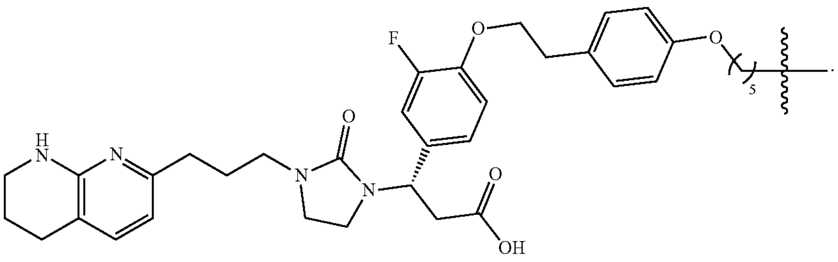

In some embodiments, the integrin targeting ligand of Structure 2.5a is linked to one or more cargo molecules (e.g., RNAi agent(s)).

In some embodiments, the integrin targeting ligand can be synthesized to include an azide reactive group, and comprises the following structure:

(Structure 2.5c)

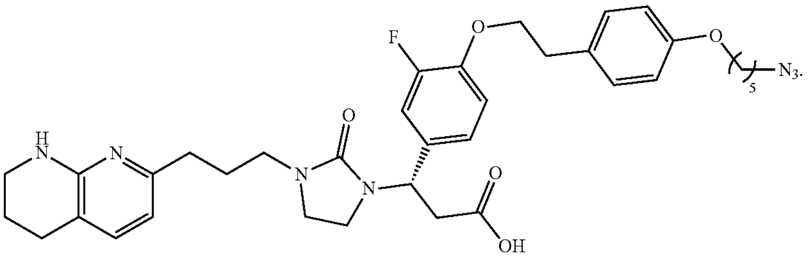

In some embodiments, an integrin targeting ligand disclosed herein comprises the following structure:

(Structure 2.6a)

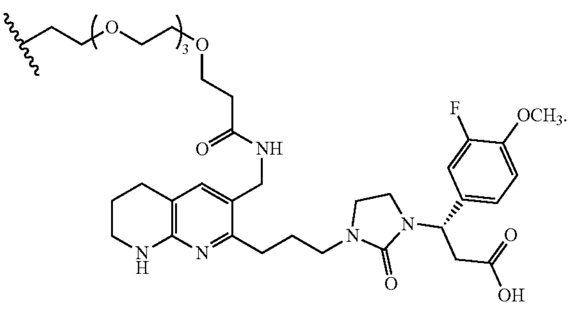

In some embodiments, the integrin targeting ligand of Structure 2.6a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 2.6b)

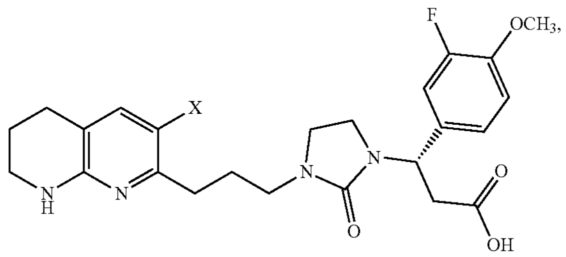

wherein X includes a reactive group, a protected reactive group, or a cargo molecule (e.g., an RNAi agent).

In some embodiments, the integrin targeting ligands can be synthesized to include an azide reactive group, and comprises the following structure:

(Structure 2.6c)

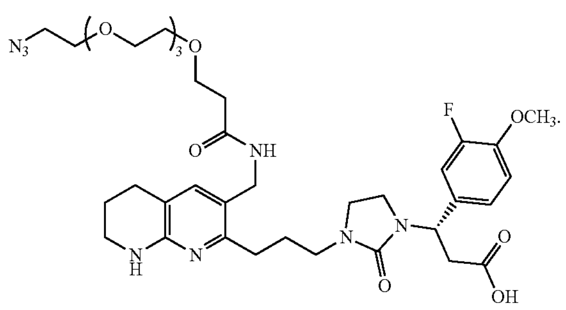

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 2.7a)

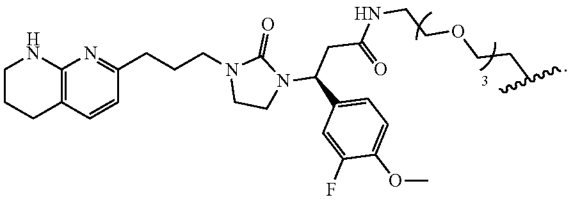

In some embodiments, the integrin targeting ligand of Structure 2.7a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 2.7b)

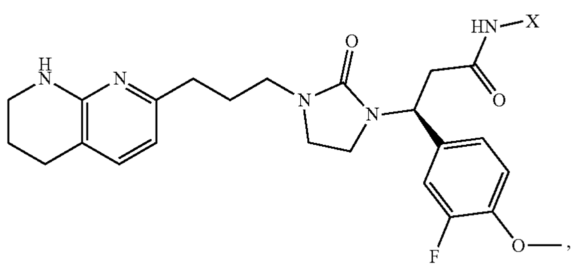

wherein X includes a reactive group, a protected reactive group, or a cargo molecule (e.g., an RNAi agent).

In some embodiments, the integrin targeting ligands can be synthesized to include an azide reactive group, and comprises the following structure:

(Structure 2.7c)

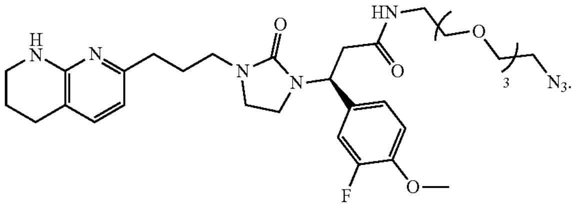

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 2.8a)

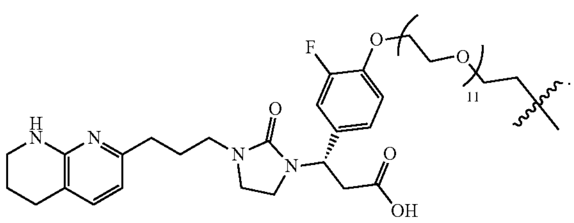

In some embodiments, the integrin targeting ligand of Structure 2.8a is linked to one or more cargo molecules (e.g., RNAi agent(s)).

In some embodiments, the integrin targeting ligands can be synthesized to include an azide reactive group, and comprises the following structure:

(Structure 2.8c)

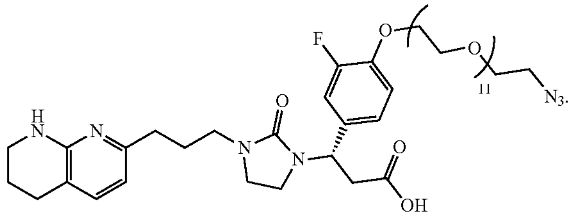

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 2.9a)

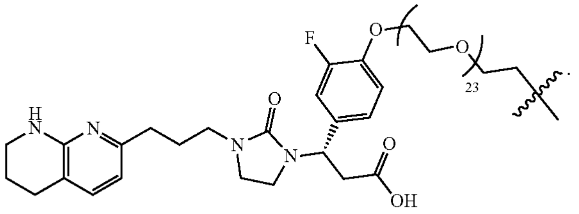

In some embodiments, the integrin targeting ligand of Structure 2.9a is linked to one or more cargo molecules (e.g., RNAi agent(s)).

In some embodiments, the integrin targeting ligands can be synthesized to include an azide reactive group, and comprises the following structure:

(Structure 2.9c)

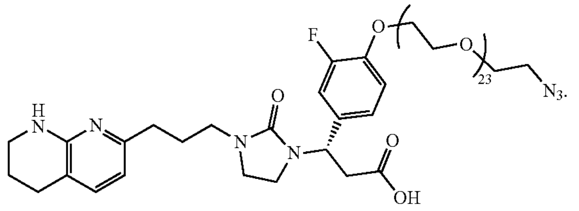

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 2.10a)

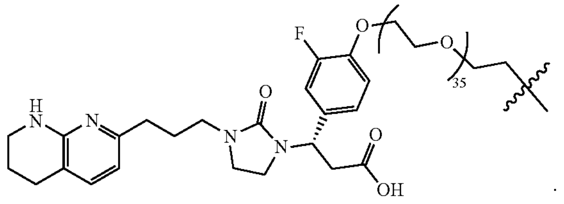

In some embodiments, the integrin targeting ligand of Structure 2.10a is linked to one or more cargo molecules (e.g., RNAi agent(s)).

In some embodiments, the integrin targeting ligands can be synthesized to include an azide reactive group, and comprises the following structure:

(Structure 2.10c)

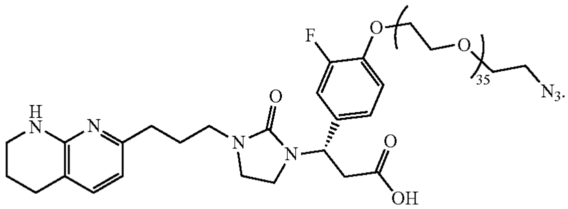

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 2.11a)

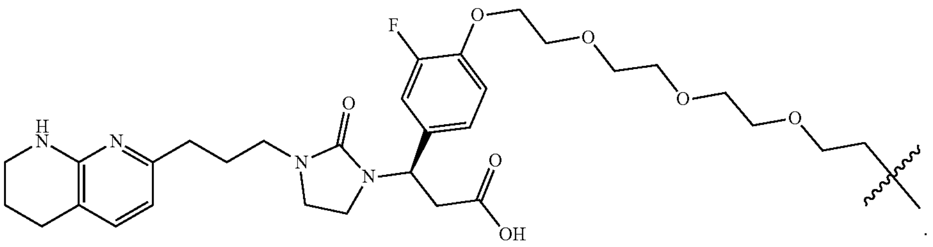

In some embodiments, the integrin targeting ligand of Structure 2.11a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 2.11b)

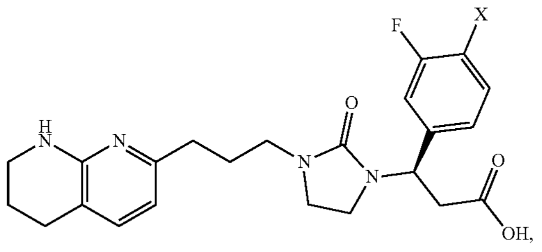

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 2.11c)

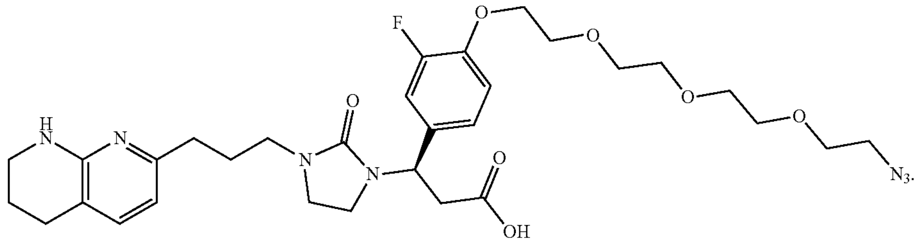

A reactive group (or protected reactive group) can be used to facilitate the conjugation of the integrin targeting ligand to a molecule of interest, e.g., to a cargo molecule (either directly or via one or more scaffolds and/or linker).

In some embodiments, an integrin targeting ligand disclosed herein comprises the following structure:

(Structure 28a)

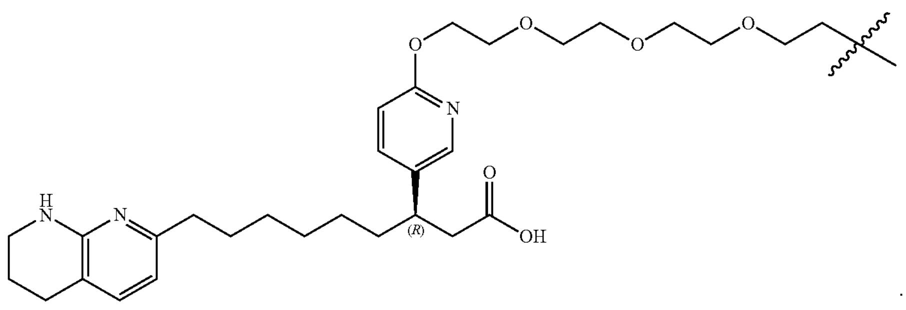

.

In some embodiments, the integrin targeting ligand of Structure 28a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 28b)

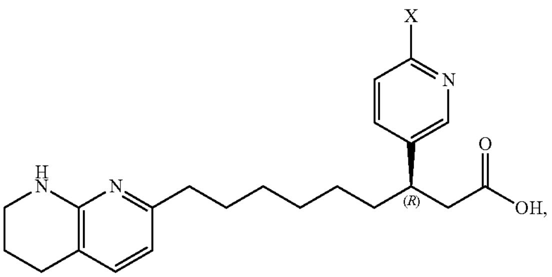

wherein X includes a reactive group, a protected reactive group, or a cargo molecule (e.g., an RNAi agent).

In some embodiments, the integrin targeting ligand can be synthesized to include an azide reactive group, and comprises the following structure:

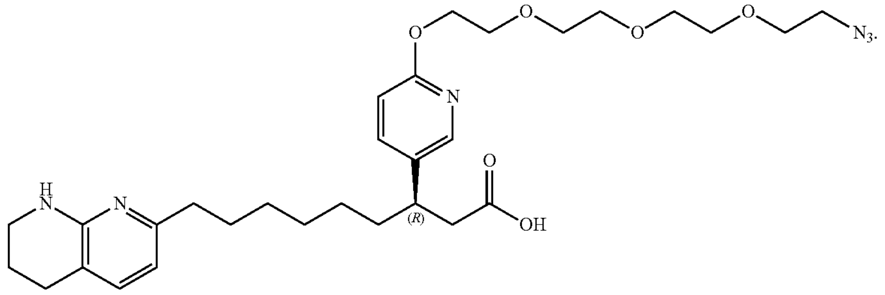

(Structure 28c).

In some embodiments, an integrin targeting ligand disclosed herein comprises the following structure:

(Structure 29a)

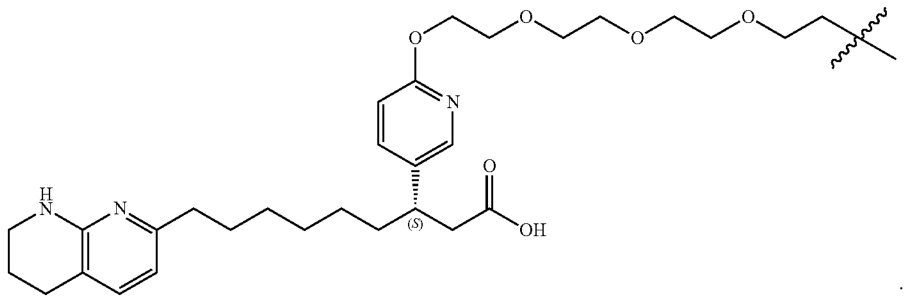

In some embodiments, the integrin targeting ligand of Structure 29a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 29b)

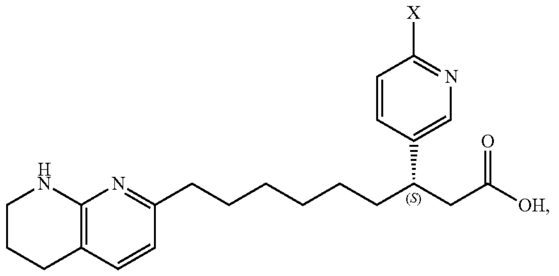

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 29c)

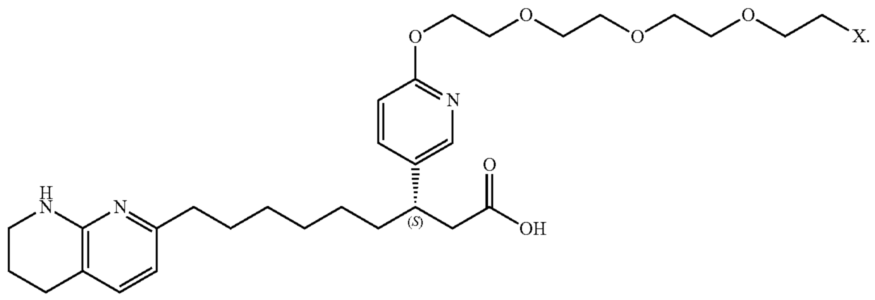

In some embodiments, an integrin targeting ligand disclosed herein comprises the following structure:

(Structure 30a)

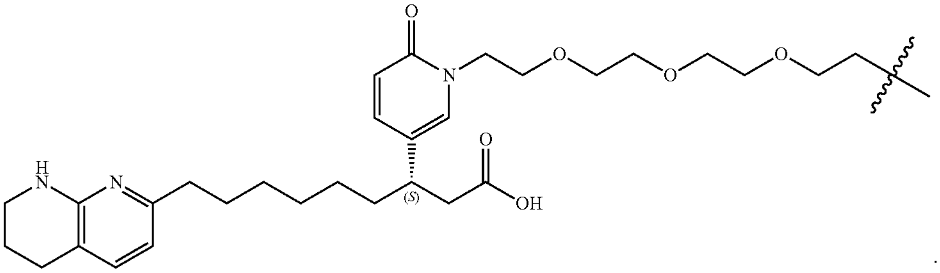

.

In some embodiments, the integrin targeting ligand of Structure 30a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 30b)

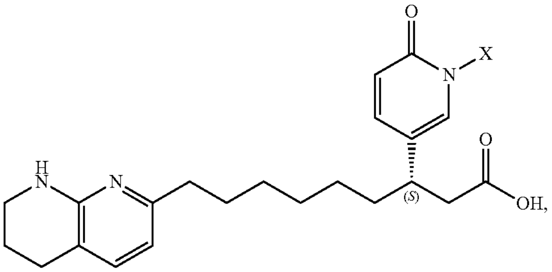

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 30c)

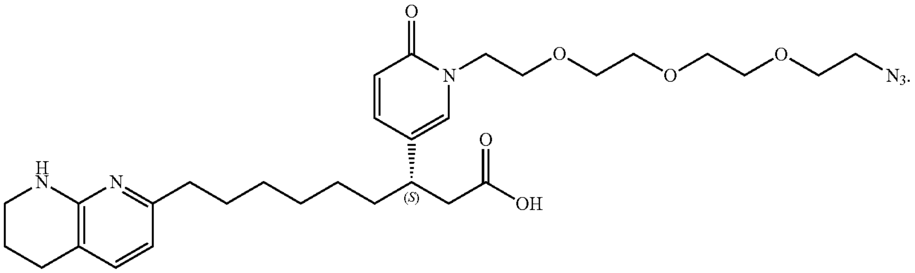

In some embodiments, an integrin targeting ligand disclosed herein comprises the following structure:

(Structure 31a)

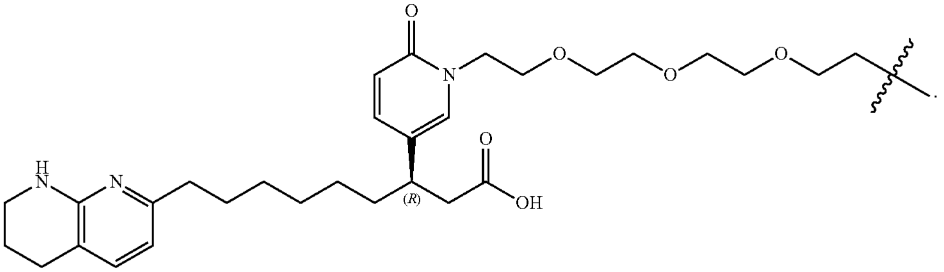

In some embodiments, the integrin targeting ligand of Structure 31a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 31b)

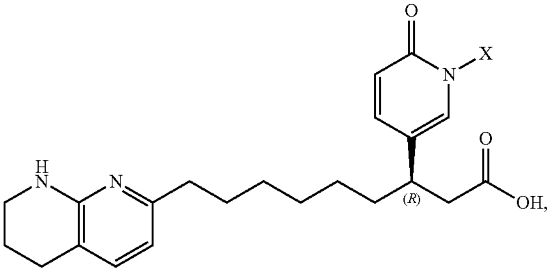

wherein X includes a reactive group, a protected reactive group, or a cargo molecule (e.g., an RNAi agent).

In some embodiments, the integrin targeting ligand can be synthesized to include an azide reactive group, and comprises the following structure:

In some embodiments, an integrin targeting ligand disclosed herein comprises the following structure:

(Structure 32a)

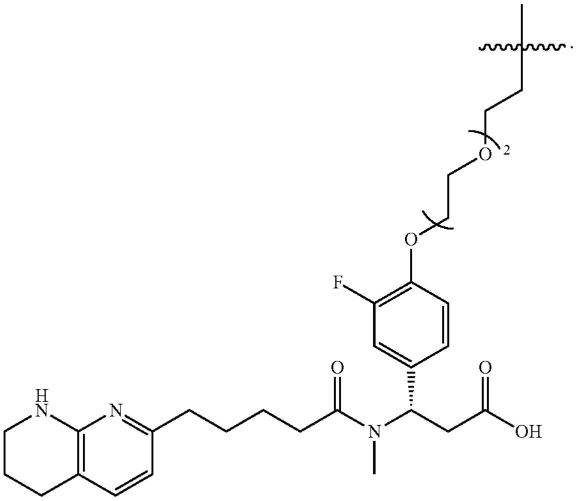

In some embodiments, the integrin targeting ligand of Structure 32a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 31c)

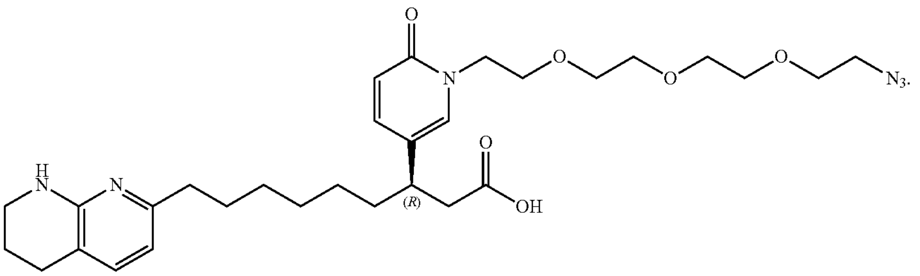

(Structure 32b)

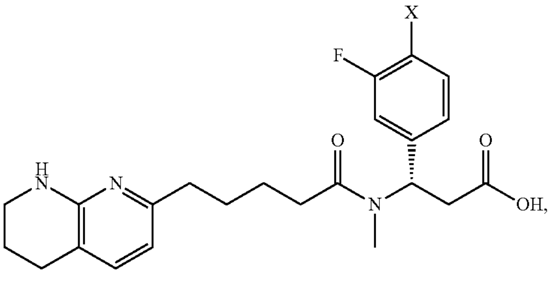

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 32c)

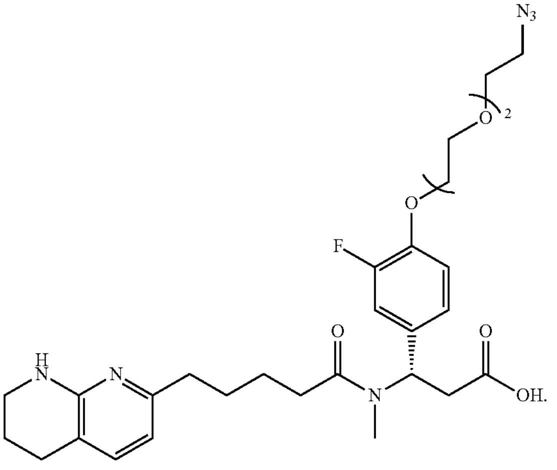

In some embodiments, an integrin targeting ligand disclosed herein comprises the following structure:

(Structure 33a)

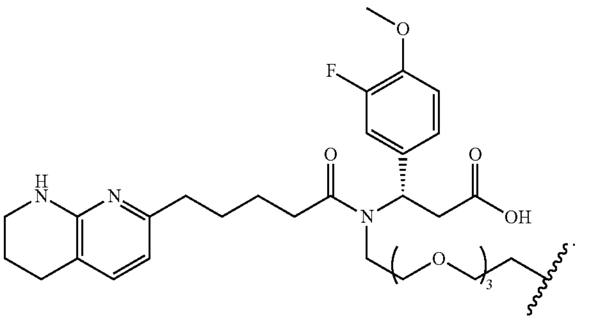

In some embodiments, the integrin targeting ligand of Structure 33a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 33b)

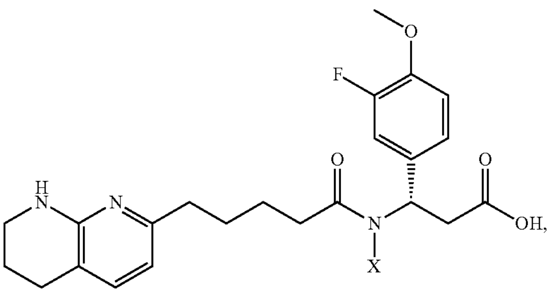

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 33c)

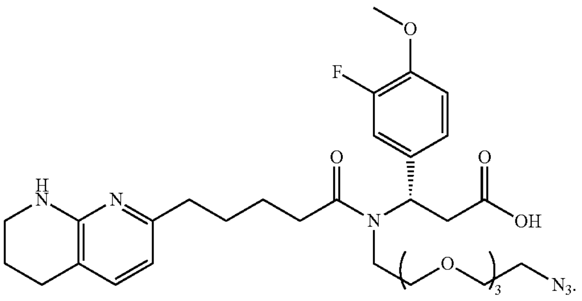

In some embodiments, an integrin targeting ligand disclosed herein comprises the following structure:

(Structure 34a)

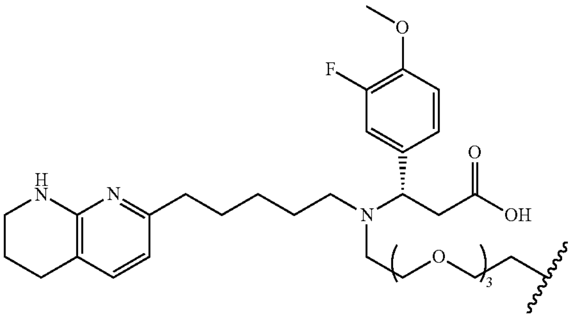

In some embodiments, the integrin targeting ligand of Structure 34a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 34b)

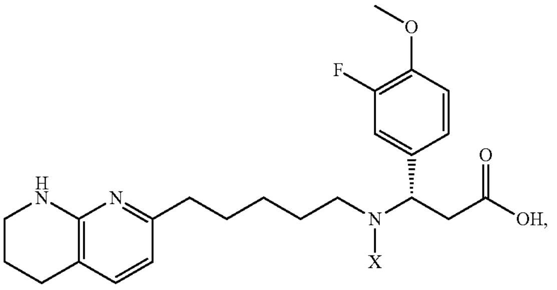

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 34c)

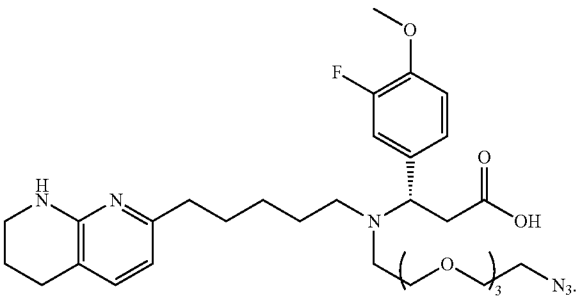

In some embodiments, an integrin targeting ligand disclosed herein comprises the following structure:

(Structure 36a)

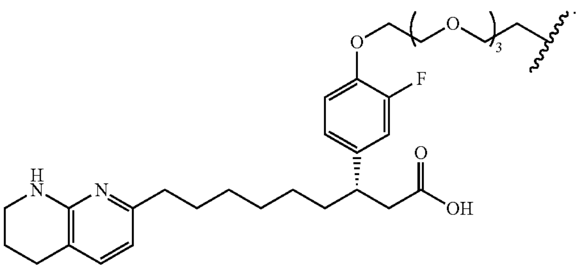

In some embodiments, the integrin targeting ligand of Structure 36a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 31b)

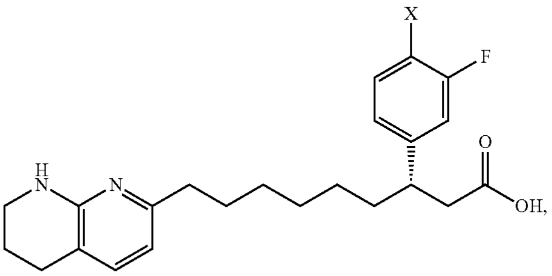

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 31c)

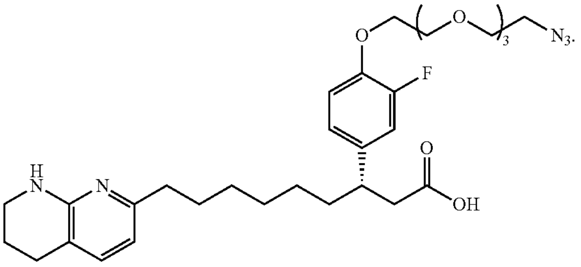

In some embodiments, an integrin targeting ligand disclosed herein comprises the following structure:

(Structure 37a)

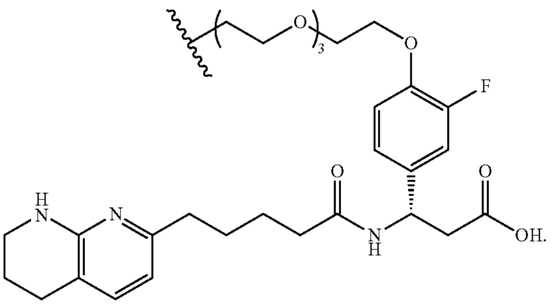

In some embodiments, the integrin targeting ligand of Structure 37a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 37b)

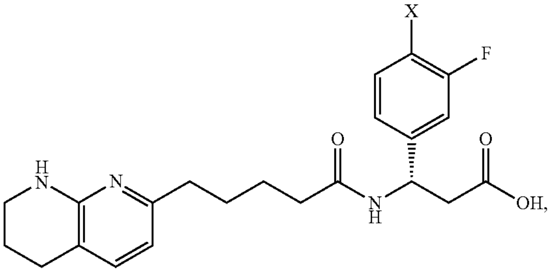

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 37c)

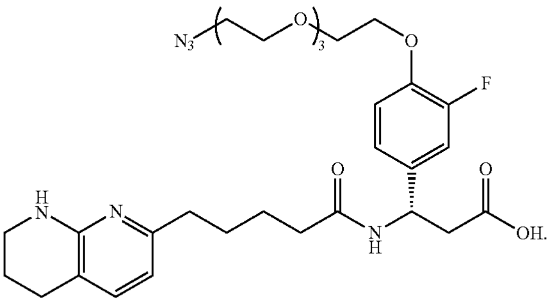

In some embodiments, an integrin targeting ligand disclosed herein comprises the following structure:

(Structure 38a)

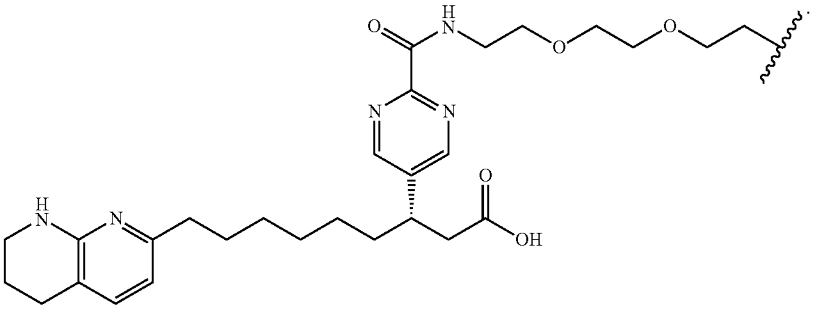

In some embodiments, the integrin targeting ligand of Structure 38a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 38b)

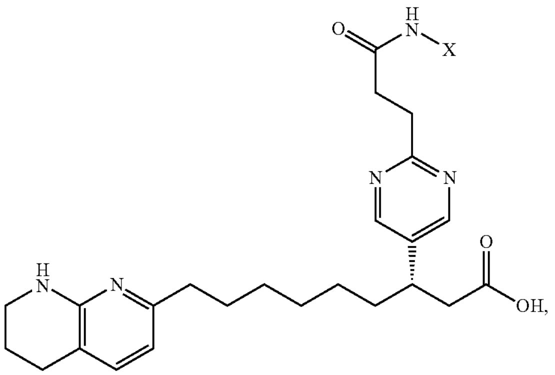

wherein X includes a reactive group, a protected reactive group, or a cargo molecule (e.g., an RNAi agent).

In some embodiments, the integrin targeting ligand can be synthesized to include an azide reactive group, and comprises the following structure.

(Structure 38c)

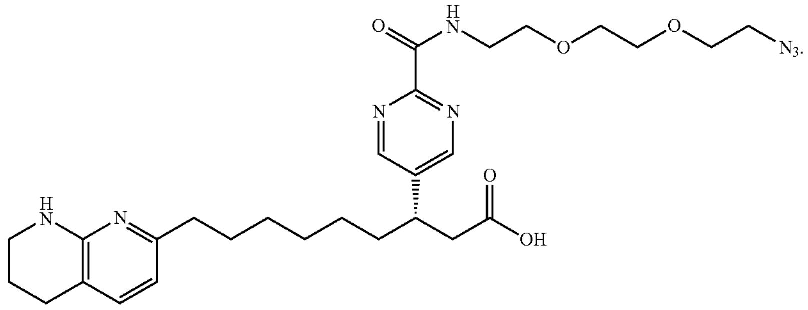

In some embodiments, an integrin targeting ligand disclosed herein comprises the following structure:

(Structure 39a)

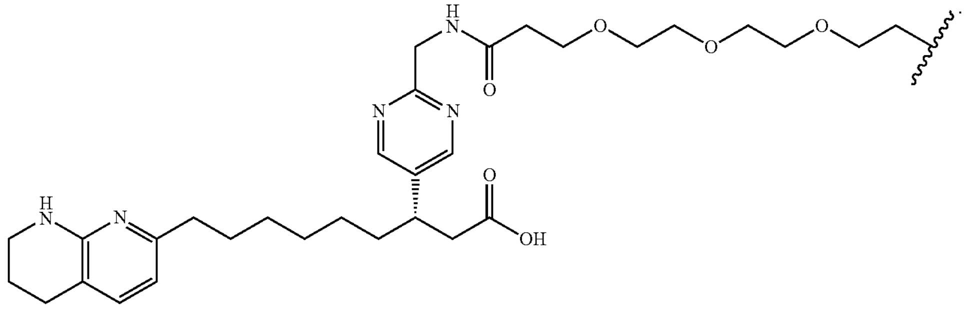

In some embodiments, the integrin targeting ligand of Structure 39a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 39b)

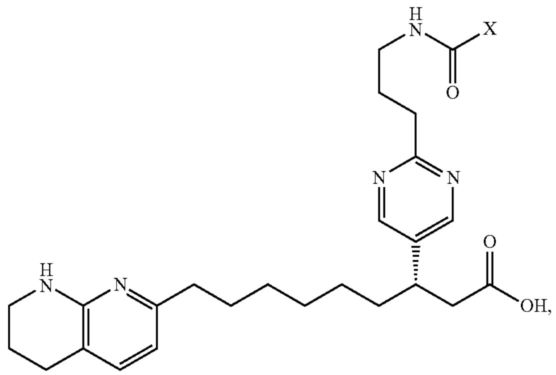

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 39c)

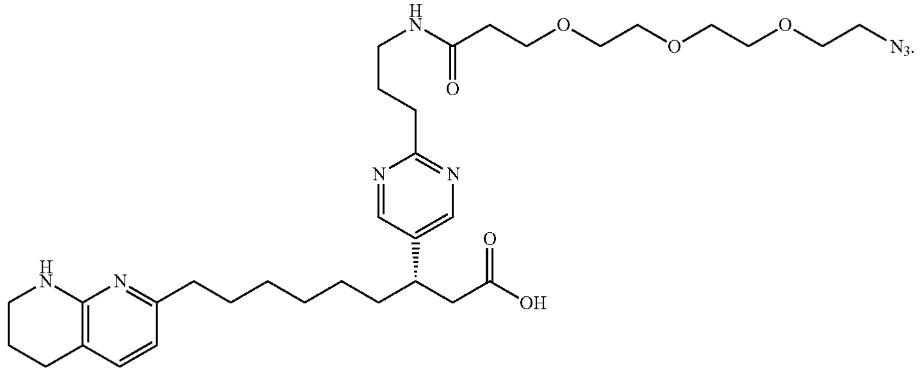

In some embodiments, an integrin targeting ligand disclosed herein comprises the following structure:

(Structure 40a)

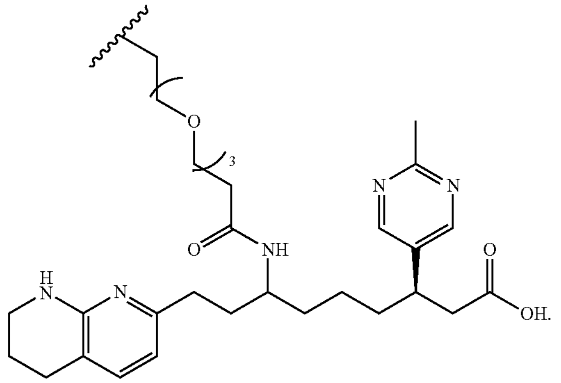

In some embodiments, the integrin targeting ligand of Structure 40a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 40b)

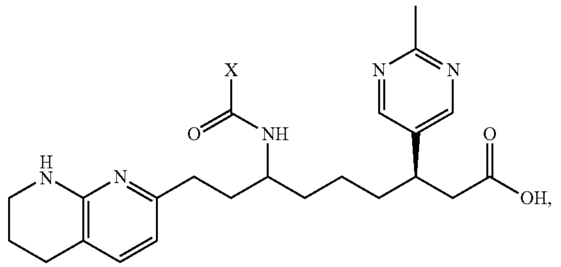

wherein X includes a reactive group, a protected reactive group, or a cargo molecule (e.g., an RNAi agent).

In some embodiments, the integrin targeting ligand can be synthesized to include an azide reactive group, and comprises the following structure.

(Structure 40c)

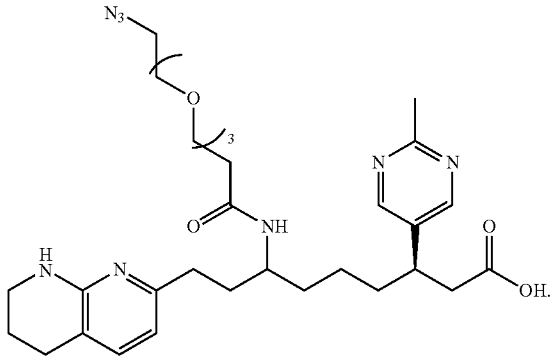

In some embodiments, an integrin targeting ligand disclosed herein comprises the following structure:

(Structure 41a)

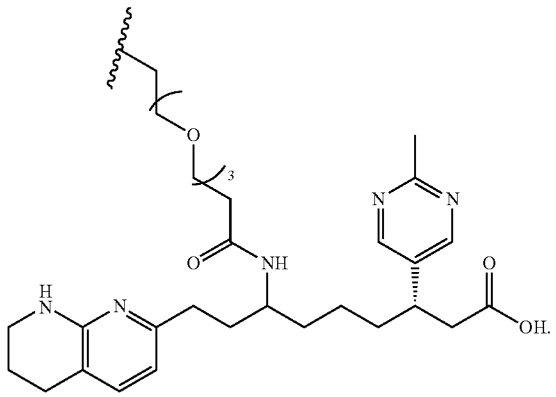

In some embodiments, the integrin targeting ligand of Structure 41a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 41b)

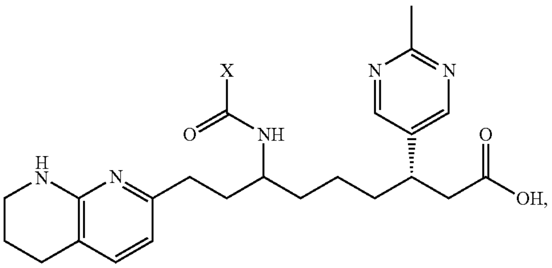

wherein X includes a reactive group, a protected reactive group, or a cargo molecule (e.g., an RNAi agent).

In some embodiments, the integrin targeting ligand can be synthesized to include an azide reactive group, and comprises the following structure:

(Structure 41c)

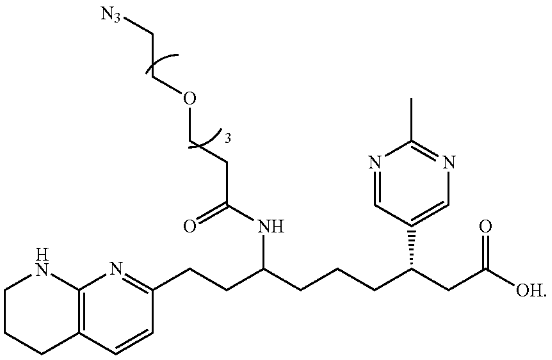

The azide reactive group as disclosed in any of Structure 1c, Structure 2c, Structure 2.1c, Structure 2.2c, Structure 2.3c, Structure 2.4c, Structure 2.5c, Structure 2.6c, Structure 2.7c, Structure 2.8c, Structure 2.9c, Structure 2.10c, Structure 2.11c, Structure 28c, Structure 29c, Structure 30c, Structure 31c, Structure 32c, Structure 33c, Structure 34c, Structure 36c, Structure 37c, Structure 38c, Structure 39c, Structure 40c, and Structure 41c can be used to attach the integrin targeting ligand to a molecule of interest, i.e., to a cargo molecule such as an RNAi agent. The cargo molecule can be any molecule that is desired to be targeted to an integrin-expressing cell.

As used herein, the term "alkyl" refers to a saturated aliphatic hydrocarbon group, straight chain or branched, having from 1 to 10 carbon atoms unless otherwise specified. For example, "$C_1$-$C_6$ alkyl" includes alkyl groups having 1, 2, 3, 4, 5, or 6 carbons in a linear or branched arrangement. Non-limiting examples of alkyl groups include methyl, ethyl, iso-propyl, tert-butyl, n-hexyl. As used herein, the term "aminoalkyl" refers to an alkyl group as defined above, substituted at any position with one or more amino groups as permitted by normal valency. The amino groups may be unsubstituted, monosubstituted, or di-substituted. Non-limiting examples of aminoalkyl groups include aminomethyl, dimethylaminomethyl, and 2-aminoprop-1-yl.

As used herein, the term "cycloalkyl" means a saturated or unsaturated nonaromatic hydrocarbon ring group having from 3 to 14 carbon atoms, unless otherwise specified. Non-limiting examples of cycloalkyl groups include, but are not limited to, cyclopropyl, methyl-cyclopropyl, 2,2-dimethyl-cyclobutyl, 2-ethyl-cyclopentyl, and cyclohexyl. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight, or branched, containing at least one carbon-carbon double bond, and having from 2 to 10 carbon atoms unless otherwise specified. Up to five carbon-carbon double bonds may be present in such groups. For example, "$C_2$-$C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "$C_2$-$C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may be optionally mono-, di-, tri-, tetra-, or penta-substituted on any position as permitted by normal valency.

As used herein, "alkoxy 1" or "alkoxy" refers to —O-alkyl radical having the indicated number of carbon atoms. For example, $C_{1-6}$ alkoxy is intended to include $C_1$, $C_2$, $C_3$, $C_4$, $C_5$, and $C_6$ alkoxy groups. For example, $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, or hexanoyl), alkenoyl (e.g., actyloyl) alkynoyl (e.g., ethanoyl, propynoyl, butynoyl, pentynoyl, or hexynoyl), aryloyl (e.g., benzoyl), heteroaryloyl (e.g., pyrroloyl, imidazoloyl, quinolinoyl, or pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxy carbonyl, benzyloxy carbonyl, or n-pentoxy carbonyl.

As used herein, "aryloxy carbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryl oxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxy carbonyl, 4-thiazolyloxy carbonyl, or pyrimidinyloxy carbonyl.

As used herein, "aryl" or "aromatic" means any stable monocyclic or poly cyclic carbon ring of up to 6 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N, and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, and tetrahydroquinoline "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N, and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxoxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyndinyl, pyridazyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition of the number, severity, and/or frequency of one or more symptoms of a disease in a subject.

As used herein, the phrase "deliver to a cell," and the like, when referring to a cargo molecule, means functionally delivering the cargo molecule to the cell. The phrase "functionally delivering," means delivering the cargo molecule to the cell in a manner that enables the cargo molecule to have the expected biological activity. When specifically referring to a cargo molecule that is an RNAi agent, the expected biological activity is, for example, sequence-specific inhibition of gene expression.

Unless stated otherwise, use of the symbol 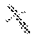 as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, a linking group is one or more atoms that connects one molecule or portion of a molecule to another to second molecule or second portion of a molecule. In the art, the terms linking group and spacers are sometimes used interchangeably. Similarly, as used in the art, the term scaffold is sometimes used interchangeably with a linking group. In some embodiments. In some embodiments, a linking group can include or consist of a PEG group or PEG moiety.

As used herein, the term "linked" or "conjugated" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1\times10^{-4}$ M (e.g., less than $1\times10^{-5}$ M, less than $1\times10^{-6}$ M, or less than $1\times10^{-7}$ M) in physiologically acceptable buffer (e.g., phosphate buffered saline). Unless stated, the term linked as used herein may refer to the connection between a first compound and a second compound either with or without any intervening atoms or groups of atoms.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Multidentate αvβ3 Integrin Ligands and Scaffolds

As disclosed herein, in some embodiments, one or more αvβ3/5 integrin ligands may be linked to one or more cargo molecules. In some embodiments, only one integrin ligand is conjugated to a cargo molecule (referred to herein as a "monodentate" or "monovalent" ligand).

In some embodiments, two integrin ligands are conjugated to a cargo molecule (referred to herein as a "bidentate" or "divalent" targeting group). In some embodiments, three integrin ligands are conjugated to a cargo molecule (referred to herein as a "tridentate" or "trivalent" targeting group). In some embodiments, four integrin ligands are conjugated to a cargo molecule (referred to herein as a "tetradentate" or "tetravalent" targeting group). In some embodiments, more than four integrin ligands are conjugated to a cargo molecule.

In some embodiments, where only one integrin ligand is conjugated to a cargo molecule (referred to herein as a "monodentate" ligand), the integrin ligand may be conjugated directly to the cargo molecule. In some embodiments, an integrin ligand disclosed herein can be conjugated to a cargo molecule via a scaffold or other linker structure.

In some embodiments, the integrin ligands disclosed herein include one or more scaffolds. Scaffolds, also sometimes referred to in the art as linking groups or linkers, can be used to facilitate the linkage of one or more cargo molecules to one or more integrin ligands disclosed herein. Useful scaffolds compatible with the ligands disclosed herein are generally known in the art. Non-limiting examples of scaffolds that can be used with the αvβ3 integrin ligands disclosed herein include, but are not limited to polymers and polyamino acids (e.g., bis-glutamic acid, poly-L-lysine, etc.). In some embodiments, scaffolds may include cysteine linkers or groups, DBCO-$PEG_{1-24}$-NHS, Propargyl-$PEG_{1-24}$-NHS, and/or multidentate DBCO and/or propargyl moieties.

In some embodiments, the scaffold used for linking one or more integrin ligands disclosed herein to one or more cargo molecules has the following structure:

(Scaffold 1)

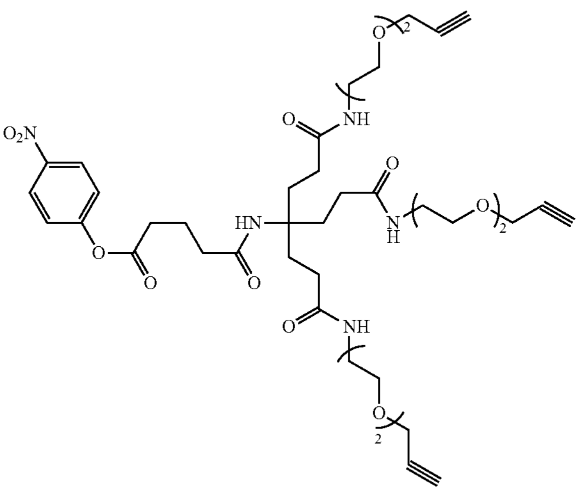

The use of Scaffold 1, for example, facilitates efficient conjugation with both the integrin ligand monomers and the one or more cargo molecules. Scaffold 1 includes an amine reactive p-nitrophenol (also called 4-nitrophenol) ester, an amide linkage, and three $PEG_2$ unit arms, as well as terminal alkynes. The 4-nitrophenol ester can be conjugated with the primary amine on a cargo molecule, such as the primary amine on an RNA trigger formulated with a terminal amine group (e.g., $NH_2$—$(CH_2)_6$), through amide formation. The terminal alkyne can be conjugated with azido modified ligands (both peptides and small molecules) through copper-catalyzed click chemistry.

In some embodiments, the cargo molecule is an RNAi agent. In some embodiments, Scaffold 1 may be attached to the terminal end of an RNAi agent, such as to the 5' terminal end of the sense strand of an RNAi agent. For example, the 5' terminal end of the sense strand of an RNAi agent may be modified to include a $C_6$ amine (—$(CH_2)_6$—$NH_2$) attached to the 5' end of the 5' terminal nucleotide of the RNAi agent. An RNAi agent having such a $C_6$ amine modification (or another other modification resulting in a terminal amine) may be readily conjugated to Scaffold 1, as shown by the representation in the following structure:

(Structure 380)

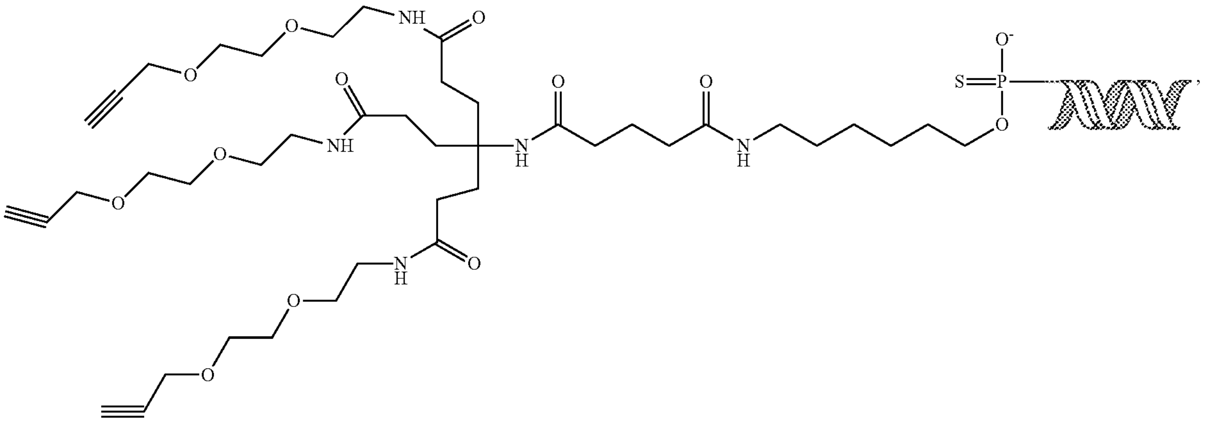

wherein 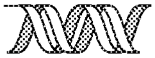 indicates an RNAi agent.

The alkyne groups of Structure 380, above, may then be conjugated to the integrin ligands disclosed herein to form tridentate integrin targeting groups.

In some embodiments, a scaffold may be synthesized using DBCO (dibenzocyclooctyne), which can be represented by the following structure:

(Structure 381)

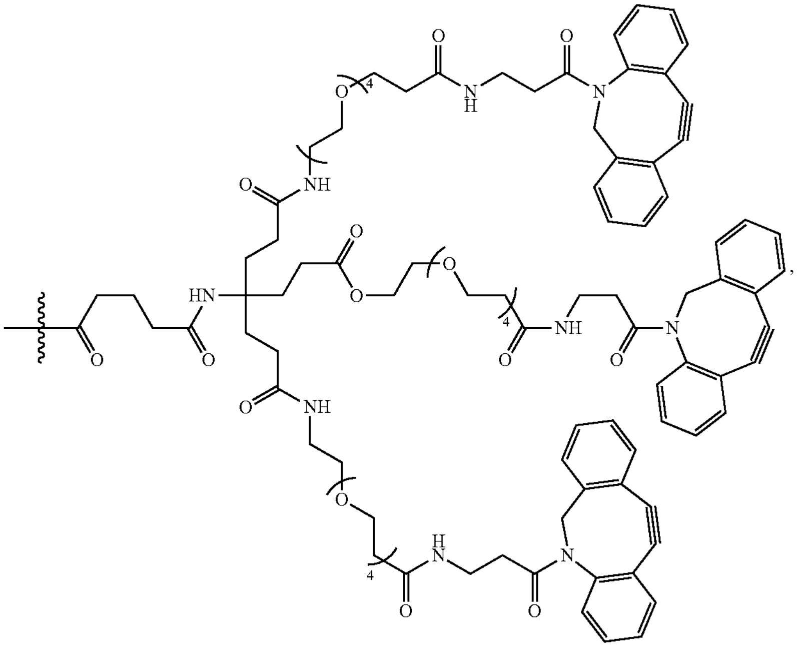

wherein  indicates attachment to a reactive group or a moiety comprising cargo molecule.

In some embodiments, triazole groups are formed between the RNAi agent and the integrin ligands disclosed herein, as shown in the following general structure:

(Structure 390)

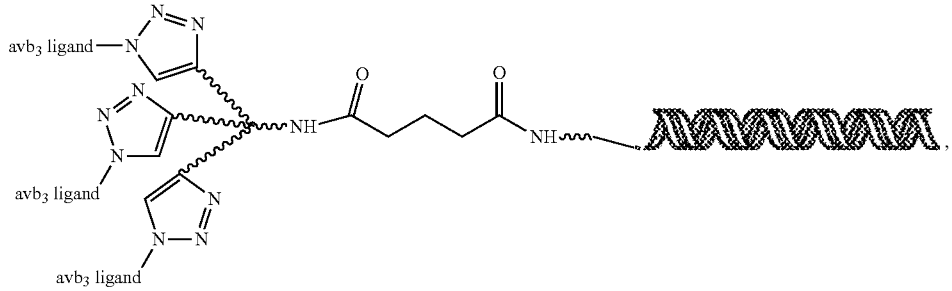

wherein 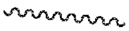 indicates any suitable scaffold or linker that can be used to bind a ligand to an RNAi agent, and 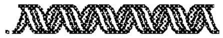 indicated an RNAi agent.

In some embodiments, a scaffold may be synthesized as a phosphoramidite compound, an example of which is shown in the following structure:

(Structure 400)

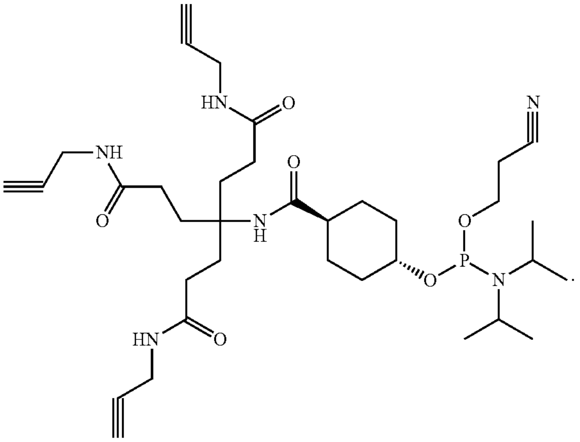

The trialkyne compound of Structure 400 allows for a tridentate ligand to be readily coupled to the 5' terminal end of the sense strand of an RNAi agent through a click reaction of an alkyne with a targeting ligand comprising an azide.

In some embodiments, an integrin targeting group disclosed herein comprises Structure 1a, Structure 2a, Structure 2.1a, Structure 2.2a, Structure 2.3a, Structure 2.4a, Structure 2.5a, Structure 2.6a, Structure 2.7a, Structure 2.8a, Structure 2.9a, Structure 2.10a, Structure 2.11a, Structure 28a, Structure 29a, Structure 30a, Structure 31a, Structure 32a, Structure 33a, Structure 34a, Structure 36a, Structure 37a, Structure 38a, Structure 39a, Structure 40a, and Structure 41a, wherein the αvβ3 integrin targeting group is a tridentate targeting group and comprises three ligands.

In some embodiments, an αvβ3 tridentate targeting group disclosed herein comprises three ligands of Structure 2a, and can be represented by the following structure:

(Structure 700)
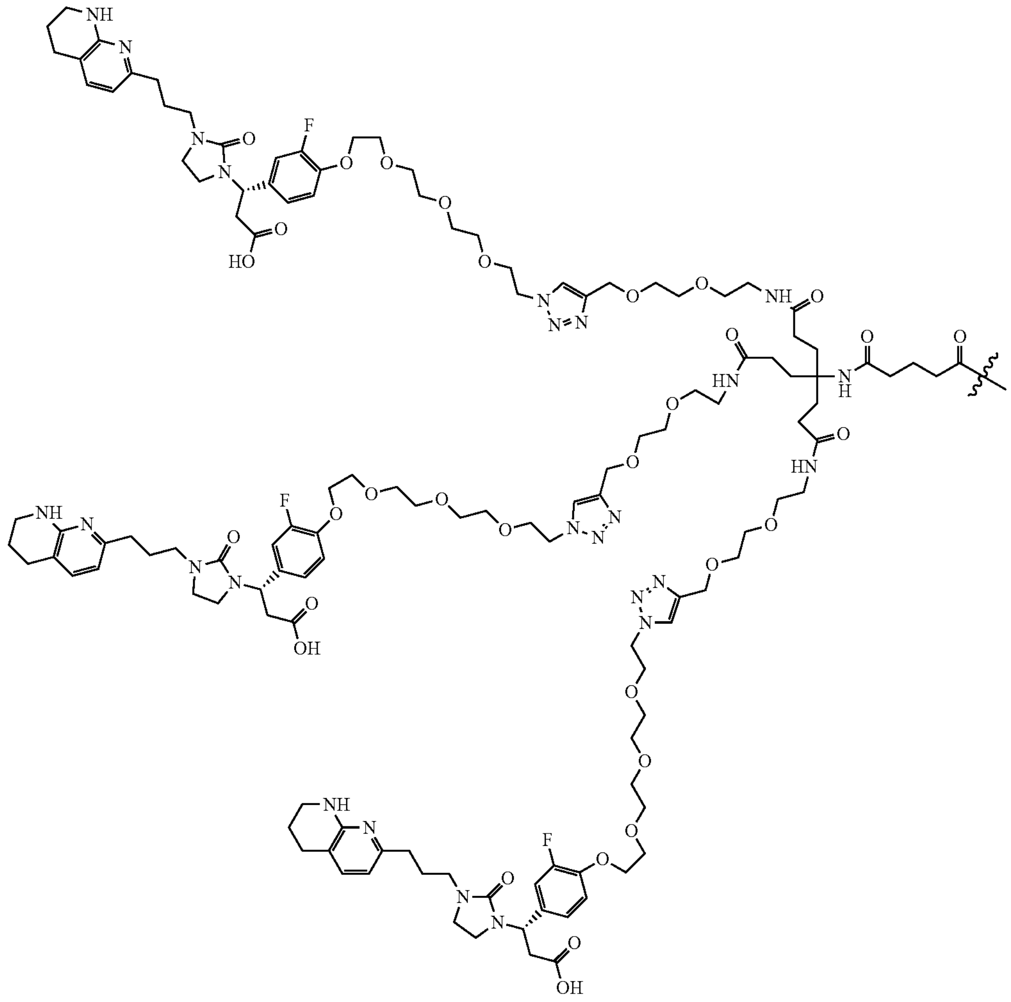
In some embodiments, a tridentate targeting group disclosed herein comprises three ligands of Structure 2a, and can be represented by the following structure:

(Structure 701)
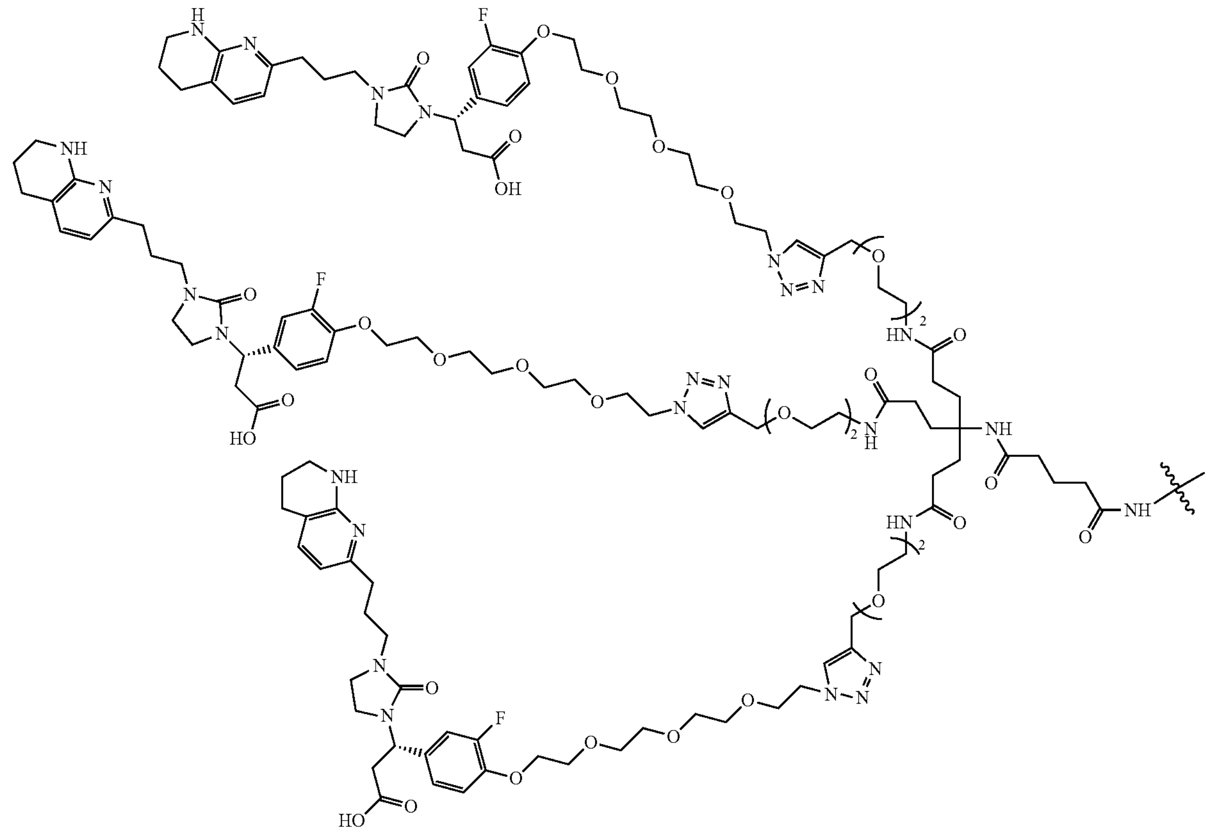
In some embodiments, a tridentate targeting group disclosed herein comprises three ligands of Structure 2a, and can be represented by the following structure:

(Structure 701a)
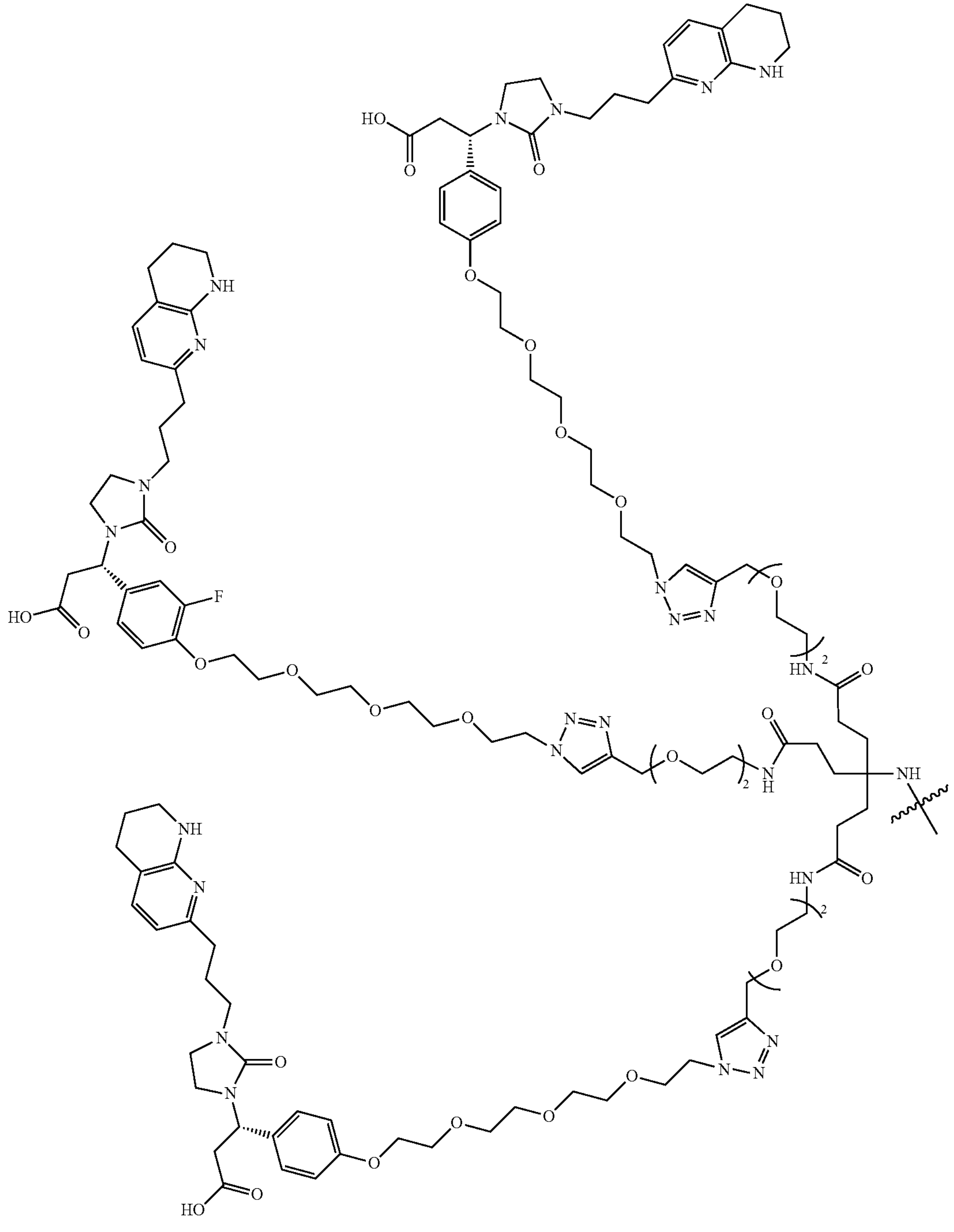
In some embodiments, a tridentate targeting group comprising a glutaric linker comprises three ligands of Structure 2a, and can be represented by the following structure:

(Structure 701b)
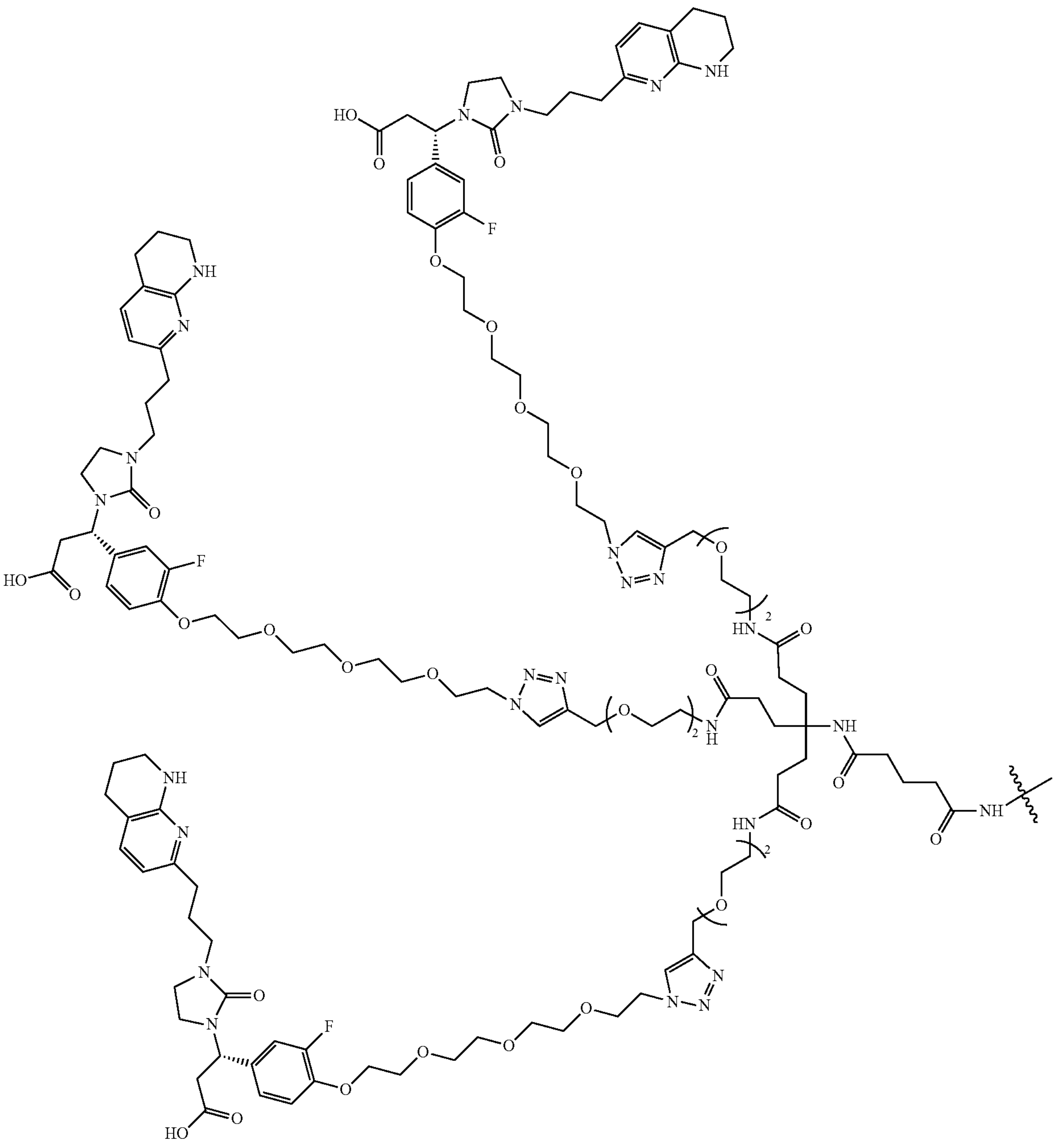
In some embodiments, a tridentate targeting group disclosed herein comprises three ligands of Structure 2a, and can be represented by the following structure:

(Structure 701c)
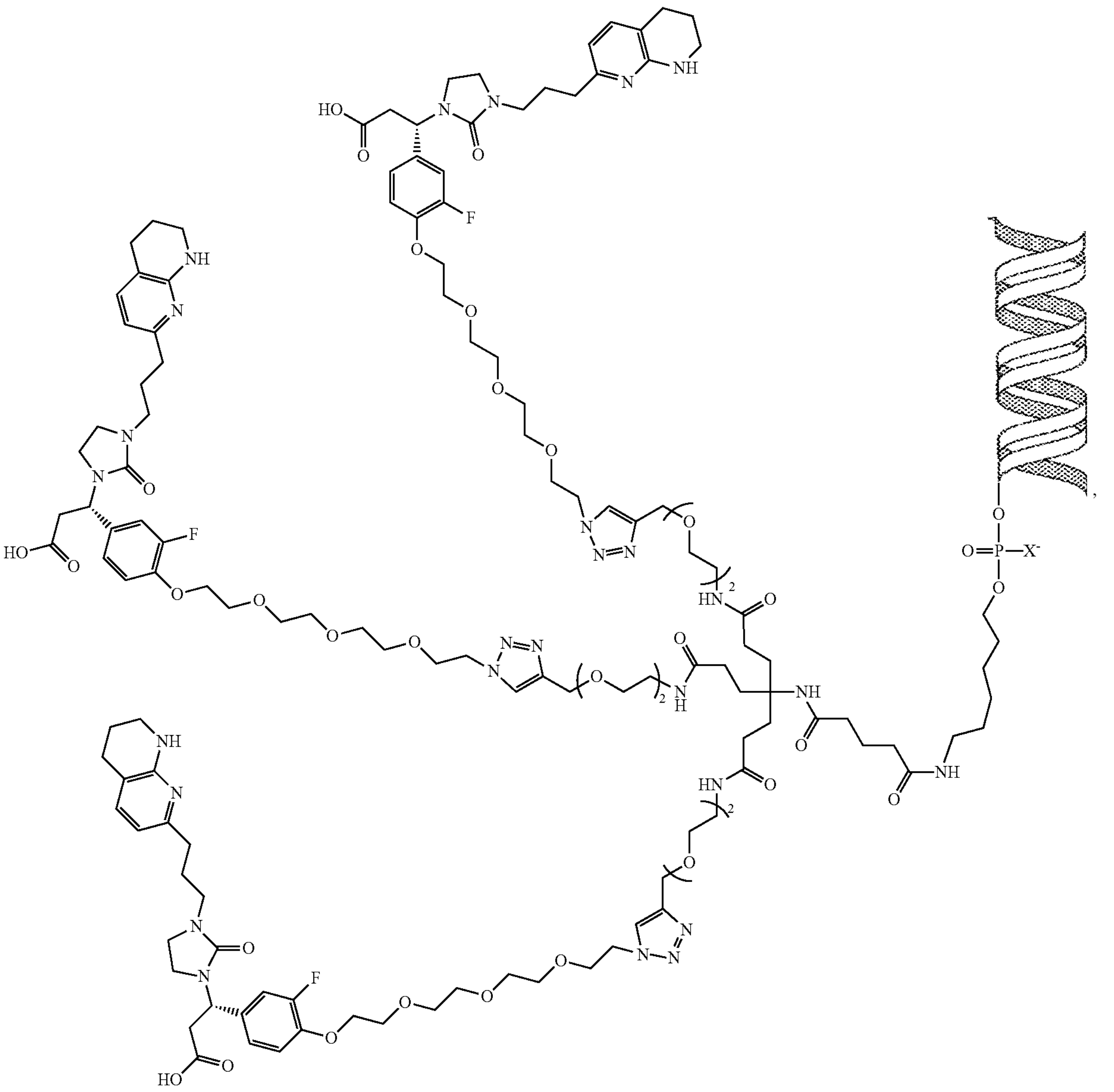
wherein 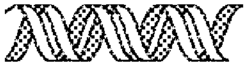 indicates an RNAi agent and X═O or S.
In some embodiments, a tridentate targeting group disclosed herein comprises three ligands of Structure 2a, and can be represented by the following structure:

(Structure 701d)

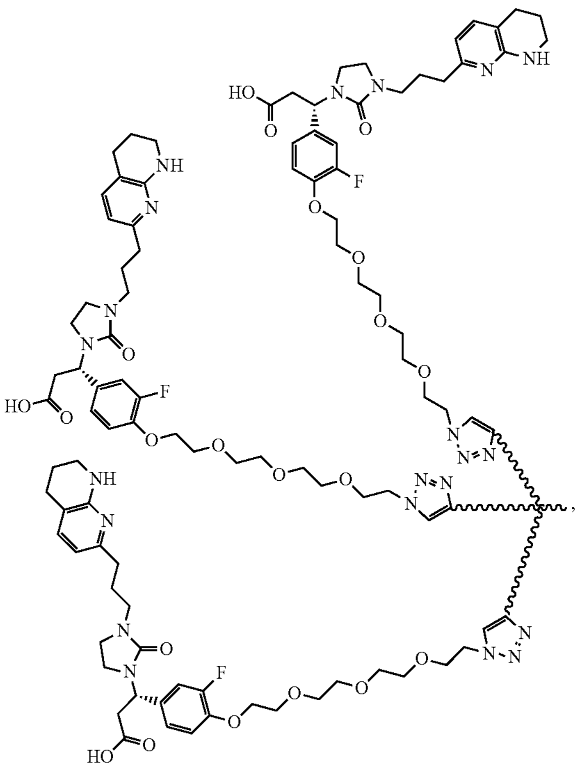

wherein indicates any suitable scaffold or linker that can be used to bind a ligand and a cargo molecule.

In some embodiments, an αvβ3 tridentate targeting group conjugated to an RNAi agent comprises three ligands of Structure 2a, and can be represented by the following structure:

(Structure 701e)

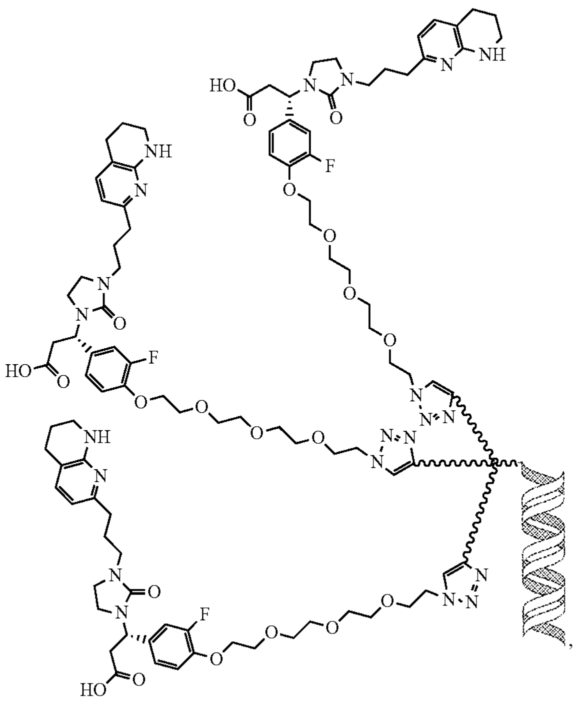

wherein; indicates any suitable scaffold or linker that can be used to bind a ligand and a RNAi agent, and 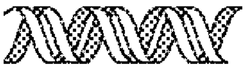 indicates a RNAi agent.

Reactive Groups and Protected Reactive Groups.

Reactive groups are well known in the art and provide for formation of covalent linkages between two molecules or reactants. Suitable reactive groups for use in the scope of the inventions herein include, but are not limited to: amino groups, amide groups, carboxylic acid groups, azides, alkynes, propargyl groups, BCN(bicyclo[6.1.0]nonyne, DBCO(dibenzocyclooctyne) thiols, maleimide groups, aminooxy groups, N-hydroxysuccinimide (NHS) or other activated ester (for example, PNP, TFP, PFP), bromo groups, aldehydes, carbonates, tosylates, tetrazines, trans-cyclooctene (TCO), hydrazides, hydroxyl groups, disulfides, and orthopyridyl disulfide groups.

Incorporation of reactive groups can facilitate conjugation of an integrin ligand disclosed herein to a cargo molecule. Conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction and click chemistry cycloaddition reaction.

In some embodiments, the integrin targeting ligands disclosed herein are synthesized as a tetrafluorophenyl (TFP) ester, which can be displaced by a reactive amino group to attach a cargo molecule. In some embodiments, the integrin targeting ligands disclosed herein are synthesized as an azide, which can be conjugated to a propargyl or DBCO group, for example, via click chemistry cycloaddition reaction, to attach a cargo molecule.

Protected reactive groups are also commonly used in the art. A protecting group provides temporary chemical trans-formation of a reactive group into a group that does not react under conditions where the non-protected group reacts, e g, to provide chemo-selectivity in a subsequent chemical reaction. Suitable protected reactive groups for use in the scope of the inventions herein include, but are not limited to, BOC groups (t-butoxycarbonyl), Fmoc (9-fluorenylmethoxycarbonyl), carboxy benzyl (CBZ) groups, benzyl esters, and PBF (2,2,4,6,7-pentamethyldihydrobenzofuran-5-sulfonyl).

Cargo Molecules (Including RNAi Agents)

A cargo molecule is any molecule which, when detached from the integrin ligands described herein, would have a desirable effect on a cell comprising an integrin receptor. A cargo molecule can be, but is not limited to, a pharmaceutical ingredient, a drug product, a prodrug, a substance with a known therapeutic benefit, a small molecule, an antibody, an antibody fragment, an immunoglobulin, a monoclonal antibody, a label or marker, a lipid, a natural or modified nucleic acid or polynucleotide, a peptide, a polymer, a polyamine, a protein, an aptamer, a toxin, a vitamin, a PEG, a hapten, a digoxigenin, a biotin, a radioactive atom or molecule, or a fluorophore. In some embodiments, one or more cargo molecules (e.g., the same or different cargo molecules) are linked to one or more integrin ligands to target the cargo molecules to a cell expressing integrin $\alpha v\beta 3$ and/or integrin $\alpha v\beta 5$.

In some embodiments, the one or more cargo molecules is a pharmaceutical ingredient or pharmaceutical composition. In some embodiments, the one or more cargo molecules is an oligonucleotide-based compound. As used herein, an "oligonucleotide-based compound" is a nucleotide sequence containing about 10-50 (e.g., 10 to 48, 10 to 46, 10 to 44, 10 to 42, 10 to 40, 10 to 38, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 50, 12 to 48, 12 to 46, 12 to 44, 12 to 42, 12 to 40, 12 to 38, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 50, 14 to 48, 14 to 46, 14 to 44, 14 to 42, 14 to 40, 14 to 38, 14 to 36, 14 to 34, 14 to 32, 14 to 30, 14 to 28, 14 to 26, 14 to 24, 14 to 22, 14 to 20, 14 to 18, 14 to 16, 16 to 50, 16 to 48, 16 to 46, 16 to 44, 16 to 42, 16 to 40, 16 to 38, 16 to 36, 16 to 34, 16 to 32, 16 to 30, 16 to 28, 16 to 26, 16 to 24, 16 to 22, 16 to 20, 16 to 18, 18 to 50, 18 to 48, 18 to 46, 18 to 44, 18 to 42, 18 to 40, 18 to 38, 18 to 36, 18 to 34, 18 to 32, 18 to 30, 18 to 28, 18 to 26, 18 to 24, 18 to 22, 18 to 20, 20 to 50, 20 to 48, 20 to 46, 20 to 44, 20 to 42, 20 to 40, 20 to 38, 20 to 36, 20 to 34, 20 to 32, 20 to 30, 20 to 28, 20 to 26, 20 to 24, 20 to 22, 22 to 50, 22 to 48, 22 to 46, 22 to 44, 22 to 42, 22 to 40, 22 to 38, 22 to 36, 22 to 34, 22 to 32, 22 to 30, 22 to 28, 22 to 26, 22 to 24, 24 to 50, 24 to 48, 24 to 46, 24 to 44, 24 to 42, 24 to 40, 24 to 38, 24 to 36, 24 to 34, 24 to 32, 24 to 30, 24 to 28, 24 to 26, 26 to 50, 26 to 48, 26 to 46, 26 to 44, 26 to 42, 26 to 40, 26 to 38, 26 to 36, 26 to 34, 26 to 32, 26 to 30, 26 to 28, 28 to 50, 28 to 48, 28 to 46, 28 to 44, 28 to 42, 28 to 40, 28 to 38, 28 to 36, 28 to 34, 28 to 32, to 28 to 30, 30 to 50, 30 to 48, 30 to 46, 30 to 44, 30 to 42, 30 to 40, 30 to 38, 30 to 36, 30 to 34, 30 to 32, 32 to 50, 32 to 48, 32 to 46, 32 to 44, 32 to 42, 32 to 40, 32 to 38, 32 to 36, 32 to 34, 34 to 50, 34 to 48, 34 to 46, 34 to 44, 34 to 42, 34 to 40, 34 to 38, 34 to 36, 36 to 50, 36 to 48, 36 to 46, 36 to 44, 36 to 42, 36 to 40, 36 to 38, 38 to 50, 38 to 48, 38 to 46, 38 to 44, 38 to 42, 38 to 40, 40 to 50, 40 to 48, 40 to 46, 40 to 44, 40 to 42, 42 to 50, 42 to 48, 42 to 46, 42 to 44, 44 to 50, 44 to 48, 44 to 46, 46 to 50, 46 to 48, or 48 to 50) nucleotides or nucleotide base pairs. In some embodiments, an oligonucleotide-based compound has a nucleobase sequence that is at least partially complementary to a coding sequence in an expressed target nucleic acid or target gene (e.g., the gene transcript or mRNA of a target gene) within a cell. In some embodiments, the oligonucleotide-based compounds, upon delivery to a cell expressing a gene, are able to inhibit the expression of the underlying gene, and are referred to herein as "expression-inhibiting oligonucleotide-based compounds." The gene expression can be inhibited in vitro or in vivo.

"Oligonucleotide-based compounds" include, but are not limited to: single-stranded oligonucleotides, single-stranded antisense oligonucleotides, short or small interfering RNAs (siRNAs), double-strand RNAs (dsRNA), micro RNAs (miRNAs), short hairpin RNAs (shRNA), ribozymes, interfering RNA molecules, and dicer substrates. In some embodiments, an oligonucleotide-based compound is a single-stranded oligonucleotide, such as an antisense oligonucleotide. In some embodiments, an oligonucleotide-based compound is a double-stranded oligonucleotide. In some embodiments, an oligonucleotide-based compound is a double-stranded oligonucleotide that is an RNAi agent.

In some embodiments, the one or more cargo molecules is/are an "RNAi agent," which as defined herein is a chemical composition that includes an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short or small interfering RNAs (siRNAs), double-strand RNAs (dsRNA), micro RNAs (miRNAs), short hairpin RNAs (shRNA), and dicer substrates. The antisense strand of the RNAi agents described herein is at least partially complementary to the mRNA being targeted. RNAi agents can include one or more modified nucleotides and/or one or more non-phosphodiester linkages.

Typically, RNAi agents can be comprised of at least a sense strand (also referred to as a passenger strand) that includes a first sequence, and an antisense strand (also referred to as a guide strand) that includes a second sequence. The length of an RNAi agent sense and antisense strands can each be 16 to 49 nucleotides in length. In some embodiments, the sense and antisense strands of an RNAi agent are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. In some embodiments, the sense and antisense strands are each 21 nucleotides in length. The sense and antisense strands can be either the same length or different lengths. The RNAi agents include an antisense strand sequence that is at least partially complementary to a sequence in the target gene, and upon delivery to a cell expressing the target, an RNAi agent may inhibit the expression of one or more target genes in vivo or in vitro.

Oligonucleotide-based compounds generally, and RNAi agents specifically, may be comprised of modified nucleotides and/or one or more non-phosphodiester linkages. As used herein, a “modified nucleotide” is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids, 2',3'-seco nucleotide mimics (unlocked nucleobase analogues, locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides, 2'-modified nucleotides (i.e. a nucleotide with a group other than a hydroxyl group at the 2' position of the five-membered sugar ring) include, but are not limited to, 2'-O-methyl nucleotides, 2'-deoxy-2'-fluoro nucleotides, 2'-deoxy nucleotides, 2'-methoxyethyl (2'-O-2-methoxylethyl) nucleotides, 2'-amino nucleotides, and 2'-alkyl nucleotides.

Moreover, one or more nucleotides of an oligonucleotide-based compound, such as an RNAi agent, may be linked by non-standard linkages or backbones (i.e., modified internucleoside linkages or modified backbones). A modified internucleoside linkage may be a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

It is not necessary for all positions in a given compound to be uniformly modified. Conversely, more than one modification may be incorporated in a single oligonucleotide-based compound or even in a single nucleotide thereof.

In some embodiments, the cargo molecule is an RNAi agent for inhibiting H1F-2 alpha (EPAS1) gene expression. The cargo molecule may be an RNAi agent described in International Patent Application Publication No. WO 2016/196239 and WO 2014/134255, each of which is herein incorporated by reference in its entirety.

The RNAi agent sense strands and antisense strands may be synthesized and/or modified by methods known in the art. For example, the disclosure of RNAi agents directed to the inhibition of HIF-2 alpha gene expression may be found, for example, in International Patent Application Publication No. WO 2016/196239, which is incorporated by reference herein in its entirety.

In some embodiments, the one or more cargo molecule(s) can include or consist of a PEG moiety that can acts as a pharmacokinetic (PK) enhancer or modulator. In some embodiments, the one or more cargo molecules can include a PEG moiety having about 20-900 ethylene oxide ($CH_2$—$CH_2$-0) units (e.g., 20 to 850, 20 to 800, 20 to 750, 20 to 700, 20 to 650, 20 to 600, 20 to 550, 20 to 500, 20 to 450, 20 to 400, 20 to 350, 20 to 300, 20 to 250, 20 to 200, 20 to 150, 20 to 100, 20 to 75, 20 to 50, 100 to 850, 100 to 800, 100 to 750, 100 to 700, 100 to 650, 100 to 600, 100 to 550, 100 to 500, 100 to 450, 100 to 400, 100 to 350, 100 to 300, 100 to 250, 100 to 200, 100 to 150, 200 to 850, 200 to 800, 200 to 750, 200 to 700, 200 to 650, 200 to 600, 200 to 550, 200 to 500, 200 to 450, 200 to 400, 200 to 350, 200 to 300, 200 to 250, 250 to 900, 250 to 850, 250 to 800, 250 to 750, 250 to 700, 250 to 650, 250 to 600, 250 to 550, 250 to 500, 250 to 450, 250 to 400, 250 to 350, 250 to 300, 300 to 900, 300 to 850, 300 to 800, 300 to 750, 300 to 700, 300 to 650, 300 to 600, 300 to 550, 300 to 500, 300 to 450, 300 to 400, 300 to 350, 350 to 900, 350 to 850, 350 to 800, 350 to 750, 350 to 700, 350 to 650, 350 to 600, 350 to 550, 350 to 500, 350 to 450, 350 to 400, 400 to 900, 400 to 850, 400 to 800, 400 to 750, 400 to 700, 400 to 650, 400 to 600, 400 to 550, 400 to 500, 400 to 450, 450 to 900, 450 to 850, 450 to 800, 450 to 750, 450 to 700, 450 to 650, 450 to 600, 450 to 550, 450 to 500, 500 to 900, 500 to 850, 500 to 800, 500 to 750, 500 to 700, 500 to 650, 500 to 600, 500 to 550, 550 to 900, 550 to 850, 550 to 800, 550 to 750, 550 to 700, 550 to 650, 550 to 600, 600 to 900, 600 to 850, 600 to 800, 600 to 750, 600 to 700, 600 to 650, 650 to 900, 650 to 850, 650 to 800, 650 to 750, 650 to 700, 700 to 900, 700 to 850, 700 to 800, 700 to 750, 750 to 900, 750 to 850, 750 to 800, 800 to 900, 850 to 900, or 850 to 900 ethylene oxide units). In some embodiments, the one or more cargo molecule(s) consist of a PEG moiety having approximately 455 ethylene oxide units (about 20 kilodalton (kDa) molecular weight). In some embodiments, a PEG moiety has a molecular weight of about 2 kilodaltons. In some embodiments, a PEG moiety has a molecular weight of about 20 kilodaltons. In some embodiments, a PEG moiety has a molecular weight of about 40 kilodaltons. The PEG moieties described herein may be linear or branched. The PEG moieties may be discrete (monodispersed) or non-discrete (polydispersed). PEG moieties for use as a PK enhancing cargo molecule may be purchased commercially. In some embodiments, the one or more cargo molecule(s) include a PEG moiety that can act as a PK modulator or enhancer, as well as a different cargo molecule, such as a pharmaceutically active ingredient or compound.

The described integrin ligands include salts or solvates thereof. Solvates of an integrin ligand is taken to mean adductions of inert solvent molecules onto the integrin ligand which form owing to their mutual attractive force. Solvates are, for example, mono- or dihydrates or addition compounds with alcohols, such as, for example, with methanol or ethanol.

Free amino groups or free hydroxyl groups can be provided as substituents of integrin ligands with corresponding protecting groups.

The αvβ3 integrin ligands also include, e.g., derivatives, i.e., integrin ligands modified with, for example, alkyl or acyl groups, sugars or oligopeptides, which are cleaved either in vitro or in an organism.

In some embodiments, an integrin ligand disclosed herein facilitates the delivery of a cargo molecule into the cytosol of a cell presenting integrin αvβ3 and/or integrin αvβ5 on its surface, either through ligand-mediated endocytosis, pinocytosis, or by other means. In some embodiments, an integrin ligand disclosed herein facilitates the delivery of a cargo molecule to the plasma membrane of a cell presenting integrin αvβ3 and/or integrin αvβ5.

Pharmaceutical Compositions

In some embodiments, the present disclosure provides pharmaceutical compositions that include, consist of, or consist essentially of, one or more of the integrin ligands disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody-, antibody-fragment, aptamers, and/or vaccine.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agent with a known therapeutic benefit.

The pharmaceutical compositions can be administered in a number of ways depending upon whether local or systemic treatment is desired and upon the area to be treated.

Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by intravenous injection or infusion or subcutaneous injection. The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, poly glycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing an αvβ3 integrin ligand are also an object of the present invention, as are processes for the manufacture of such medicaments, which processes comprise bringing one or more compounds containing a αvβ3 integrin ligand, and, if desired, one or more other substances with a known therapeutic benefit, into a pharmaceutically acceptable form.

The described integrin ligands and pharmaceutical compositions comprising integrin ligands disclosed herein may be packaged or included in a kit, container, pack, or dispenser. The integrin ligands and pharmaceutical compositions comprising the integrin ligands may be packaged in pre-filled syringes or vials.

Linking Groups, Pharmacokinetic (PK) Enhancers, Pharmacodynamic (PD) Modulators, Delivery Vehicles, and Targeting Groups In some embodiments, an αvβ3 ligand is conjugated to one or more non-nucleotide groups including, but not limited to, a linking group, a pharmacokinetic (PK) enhancer (also referred to as a PK modulator), a pharmacodynamic (PD) modulator, a delivery polymer, or a delivery vehicle. The non-nucleotide group can enhance targeting, delivery, or attachment of the cargo molecule. Examples of scaffolds for targeting groups and linking groups are disclosed herein. The non-nucleotide group can be covalently linked to the 3' and/or 5' end of either the sense strand and/or the antisense strand. In embodiments where the cargo molecule is an RNAi agent, the RNAi agent contains a non-nucleotide group linked to the 3' and/or 5' end of the sense strand. In some embodiments, a non-nucleotide group is linked to the 5' end of an RNAi agent sense strand. An integrin ligand disclosed herein can be linked directly or indirectly to the cargo molecule via a linker/linking group. In some embodiments, an integrin ligand is linked to the cargo molecule via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent. In some embodiments a non-nucleotide group enhances or modulates the pharmacodynamic properties of an RNAi agent or conjugate to which it is attached to improve cell- or tissue-specific distribution and cell-specific uptake of the RNAi agent or conjugate.

Targeting groups or targeting moieties enhance the pharmacokinetic or biodistribution properties of a cargo molecule to which they are attached to improve cell-specific (including, in some cases, organ specific) distribution and cell-specific (or organ specific) uptake of the cargo molecule. In some embodiments, a targeting group may comprise an αvβ3 ligand as described herein. In some embodiments, a targeting group comprises a linker. In some embodiments, a targeting group comprises a PK enhancer. In some embodiments, an αvβ3 integrin ligand is linked to a cargo molecule using a linker, such as a PEG linker or one, two, or three abasic and/or ribitol (abasic ribose) residues, which in some instances can serve as linkers. Targeting groups may comprise one or more targeting ligands. In some embodiments, a targeting group may comprise one to four integrin ligands disclosed herein. In some embodiments, a targeting group is a tridentate targeting group and comprises three integrin ligands disclosed herein.

Cargo molecules can be synthesized having a reactive group, such as an amino group (also referred to herein as an amine). In embodiments where the cargo molecule is an RNAi agent, the reactive group may be linked at the 5'-terminus and/or the 3'-terminus. The reactive group can be used subsequently to attach an αvβ3 integrin ligand using methods typical in the art.

For example, in some embodiments, an RNAi agent is synthesized having an $NH_2$—$C_6$ group at the 5'-terminus of the sense strand of the RNAi agent. The terminal amino group subsequently can be reacted to form a conjugate with, for example, a group that includes an integrin targeting ligand. In some embodiments, an RNAi agent is synthesized having one or more alky ne groups at the 5'-terminus of the sense strand of the RNAi agent. The terminal alkyne group (s) can subsequently be reacted to form a conjugate with, for example, a group that includes an αvβ3 integrin targeting ligand.

In some embodiments, a linking group is conjugated to the αvβ3 ligand. The linking group facilitates covalent linkage of the αvβ3 ligand to a cargo molecule, PK enhancer, delivery polymer, or delivery vehicle. Examples of linking groups, include, but are not limited to: Alk-SMPT-C6, Alk-SS-C6, DBCO-TEG, Me-Alk-SS-C6, and C6-SS-Alk-Me, reactive groups such a primary amines and alkynes, alkyl groups, abasic residues/nucleotides, amino acids, tri-alkyne functionalized groups, ribitol, and/or PEG groups.

A linker or linking group is a connection between two atoms that links one chemical group (such as an RNAi agent) or segment of interest to another chemical group (such as an αvβ3 integrin ligand, PK enhancer, PD modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups: each of which can contain one or more heteroatoms, heterocycles, amino acids, nucleotides, and saccharides. Spacer groups are well known in the art and the preceding list is not meant to limit the scope of the description.

In some embodiments, αvβ3 ligands are linked to cargo molecules without the use of an additional linker. In some embodiments, the αvβ3 ligand is designed having a linker readily present to facilitate the linkage to a cargo molecule. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Examples of certain linking groups and scaffolds are provided in Table A.

TABLE A

Structures Representing Various Linking Groups and Scaffolds

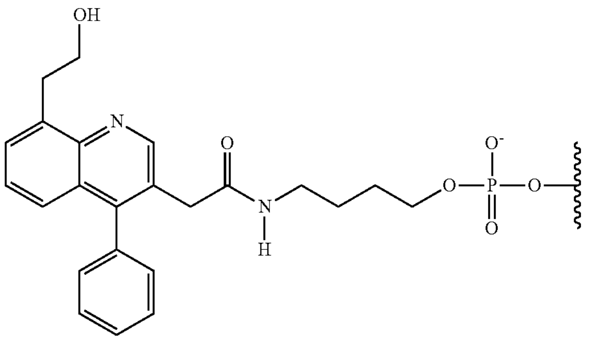

(PAZ)

When positioned at the 3' terminal end of oligonucleotide:

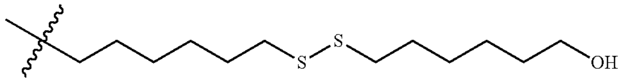

(C6-SS-C6)

When positioned internally in oligonucleotide:

linkage towards 5′ end of oligonucleotide linkage towards 3′ end of oligonucleotide

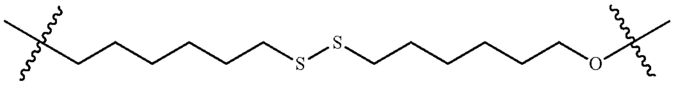

(C6-SS-C6)

When positioned at the 3' terminal end of oligonucleotide:

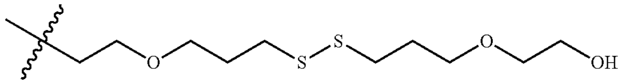 [SMILES: *CCOCCCSSCCCOCCO]

When positioned internally in oligonucleotide:

linkage towards 5′ end of oligonucleotide linkage towards 3′ end of oligonucleotide

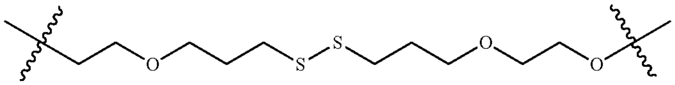

(6-SS-6)

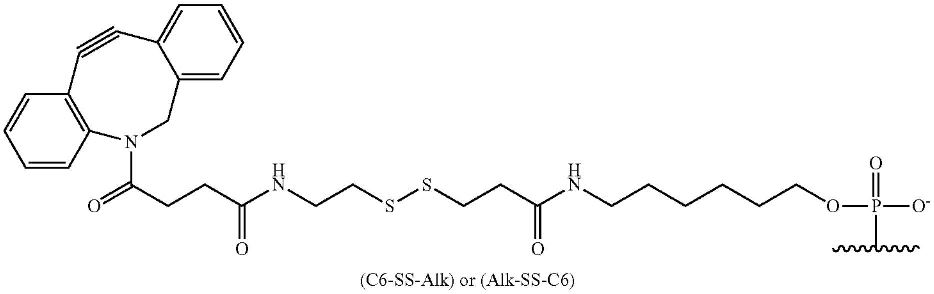 [SMILES: *P(=O)([O-])OCCCCCCNC(=O)CCSSCCNC(=O)CCC(=O)N1Cc2ccccc2C#Cc2ccccc21]

(C6-SS-Alk) or (Alk-SS-C6)

TABLE A-continued
Structures Representing Various Linking Groups and Scaffolds
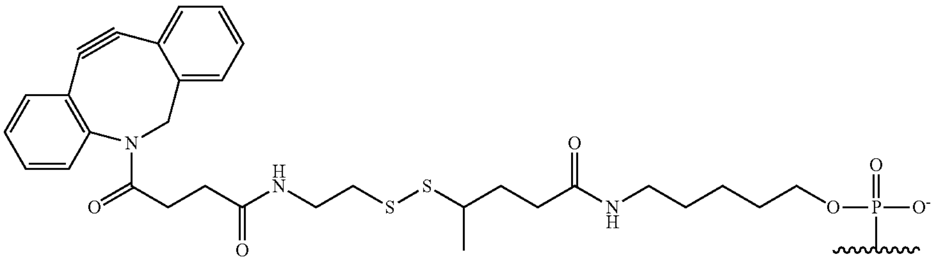
(C6-SS-Alk-Me)
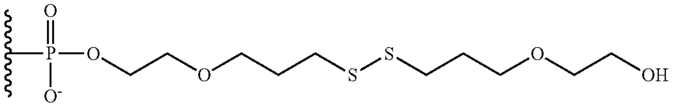
(PEG-C3-SS)
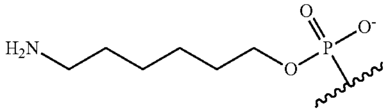
(NH2-C6)
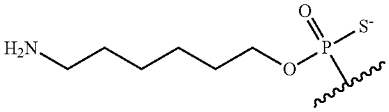
(NH2-C6)s
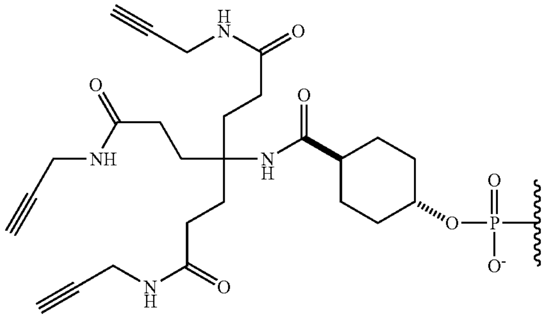
(TriAlk1)
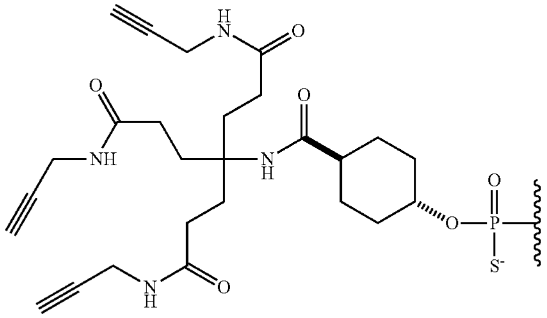
(TriAlk1)s TABLE A-continued
| Structures Representing Various Linking Groups and Scaffolds |
| --- |
| 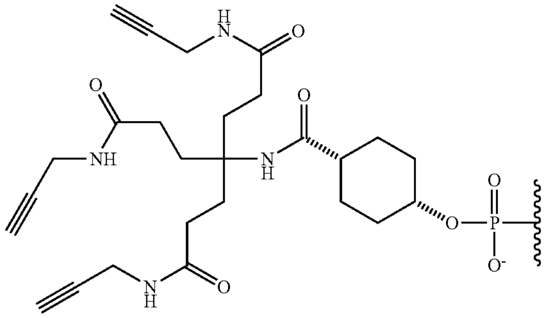 |
| (TriAlk2) |
| 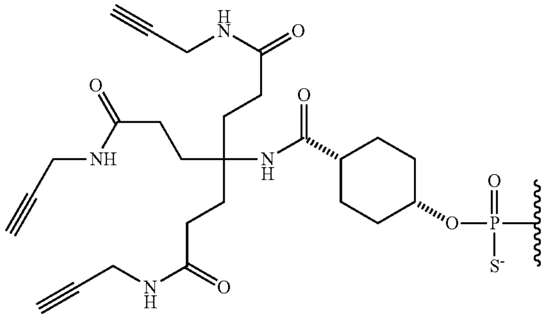 |
| (TriAlk2)s |
| 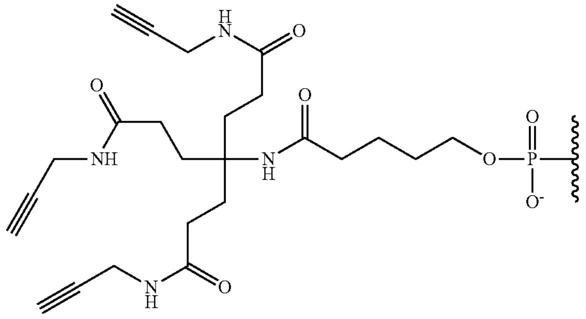 |
| (TriAlk3) |
| 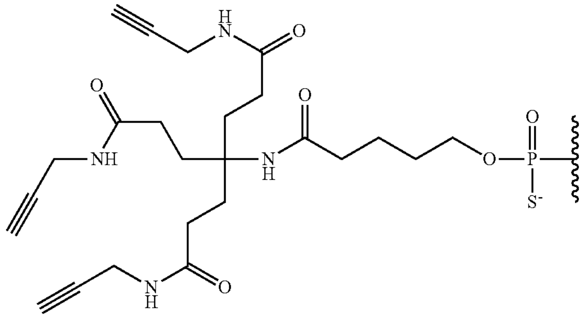 |
| (TriAlk3)s |

TABLE A-continued
Structures Representing Various Linking Groups and Scaffolds
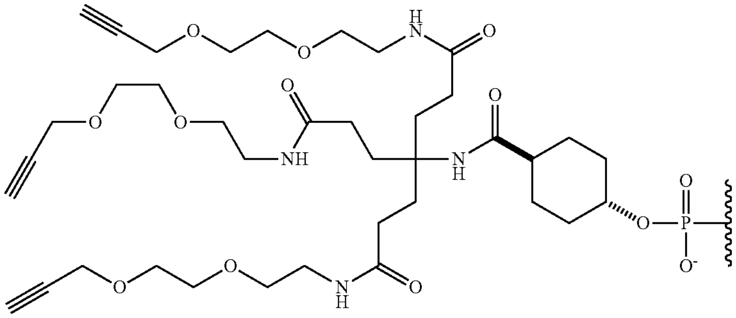
(TriAlk4)
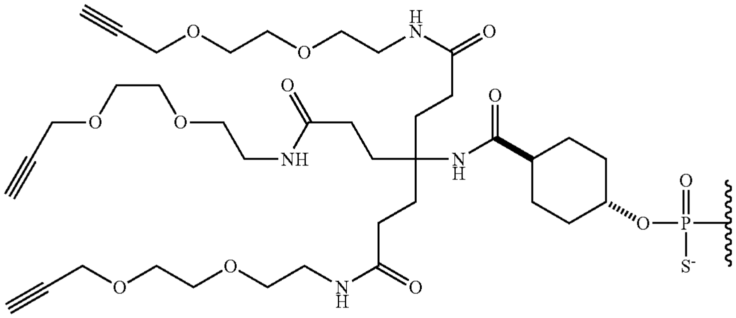
(TriAlk4)s
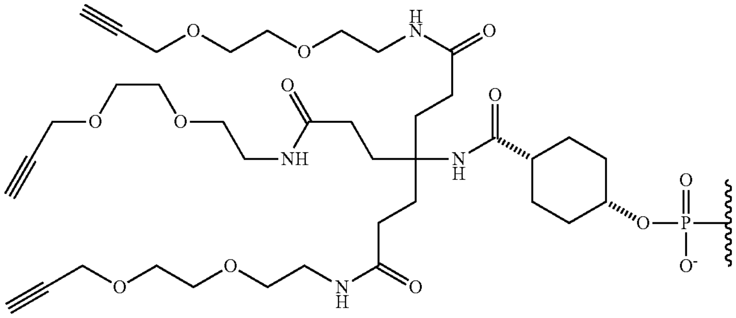
(TriAlk5)
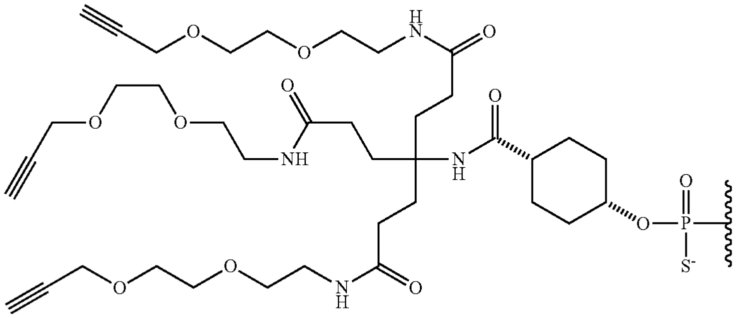
(TriAlk5)s TABLE A-continued
| Structures Representing Various Linking Groups and Scaffolds |
| --- |
| 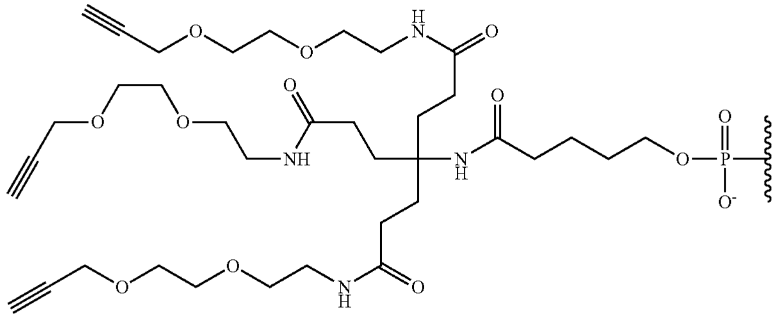 |
| (TriAlk6) |
| 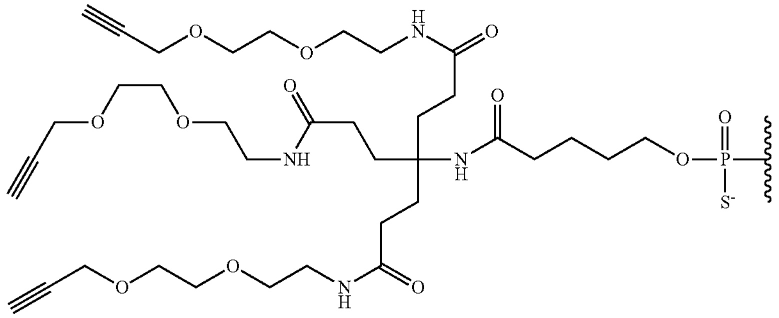 |
| (TriAlk6)s |
| 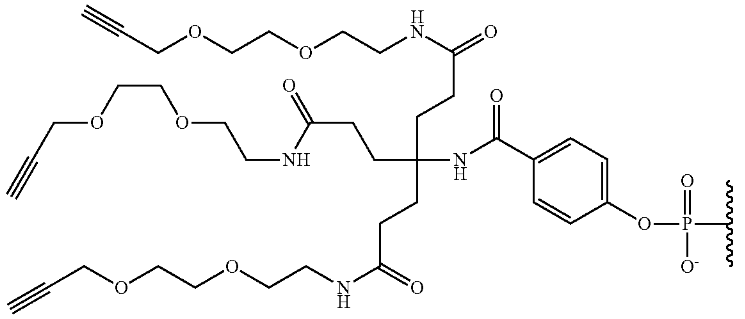 |
| (TriAlk7) |
| 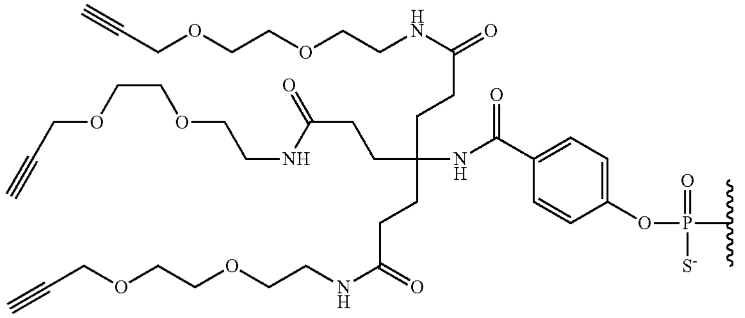 |
| (TriAlk7)s |

TABLE A-continued
Structures Representing Various Linking Groups and Scaffolds
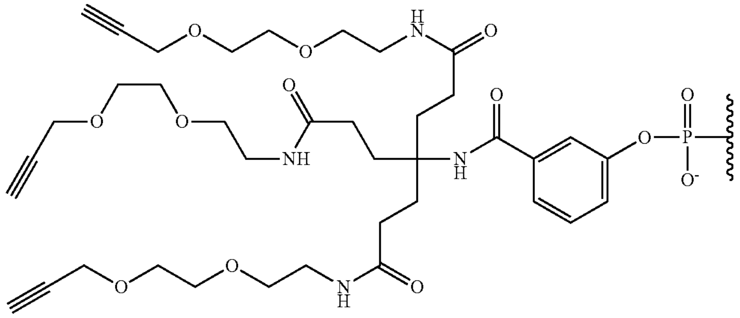
(TriAlk8)
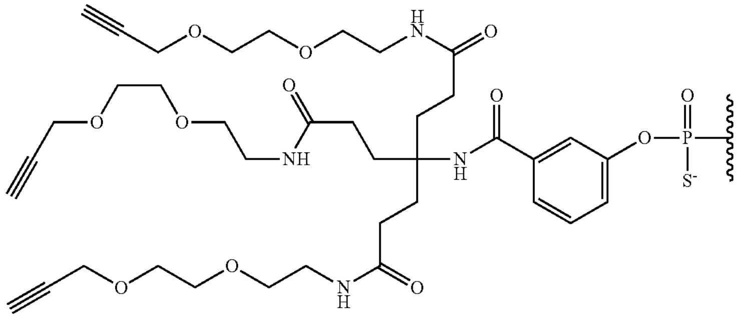
(TriAlk8)s
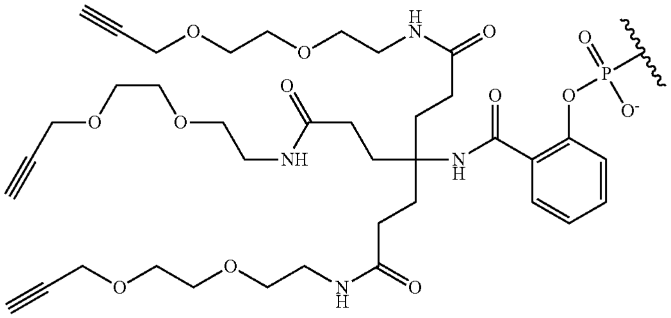
(TriAlk9)
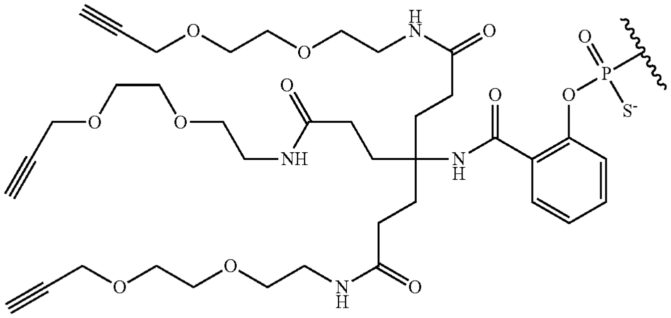
(TriAlk9)s TABLE A-continued
| Structures Representing Various Linking Groups and Scaffolds |
|---|
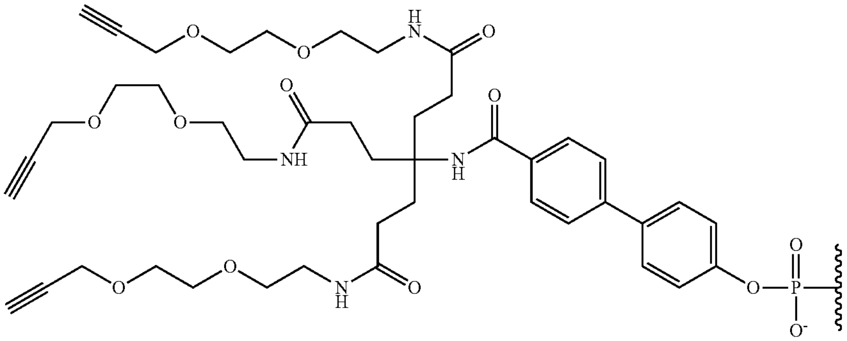
(TriAlk10)
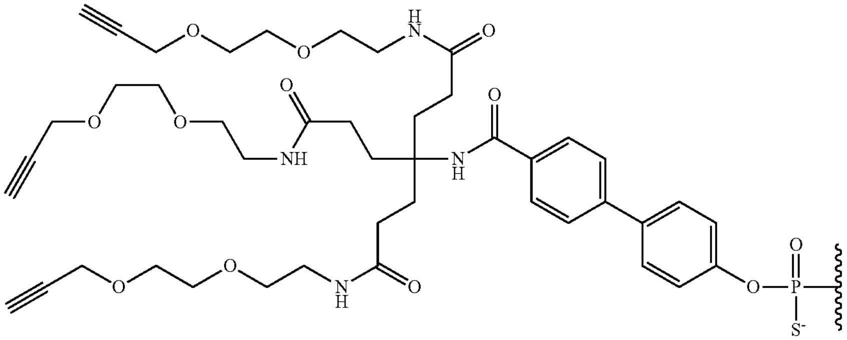
(TriAlk10)s
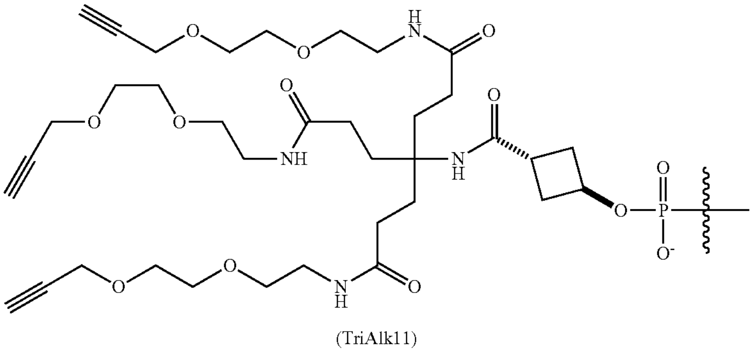
(TriAlk11)
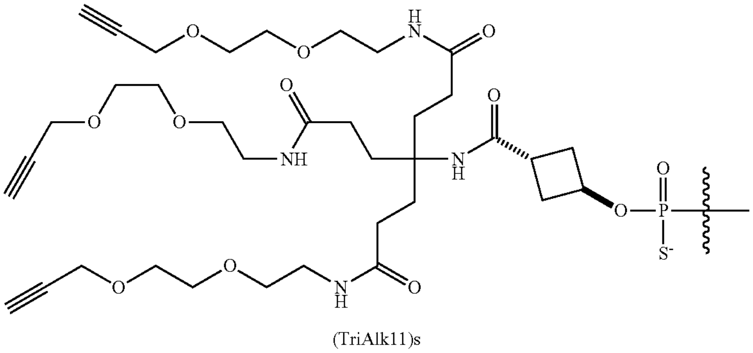
(TriAlk11)s TABLE A-continued
| Structures Representing Various Linking Groups and Scaffolds |
| --- |
| 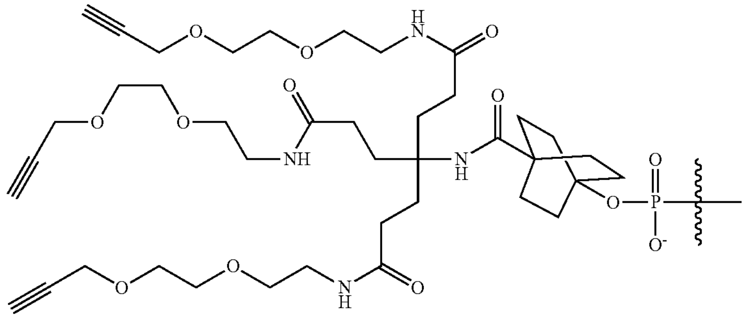 |
| (TriAlk12) |
| 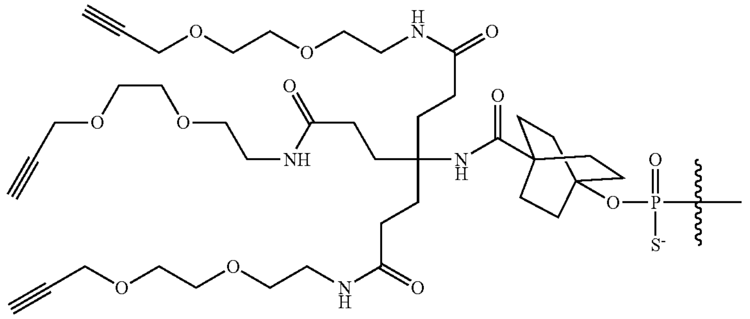 |
| (TriAlk12)s |
| 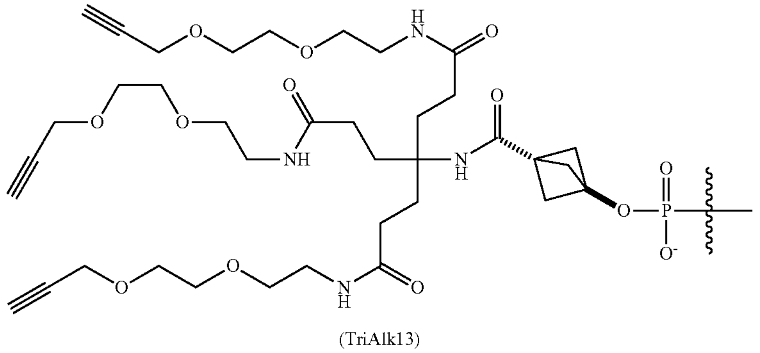 |
| (TriAlk13) |
| 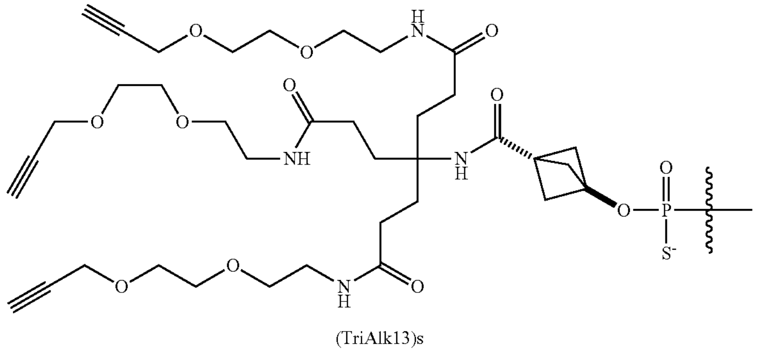 |
| (TriAlk13)s |

TABLE A-continued

Structures Representing Various Linking Groups and Scaffolds

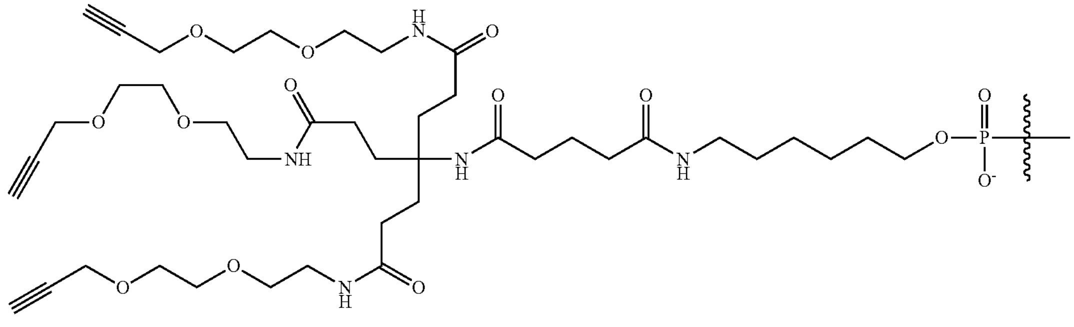

(TriAlk14)

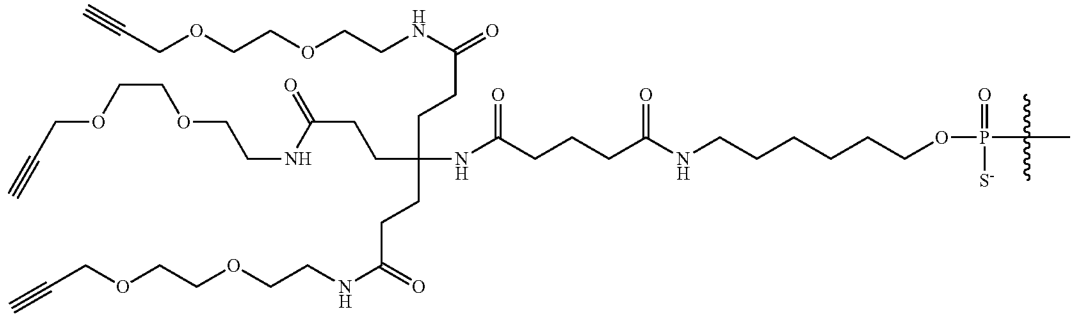

(TriAlk14)s wherein indicates the point of attachment to a cargo molecule.

Alternatively, other linking groups known in the art may be used. Examples of suitable linking groups are provided in PCT Application No. PCT/US19/18232, which is incorporated by reference herein in its entirety.

The above provided embodiments and items are now illustrated with the following, non-limiting examples.

Internally Linked Targeting Ligands

In some embodiments when the integrin targeting ligands described herein are bound or linked to an RNAi molecule, the integrin targeting ligand may be bound to internal nucleotides of the sense strand or the antisense strand. In some embodiments, up to 15 targeting ligands may be conjugated to internal nucleotides on the sense strand of an RNAi agent. In some embodiments, 1, 2, 3, 4, 5, 6, 7, 8, 9, 10, 11, 12, 13, 14, or 15 targeting ligands may be conjugated to internal nucleotides on the sense strand of a HIF-2 alpha RNAi agent. In some embodiments, 1 to 5 (e.g., 1, 2, 3, 4, or 5) targeting ligands are conjugated to internal nucleotides on the sense strand of an RNAi agent. In some embodiments, 3 to 4 targeting ligands are conjugated to internal nucleotides on the sense strand of an RNAi agent.

In some embodiments, placement of internal targeting ligands may impact the efficacy or potency of an RNAi agent. In some embodiments of αvβ3 integrin targeting ligands bound to RNAi agents, a targeting group is conjugated to the 5' end of the sense strand, and at least 10 nucleotides are positioned between the tridentate targeting group located on the 5' end of the sense strand and the next closest targeting ligand located on the sense strand. In some embodiments, at least 3 nucleotides are positioned between the tridentate targeting group located on the 5' end of the sense strand and the next closest targeting ligand located on the sense strand.

In some embodiments where two or more targeting ligands are conjugated to internal nucleotides located on the sense strand of an RNAi agent, there is a space of at least one nucleotide that is not conjugated to a targeting ligand positioned between the two internal nucleotides that are conjugated to targeting ligands. In some embodiments where two or more targeting ligands are conjugated to the sense strand of an RNAi agent, at least two nucleotides that are not conjugated to a targeting ligand are positioned between two internal nucleotides that are conjugated to targeting ligands.

In some embodiments, targeting ligands are conjugated to the 2nd, 4th, and 6th nucleotides on the sense strand as numbered from 3' to 5', starting from the farthest 3' nucleotide that forms a base pair with a nucleotide on the antisense strand. In some embodiments, targeting ligands are conjugated to the 2nd, 4th, 6th, and 8th nucleotides (3'→5') from the 3' terminal nucleotide on the sense strand that forms a base pair with the antisense strand.

Examples of modified nucleotides for attaching internal targeting ligands are shown in Table B below:

TABEL B
| Structures Representing Modified Nucleotides for Attaching Targeting Ligands. |
| --- |
| 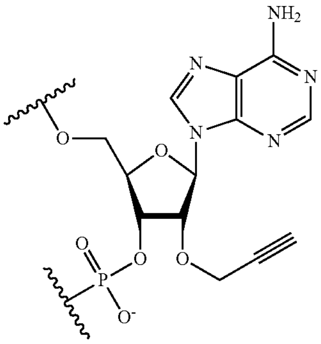 |
| aAlk |
| 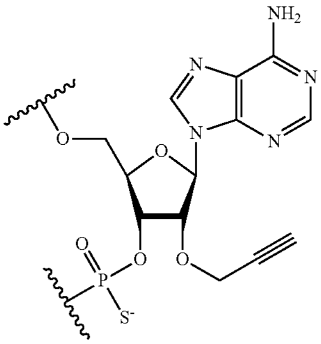 |
| aAlks |
| 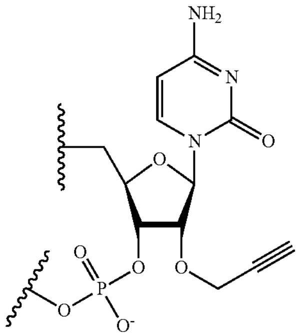 |
| cAlk |
| 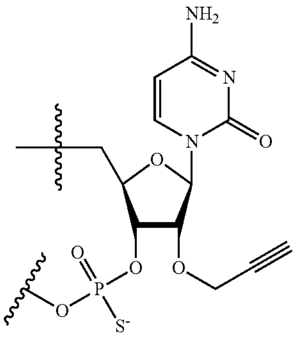 |
| cAlks |
TABEL B-continued
| Structures Representing Modified Nucleotides for Attaching Targeting Ligands. |
| --- |
| 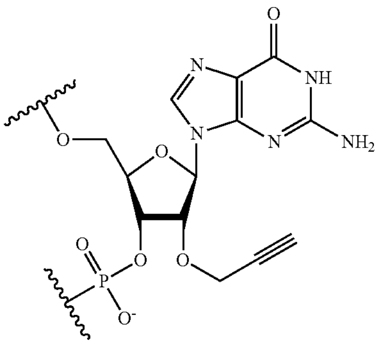 |
| gAlk |
| 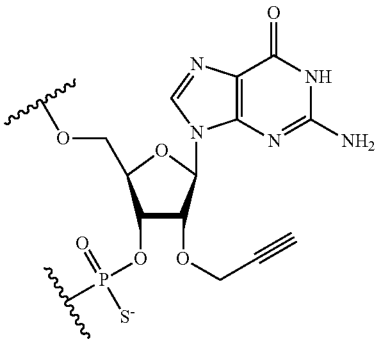 |
| gAlks |
| 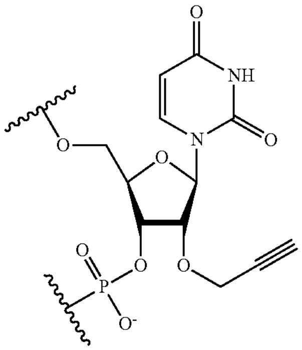 |
| uAlk |
| 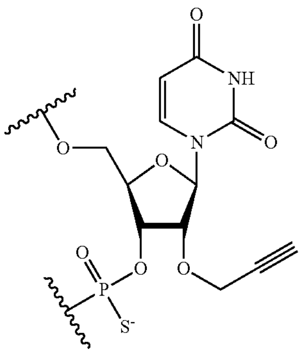 |
| aAlks |

EXAMPLES

The following examples are not limiting and are intended to illustrate certain embodiments disclosed herein.

Example 1. Synthesis of Integrin Targeting Ligands

Some of the abbreviations used in the following experimental details of the synthesis of the examples are defined as follows: h or hr=hour(s); min=minute(s); mol=mole(s); mmol=millimole(s); M=molar; μM=micromolar; g=gram (s); μg=microgram(s); rt or RT=room temperature; L=liter (s); mL=milliliters); wt=weight; $Et_2O$=diethyl ether; THF=tetrahydrofuran; DMSO=dimethyl sulfoxide; EtOAc=ethyl acetate; $Et_3N$ or TEA=triethylamine; i-$Pr_2NEt$ or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl or TBDMSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; $N_2$=nitrogen; $SiO_2$=silica; $R_T$=retention time; PTSA=para-toluenesulfonic acid; PPTS=pyridinium para-toluenesulfonate.

Synthesis of Structure 1c ((S)-3-(6-((1-azido-15-oxo-3,6,9,12-tetraoxa-16-azanonadecan-19-yl)oxy)pyridin-3-yl)-3-(2-oxo-3-(3-(5,6,7,8-tetrahydro-1,8-naphthyridin-2-yl)propyl)imidazolidin-1-yl)propanoic acid)

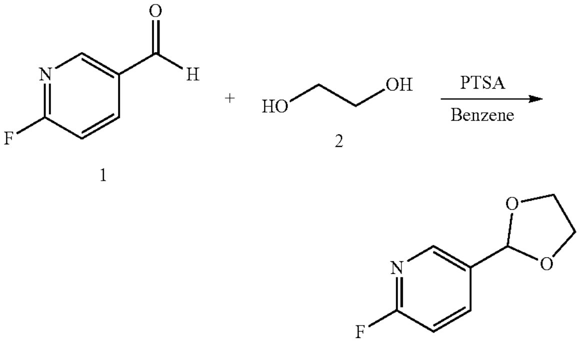

1 2

3

A mixture containing compound 1 (1.03 g, 8.23 mmol), compound 2 (0.92 g 14.8 mol), and PTSA hydrate (156 mg, 0.82 mmol) in benzene (25 mL) was refluxed in a dean stark apparatus overnight. The following morning, the reaction mixture was poured into saturated sodium bicarbonate, and ethyl acetate was subsequently added. The organic phase was separated, filtered over sodium sulfate, and concentrated to afford compound 3 in 95% yield, which was subsequently used without further purification.

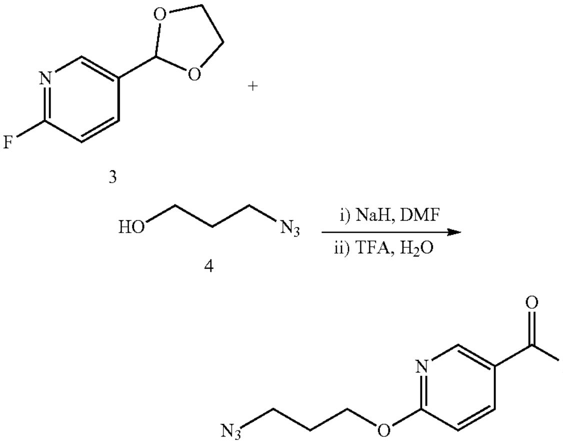

3

4

5

To a solution containing compound 4 (5.39 g, 53.3 mmol) and 3 Å molecular sieves in DMF (100 mL) was added sodium hydride (60 wt %, 2.13 g, 53.3 mmol), and the reaction was agitated for 1 hour. A solution of compound 3 (7.52 g, 7.52 g) in DMF (20 mL) was subsequently added and the suspension was heated at 80° C. overnight. Upon completion, the suspension was filtered over a cotton plug and concentrated under reduced pressure. The residue was partitioned between diethyl ether and water, and the organic phase was separated, filtered over sodium sulfate, and concentrated under reduced pressure. The residue was treated with 20 ml of 10% $H_2O$ in TFA and stirred for 30 minutes. Upon completion, the solution was chilled to 0° C. and the pH was adjusted to 11 with 6M NaOH, upon which the product precipitated as an oil. Compound 5 was extracted three times from the oily suspension with diethyl ether. The organic phases were combined, filtered over sodium sulfate, and concentrated. Compound 5 was then isolated in 26% yield by separation on silica eluting a gradient of ethyl acetate in hexanes.

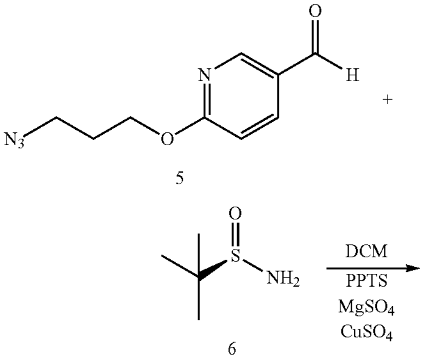

5

6

-continued

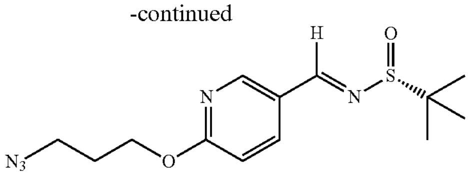

7

A mixture containing compound 5 (2.29 g, 9.94 mmol), compound 6 (4.82 g, 39.8 mmol), PPTS (125 mg, 0.50 mmol), magnesium sulfate (3 g, 24.9 mmol), copper sulfate (3.97 g, 24.9 mmol), and 3 angstrom molecular sieves in DCM (22 mL) was heated to reflux overnight. Upon completion, the mixture was filtered and concentrated under reduced pressure. Compound 7 was then isolated in 76% yield by separation on silica eluting a gradient of ethyl acetate in hexanes.

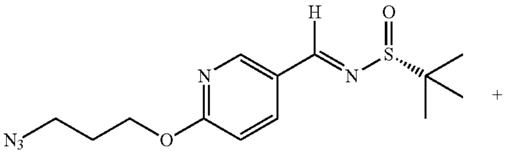

7

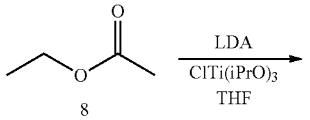

8

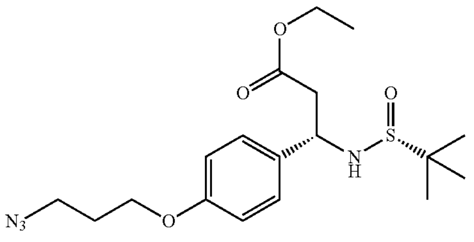

9

A flame dried flask was charged with THF (40 mL) and diisopropylamine (2.29 g, 22.6 mmol). It was cooled to −20° C. and n-BuLi (2.5 M, 8.64 mL, 21.6 mmol) was added via cannula. The solution was stirred for 10 min at −20° C. then cooled to −78° C. Compound 8 (2.02 mL, 20.6 mmol) was added dropwise with vigorous stirring. After addition, the solution was stirred for 30 min at −78° C. Next, $ClTi(iPrO)_3$ (11.26 g, 43.2 mmol) as a solution in THF (10 mL) was added via addition funnel over approximately 10 minutes with vigorous stirring. The reaction was stirred for 30 minutes at −78° C. Finally, compound 7 (2.29 g. 6.86 mmol) was added dropwise as a suspension in THF and stirred at −78° C. for 1.25 hours until the reaction was complete. To the reaction at −78° C. was added saturated aqueous ammonium chloride. The reaction was then removed from cooling and the aqueous phase was allowed to gradually thaw and quench (yellow orange color disappears). The mixture was portioned between EtOAc and saturated aqueous ammonium chloride. The organic phase was separated and aqueous phase was extracted two times with EtOAc. The organic phases were combined and dried over brine, then over sodium sulfate, and then filtered and concentrated. The residue was purified over silica eluting a gradient of ethyl acetate in hexanes. Compound 9 was obtained in 75% yield as single diastereomer after purification.

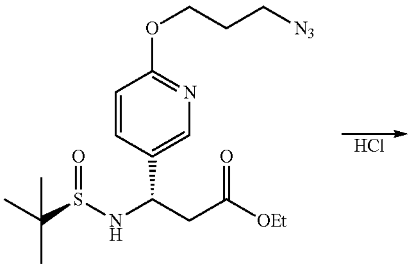

9

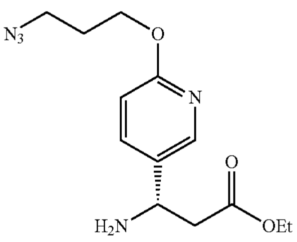

10

Compound 9 (1.28 g, 3.21 mmol) in MeOH (3.2 mL) was treated with HCl in dioxane (4M, 3.2 mL, 12.9 mmol) and stirred at room temperature for 30 minutes. Upon completion, the reaction mixture was diluted with water and washed with diethyl ether. Subsequently, the pH was adjusted to 11 using 2 N aqueous NaOH and the product was extracted with ethyl acetate. The organic phase was dried over sodium sulfate, filtered, and concentrated, yielding compound 10 in 92% yield, which was subsequently used without further purification.

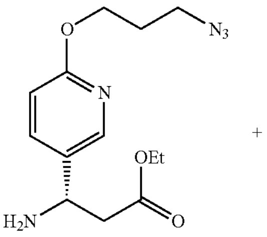

10

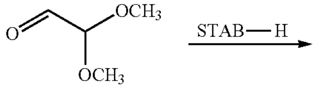

11

-continued

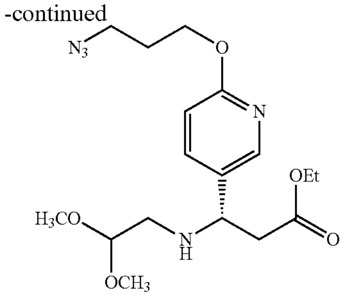

12

To mixture of compound 10 (0.78 g, 2.67 mmol) and compound 11 (0.60 g, 3.46 mmol) in THF (6 mL) at 15° C. was added STAB-H (1.29 g, 6.12 mmol) portion-wise as solid. After the addition, cooling was removed and the mixture was stirred for approximately 2.5 hours to completion. The reaction was quenched by addition of saturated aqueous sodium bicarbonate and pH was brought to 9. The product was extracted three times with EtOAc, the organic phases were combined, dried with brine, then filtered over sodium sulfate and concentrated. Compound 12 was isolated in 85% yield by separation on silica eluting a gradient of ethyl acetate in hexanes.

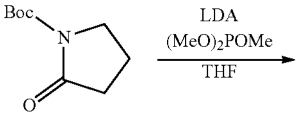

13

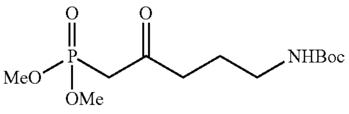

14

To DIPEA (7.53 mL, 53.75 mmol) in THF (35 mL) was added n-BuLi (2.5 M, 19.9 mL, 49.8 mmol) via oven dried gastight syringe over 2 minutes at −10° C. The mixture was stirred for 10 minutes at −10° C., then cooled to −60° C. and a solution of dimethyl methylphosphonate (6.42 g, 51.8 mmol) in THF (8 mL) was added dropwise over 5-10 minutes. After aging at −60° C. for about 1 hour, compound 13 (7.37 g. 39.82 mmol) was added as solution in THF (15 mL) dropwise over 5 minutes at −60° C. The reaction mixture was stirred at −60° C. for 1 hour and then −41° C. for about 1.5 hours. The reaction was quenched by addition of 2.6 equivalents of $H_2SO_4$ (2.0 M) and extracted three times with ethyl acetate (50 mL). The organic phases were combined and dried with brine, filtered over sodium sulfate, and concentrated briefly to determine crude weight and take sample for NMR. Upon determination of dry weight, compound 14 was dissolved in MeOH for use in next reaction without further purification. Calculated to be 75.83% yield. Crude wt/wt % 76.3% by NMR. $^1$H NMR: 400 MHz $CDCl_3$ δ 4.75 (s, 1H), 3.81 (s, 3H), 3.78 (s, 3H), 3.10-3.14 (m, 2H), 3.04-3.09 (m, 2H), 2.68 (t, 2H), 1.82-1.75 (m, 2H), 1.44 (s, 9H).

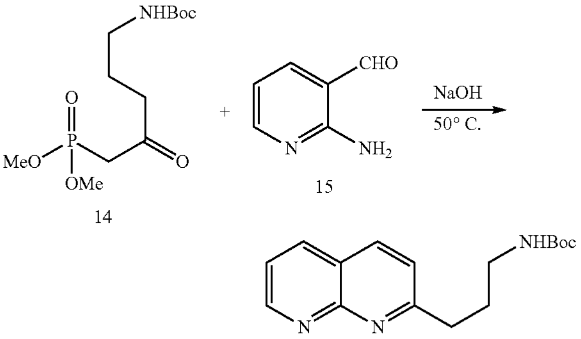

14 15

16

To compound 14 (9.33 g by weight from NMR of 12 g crude, 30.16 mmol) in MeOH (40 mL), was added solution of NaOH (1.45 g, 36.2 mmol) in water (1.5 mL). The mixture was heated to 50° C. and compound 15 (2.76 g, 22.62 mmol) was added. After stirring for 30 minutes, a second portion of compound 15 (736 mg, 6.03 mmol) was added, and the reaction mixture was stirred overnight at 50° C. The reaction mixture was then concentrated to an oil and partitioned between 2 volumes EtOAc and 1 volume $H_2O$. The organic phase was separated and washed with 1 volume of water. The aqueous washes were combined and back extracted (2×, 1 vol) with EtOAc. The combined organic phase was dried over sodium sulfate, filtered, and concentrated. The crude was dried onto approximately 20 g of silica compound 16 was isolated in 69% yield by separation on silica eluting a gradient of ethyl acetate in hexanes containing 1% triethylamine. $^1$H NMR: 400 MHz $CDCl_3$ δ 9.09 (dd, 1H), 8.17 (dd, 1H), 8.12 (d, 1H), 7.46 (dd, 1H), 7.41 (d, 1H), 4.78 (s, 1H), 3.24 (q, 2H), 3.10 (t, 2H), 2.12 (quin, 2H), 1.43 (S, 9H).

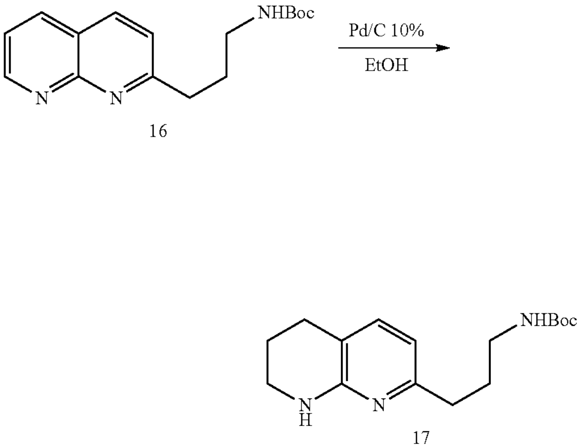

16

17

To a solution of compound 16 (5.98 g, 20.8 mmol) in EtOH (50 mL) was charged with palladium (10% on Carbon, 2.22 g, 2.08 mmol) and hydrogen at 1 atmosphere. The reaction mixture was stirred at room temperature overnight. Upon completion, the reaction mixture was filtered over Celite® and concentrated. Compound 17 was isolated in 79% yield by separation on silica eluting a gradient of ethyl acetate in hexanes containing 1% triethylamine. $^1$H NMR: 400 MHz $CDCl_3$ δ 7.05 (d, 1H), 6.34 (d, 1H), 5.48 (s, 1H), 4.81 (s, 1H), 3.36-3.43 (m, 2H), 3.16 (q, 2H), 2.68 (t, 2H), 2.59 (t, 2H), 1.90 (dt, 2H), 1.83 (quin, 2H), 1.44 (s, 9H).

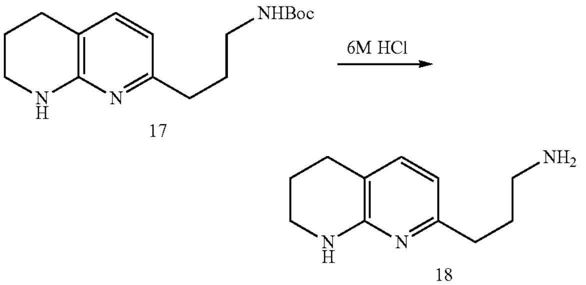

17
18

Compound 17 (4.81 g, 16.53 mmol) was dissolved in aqueous 6 M HCl (16.4 mL) and heated at 42° C. for 2 hours. An additional portion of 6 M HCl (2.8 mL) was then added and the reaction mixture was stirred for an additional 2 hours. To the reaction was added sodium chloride followed by aqueous 2 N NaOH until the product precipitated as an oil (pH was greater than 12). The mixture was extracted three times with 2-Butanol. The combined organic phase was dried over sodium sulfate, filtered and concentrated. Compound 18 was obtained in 85% yield and subsequently used without further purification. $^1$H NMR. 400 MHz $CDCl_3$ δ 7.06 (d, 1H), 6.35 (d, 1H), 4.83 (s, 1H), 3.35-3.46 (m, 2H), 2.75-2.67 (m, 4H), 2.58 (t, 2H), 1.88-195 (m, 2H), 1.84-1.76 (m, 4H).

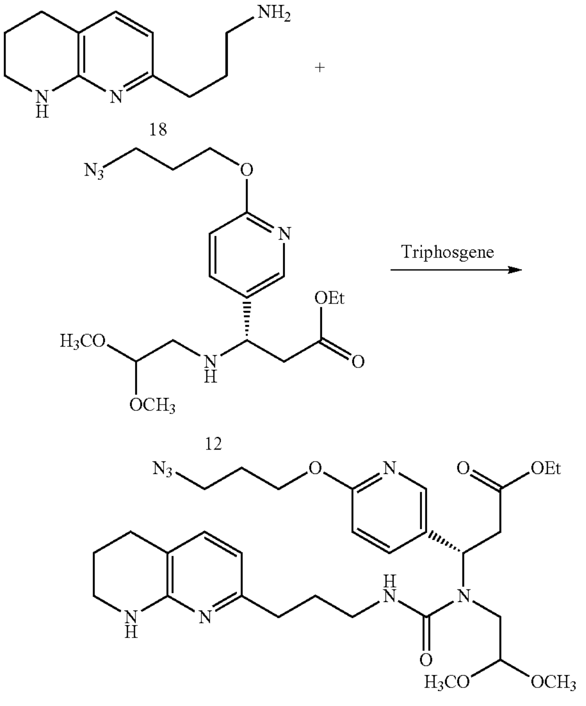

18
12
19

To a solution of triphosgene (85 mg, 0.28 mmol) in THF (0.9 mL) in a flame dried flask at −10° C. was added dropwise a solution of compound 18 (236 mg, 0.62 mmol) and TEA (0.134 mL, 0.96 mmol) in THF (0.5 mL). The reaction mixture was warmed to room temperature. After TLC indicated a complete reaction, additional TEA (0.134 mL) was added followed by addition of compound 12 (166 mg, 0.87 mmol) as a solid. The heterogenous mixture was heated at 50° C. for 2 hours with vigorous stirring. Upon completion, the reaction mixture was quenched with 1 volume of water and extracted three times with EtOAc. The combined organic phase was dried with brine, filtered over sodium sulfate and concentrated. Compound 19 was obtained assuming 100% yield and subsequently used without further purification.

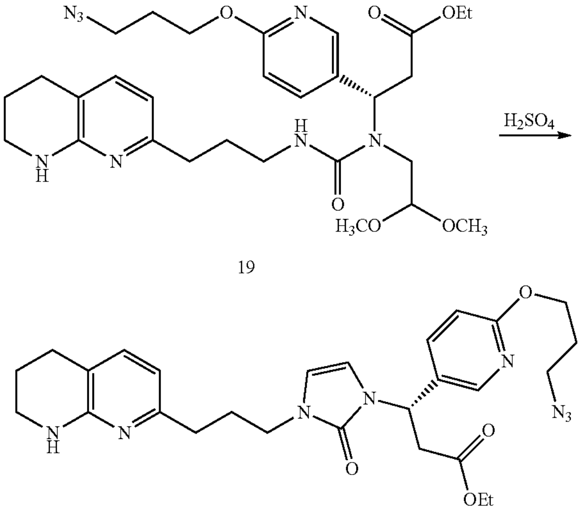

19

Crude compound 19 (400 mg, 0.62 mmol assumed) dissolved in THF (37 mL) was added $H_2SO_4$ (2M, 0.6 mL) and the mixture was stirred at room temperature overnight. The following morning, an additional portion of $H_2SO_4$ (0.65 equivalents) was added. Four hours later the reaction was complete. The reaction mixture was diluted with ethyl acetate. The organic phase was separated and the aqueous phase was back extracted once with ethyl acetate. The combined organic phase was filtered over sodium sulfate and concentrated. Compound 20 was isolated in 75% yield by separation over silica eluting a gradient of MeOH in DCM.

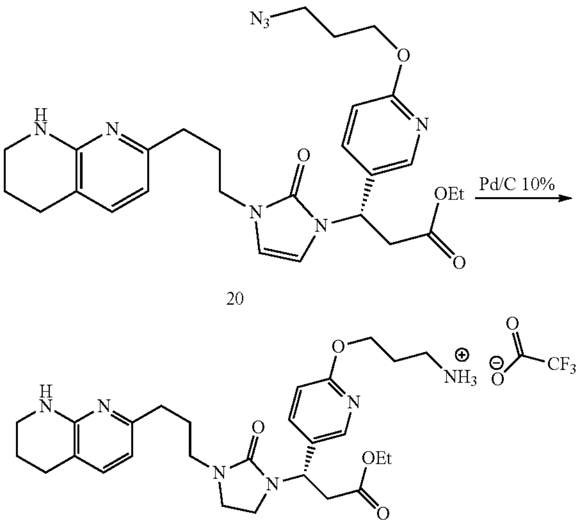

20
21

To a suspension of compound 20 (251 mg, 0.47 mmol) and Pd/C (10 wt %, 100 mg, 0.094 mmol) in ethanol (9 mL) was charged $H_2$ to 1 atmosphere and stirred at 35° C. overnight. Upon completion, palladium was removed by filtration over Celite®. Compound 21 was isolated in 20% yield as TFA salt by reverse phase HPLC using a $C_{18}$ 5 u 19×250 mm BEH column (Waters Corp.) eluting a gradient of acetonitrile in $H_2Q$ containing 1% TFA.

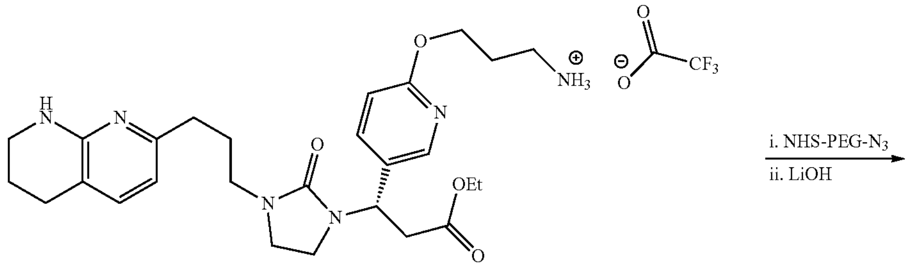

21

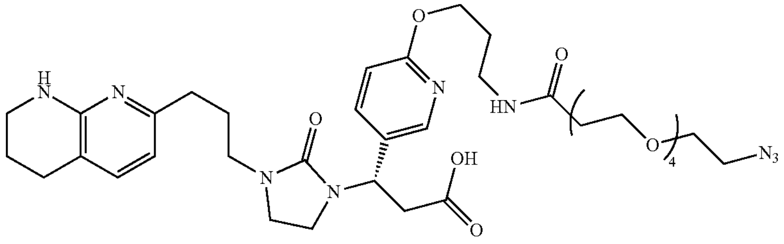

22

To a solution of compound 21 (61 mg, 0.097 mmol) in DCM (250 uL) was added TEA (8 uL, 0.24 mmol) followed by addition of NHS-PEG$_4$-N$_3$ (41.4 mg, 0.11 mmol) as a solution in DCM (275 μL). The reaction mixture was stirred for 15 minutes and checked LC-MS, which showed reaction was complete. All volatiles were removed, and the residue was dissolved in EtOH (0.4 mL) and water (0.4 mL). LiOH (11.2 mg, 0.47 mmol) was added and the reaction mixture was heated at 40° C. for 2 hours. Upon completion, the reaction mixture was concentrated under reduced pressure. Compound 22 (Structure 1c) was isolated in 42% yield by reverse phase HPLC using a $C_{18}$ 5 u 19×250 mm BEH column (Waters Corp.) eluting a gradient of acetonitrile in $H_2O$ containing 1% TFA.

Synthesis of Structure 2c ((S)-3-(4-(2-(2-(2-(2-azidoethoxy)ethoxy)ethoxy)ethoxy)-3-fluorophenyl)-3-(2-oxo-3-(3-(5,6,7,8-tetrahydro-1,8-naphthyridin-2-yl)propyl)imidazolidin-1-yl)propanoic acid)

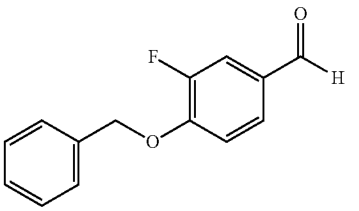

+

23

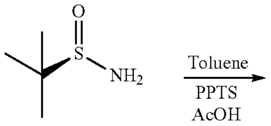

6

-continued

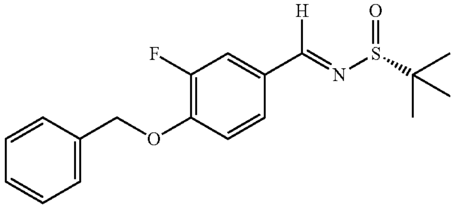

24

To a solution of compound 23 (10 g, 43.4 mmol) in toluene (80 mL) was added compound 6 (21.1 g, 0.17 mol), PPTS (0.55 g, 2.2 mmol), and then acetic acid (1.24 mL, 21.7 mmol)). The reaction vessel was equipped with a Dean Stark trap and then heated to reflux overnight. Upon completion the reaction mixture was concentrated and dried onto 60 grams of silica and purified over $SiO_2$ with a gradient of ethyl acetate in hexanes, yielding compound 24 in 66% yield. $^1$H NMR: 400 MHz $CDCl_3$ δ 8.47 (s, 1H), 7.68 (d, 1H), 7.31-7.56 (m, 6H), 6.98-7.16 (m, 1H), 5.23 (s, 2H), 1.26 (s, 9H).

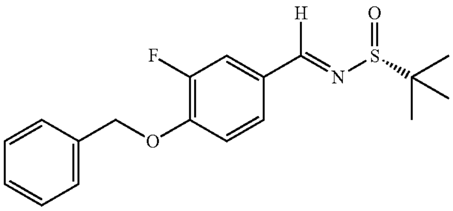

+

24

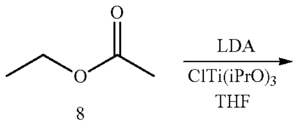

8

-continued

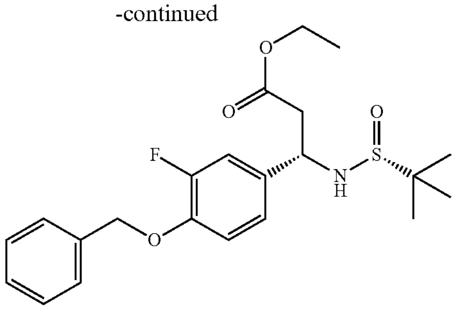

25

A flame dried flask was charged with THF (190 mL) and DIPEA (9.07 g, 89.7 mmol), cooled to −20° C., and then charged with n-BuLi (2.5M, 34.2 mL, 85.6 mmol) via cannula. The solution was stirred for 10 min at −20° C. then cooled to −78° C. Compound 8 (8 mL, 81.5 mmol) was added dropwise with vigorous stirring. After addition, stirred for 30 min at −78° C. Next, $ClTi(iPrO)_3$ (44.6 g, 0.171 mol) as solution in THF (40 mL) was added via addition funnel over 10 minutes. The reaction was stirred for 30 minutes at −78° C. Finally, compound 24 (9.06 g, 27.2 mmol) was added dropwise as a suspension in THF (20 mL) and stirred at −78° C. for 1.25 hour until the reaction was complete. To the reaction at −78° C. was added saturated aqueous ammonium chloride. The reaction was then removed from cooling and the aqueous phase was allowed to gradually thaw and quench (yellow orange color disappears). The mixture was partitioned between EtOAc and saturated aqueous ammonium chloride. The organic phase was separated and aqueous was washed two times with EtOAc. The organic phases were combined and dried over brine, then over sodium sulfate, filtered, and concentrated. Compound 25 was obtained in 70% yield as a single diastereomer by separation on silica eluting a gradient of ethyl acetate in hexanes. $^1H$ NMR: 400 MHz $CDCl_3$ δ 7.31-7.48 (m, 5H), 7.09 (dd, 1H), 6.89-7.04 (m, 2H), 5.13 (s, 2H), 4.59-4.76 (m, 2H), 4.13 (q, 2H), 2.81 (dd, 2H), 1.21-1.25 (m, 12H).

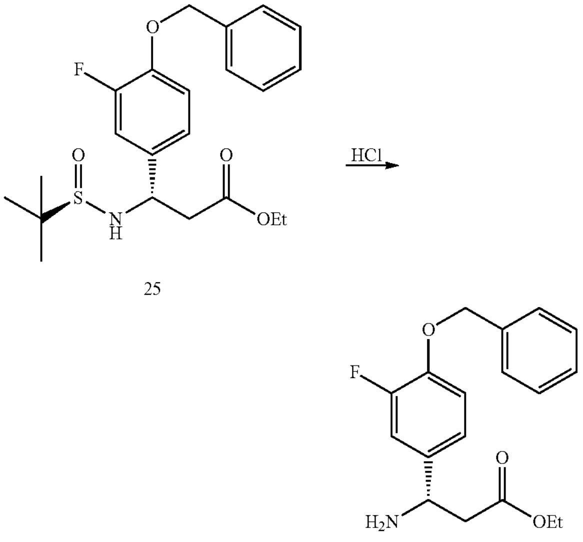

25

26

To compound 25 (8.07 g, 19.1 mmol) was added aqueous HCl (6M, 20.7 mL, 0.124 mol) followed by MeOH (60 mL). THF was added until homogenous solution was obtained and the reaction mixture was stirred for 6 hours at room temperature. The reaction mixture was basified to a of pH 10 with aqueous 2 N NaOH and then was extracted three times with EtOAc. The combined organic phases were dried with brine, filtered over sodium sulfate, and concentrated. Compound 26 was obtained in 95% yield and was subsequently used without further purification. $^1H$ NMR: 400 MHz $CDCl_3$ δ 7.28-7.46 (m, 6H), 7.18 (d, 1H), 6.99 (t, 1H), 5.11 (s, 2H), 4.57 (t, 1H), 4.09 (q, 2H), 2.97-3.09 (m, 1H), 2.81-2.93 (m, 1H), 1.18 (t, 3H).

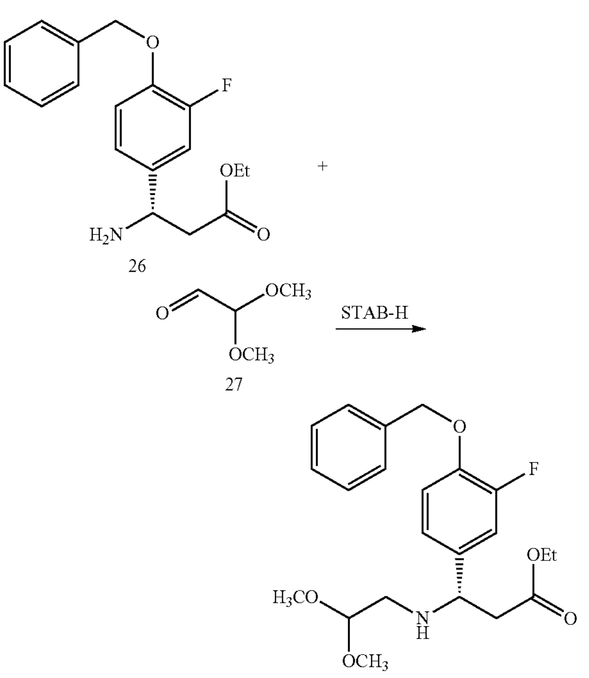

26 + 27

28

To a mixture of compound 26 (5.76 g, 18.2 mmol) and compound 27 (4.09 g, 23.6 mmol) in THF (40 mL) at 0° C. was added STAB-H (8.85 g, 41.8 mmol) portionwise as solid. After final addition cooling was removed and the mixture was stirred for approximately 2.5 hours to completion. The reaction mixture was quenched by addition of saturated aqueous sodium bicarbonate. The mixture was extracted three times with EtOAc. The combined organic phases were dried with brine, filtered over sodium sulfate, and concentrated. Compound 28 was isolated in 73% yield by separation on silica eluting a gradient of ethyl acetate in hexanes. $^1H$ NMR. 400 MHz $CDCl_3$ δ 7.30-7.49 (m, 5H), 7.11 (dd, 1H), 6.88-7.02 (m, 2H), 5.13 (s, 2 H), 4.40 (t, 1H), 4.10 (q, 2H), 4.00 (dd, 1H), 3.35 (s, 3H), 3.31 (s, 3H), 2.47-2.75 (m, 4H), 1.20 (t, 3H).

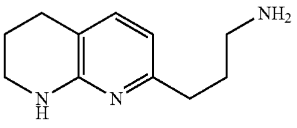

19

+

-continued

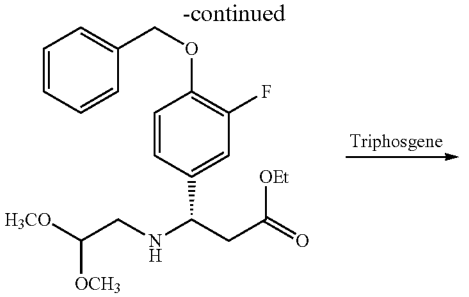

28

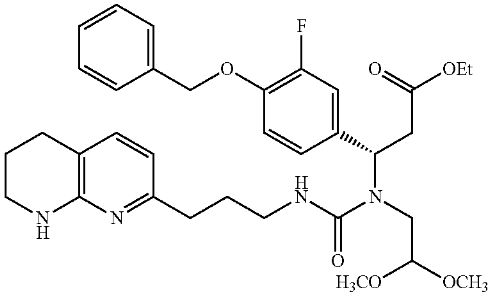

29

To a solution of triphosgene (1.2 g, 4.04 mmol) in THF (24 mL) in flame dried flask at −10° C. was added drop wise a solution of compound 19 (3.64 g, 8.99 mmol) and TEA (1.94 mmol, 13.9 mmol) in THF (6 mL). The reaction mixture was warmed to room temperature. After TLC indicated a complete reaction, additional TEA (3.3 mL, 23.6 mmol) was added followed by the addition of compound 28 (2.61 g, 13.7 mmol) as a solid. The heterogenous mixture was heated at 50° C. for 2 hours with vigorous stirring. Upon completion, the reaction mixture was quenched with 1 volume of water and extracted three times with EtOAc. The combined organic phase was dried with brine, filtered over sodium sulfate and concentrated. Compound 29 was obtained assuming 100% yield and the crude was subsequently used without further purification.

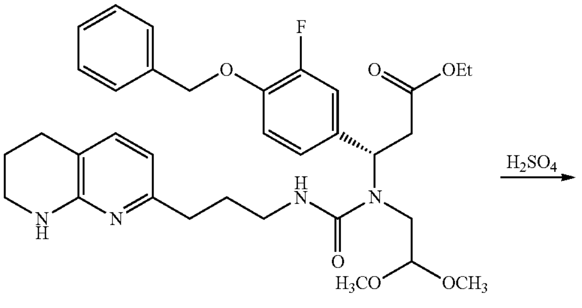

29

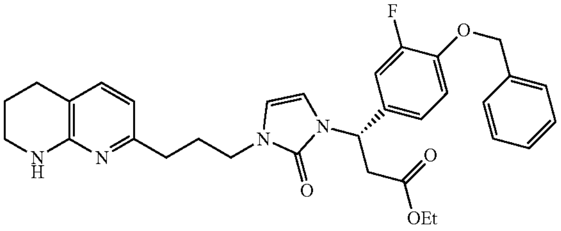

30

To compound 29 (5.59 g, 8.97 mmol) dissolved in THF (37 mL) was added water (0.8 mL) and $H_2SO_4$ (2M, 8.07 ml, 16.2 mmol) and the reaction mixture was stirred at 28° C. overnight. The following morning, the pH of the mixture was adjusted to 9 using sodium bicarbonate and extracted three times with DCM. The combined organic phases were dried with brine, filtered over sodium sulfate, and concentrated. Compound 30 was isolated in 82% yield by separation on silica eluting a gradient of MeOH in DCM containing 1% TEA.

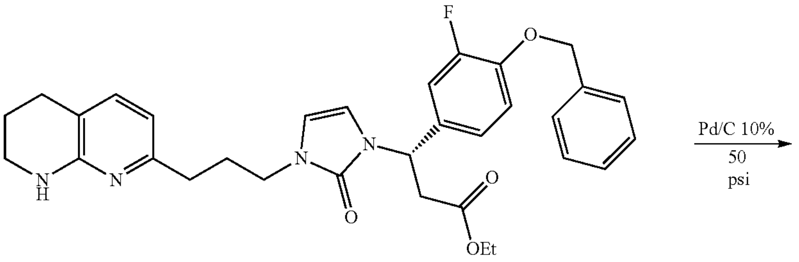

30

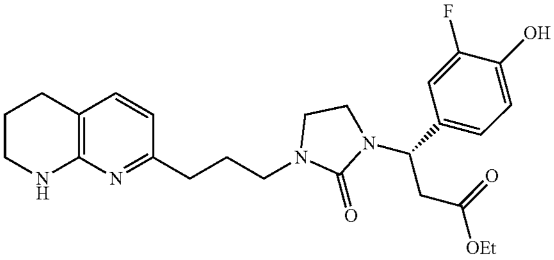

31

To compound 30 (4.13 g, 7.39 mmol) dissolved in EtOH (30 mL) was charged Degussa® palladium (10 wt %, 3.15 g, 2.% mmol) and hydrogen to 50 psi. The mixture was stirred at room temperature overnight. The next day, reaction was 64% complete. The reaction mixture was filtered over Celite® and concentrated. The residue was dissolved in EtOH and charged with palladium (10 wt %, 1.57 g, 1.48 mmol)) and hydrogen to 50 psi. After stirring for 48 hours the reaction mixture was heated to 30° C. and stirred for a further 24 hours. Upon completion the suspension was filtered over Celite® and all volatiles were removed in vacuo. The residue was purified over silica eluting a gradient of MeOH in DCM, yielding compound 31 in 72% yield. $^{1}H$ NMR. 400 MHz DMSO-do δ 9.88 (s, 1H), 7.02-7.14 (m, 2H), 6.86-6.93 (m, 2H), 6.50-6.76 (m, 1H), 6.31 (d, 1H), 5.17 (t, 1H), 4.00 (q, 2H), 3.23-3.28 (m, 4H), 2.79-3.18 (m, 7H), 2.61 (t, 2H), 2.41 (t, 2H), 1.65-1.78 (m, 4H), 1.09 (t, 3H).

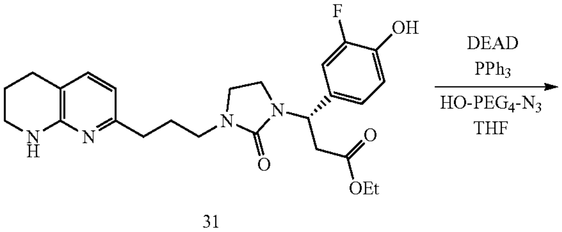

31

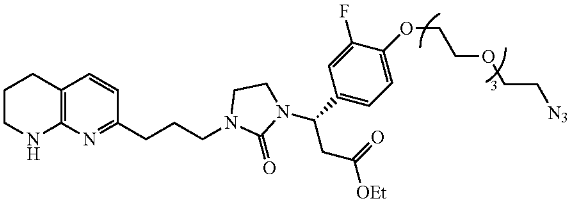

32

To a solution of $PPh_3$ (699 mg, 2.66 mmol) in THF (0.47 mL) at −10° C. was added dropwise a solution of DEAD. The mixture was warmed to room temperature and added to a neat mixture of compound 31 (600 mg, 1.33 mmol) and HO-$PEG_4$-$N_3$, (466 mg, 3.06 mmol) and stirred overnight. The reaction mixture was then concentrated under reduced pressure, and the residue was purified over silica eluting a gradient of MeOH in DCM, yielding compound 32 in 50% yield. $^{1}H$ NMR. 400 MHz DMSO-$d_6$ δ 7.10-7.19 (m, 2H), 6.97-7.06 (m, 2H), 6.18-6.31 (m, 2H), 5.20 (t, 1H), 4.13-4.16 (m, 1H), 3.98-4.04 (m, 2H), 3.71-3.80 (m, 2H), 3.52-3.61 (m, 8H), 3.38-3.37 (m, 5H), 3.10-3.25 (m, 5H), 2.79-3.08 (m, 5H), 2.59 (t, 2H), 2.31-2.42 (m, 2H), 1.65-1.75 (m, 4H), 1.10 (t, 3H).

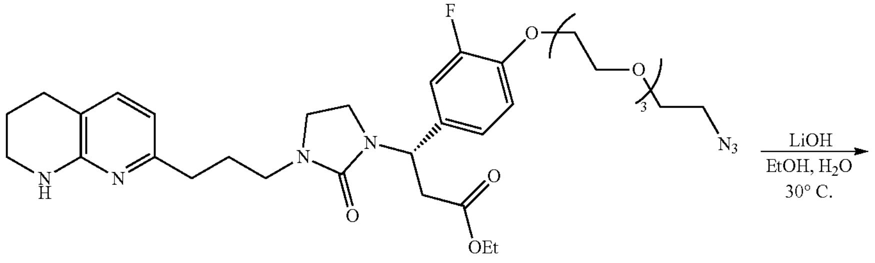

32

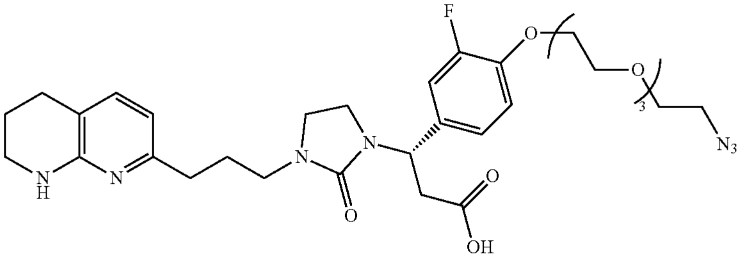

33

To compound 32 (826 mg, 1.23 mmol) was added EtOH (3 mL) and $H_2O$ (3 mL), followed by LiOH (97 mg, 4.05 mmol). The mixture was stirred at 30° C. overnight. Upon completion the mixture was neutralized to pH=5 using 6 M aqueous HCl and concentrated. The residue was purified by reverse phase HPLC with a Phenomenex Gemini C18, 50×250 mm, 10 μm column eluting a gradient of acetonitrile in water containing 0.1%, yielding compound 33 (Structure 2c) in 81% yield. $^{1}H$ NMR: 400 MHz $D_2O$ δ 7.30 (d, 1H), 7.01-7.19 (m, 3H), 6.45 (d, 1H), 5.24 (t, 1H), 4.14-4.32 (m, 2H), 3.84-3.92 (m, 2H), 3.59-3.77 (m, 10H), 3.14-3.45 (m, 8H), 0.02-3.12 (m, 1H), 2.97 (d, 2H), 2.85 (q, 1H), 2.50-2.72 (m, 4H), 1.68-1.94 (m, 4H).

Synthesis of Structure 2.1c ((S)-3-(4-((11-azidoundecyl)oxy)-3-fluorophenyl)-3-(2-oxo-3-(3-(5,6,7,8-tetrahydro-1,8-naphthyridin-2-yl)propyl)imidazolidin-1-yl)propanoic acid)

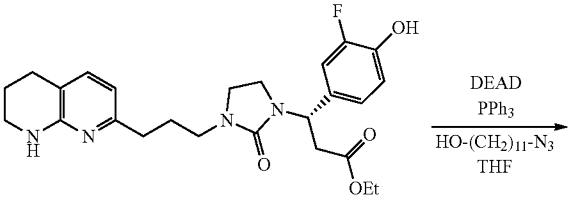

31

-continued

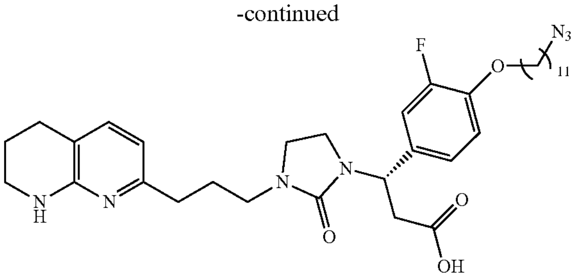

34

To a solution of $PPh_3$ in THF was added dropwise a solution of DEAD at room temperature. The mixture was transferred to a vial containing mixture of compound 31 and $OH—(CH_2)_{11}—N_3$, and the reaction mixture was stirred at room temperature overnight. Volatiles were removed from the reaction mixture and the crude was dissolved in EtOH. LiOH was added as a solution in $H_2O$, and additional water/EtOH was added until the reaction mixture became homogenous. After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile-water, gradient elution).

Synthesis of Structure 2.2c ((S)-3-(4-(2-(1-(6-azidohexanoyl)piperidin-4-yl)ethoxy)-3-fluorophenyl)-3-(2-oxo-3-(3-(5,6,7,8-tetrahydro-1,8-naphthyridin-2-yl)propyl)imidazolidin-1-yl)propanoic acid)

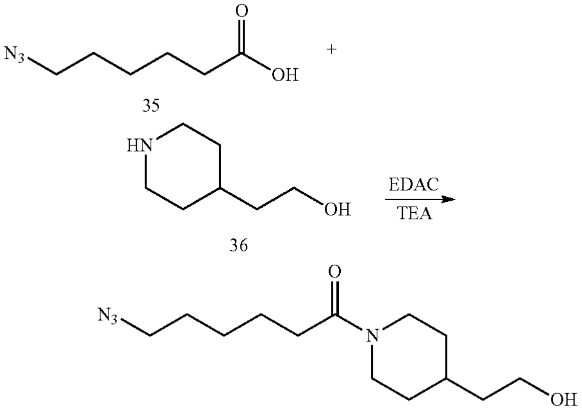

35

36

37

Compound 35 dissolved in DCM at 0° C. was treated with EDAC and acetonitrile was added to aid in solubility. After 5 minutes, TEA and compound 36 were added, cooling was removed, and stirring continued for 2 hours. Upon completion, saturated ammonium chloride was added and the organic phase was separated, filtered over sodium sulfate, and concentrated. The crude obtained was used subsequently without further purification.

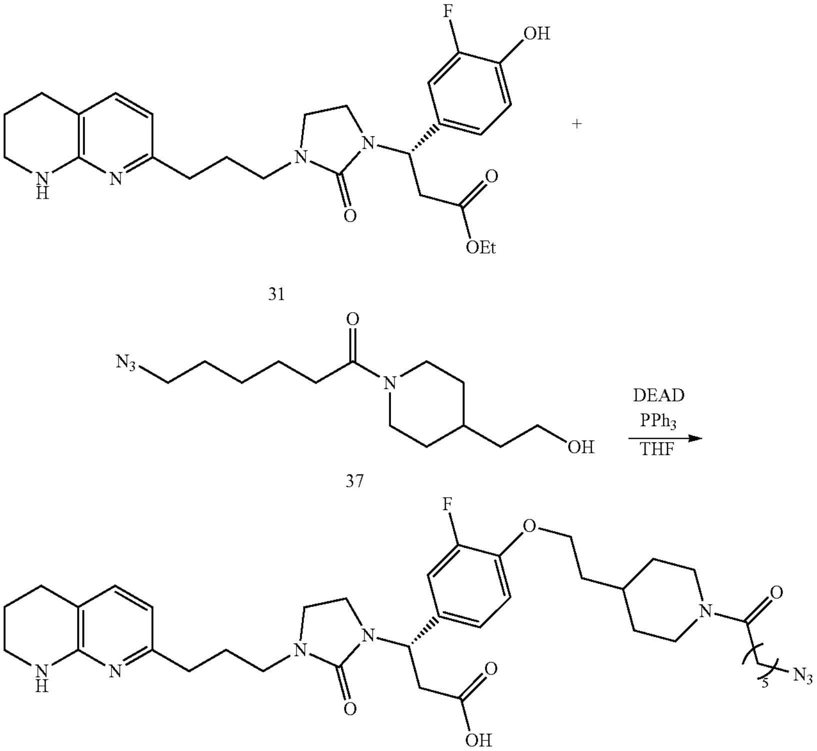

31

37

38

To a solution of $PPh_3$ in THF was added dropwise a solution of DEAD at room temperature with vigorous stirring. The mixture was transferred to a vial containing a mixture of compound 31 and compound 37, and the reaction mixture was stirred at room temperature overnight. Volatiles were removed from the reaction mixture and the crude was dissolved in EtOH. LiOH was added as a solution in $H_2O$, and additional water was added until the reaction mixture was removed and compound 39 was added, followed by the addition of TEA. The heterogeneous mixture was stirred overnight at room temperature. The next day, the reaction was diluted with DCM and the precipitate dissolved. The mixture was washed twice with 5% $KHSO_4$ and once with brine. The organic phase was filtered over sodium sulfate and concentrated. The crude residue containing compound 40 was used without further purification.

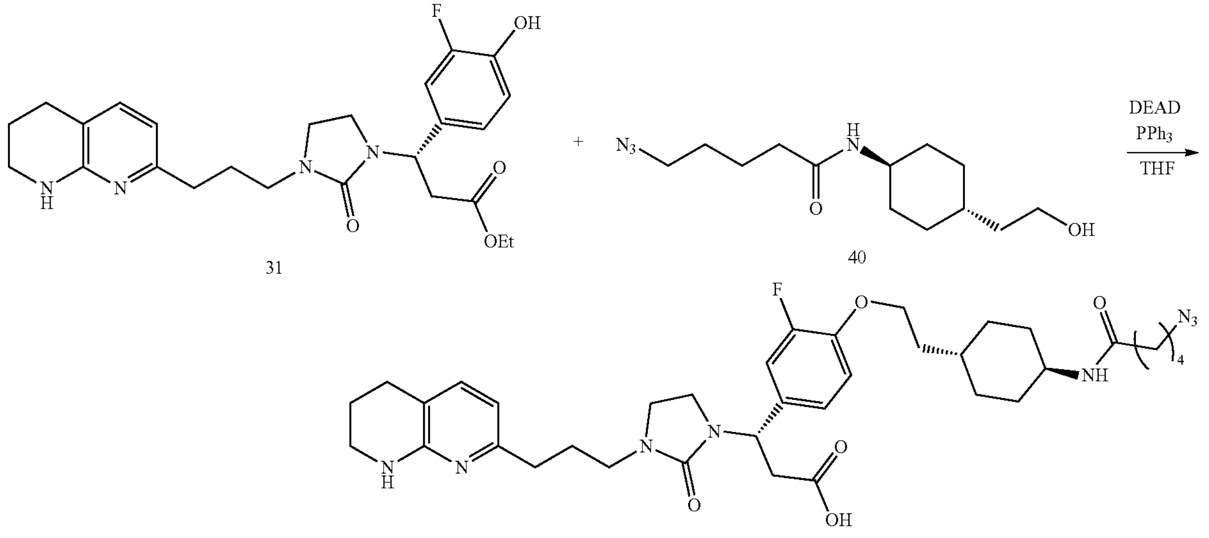

31

40

41 became homogeneous After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 38 (Structure 2.2c).

Synthesis of Structure 2.3c ((S)-3-(4-(2-((1r,4S)-4-(S-azidopentanamido)cyclohexyl)ethoxy)-3-fluorophenyl)-3-(2-oxo-3-(3-(5,6,7,8-tetrahydro-1,8-naphthyridin-2-yl)propyl)imidazolidin-1-yl)propanoic acid)

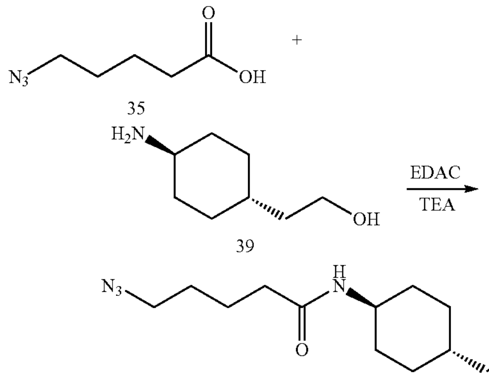

35

39

40

To suspension of compound 35 in DCM at 0° C. was added EDAC as a solution in DCM. After 5 minutes, cooling To a solution of $PPh_3$ in THF was added dropwise a solution of DEAD at room temperature with vigorous stirring. The mixture was transferred to a vial containing a mixture of compound 31 and compound 40, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 41 (Structure 2.3c).

Synthesis of Structure 2.4c ((S)-3-(4-(4-(5-azidopentanamido)phenethoxy)-3-fluorophenyl)-3-(2-oxo-3-(3-(5,6,7,8-tetrahydro-1,8-naphthyridin-2-yl)propyl)imidazolidin-1-yl)propanoic acid)

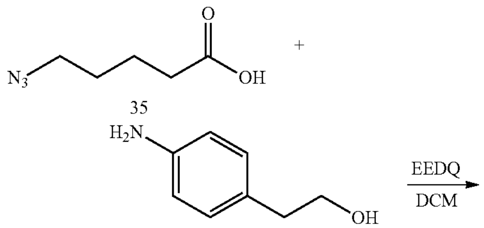

35

42

-continued

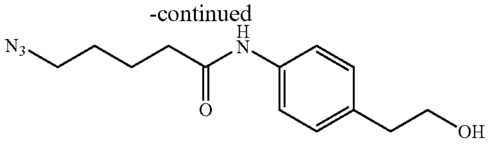

43

To a mixture of compound 35 and compound 42 in DCM was added EEDQ, and the solution was stirred at room temperature overnight. The reaction mixture was then diluted with DCM, washed three times with 1M HCl, and washed once with brine. The organic phase was dried over sodium sulfate, filtered, and concentrated. Compound 43 was then used without further purification.

-continued

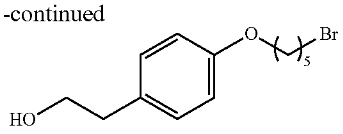

47

To a solution of compound 45 and compound 46 in acetone was added potassium carbonate. The mixture was heated to 65° C. in a sealed vial as a suspension with vigorous stirring overnight under $N_2$ protection. The reaction was then filtered, concentrated, and purified over silica eluting a gradient of ethyl acetate in hexanes, yielding compound 47.

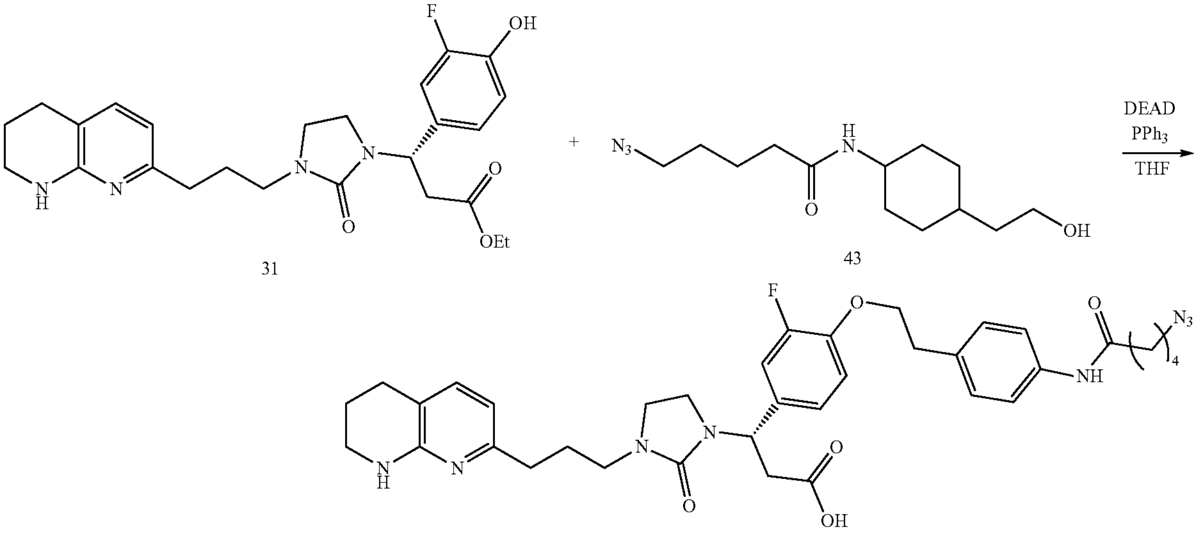

31 43 44

To a solution of $PPh_3$ in THF was added dropwise a solution of DEAD at room temperature with vigorous stirring. The mixture was transferred to a vial containing a mixture of compound 31 and compound 43, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 44 (Structure 2.4c).

Synthesis of Structure 2.5c ((S)-3-(4-(4-((5-azidopentyl)oxy)phenethoxy)-3-fluorophenyl)-3-(2-oxo-3-(3-(5,6,7,8-tetrahydro-1,8-naphthyridin-2-yl)propyl)imidazolidin-1-yl)propanoic acid)

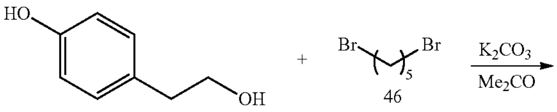

45 46

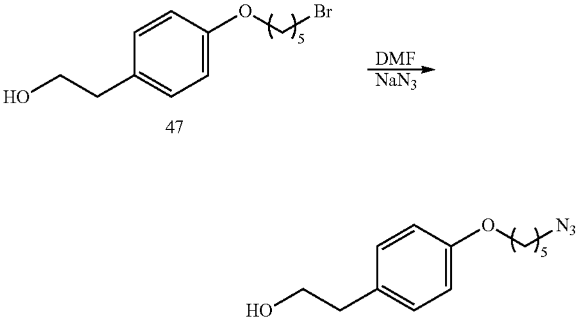

47 48

To a solution of compound 47 in DMF was added sodium azide and the mixture was stirred at 80° C. in a sealed vial under nitrogen protection overnight. Upon completion, 1 volume of water was added and the product was extracted with ethyl acetate. The separated organic phase was filtered over sodium sulfate and concentrated. Crude of compound 48 was used without further purification.

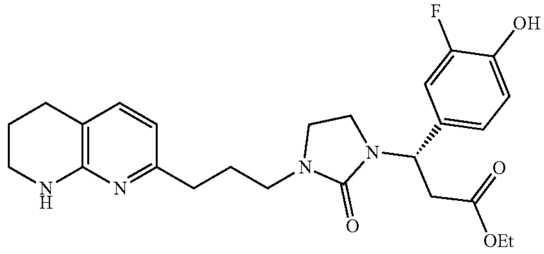

31

+

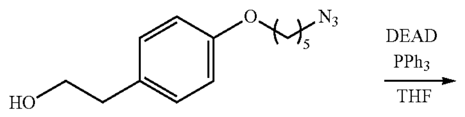

48

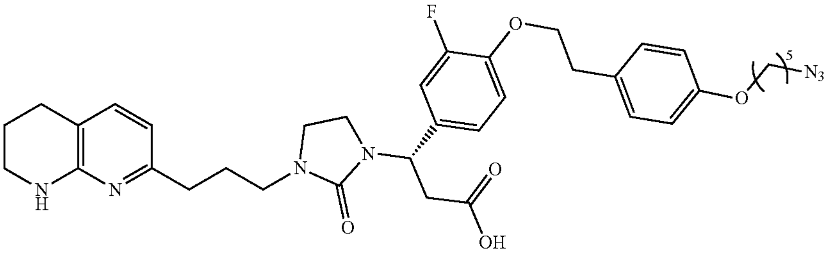

49

To a solution of $PPh_3$ in THF was added dropwise a solution of DEAD at room temperature with vigorous stirring. The mixture was transferred to a vial containing a mixture of compound 31 and compound 48, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 49 (Structure 2.5c).

Synthesis of Structure 2.6c ((S)-3-(3-(3-(3-(17-azido-3-oxo-6,9,12,15-tetraoxa-2-azaheptadecyl)-5,6,7,8-tetrahydro-1,8-naphthyridin-2-yl)propyl)-2-oxoimidazolidin-1-yl)-3-(3-fluoro-4-methoxyphenyl)propanoic acid)

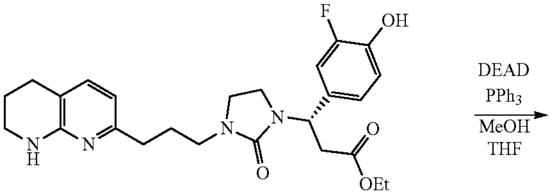

31

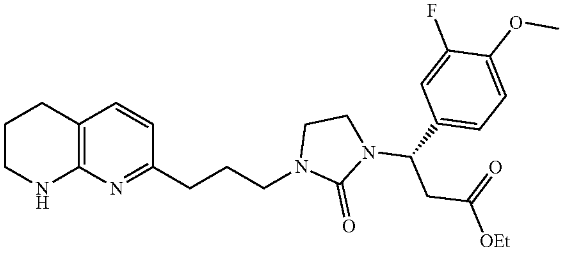

50

To a solution of $PPh_3$ in THF was added dropwise a solution of DEAD at 0° C. After complete addition, the mixture was transferred to a vial containing a neat mixture of compound 31 and MeOH. The vial was capped with $N_2$ and stirred at room temperature overnight. Upon completion all volatiles were removed and the crude obtained was purified over silica eluting a gradient of MeOH in DCM, yielding compound 50.

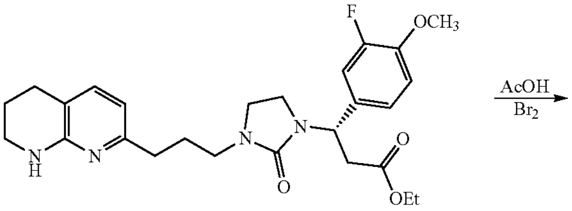

50

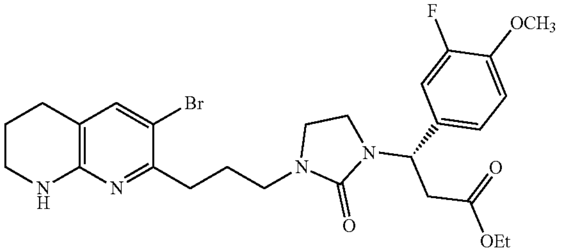

51

To a solution of compound 50 in AcOH was added bromine, and the mixture was stirred for 0.5 hours. Upon completion, the reaction was diluted with 5 volumes of ethyl acetate and 2.5 volumes of water. The aqueous layer was neutralized to pH 7 with saturated aqueous sodium bicarbonate, and the organic phase was separated. The aqueous layer was extracted two additional times with ethyl acetate. The combined organic phases were dried over sodium sulfate, filtered, and concentrated. Crude obtained of compound 51 was subsequently used without further purification.

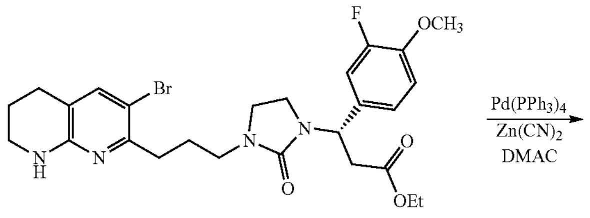

51

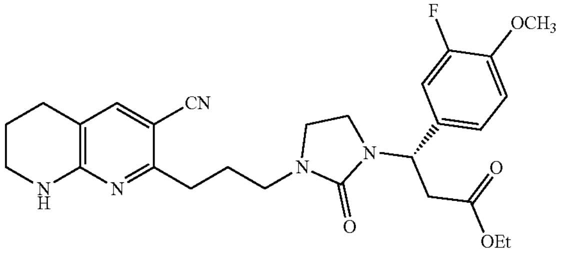

52

A solution of compound 51, $Pd(PPh_3)_4$, and $Zn(CN)_2$ in DMAC was degassed with nitrogen for 30 minutes The mixture was heated at 128° C. in a sealed vial overnight. Upon completion, mixture was diluted with 5 volumes of EtOAc. The organic phase was separated then washed two times with water, washed two times with brine, and then the organic phase was filtered over sodium sulfate and concentrated. The residue was purified over silica eluting 100% EtOAc, yielding compound 52.

To a solution of compound 52 in MeOH was added ammonia, then a slurry of Raney nickel that was pre-rinsed three times with methanol. A Parr® flask was charged to 60 psi with hydrogen and stirred at room temperature for 16 hours. Upon completion, the suspension was filtered and concentrated. The crude residue obtained was redissolved in DMF. DIEA and NHS-$PEG_4$-$N_3$ were added and the mixture was stirred for one hour. Upon completion, all volatiles were removed and the crude residue was redissolved in a mixture of MeOH and THF. LiOH in $H_2O$ was added and the mixture was stirred at room temperature for 17 hours. Upon reaction completion, the pH was adjusted to 3 with TFA and the mixture was directly injected onto semi-preparative reverse phase HPLC (Phenomenex Gemini C18, 250×21.2 mm, 5 μm, 0.1% TFA in water/ACN, gradient elution), yielding compound 53 (Structure 2.6c).

Synthesis of Structure 2.7c ((S)—N-(2-(2-(2-(2-azidoethoxy)ethoxy)ethoxy)ethyl)-3-(3-fluoro-4-methoxyphenyl)-3-(2-oxo-3-(3-(5,6,7,8-tetrahydro-1,8-naphthyridin-2-yl)propyl)imidazolidin-1-yl)propanamide), Structure 2.8c, Structure 2.9c, and Structure 2.10c

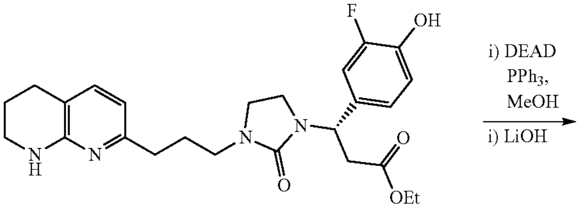

31

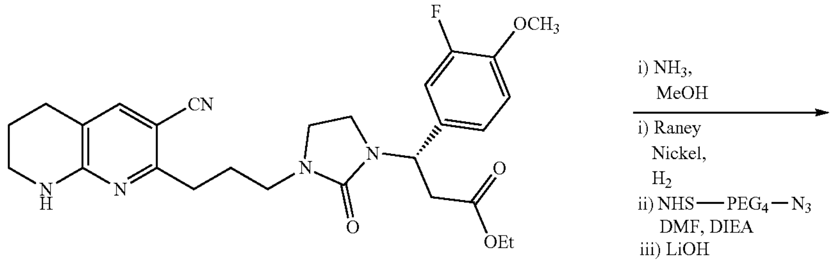

52

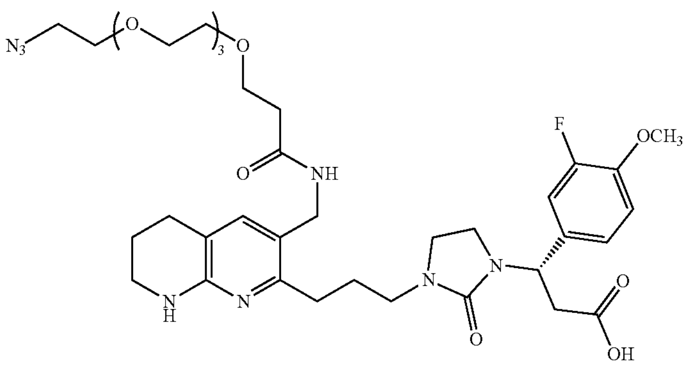

53

-continued

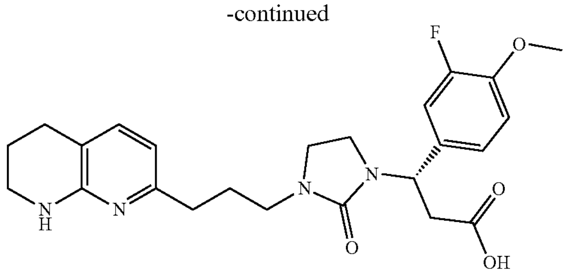

54

To compound 31 was added sequentially THF, $PPh_3$, and a solution of DEAD dropwise at 0° C. The mixture was stirred for 16 hours at room temperature. The mixture was then cooled to −20° C. for 1 hour and filtered to remove triphenylphosphine oxide. The filtrate was concentrated and intermediate of O-alkylation isolated by purification on silica eluting a gradient of ethyl acetate in hexanes containing 1% TEA. Isolated intermediate was then suspended in a mixture of THF and $H_2O$, treated with LiOH in $H_2O$, and stirred at 35° C. for 16 hours. Upon completion, the pH was adjusted to 7 with 2 M HCl and all volatiles were removed. Crude was suspended in $H_2O$; sodium chloride was added and compound 54 was extracted with ethyl acetate five times. The organic phases were combined, filtered over sodium sulfate and concentrated. Compound 54 was subsequently used without further purification.

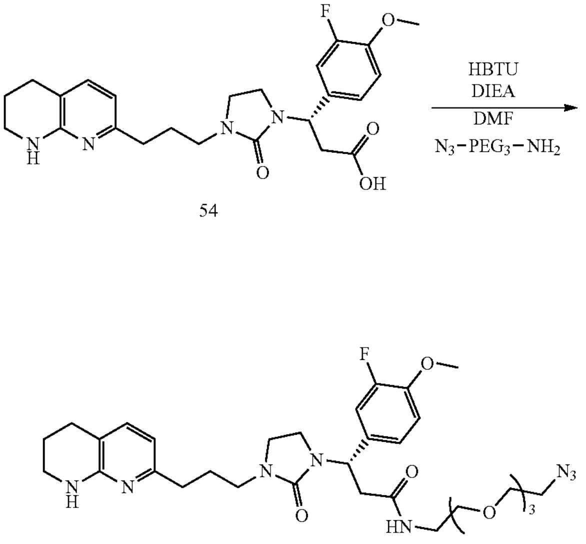

54

55

A solution of compound 54 in DMF was treated with HBTU and stirred for 5 minutes. DIEA and $N_3$-$PEG_3$-$NH_2$ were subsequently added, and the mixture was stirred at room temperature for 16 hours. Upon completion, the pH was adjusted to 3 with TFA and compound 55 was isolated by direct injection into semi-preparative reverse phase HPLC (Phenomenex Gemini $C_{1-8}$, 250x21.2 mm, 5 μm, 0.1% TFA in water/ACN, gradient elution), yielding compound 55.

Similar procedures were used to synthesize compounds 2.8c, 2.9c and 2.10c, using $N_3$-$PEG_{11}$-$NH_2$, $N_3$-$PEG_{23}$-$NH_2$ and $N_3$-$PEG_{35}$-$NH_2$, respectively.

Synthesis of Structure 2.11c ((R)-3-(4-(2-(2-(2-(2-azidoethoxy)ethoxy)ethoxy)ethoxy)-3-fluorophenyl)-3-(2-oxo-3-(3-(5,6,7,8-tetrahydro-1,8-naphthyridin-2-yl)propyl)imidazolidin-1-yl)propanoic acid)

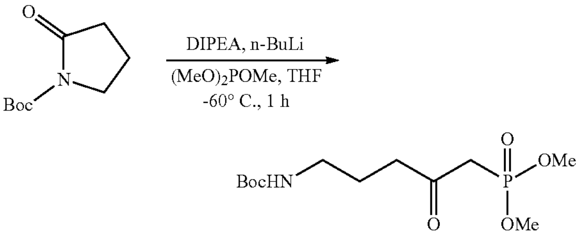

174

Into a 3-L 4-necked round-bottom flask purged and maintained with an inert atmosphere of nitrogen, was placed THF (1.50 L), DIPEA (150.00 mL, 716.000 mmol, 0.88 equiv.), n-BuLi (430.00 mL, 680.000 mmol, 0.84 equiv.) This was followed by the addition of trimethyl phosphite (195.00 mL) at −60° C. and stirred for 1 h at −60° C. To this was added tert-butyl 2-oxopyrrolidine-1-carboxylate (150.00 g, 809.835 mmol, 1.00 equiv.) at −60° C. The resulting solution was stirred for 1 h at −60° C. in a liquid nitrogen bath. The reaction was then quenched by the addition of 350 mL of $H_2SO_4$ (2N) and diluted with 1.5 L of $H_2O$. The resulting solution was extracted with 2x1 L of ethyl acetate. The resulting mixture was washed with 1x1 L of $H_2O$, dried over anhydrous sodium sulfate and concentrated under vacuum. This resulted in 200 g (crude) of tert-butyl N-[5-(dimethoxyphosphoryl)-4-oxopentyl]carbamate as yellow oil.

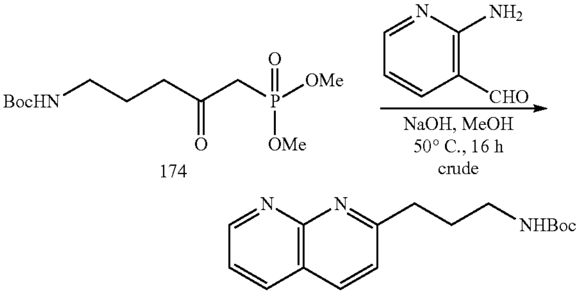

174

175

Into a 3-L round-bottom flask, was placed tert-butyl N-[5-(dimethoxyphosphoryl)-4-oxopentyl]carbamate (200.00 g, 1500.00 mmol, 1.50 equiv.), MeOH (1.50 L), 2-aminopyridine-3-carbaldehyde (53.00 g, 1000.00 mmol, 1.00 equiv), NaOH (50.00 g, 1500.00 mmol, 1.50 equiv.). The resulting solution was stirred for 16 h at 50° C. in an oil bath. The pH value of the solution was adjusted to 8 with $NaHCO_3$ (aq.). The resulting mixture was concentrated. The reaction was then quenched by the addition of 1.5 L of water and extracted with 2x1.5 L of ethyl acetate. The combined organic layers were dried over anhydrous sodium sulfate and concentrated under vacuum. This resulted in 160 g (crude) of tert-butyl N-[3-(1,8-naphthyridin-2-yl)propyl]carbamate as yellow oil.

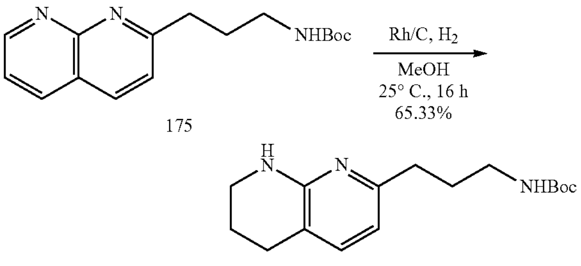

175

176

Into a 5-L round-bottom flask, was placed tert-butyl N-[3-(1,8-naphthyridin-2-yl)propyl]carbamate (160.00 g, 556.787 mmol, 1.00 equiv.), MeOH (2.00 L), Rh/C (140.00 g, 1.360 mmol), $H_2$ (40 Psi). The resulting solution was stirred for 16 h at 25° C. The solids were filtered out. The resulting mixture was concentrated. This resulted in 106 g (65.33%) of tert-butyl N-[3-(5,6,7,8-tetrahydro-1,8-naphthyridin-2-yl)propyl]carbamate as a yellow solid.

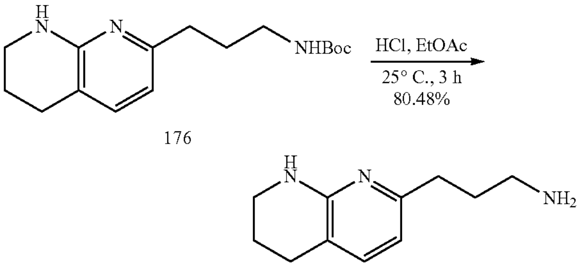

176

177

Into a 1-L round-bottom flask, was placed tert-butyl N-[3-(5,6,7,8-tetrahydro-1,8-naphthyridin-2-yl)propyl]carbamate (106.00 g, 363.767 mmol, 1.00 equiv.), EtOAc (500.00 mL), HCl in EtOAc (4M, 400.00 mL). The resulting solution was stirred for 3 h at 25° C. The resulting solution was diluted with 1 L of $H_2O$. NaOH (aq.) was employed to adjust the pH to 11. The resulting solution was extracted with 2×1 L of ethyl acetate. The combined organic layers were dried over anhydrous sodium sulfate and concentrated under vacuum. This resulted in 56 g (80.48%) of 3-(5,6,7,8-tetrahydro-1,8-naphthyridin-2-yl)propan-1-amine as a yellow solid.

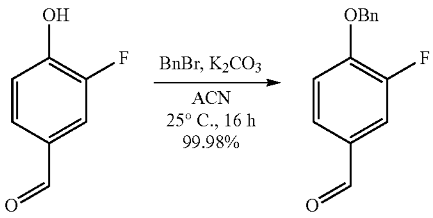

178

Into a 2-L round-bottom flask, was placed 3-fluoro-4-hydroxybenzaldehyde (140.00 g, 999.194 mmol, 1.00 equiv.), ACN (1000 mL), (bromomethyl)benzene (205.08 g, 1199.039 mmol, 1.20 equiv.), $K_2CO_3$ (414.28 g, 2997.581 mmol, 3.00 equiv.). The resulting solution was stirred for 16 h at 25° C. The solids were filtered out. The resulting mixture was concentrated. This resulted in 230 g (99.98%) of 4-(benzyloxy)-3-fluorobenzaldehyde as a white solid.

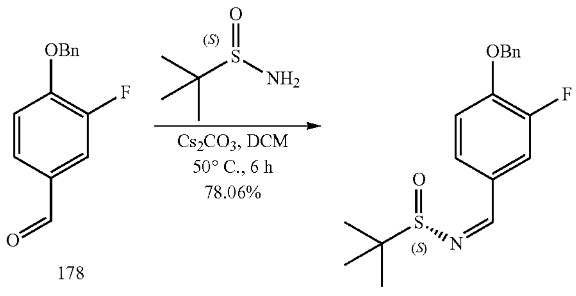

178

179

Into a 3-L round-bottom flask, was placed 4-(benzyloxy)-3-fluorobenzaldehyde (230.00 g, 998.966 mmol, 1.00 equiv.), DCM (1600 mL), (S)-2-methylpropane-2-sulfinamide (145.29 g, 1198.762 mmol, 1.20 equiv.), $Cs_2CO_3$ (650.97 g, 1997.933 mmol, 2.00 equiv.). The resulting solution was stirred for 6 h at 50° C. in an oil bath. The solids were filtered out. The resulting mixture was concentrated. This resulted in 260 g (78.06%) of (S)—N-[[4-(benzyloxy)-3-fluorophenyl]methylidene]-2-methylpropane-2-sulfinamide as a white solid.

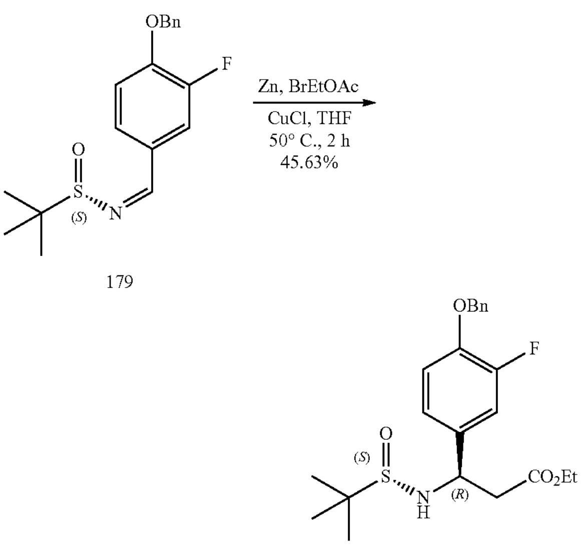

179

180

Into a 3-L round-bottom flask purged and maintained with an inert atmosphere of nitrogen, was placed THF (2.0 L), Zn (1.02 kg, 15595.945 mmol, 20.00 equiv.), CuCl (115.80 g, 1169.6% mmol, 1.50 equiv.), ethyl 2-bromoacetate (325.57 g, 1949.498 mmol, 2.50 equiv.), (S)—N-[[4-(benzyloxy)-3-fluorophenyl]methylidene]-2-methylpropane-2-sulfinamide (260.00 g, 779.797 mmol, 1.00 equiv.). The resulting solution was stirred for 30 min at 0° C. in a water/ice bath. The resulting solution was allowed to react, with stirring, for an additional 2 h while the temperature was maintained at 50° C. in an oil bath. The solids were filtered out. The resulting mixture was concentrated. The reaction was then quenched by the addition of 2 L of water and extracted with 2×2 L of ethyl acetate. The combined organic layers were dried over anhydrous sodium sulfate and concentrated under vacuum. This resulted in 150 g (45.63%) of ethyl (3R)-3-[4-(benzyloxy)-3-fluorophenyl]-3-[[(S)-2-methylpropane-2-sulfinyl]amino]propanoate as yellow oil.

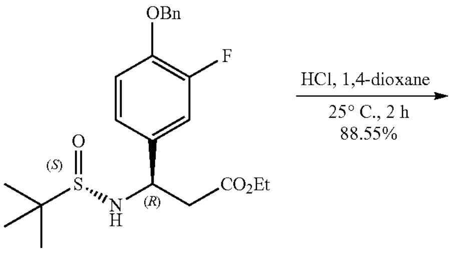

180

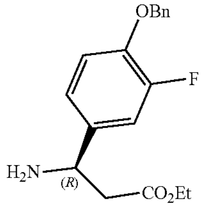

181

Into a 1-L round-bottom flask, was placed ethyl (3R)-3-[4-(benzyloxy)-3-fluorophenyl]-3-[[(S)-2-methylpropane-2-sulfinyl]amino]propanoate (150.00 g, 355.847 mmol, 1.00 equiv.), HCl in 1,4-dioxane (400.00 mL, 4M). The resulting solution was stirred for 2 h at 25° C. The resulting mixture was concentrated. The reaction was then quenched by the addition of 1 L of water. $NaHCO_3$ (aq.) was employed to adjust the pH to 8. The resulting solution was extracted with 2×1 L of ethyl acetate dried over anhydrous sodium sulfate and concentrated. This resulted in 100 g (88.55%) of ethyl (3R)-3-amino-3-[4-(benzyloxy)-3-fluorophenyl]propanoate as yellow oil.

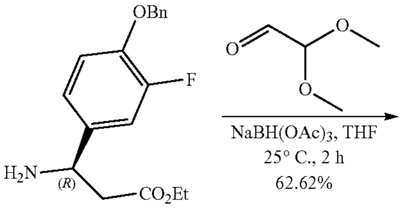

181

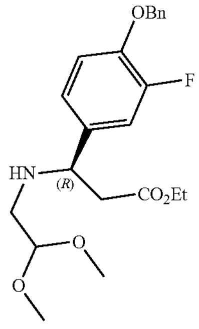

182

Into a 2-L round-bottom flask, was placed ethyl (3R)-3-amino-3-[4-(benzyloxy)-3-fluorophenyl]propanoate (100.00 g, 315.100 mmol, 1.00 equiv.), THF (1.00 L), 2,2-dimethoxyacetaldehyde (49.21 g, 472.696 mmol, 1.50 equiv.), $NaBH(OAc)_3$ (133.57 g, 630.199 mmol, 2.00 equiv.). The resulting solution was stirred for 2 h at 25° C. The reaction was then quenched by the addition of 1 L of water. The resulting solution was extracted with 2×1 L of ethyl acetate dried over $Na{:}SO_4$ and concentrated under vacuum. This resulted in 80 g (62.62%) of ethyl (3R)-3-[4-(benzyloxy)-3-fluorophenyl]-3-[(2,2-dimethoxyethyl)amino]propanoate as yellow oil.

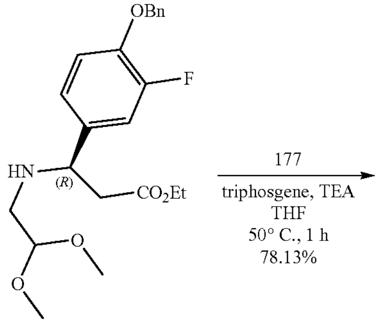

182

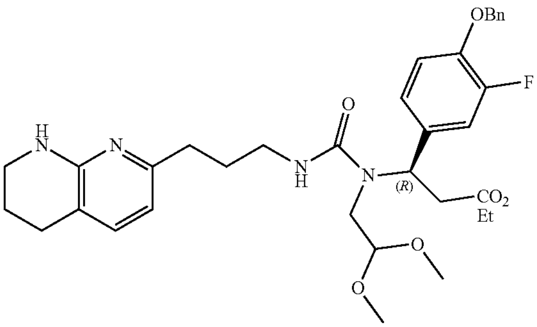

183

Into a 2-L 3-necked round-bottom flask, was placed Triphosgene (22.25 g, 74.975 mmol, 0.38 equiv.), THF (500 mL), ethyl (3R)-3-[4-(benzyloxy)-3-fluorophenyl]-3-[(2,2-dimethoxyethyl)amino]propanoate (80.00 g, 197.304 mmol, 1.00 equiv.), TEA (29.95 g, 295.956 mmol, 1.50 equiv.), 3-(5,6,7,8-tetrahydro-1,8-naphthyridin-2-yl)propan-1-amine (Compound 177, 33.97 g, 177.573 mmol, 0.90 equiv.). The resulting solution was stirred for 1 h at 50° C. in an oil bath. The reaction was then quenched by the addition of 1 L of water. $NaHCO_3$ (aq.) was employed to adjust the pH to 8. The resulting solution was extracted with 2×1 L of ethyl acetate dried over anhydrous sodium sulfate and concentrated. This resulted in 96 g (78.13%) of ethyl (3R)-3-[4-(benzyloxy)-3-fluorophenyl]-3-[(2,2-dimethoxyethyl)([[3-(5,6,7,8-tetrahydro-1,8-naphthyridin-2-yl)propyl]carbamoyl])amino]propanoate as yellow crude oil.

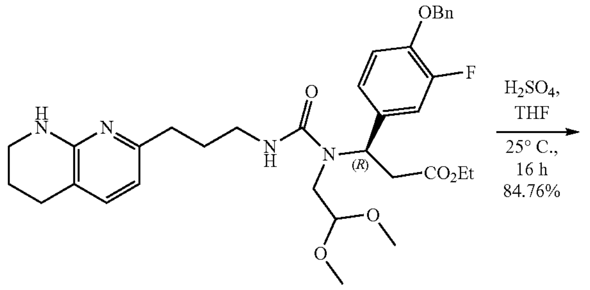

183

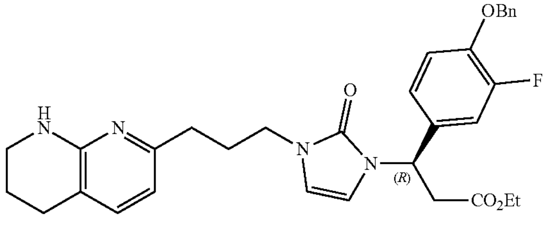

184

Into a 1000-mL round-bottom flask, was placed ethyl (3R)-3-[4-(benzyloxy)-3-fluorophenyl]-3-[(2,2-dimethoxyethyl)([[3-(5,6,7,8-tetrahydro-1,8-naphthyridin-2-yl)propyl]carbamoyl])amino]propanoate (96.00 g, 154.158 mmol, 1.00 equiv.), THF (500.00 mL), $H_2SO_4$ (180.00 mL, 2M). The resulting solution was stirred for 16 h at 25° C. NaOH (5M) was employed to adjust the pH to 8. The resulting solution was extracted with 2×1 L of dichloromethane dried over anhydrous sodium sulfate and concentrated. The residue was applied onto a silica gel column with dichloromethane/methanol (50/1). The collected fractions were combined and concentrated. This resulted in 73 g (84.76%) of ethyl (3R)-3-[4-(benzyloxy)-3-fluorophenyl]-3-[2-oxo-3-[3-(5,6,7,8-tetrahydro-1,8-naphthyridin-2-yl)propyl]-2,3-dihydro-1H-imidazol-1-yl]propanoate as yellow oil.

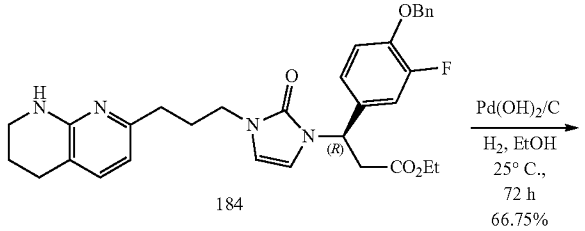

184

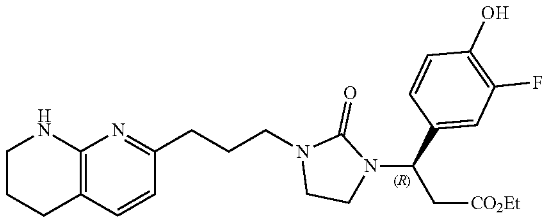

185

Into a 3-L round-bottom flask, was placed ethyl (3R)-3-[4-(benzyloxy)-3-fluorophenyl]-3-[2-oxo-3-[3-(5,6,7,8-tetrahydro-1,8-naphthyridin-2-yl)propyl]-2,3-dihydro-1H-imidazol-1-yl]propanoate (73.00 g, 130.671 mmol, 1.00 equiv.), EtOH (1.50 L), $Pd(OH)_2/C$ (60.00 g, 427.259 mmol, 3.27 equiv.), $H_2$ (50 atm). The resulting solution was stirred for 72 h at 25° C. The solids were filtered out. The residue was applied onto a silica gel column with dichloromethane/methanol (9/1). The collected fractions were combined and concentrated. This resulted in 41.0415 g (66.75%) of ethyl (3R)-3-(3-fluoro-4-hydroxyphenyl)-3-[2-oxo-3-[3-(5,6,7,8-tetrahydro-1,8-naphthyridin-2-yl)propyl]imidazolidin-1-yl]propanoate as yellow oil.

LCMS-PH-ARP-052-0: [MS+1]+=471

Rotation Optical $[a]_D^{20.0}$=+37.5° (C=1 g/100 ml in MeOH)

H-NMR: (300 MHz, DMSO-$d_6$, ppm) δ 9.84 (s, 1H), 7.07-7.00 (m, 2H), 6.95-6.850 (m, 2H), 6.24 (d, 2H), 5.18 (t, 1H), 4.06-3.% (m, 2H), 3.32-2.75 (m, 10H), 2.60 (t, 2H), 2.37 (t, 2H), 1.77-1.67 (m, 4H), 1.10 (t, 3H).

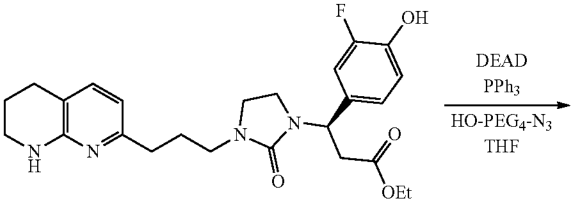

185

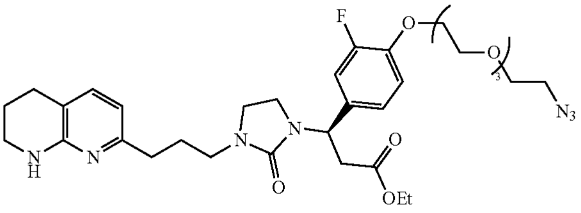

186

To a solution of $PPh_3$ in THF at −10° C. was added dropwise a solution of DEAD. The mixture was warmed to room temperature and added to a neat mixture of compound 185 and HO-$PEG_4$-$N_3$, and stirred overnight. The reaction mixture was then concentrated under reduced pressure, and the residue was purified over silica eluting a gradient of MeOH in DCM, yielding compound 186.

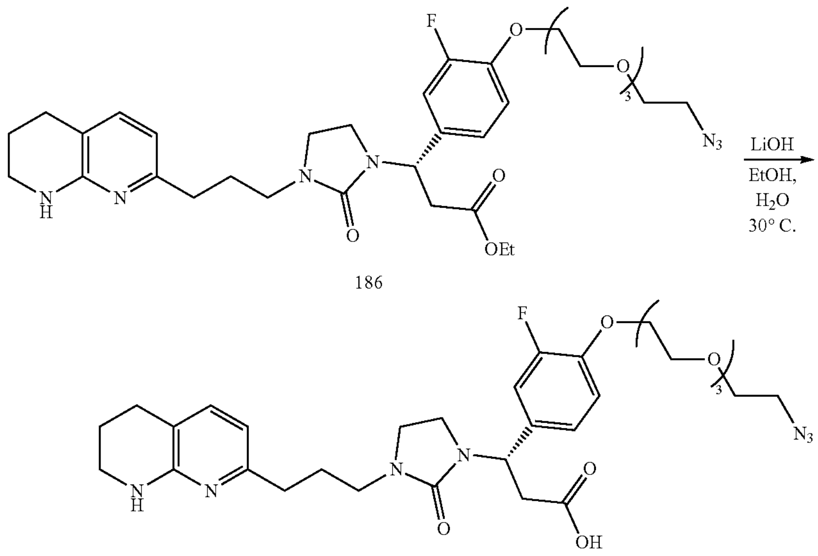

186

187

To compound 186 was added EtOH and $H_2O$, followed by LiOH. The mixture was stirred at 30° C. overnight. Upon completion the mixture was neutralized to pH=5 using 6 M aqueous HCl and concentrated. The residue was purified by reverse phase HPLC with a Phenomenex Gemini C18, 50×250 mm, 10 μm column eluting a gradient of acetonitrile in water containing 0.1%, yielding compound 187 (Structure 2.11c).

Synthesis of Structure 28c (Compound 118a) Structure 29c (Compound 118b), Structure 31c (Compound 119a), and Structure 30c (Compound 119b)

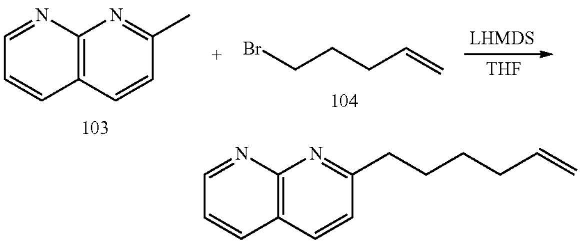

103

104

105

To a solution of LHMDS (1.0 M in THE, 95 mL, 95 mmol) and THF (60 mL) was added a solution of compound 103 (2-methyl-[1,8]naphthyridine (12.5 g, 86.7 mmol)) in THF (180 mL) dropwise at −78° C. After stirring for 30 minutes, a solution of compound 104 (5-bromo-1-pentene (19.4 g, 130 mmol)) in THF (120 mL) was added to the reaction mixture dropwise. The reaction mixture was warmed to 0° C. and stirred for 4 hours. The reaction mixture was quenched with saturated aqueous $NH_4Cl$ solution (100 mL) and deionized water (100 mL), then extracted with ethyl acetate (2×400 mL). The combined organic phase was dried over $Na_2SO_4$, filtered, concentrated, and compound 105 was isolated by CombiFlash® eluting a gradient of 50-100% ethyl acetate in hexanes. Yield of compound 105: 7.93 g (43%).

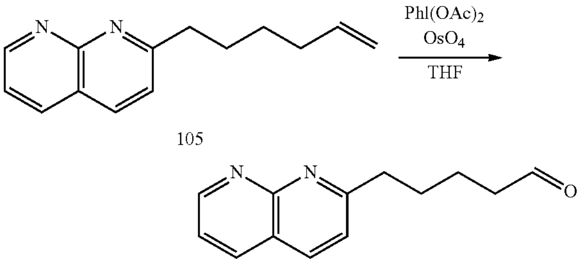

105

106

To a solution of compound 105 (2.50 g, 11.8 mmol) in acetone (67.5 mL), water (7.5 mL), and 2,6 lutidine (2.74 mL, 23.6 mmol) was added 4-methylmorpholine N-oxide (2.07 g, 17.7 mmol) and osmium tetroxide (2.5 wt % in t-butanol, 2.40 g, 0.24 mmol) at room temperature. After stirring for 75 minutes, (diacetoxyiodo)benzene (5.69 g, 17.7 mmol) was added to the reaction mixture. The reaction mixture was stirred for 2 hours then quenched with saturated aqueous sodium thiosulfate solution (100 mL) and extracted with ethyl acetate (2×100 mL). The combined organic phase was dried over $Na_2SO_4$, filtered, concentrated, and compound 106 was isolated by Combi Flash® eluting a gradient of 0-5% methanol in ethyl acetate. Yield of compound 106: 1.12 g (44%).

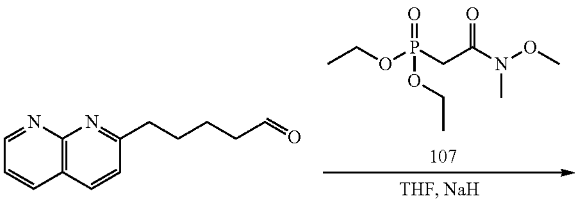

106

-continued

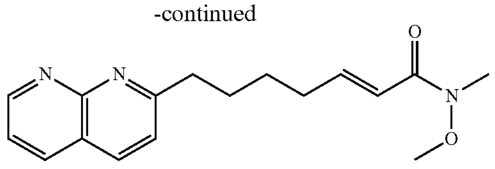

108

To a suspension of sodium hydride (60% dispersion in mineral oil, 0.185 g, 4.64 mmol) in THF (9 mL) was added a solution of compound 107 (diethyl (N-methoxy-N-methylcarbamoyl methyl)phosphonate) (1.06 g, 4.43 mmol) in THF (5 mL) at 0° C. After stirring for 30 minutes, a solution of compound 106 (0.903 g, 4.21 mmol) in THF (9 mL) was added dropwise. The reaction mixture was stirred for 10 minutes at 0° C. then quenched with saturated aqueous $NH_4Cl$ solution (30 mL) and extracted with ethyl acetate (3x30 mL). The combined organic phase was washed twice with half saturated aqueous $NaHCO_3$ solution. The organic phase was dried over $Na_2SO_4$, filtered, and concentrated. Yield of compound 10: 1.40 g (assumed 100% yield and used in the subsequent step without further purification).

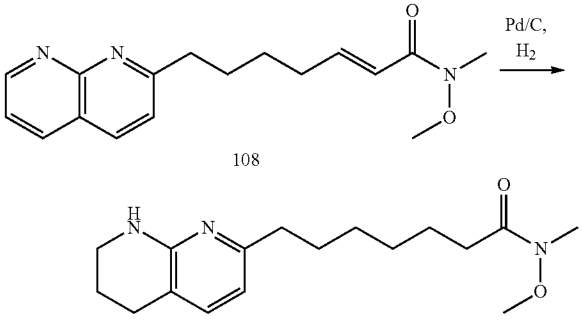

108

109

To a solution of compound 108 (1.31 g, 4.38 mmol) in ethyl acetate (20 mL) was added Pd/C (10% loading, 0.466 g, 0.44 mmol). The reaction vessel was pressurized with $H_2$ to 50 PSI. After stirring for 3.5 hours, the reaction mixture was filtered over Celite® and rinsed with methanol. The filtrate was concentrated and compound 109 was isolated by CombiFlash®eluting a gradient of 50-100% ethyl acetate in hexanes containing 1% triethylamine. Yield of compound 109: 0.833 g (62%).

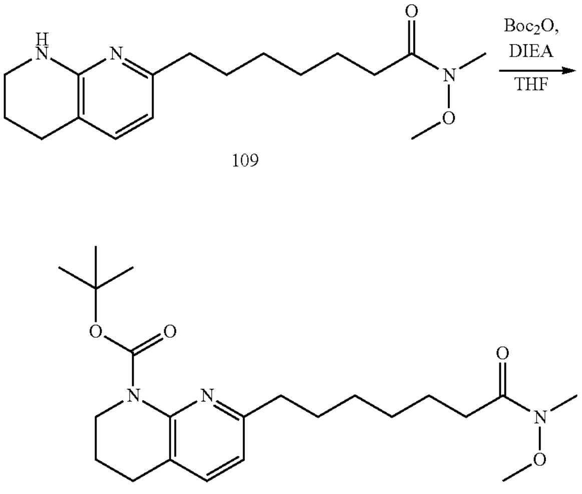

109

110

To a solution of compound 109 (0.833 g, 2.73 mmol) in THF (10 mL) was added DIEA (0.590 mL, 3.41 mmol) and di-tert-butyl dicarbonate (0.744 g, 3.41 mmol). The reaction mixture was heated to 50° C. for 5 hours. The reaction was incomplete based on LC/MS and additional portions of DIEA (0.590 mL, 3.41 mmol) and di-tert-butyl dicarbonate (0.744 g, 3.41 mmol) were added. The reaction mixture was heated at 50° C. for an additional 16 hours. The reaction mixture was concentrated and compound 110 was isolated by CombiFlash® eluting a gradient of 50-100% ethyl acetate in hexanes. Yield of compound 110: 0.934 g (84%).

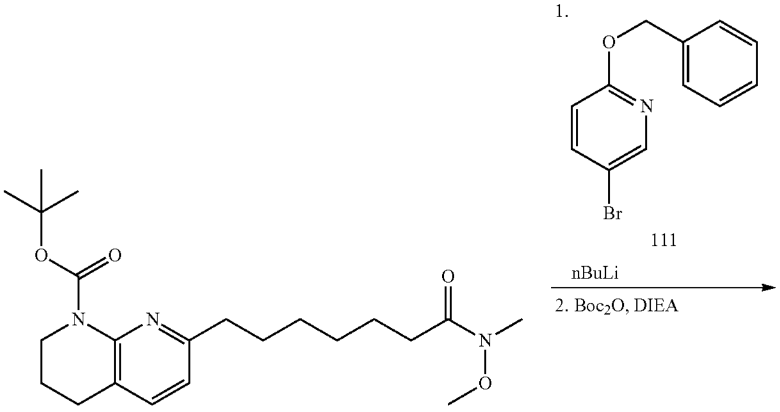

110

-continued

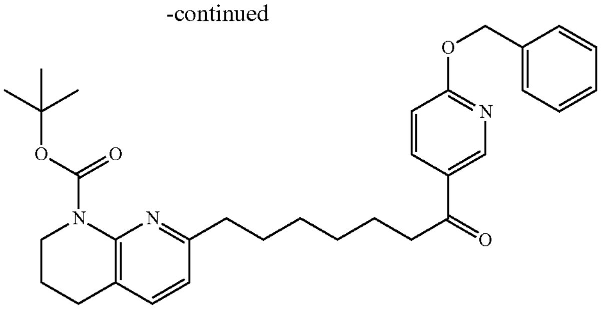

112

To a solution of n-butyl lithium (2.5 M in hexanes, 0.70 mL, 1.8 mmol) and THF (1.5 mL) was added compound 111 (5-bromo-2-(phenylmethoxy)-pyridine) (0.465 g, 1.8 mmol) as a solution in THF (0.8 mL) dropwise over 3 minutes at −78° C. Compound 110 (0.535 g, 1.3 mmol) was then added as a solution in THF (1 mL). After stirring for 30 minutes, the reaction was warmed to 0° C., quenched with saturated aqueous $NH_4Cl$ solution (10 mL), and acidified further with 6 M aqueous HCl to a pH of 7. The mixture was extracted with ethyl acetate (3×10 mL). The combined organic phase was dried over $NH_4Cl$, filtered, and concentrated. To a solution of the crude in THF (8 mL) was added DIEA (0.94 mL, 5.4 mmol) and di-tert-butyl dicarbonate (1.18 g, 5.4 mmol). The mixture was stirred at 40° C. overnight. The reaction mixture was concentrated and compound 112 was isolated by Combi Flash® eluting a gradient of 0-40% ethyl acetate in hexanes. Yield of compound 112: 471 mg (50%).

To a suspension of sodium hydride (60% dispersion in mineral oil, 0.106 g, 2.65 mmol) in dimethoxyethane (2 mL) was added compound 113 (triethyl phosphonoacetate) (0.593 g, 2.65 mmol) as a solution in dimethoxyethane (1 mL) at 0° C. After stirring for 20 minutes, the reaction mixture was warmed to room temperature and a solution of compound 112 (0.467 g, 0.88 mmol) in dimethoxyethane (2 mL) was added. The reaction mixture was heated at 70° C. for 4 hours. The reaction was quenched with saturated aqueous $NH_4Cl$ solution (10 mL) and the product was extracted with ethyl acetate (3×15 mL). The organic phase was dried over $Na_2SO_4$, filtered, concentrated, and compound 114 was isolated as a 1:1 mixture of cis:trans isomers by CombiFlash® eluting a gradient of 0-30% ethyl acetate in hexanes. Yield of compound 114: 392 mg (74%).

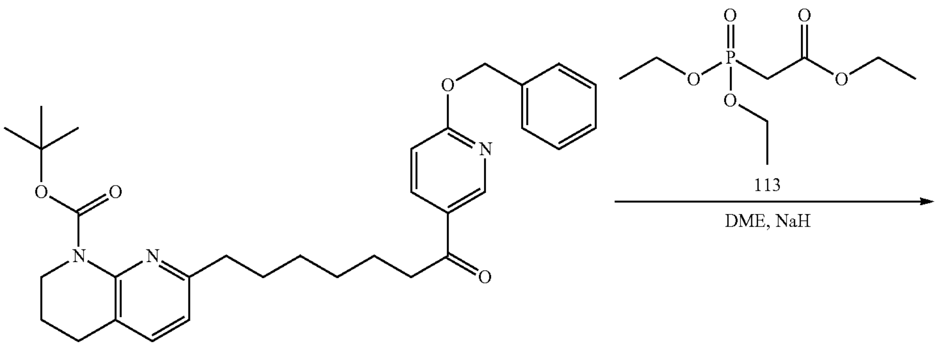

112

113

DME, NaH

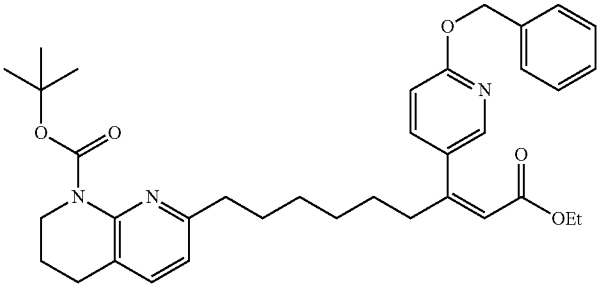

114

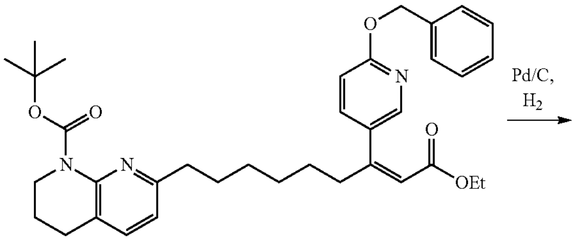

114

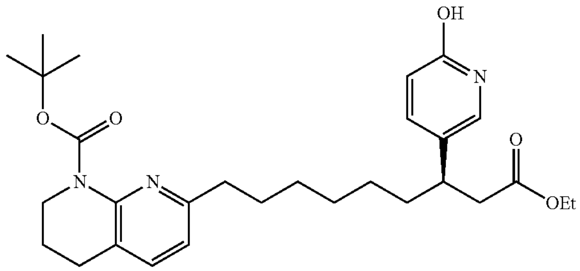

115a

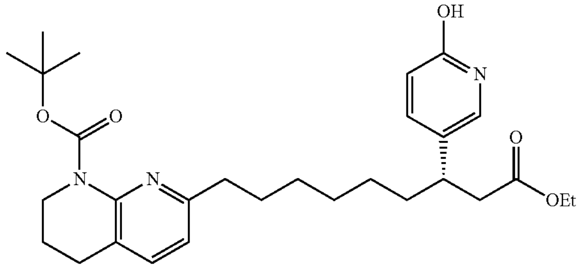

115b

To a solution of compound 114 (390 mg, 0.65 mmol) in ethanol (6 mL) was added Pd/C (10% loading, 69 mg, 0.07 mmol). The reaction vessel was pressurized with $H_2$ to 50 PSI. After stirring for 4 hours, the reaction mixture was filtered over Celite® and rinsed with methanol. The filtrate was concentrated and compound 115 was isolated as a racemic mixture by CombiFlash® eluting a gradient of 0-10% methanol in DCM. Yield of compound 115: 95 mg (29%). Chiral semi-preparative HPLC (250×21 mm Chiralpak® AD column, 5 μm, 90/10 hexanes/EtOH, 40 mL/min) was used to isolate 42 mg of the first eluting R-isomer ($R_T$=12-14 m, >99% ee, compound 115a) and 40 mg of the second eluting S-isomer ($R_T$=15-18 m, >98% ee, compound 115b). The identity of the R- and S-isomers were assigned based on the order of elution of a structurally similar compound reported by Coleman et al. 47 J. Med Chem. 4834 (2004).

Structures 28c ((R)-3-(6-(2-(2-(2-(2-azidoethoxy)ethoxy)ethoxy)ethoxy)pyridin-3-yl)-9-(5,6,7,8-tetrahydro-1,8-naphthyridin-2-yl)nonanoic acid) and 31c ((R)-3-(1-(2-(2-(2-(2-azidoethoxy)ethoxy)ethoxy)ethyl-6-oxo-1,6-dihydropyridin-3-yl)-9-(5,6,7,8-tetrahydro-1,8-naphthyridin-2-yl)nonanoic acid)

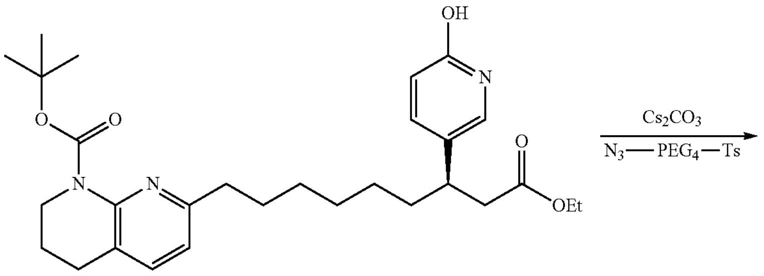

115a

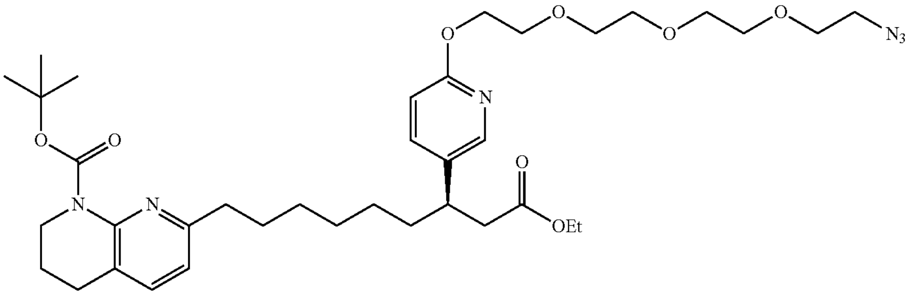

116a

+

-continued

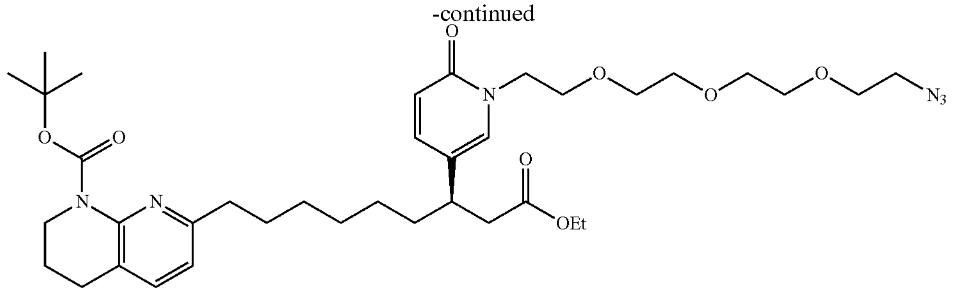

117a

To a solution of compound 115a (41 mg, 0.08 mmol) and $N_3$-$PEG_4$-OTs (61 mg, 0.16 mmol) in DMF (0.5 mL) was added cesium carbonate (53 mg, 0.16 mmol). The reaction mixture was stirred at 40° C. for 1 hour. The reaction mixture was quenched with aqueous $NaHCO_3$ solution (1 mL) then extracted with ethyl acetate (3×3 mL). The organic phase was concentrated under reduced pressure. The crude mixture of N- and O-alkylated regioisomers was subsequently used without further purification.

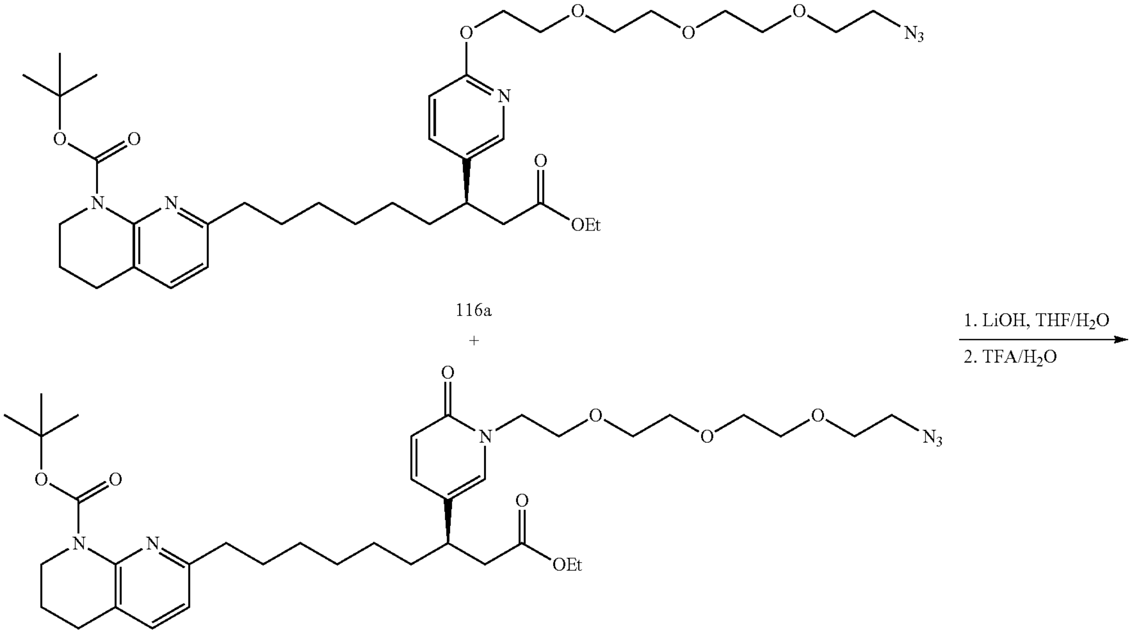

116a

+

117a

-continued

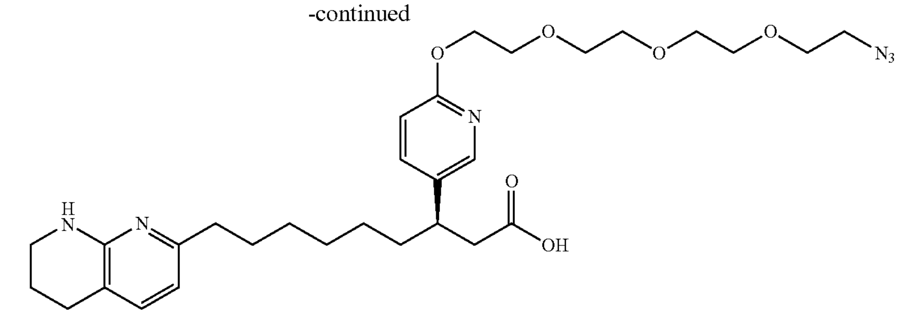

118a

+

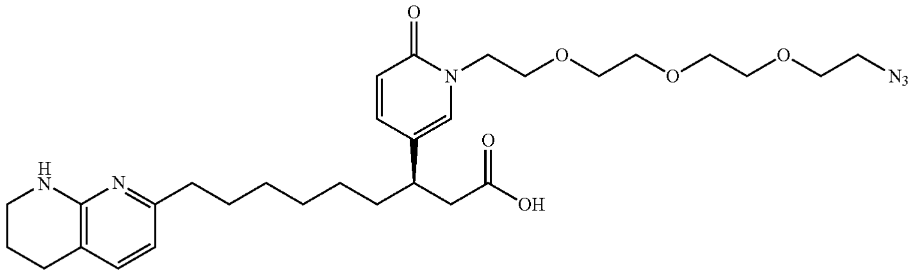

119a

To a solution of compounds 116a and 117a (58 mg, 0.08 mmol, 4:6 mixture of 9a: 10a) in THF (1.0 mL) and deionized water (1.0 mL) was added lithium hydroxide (6 mg, 0.25 mmol). The reaction mixture was stirred at room temperature for 1 hour and then at 35° C. for 2 hours. An additional portion of lithium hydroxide (4 mg, 0.16 mmol) was added and the reaction temperature was increased to 40° C. After stirring for 3 hours, a final portion of lithium hydroxide (4 mg, 0.25 mmol, total 16 mg, 0.66 mmol) was added. The reaction mixture was stirred at 50° C. for 3 hours. The reaction mixture was acidified to a pH of 7 with 6 N aqueous HCl and concentrated under reduced pressure. The regioisomers, compounds 118a and 119a, were separated by CombiFlash® eluting a gradient of 0-5% methanol in DCM containing 0.5% acetic acid. Compound 118a was further purified by reverse phase HPLC (Thermo Scientific™ Aquasil™ C18, 250×21.2 mm, 5 µm, 20 mL/min, 0.1% TFA in water/ACN, gradient elution), yielding 13 mg of compound 118a (Structure 28c). Compound 119a was purified under the same conditions, yielding 16 mg of compound 119a (Structure 31c).

Structures 29c ((S)-3-(6-(2-(2-(2-(2-azidoethoxy)ethoxy)ethoxy)ethoxy)pyridin-3-yl)-9-(5,6,7,8-tetrahydro-1,8-naphthyridin-2-yl)nonanoic acid) and 30c ((S)-3-(1-(2-(2-(2-(2-azidoethoxy)ethoxy)ethoxy)ethyl)-6-oxo-1,6-dihydropyridin-3-yl)-9-(5,6,7,8-tetrahydro-1,8-naphthyridin-2-yl)nonanoic acid)

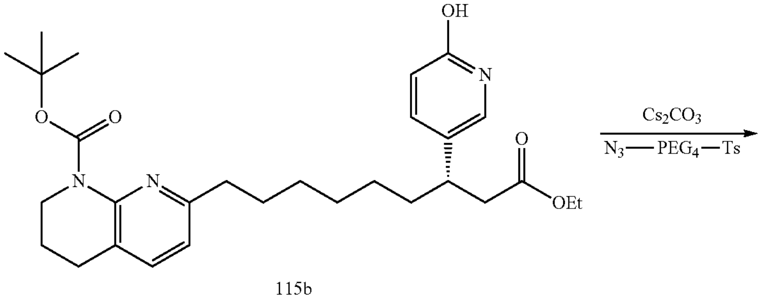

115b

-continued

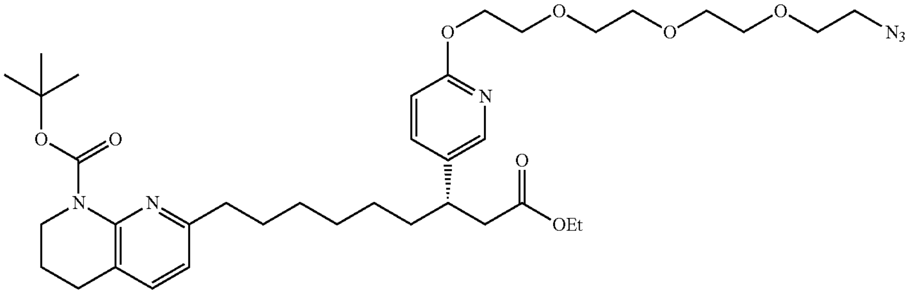

116b

+

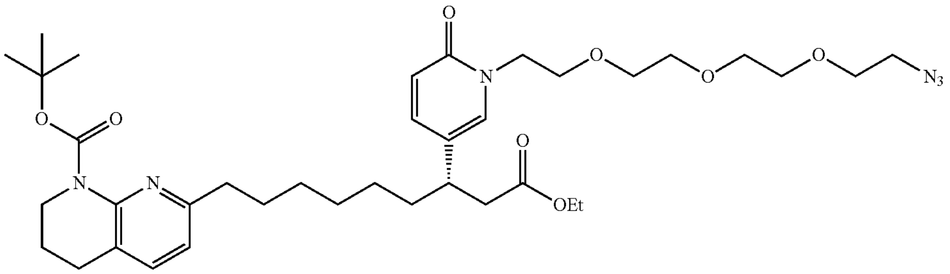

117b

To a solution of compound 115b (40 mg, 0.08 mmol) and $N_3$-$PEG_4$-OTs (58 mg, 0.16 mmol) in DMF (0.5 mL) was added cesium carbonate (51 mg, 0.16 mmol). The reaction mixture was stirred at 40° C. for 30 minutes. The reaction mixture was quenched with aqueous $NaHCO_3$ solution (1 mL) then extracted with ethyl acetate (3×3 mL). The organic phase was concentrated under reduced pressure. The crude mixture of N- and O-alkylated regioisomers was subsequently used without further purification.

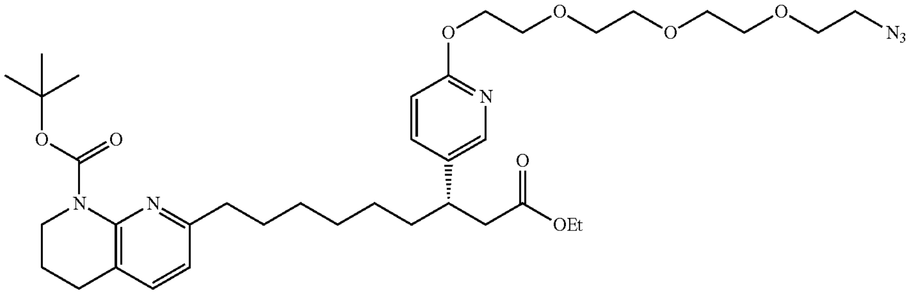

116b

+

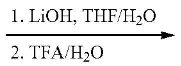

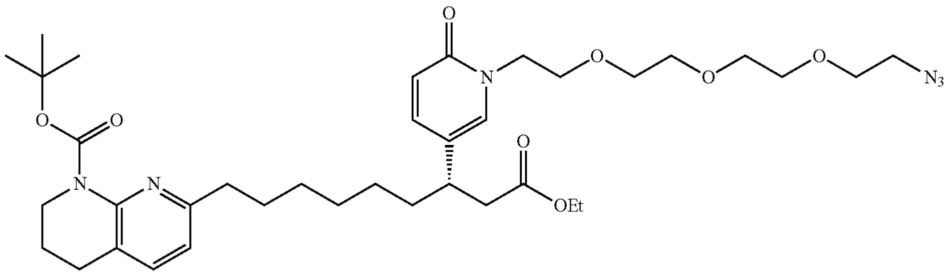

117b

-continued

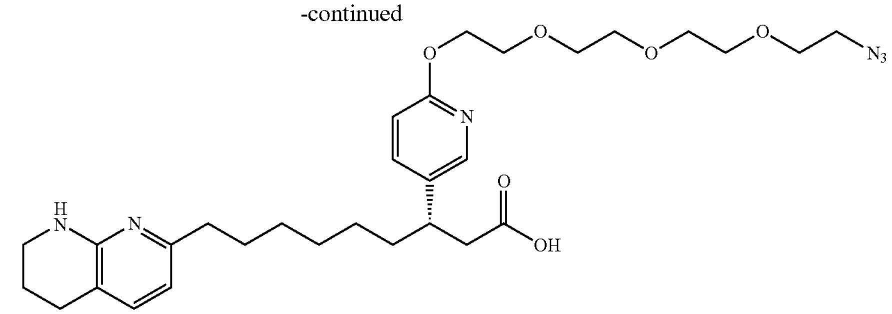

118b

+

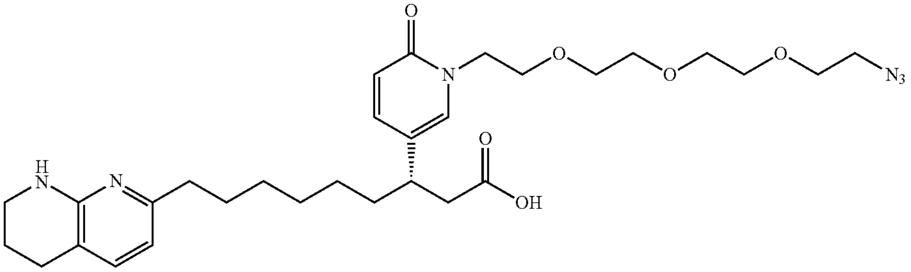

119b

To a solution of compounds 116b and 117b (56 mg, 0.08 mmol, 4:6 mixture of 9a: 10a) in THF (0.75 mL) and deionized water (0.75 mL) was added lithium hydroxide (6 mg, 0.25 mmol). The reaction mixture was stirred at 45° C. for 2.5 hours. An additional portion of lithium hydroxide (6 mg, 0.25 mmol) was added and the reaction mixture was stirred for 2.5 hours. The reaction temperature was lowered to 35° C. and the mixture was stirred overnight. The reaction mixture was acidified to pH=7 with 6 N aqueous HCl and concentrated under reduced pressure. The regioisomers, compounds 118b and 119b, were separated by CombiFlash eluting a gradient of 0-5% methanol in DCM containing 0.5% acetic acid. Compound 118b was further purified by reverse phase HPLC (Thermo Scientific™ Aquasil™ C18, 250×21.2 mm, 5 μm, 20 mL/min, 0.1% TFA in water/ACN, gradient elution), yielding 14 mg of compound 118b (Structure 29c). Compound 119b was purified under the same conditions, yielding 18 mg of compound 119b (Structure 30c).

Synthesis of Structure 32c ((R)-3-(4-(2-(2-(2-azido-ethoxy)ethoxy)ethoxy)-3-fluorophenyl)-3-(N-methyl-5-(5,6,7,8-tetrahydro-1,8-naphthyridin-2-yl) pentanamido)propanoic acid)

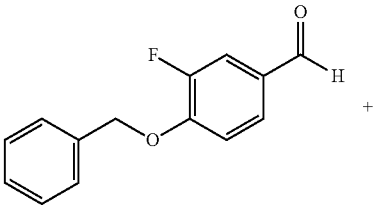

120

+

-continued

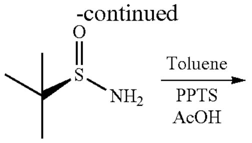

121

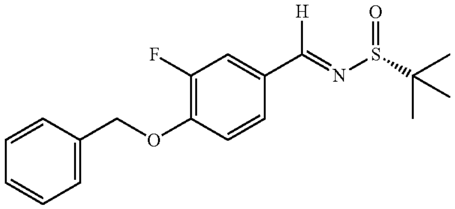

122

To compound 120 (2.75 g, 11.94 mmol) in toluene (80 mL) over 3 Å sieves was added compound 121 (5.79 g, 47.78 mmol), followed by PPTS (300 mg, 1.19 mmol) then AcOH (683 uL, 11.94 mmol). The reaction was brought to reflux overnight. Upon completion the reaction was quenched by addition of saturated sodium bicarbonate. The organic layer was diluted with 2 volumes of ethyl acetate, separated, and filtered over sodium sulfate. The product was isolated over silica eluting a gradient of ethyl acetate (0-30%) in hexane to yield 2.054 g (54%).

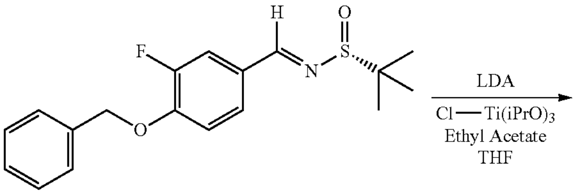

122

-continued

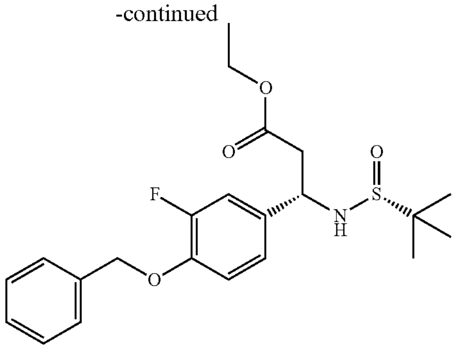

123

To DIA (2.85 mL, 20.33 mmol) in THF (15 mL) at −78° C. was added a 2.5M solution of n-BuLi (7.76 mL, 19.41 mmol) was added dropwise. Stirring was continued for 5 minutes at −78 C and ethyl acetate (1.81 mL, 18.48 mmol) was added dropwise. Stirring was continued for a further 10 minutes at −78° C. and a solution of chloro titanium triisopropoxide (9.27 mL, 38.381 mmol) in THF (10 mL) was added dropwise. Stirring was continued for a further 15 minutes at −78° C. and a solution of compound 122 (2.054 g, 6.16 mmol) in THF (10 mL) was added dropwise. Stirring was continued for 1.5 hours at −78° C. Upon completion the reaction was quenched by addition of saturated ammonium bicarbonate. The suspension was diluted with 6 volumes of ethyl acetate and the organic layer was separated, dried over sodium sulfate, filtered and concentrated. The product was isolated over silica eluting a gradient of ethyl acetate in hexanes to yield 1.043 g (53%).

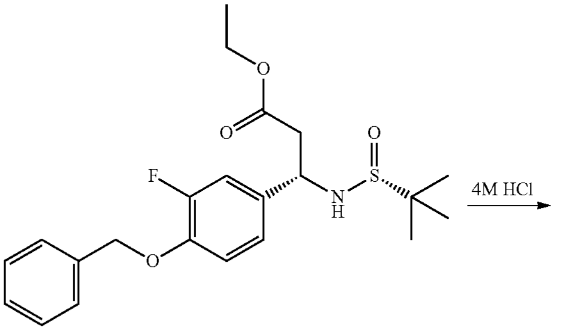

123

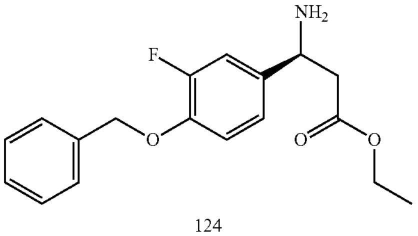

124

To compound 123 (1.043 g, 2.47 mmol) stirring in MeOH (3 mL) was added a 4M HCl solution in dioxane (3.09 mL, 12.37 mmol). Upon completion of deprotection the solution was diluted with water (8 mL) and washed twice with diethyl ether (6 mL). The aqueous layer was subsequently adjusted to a pH of 11 with sodium hydroxide. The precipitate was extracted with ethyl acetate, and the combined organic extracts were dried over sodium sulfate, filtered, and concentrated yielding 0.616 g (78.5%) of product 124 that was used without further purification.

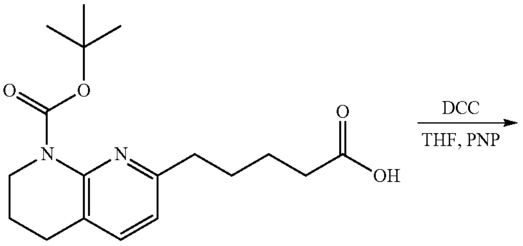

125

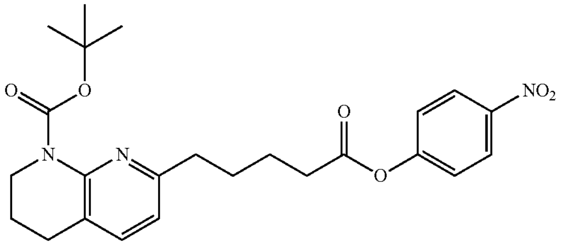

126

To compound 125 (92.1 mg, 0.275 mmol) in THF (1.5 mL) at 0° C. was added DCC (68.1 mg, 0.331 mmol). After 5 minutes PNP (106.1 mg, 0.331 mmol) was added, the ice bath was removed, and stirring continued for 1 hour. Upon completion the suspension was chilled to −20° C. for 1 hour and the precipitate was removed by filtration. The supernatant was concentrated and to yield 129 mg (103%) of crude product 126 that was subsequently used without further purification.

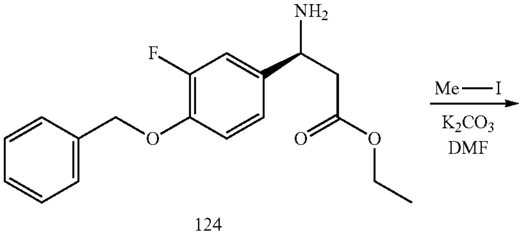

124

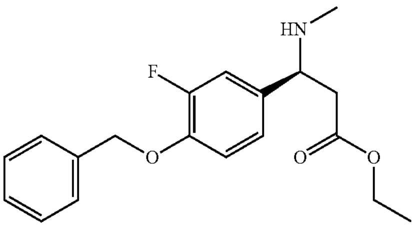

127

A mixture containing compound 124 (148.6 mg, 0.468 mmol) and potassium carbonate (129 mg, 0.937 mmol) in DMF (2 mL) was treated with methyl iodide (66.5 mg, 0.468 mmol) and stirred at 50° C. for 3 hours. Upon completion of alkylation all volatiles were removed and the product was isolated over silica eluting a gradient of ethyl acetate in hexanes, each buffered with 1% TEA, to yield 94.6 mg (61%).

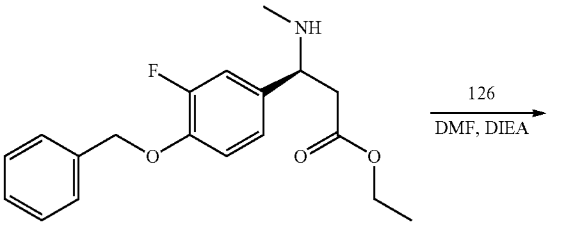

127

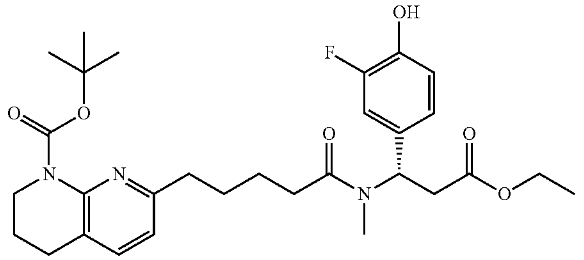

128

To compound 127 (94.5 mg, 0.285 mmol) in DMF (2 mL) was added DIEA (149 uL, 0.856 mmol) followed by Compound 126 (129.9 mg, 0.285 mmol) and the mixture was stirred for 1 hour at 80° C. Upon completion all volatiles were removed and the crude was dissolved in MeOH, treated with 10% palladium on carbon (20 mg), and the flask was charged with 60 PSI of hydrogen. Upon completion the suspension was filtered. The supernatant was concentrated and the crude product obtained was used subsequently without further purification.

A mixture containing compound 128 (159 mg, 0.285 mmol), Bromo-$PEG_2$-Azide (74.7 mg, 0.314 mmol) and cesium carbonate (204 mg, 0.627 mmol) in DMF (2 mL) was heated to 60° C. for 2 hours. Upon completion all volatiles were removed and the crude was treated with 4M HCl in dioxane (0.5 mL, 2 mmol) and heated to 40° C. for 3 hours. Upon completion all volatiles were removed. The crude was suspended in a mixture of THF (1 mL), MeOH (1.5 mL) and $H_2O$ (1.5 mL), treated with lithium hydroxide (83.5 mg, 3.48 mmol) and heated to 40° C. for 16 hours. Upon completion the pH was adjusted to 3 with TFA, and the product was isolated by separation over a Phenomenex® Gemini® C18 column (21.2×250 mm, 5 micron) eluting a gradient of acetonitrile in water containing 0.1% TFA to yield 33.1 mg (20%).

Synthesis of Structure 33c ((R)-1-azido-13-(3-fluoro-4-methoxyphenyl)-12-(5-(5,6,7,8-tetrahydro-1,8-naphthyridin-2-yl)pentanoyl)-3,6,9-trioxa-12-azapentadecan-15-oic acid)

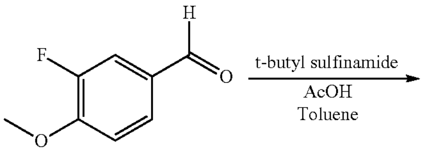

130

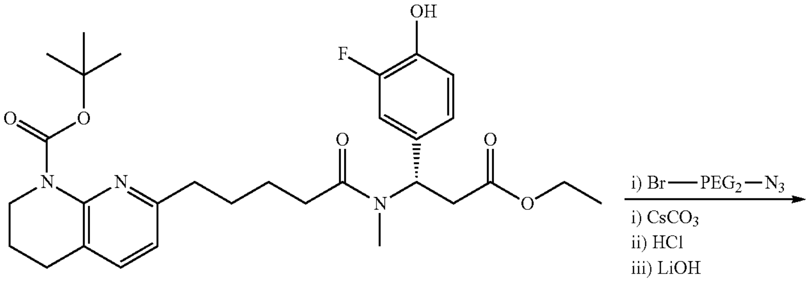

128

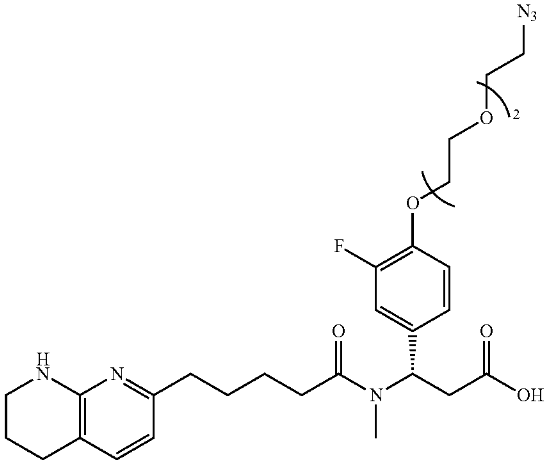

129

-continued

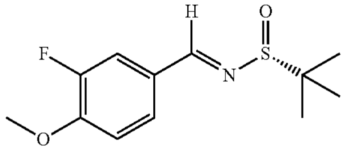

131

A mixture containing compound 130 (1.5 g, 9.73 mmol), (R) t-butyl sulfinamide (2.36 g, 19.46 mmol), and AcOH (0.14 mL) in toluene (45 mL) was refluxed in a flask fitted with a Dean-Stark trap for 16 hours. Upon completion the reaction was quenched by addition of saturated sodium bicarbonate. The organic layer was separated, dried over sodium sulfate, filtered and concentrated. The product was isolated by separation over silica eluting a gradient of ethyl acetate in hexanes to yield 1.714 g (68.4%).

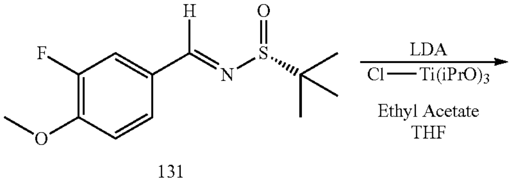

131

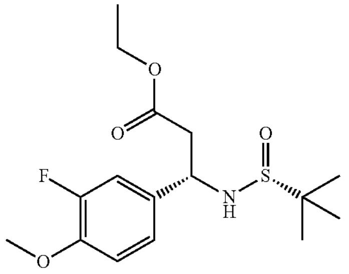

132

To DIA (3.056 mL, 21.80 mmol) in THF (18 mL) at −78° C. was added a 2.5M solution of n-BuLi (8.324 mL, 20.81 mmol) was added dropwise. Stirring was continued for 5 minutes at −78° C. and ethyl acetate (1.94 mL, 19.82 mmol) was added dropwise. Stirring was continued for a further 10 minutes at −78° C. and a solution of chloro titanium triisopropoxide (9.94 mL, 41.62 mmol) in THF (10 mL) was added dropwise. Stirring was continued for a further 15 minutes at −78° C. and a solution of compound 131 (1.70 g, 6.61 mmol) in THF (12 mL) was added dropwise. Stirring was continued for 1.5 hours at −78° C. Upon completion the reaction was quenched by addition of saturated ammonium bicarbonate. The suspension was diluted with 7 volumes of ethyl acetate and the organic layer was separated, dried over sodium sulfate, filtered and concentrated. The product was isolated over silica eluting a gradient of ethyl acetate in hexanes to yield 0.984 g (43%).

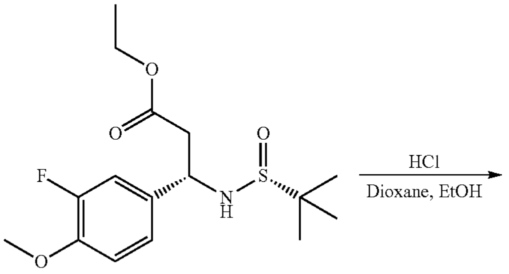

132

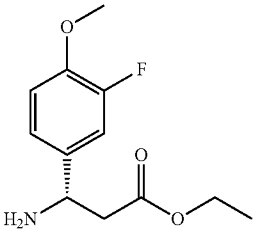

133

To compound 132 (0.975 g, 2.82 mmol) in EtOH (6 mL) at 0° C. was added 4 M HCl (2.12 mL, 8.47 mmol) in dioxane and stirred for 30 minutes. Upon completion the reaction was diluted with water (15 mL) and washed with diethyl ether. The organic layer was separated and the pH of the aqueous layer was adjusted to 12 with sodium hydroxide. The aqueous layer was washed with 5 volumes of ethyl acetate and the organic layer was separated, filtered over sodium sulfate and concentrated. The product was isolated by separation over silica eluting a gradient of ethyl acetate in hexanes containing 1% TEA to yield 0.434 g (64%).

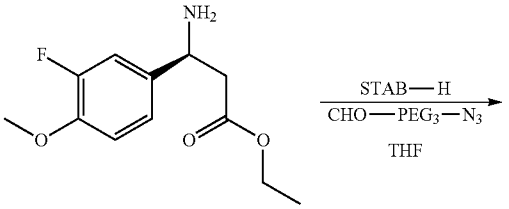

133

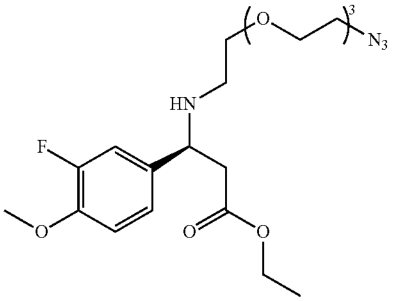

134

To a mixture of compound 133 (0.120 g, 0.497 mmol) and PEG (0.151 g, 0.696 mmol) in THF (2 mL) over 3 Å molecular sieves was added STAB-H (0.253 g, 1.19 mmol) and the suspension was stirred for 16 hours at room temperature. Upon completion the reaction was quenched by addition of saturated sodium bicarbonate and the crude was extracted with three portions of ethyl acetate. The separated organic extracts were combined, dried over sodium sulfate, filtered and concentrated. The crude obtained was used subsequently without further purification.

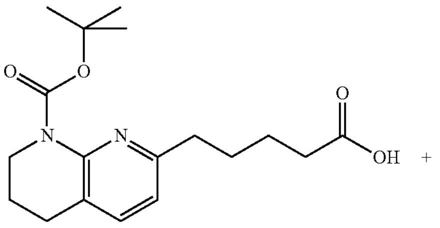

125

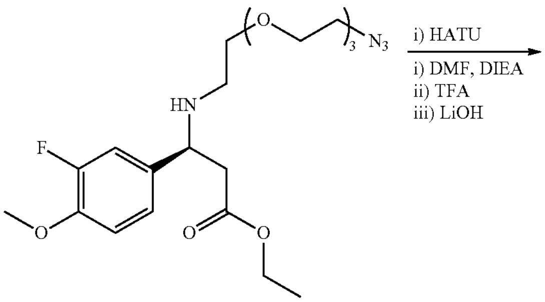

134

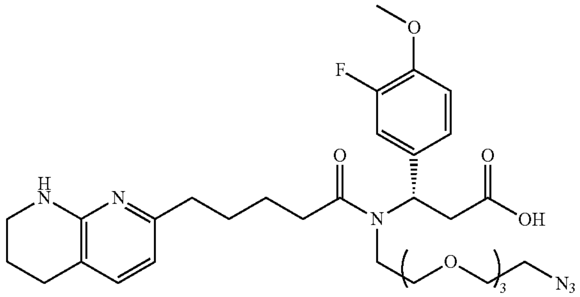

135

Compound 134 (0.200 g, 0.597 mmol) in DMF (2 mL) was treated with HATU (0.227 g, 0.597 mmol) and stirred for 5 minutes. To the activated ester was added DIE A (0.259 mL, 1.49 mmol) followed by compound 125 (0.220 g, 0.497 mmol) in DMF (1 mL) and the resulting mixture was stirred for 1 hour. All volatiles were removed and the resulting crude was treated with neat TFA (3.8 mL) and stirred for 3 hours at 40° C. Upon completion of BOC removal all volatiles were removed and the crude was suspended in a mixture of THF (4 mL), water (8 mL), and MeOH (8 mL). The resulting mixture was treated with LiOH (71.6 mg, 2.98 mmol) and heated to 40° C. for 16 hours. Upon completion the pH was adjusted to 3 with TFA, and the product was isolated by separation over a Phenomenex® Gemini® c18 column (21.2×250 mm, 5 micron) eluting a gradient of acetonitrile in water containing 0.1% TFA to yield 56.2 mg (18%, 3-Steps).

Synthesis of Structure 34c ((S)-1-azido-13-(3-fluoro-4-methoxyphenyl)-12-(5-(5,6,7,8-tetrahydro-1,8-naphthyridin-2-yl)pentyl)-3,6,9-trioxa-12-aza-pentadecan-15-oic acid)

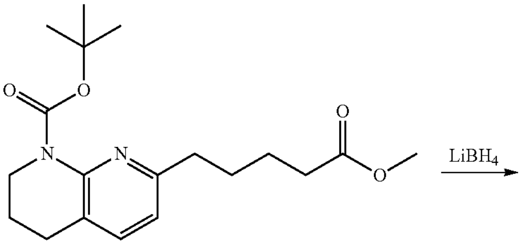

136

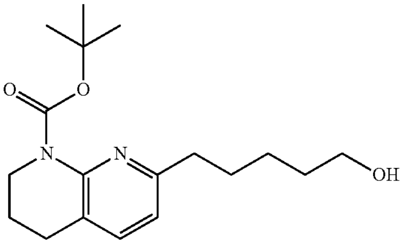

137

Compound 136 (0.500 g, 1.45 mmol) in a mixture of THF (9.0 mL) and MeOH (0.5 mL) at 0° C. was treated with lithium borohydride (94.5 mg, 4.34 mmol). Cooling was removed and stirring was continued until gas evolution ceased. The reaction mixture was diluted with 5 volumes of EtOAc. The organic layer was washed with ammonium bicarbonate, dried over sodium sulfate, filtered, and concentrated. The product was isolated by elution over silica using a gradient of ethyl acetate in hexanes to yield 309 mg (67%).

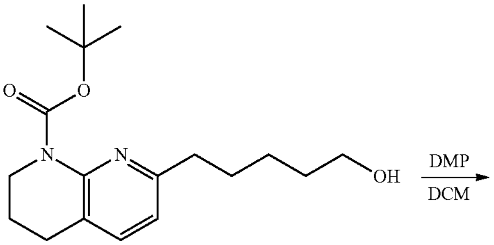

137

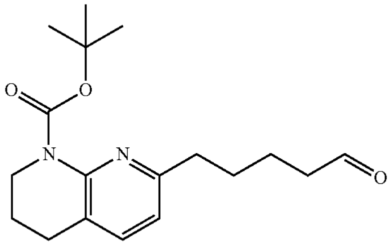

138

To a solution containing compound 137 (0.305 g, 0.952 mmol) in DCM (9 mL) at 0° C. was added Martin's reagent in several portions. Several drops of water were added, cooling was removed, and the reaction was stirred for 3 hours. Upon completion the mixture was washed with saturated sodium bicarbonate then saturated sodium thiosulfate. The separated organic was dried over sodium sulfate, over sodium sulfate, filtered and concentrated. The product was isolated by separation over silica eluting a gradient of MeOH in DCM containing 1% TEA to yield 64 mg (33%).

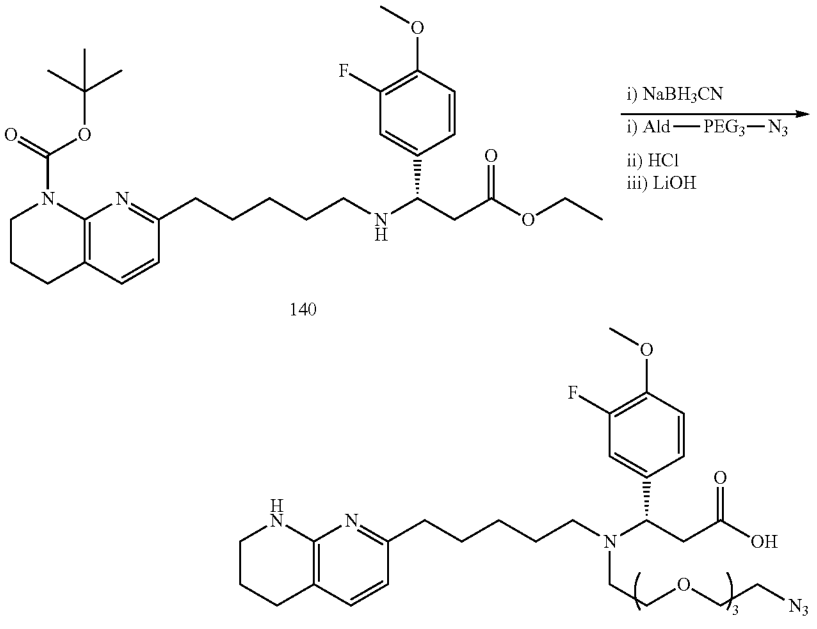

140

141 filtered and concentrated. The product 138 was separated over silica eluting a gradient of MeOH in DCM to yield 140 mg (46%).

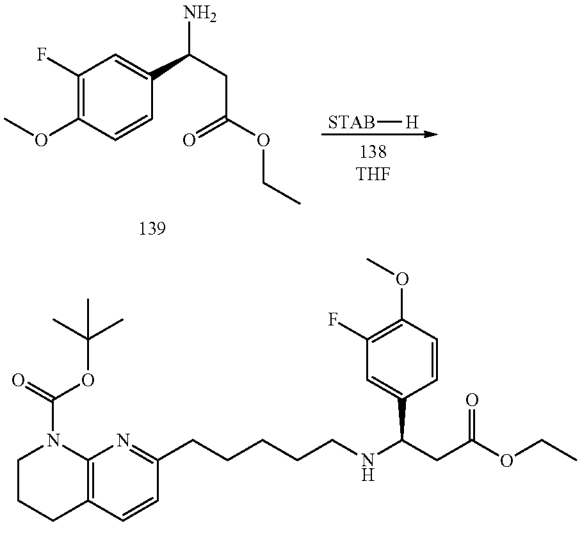

139

140

To a mixture containing compound 1 (85.2 mg, 0.353 mmol) and 138 (134.9 mg, 0.424 mmol) in THF (2.5 mL) over 3 Å molecular sieves was added STAB-H (0.150 g, 0.706 mmol) and the resulting suspension was heated to 40° C. for 16 hours. Upon completion the reaction was diluted with 5 volumes of ethyl acetate and treated with saturated sodium bicarbonate. The organic layer was separated, dried To a mixture containing compound 140 (60 mg, 0.110 mmol), Ald-$PEG_3$-$N_3$ (71.9 mg, 0.331 mmol) and AcOH (3 μL, 0.0276 mmol) in MeOH (1 mL) over 3 Å molecular sieves was added sodium cyanoborohydride (28.9 mg, 0.276 mmol) and the reaction was stirred at 40° C. for 3 hours. Upon completion the mixture was cooled to 0° C., water was added (0.15 mL) and the solution was acidified to a pH of 7 using HCl (4M) in dioxane. All methanol was subsequently removed, 4M HCl (0.138 mL, 0.552 mmol) in dioxane was added and the mixture was stirred at 40° C. for 2 hours. Upon completion of BOC removal all volatiles were removed and the crude was suspended in a mixture of THF (1 mL), water (2 mL) and MeOH (2 mL) and treated with lithium hydroxide (26.5 mg, 1.104 mmol). Upon completion of ester removal the pH was adjusted to 3 by addition of TFA and the product was isolated by separation on a Phenomenex® (21.2×250 mm) C18 column eluting a gradient of acetonitrile in water containing 0.1% TFA to yield 16.4 mg (24%, 3-Steps).

Synthesis of Structure 36c ((S)-3-(4-(2-(2-(2-(2-azidoethoxy)ethoxy)ethoxy)ethoxy)-3-fluorophenyl)-9-(5,6,7,8-tetrahydro-1,8-naphthyridin-2-yl) nonanoic acid)

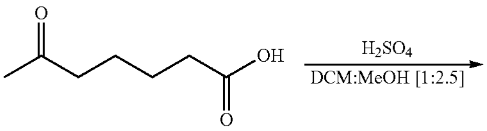

-continued

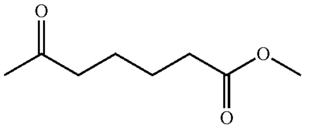

141

To a solution of 6-oxoheptanoic acid (9.74 g, 68 mmol) in DCM (30 mL) and MeOH (75 mL) was added cone. $H_2SO_4$ (0.18 mL, 3.4 mmol) at room temperature. The reaction mixture was refluxed overnight. The reaction mixture was then concentrated to an oil, redissolved in DCM (150 mL), and washed with sat. aq. $NaHCO_3$ (2x40 mL) and brine (40 mL). The organic layer was dried over $Na_2SO_4$, filtered, and concentrated. The product was used in the next step without further purification. Yield of compound 141: 10.2 g (95%). $^1H$ NMR (400 MHz, DMSO-d6): δ 3.58 (s, 3H), 2.43 (t, 2H), 2.29 (t, 2H), 1.46 (m, 4H).

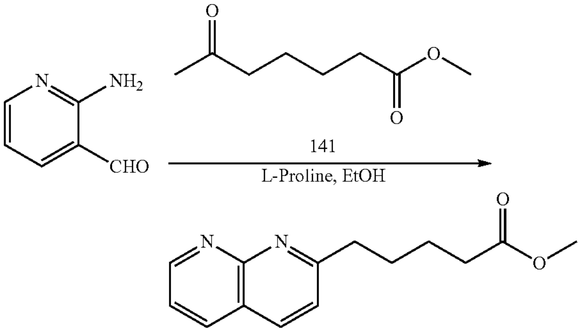

142

To a solution of compound 141 (10.2 g, 65 mmol) and 2-amino-3-formylpyridine (7.89 g, 65 mmol) in EtOH (80 mL) was added L-proline (3.72 g, 32 mmol). The reaction mixture was heated at reflux overnight. The reaction mixture was then concentrated, dissolved in EtOAc (50 mL), and washed with water (3x30 mL). The organic phase was dried over $Na_2SO_4$, filtered, and concentrated. The residue was purified by CombiFlash using silica gel as the stationary phase and was eluted with a gradient of EtOAc in DCM (10-100%). Yield of compound 142: 6.08 g (39%). Mass calculated for $C_{14}H_{16}N_2O_2$ $[M+H]^+$: 245.13, found: 245.21.

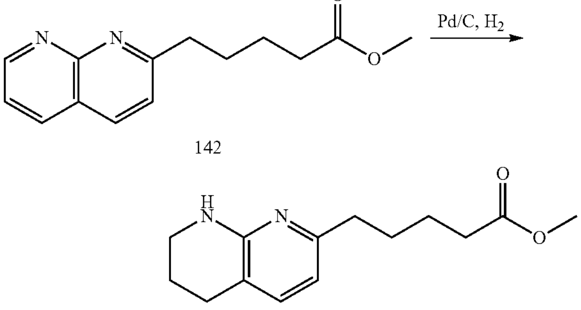

143

To a solution of compound 142 (6.08 g, 24.9 mmol) in MeOH (50 mL) was added Pd/C (10% loading, Degussa type, 1.99 g, 1.87 mmol). The reaction flask was charged with nitrogen, evacuated, and backfilled with nitrogen three times. This process was repeated with hydrogen, and the reaction vessel was finally charged with hydrogen (1 atm) and stirred overnight at room temperature. The reaction mixture was filtered over Celite®, the pad rinsed with MeOH, and the filtrate concentrated. The product, compound 143, was used in the next step without further purification assuming 100% yield. Mass calculated for $C_{14}H_{20}N_2O_2$ $[M+H]^+$: 249.16, found: 249.08.

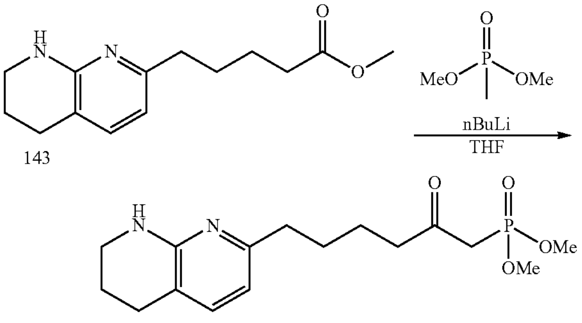

144

To a solution of dimethyl methylphosphonate (12.3 g, 100 mmol) in anhydrous THF (120 mL) was added n-BuLi solution (2.5 M in hexanes, 40 mL, 100 mmol) via syringe pump over 1 h at −78° C. A solution of compound 143 (6.175 g, 24.9 mmol) in THF (40 mL) was added to the reaction mixture over 45 m at −78° C. After stirring for 20 m at −78° C., the reaction mixture was quenched with sat. aq. $NH_4Cl$ solution (200 mL), warmed to rt, and extracted with EtOAc (400 mL). The organic layer was washed with water (200 mL) and brine (200 mL). The organic phase was separated, dried over $Na_2SO_4$, filtered, and concentrated. The product was used in the next step without further purification. Yield of compound 144 7.86 g (93%). Mass calculated for $C_{16}H_{25}N_2O_4P$ $[M+H]^+$: 341.17, found: 341.17.

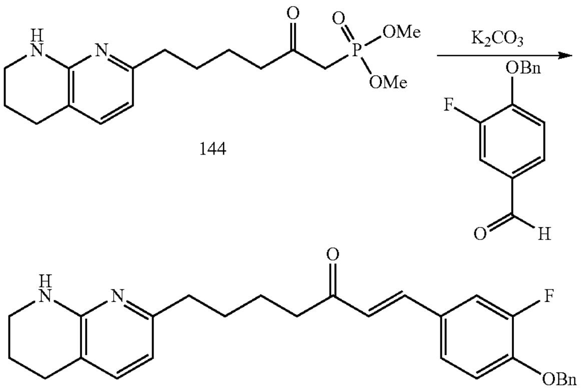

145

A suspension of 3-fluoro-4-(phenylmethoxy)-benzaldehyde (0.38 g, 1.65 mmol), compound 144 (0.67 g, 1.98 mmol), and anhydrous potassium carbonate (0.547 g, 3.96 mmol) in THF (13.5 mL) was heated at reflux overnight. Additional 3-fluoro-4-(phenylmethoxy)-benzaldehyde (0.19 g, 0.83 mmol) and potassium carbonate (0.23 g, 1.65 mmol) were added and the reaction mixture was refluxed for an additional 4 h. The mixture was diluted with EtOAc (100 mL) and washed with water (30 mL) and brine (30 mL). The organic phase was separated, dried over $Na_2SO_4$, filtered, and concentrated. The residue was purified by CombiFlash using silica gel as the stationary phase and was eluted with a gradient of MeOH in DCM (0-10%). Yield of compound 145: 446 mg (61%). Mass calculated for $C_{28}H_{29}FN_2O_2$ $[M+H]^+$: 445.23, found: 445.41.

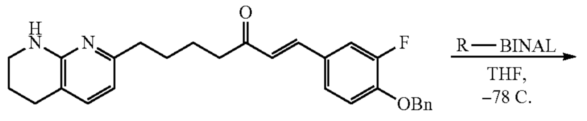

145 warmed to room temperature. The mixture was further acidified to pH=7 using 6 N HCl then extracted with EtOAc (2×250 mL). The combined organic phase was washed with water (125 mL) and brine (125 mL). The organic phase was dried over $Na_2SO_4$, filtered, and concentrated. The residue was purified by CombiFlash using silica gel as the stationary phase and was eluted with a gradient of MeOH in DCM (0-5%). Yield of compound 146: 634 mg (53%). Chiral purity was determined by analytical chiral HPLC, Chiralpak AD-H column 4.6x250 mm, 5 micron, EtOH 0.1% diethylamine isocratic, 1.75 mL/min. The first eluting R isomer was 86 area % pure, corresponding to 72% ee. Compound 6 was further purified by chiral semi-preparative HPLC (Chiralpak AD-H 21.2x250 mm, 5 micron, EtOH 0.1% diethylamine, 20 mL/min). Final yield of compound 146: 445 mg (98% ee). Mass calculated for $C_{28}H_{31}FN_2O_2$ $[M+H]^+$: 447.25, found: 447.30.

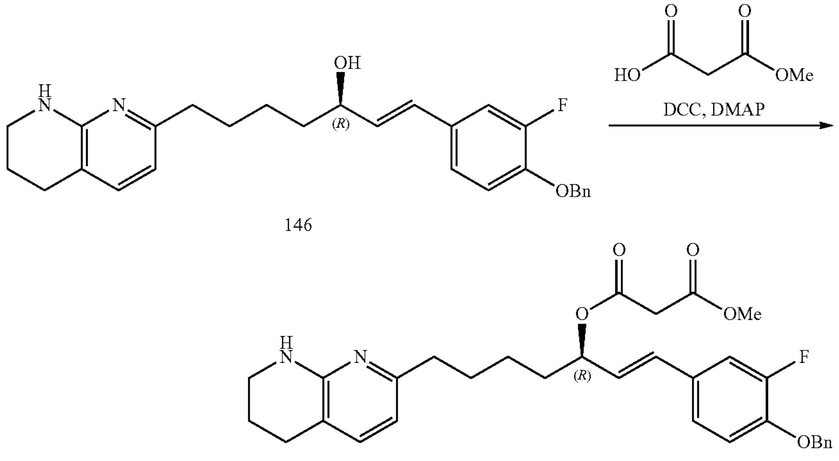

146

147

-continued

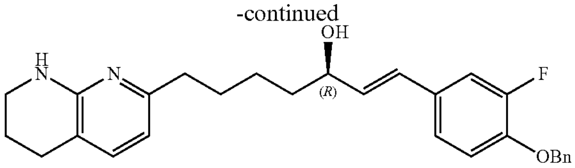

146

Preparation of R-BINAL: To a slurry of LAH (0.3% g, 10.4 mmol, 0.98 eq) dry THF (34 mL) was added EtOH (0.492 g, 10.65 mmol, 1.00 eq) as a solution in THF (3.2 mL) over 10 m while maintaining an internal temperature <35° C. After aging for 30 m, R-BINOL (3.05 g, 10.65 mmol, 1.00 eq) was added as a solution in THF (10 mL), maintaining an internal temperature <35° C. (ca 10 minutes). After stirring for 2 h at room temperature, the reaction mixture was cooled on a dry ice/acetone bath to −78° C.

Compound 145 (1.18 g, 2.65 mmol) was dried azeotropically with anhydrous toluene (50 mL) and was dissolved in anhydrous THF (12 mL). The solution of compound 145 was added dropwise to the solution of R-BINAL via syringe pump over 45 m at −78° C. After 1.5 h, the reaction vessel was transferred to a very large dewer, filled with dry ice/acetone, and covered with aluminum foil. The reaction mixture was stirred ON at −78° C. The majority of the reduction occurred within the first 1.5 h with only a small amount additional conversion overnight. The reaction was quenched by addition of sat. aq. $NH_4Cl$ (150 mL) and To a solution of compound 146 (0.325 g, 0.73 mmol) and malonic acid monomethyl ester (0.103 g, 0.87 mmol) in DCM (3 mL) was added a solution of DMAP (9 mg, 0.073 mmol) in DCM. The mixture was cooled to 0° C. and DCC (0.180 g, 0.87 mmol) was added. The cooling bath was removed, and the reaction was stirred at RT ON. The reaction mixture was then diluted with DCM (10 mL) and filtered. The filtrate was concentrated and purified by CombiFlash using silica gel as the stationary phase, eluting with a gradient of MeOH (0-5%) in DCM. Yield of compound 147: 142 mg (37%). Mass calculated for $C_{32}H_{35}FN_2O_5$ $[M+H]^+$: 547.26, found: 547.58.

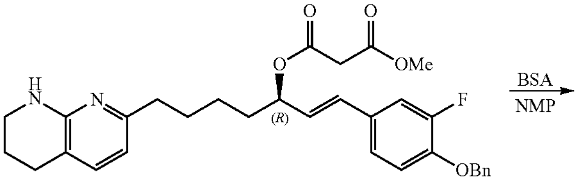

147

-continued

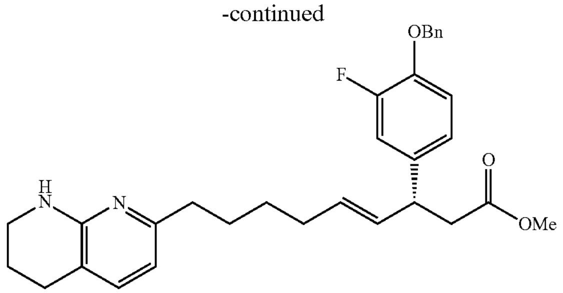

148

To a solution of compound 147 (0.232 g, 0.42 mmol) in NMP (0.5 mL) was added N,O-bis(trimethylsilyl)acetamide (0.229 g, 1.12 mmol) at room temperature. The mixture was heated at 60° C. for 30 m. Brine (58 μL) was added in two portions over 5 m. The reaction mixture was then heated at 90° C. for 3 h then room temperature overnight. The reaction mixture was diluted with EtOAc (12 mL) and washed with water (3 mL). The aqueous layer was back extracted with EtOAc (12 mL). The combined organic layer was concentrated. The residue was purified by CombiFlash using silica gel as the stationary phase and was eluted with a gradient of MeOH in DCM. Yield of compound 148: 140 mg (66%). Mass calculated for $C_{31}H_{35}FN_2O_3$ $[M+H]^+$: 503.27, found: 503.29.

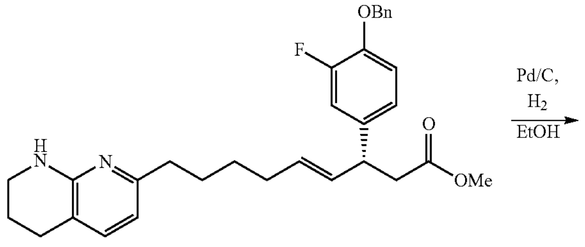

148

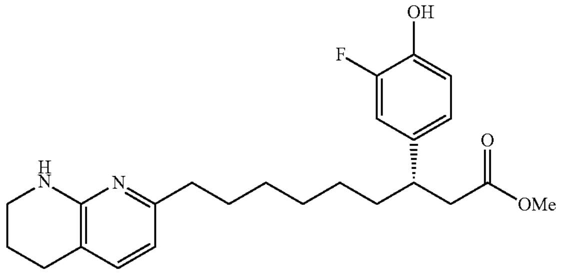

149

To a solution of compound 148 (0.169 g, 0.34 mmol) in EtOH (3 mL) was added a slurry of Pd/C (10% loading, 36 mg, 0.034 mmol) in EtOH (1 mL). The reaction vessel was pressurized and vented with hydrogen three times. The reaction vessel was repressurized to 55 psi for 3 h. The reaction mixture was diluted with MeOH (5 mL) and filtered. The filtrate was concentrated and the product, compound 149, was used in the next step without further purification assuming 100% yield. Mass calculated for $C_{24}H_{31}FN_2O_3$ $[M+H]^+$: 415.24, found: 415.07.

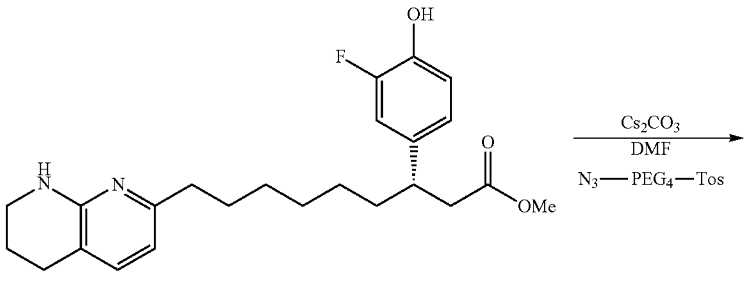

149

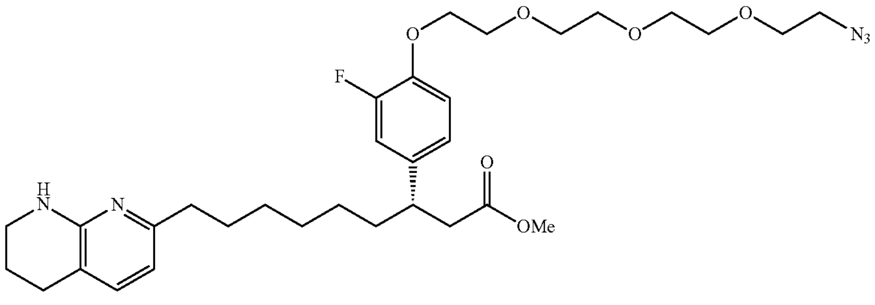

150

To a solution of compound 149 (139 mg, 0.34 mmol) and azido-$PEG_4$-tosylate (0.188 mg, 0.50 mmol) in DMF (2.5 mL) was added cesium carbonate (164 mg, 0.50 mmol). The reaction mixture was heated at 40° C. for 1 h then quenched with sat. aq. $NaHCO_3$ (3 mL). The mixture was extracted with EtOAc, (3×10 mL). The combined organic phase was washed with water (2×5 mL). The organic phase was dried over $Na_2SO_4$, filtered, concentrated, and used in the next step without further purification. Mass calculated for $C_{32}H_{46}FN_5O_6$ $[M+H]^+$: 616.35, found: 616.90.

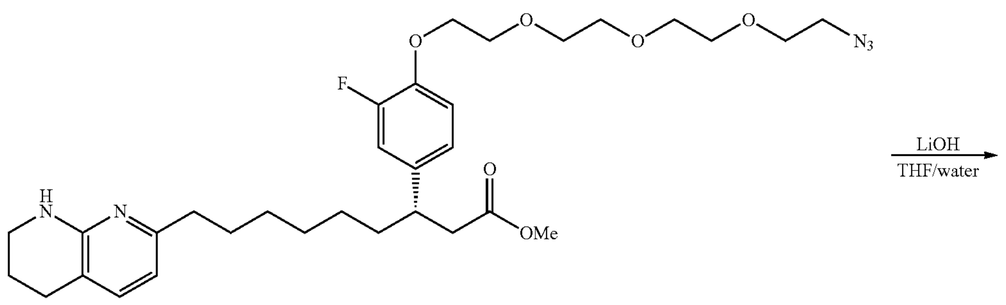

150

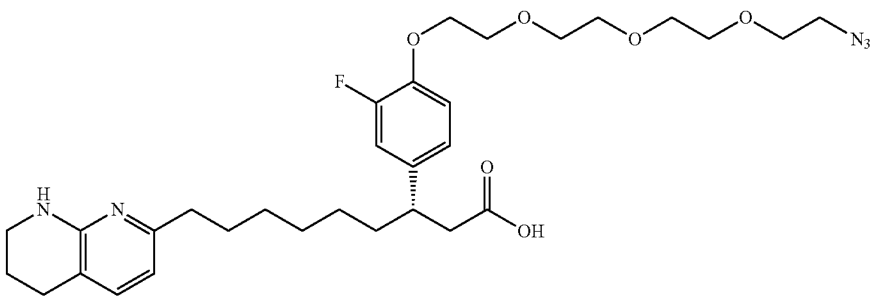

151

To a solution of compound 150 (0.207 mg, 0.34 mmol) in THF (1.5 mL) and water (1.5 mL) was added lithium hydroxide (0.040 g, 1.68 mmol). The reaction mixture was heated to 40° C. overnight. The next morning the reaction mixture was acidified with 6 N HCl to pH=7 and concentrated under reduced pressure. The residue was dissolved in 35% ACN in $H_2O$, 0.1% TFA, and purified by RP-HPLC (Thermo Aquasil C18, 250×21 mm, 5 μm, 20 mL/min, gradient of ACN in $H_2O$ containing 0.1% TFA). Yield of compound 151 (SM 36): 125 mg (52% over 3 steps). Mass calculated for $C_{31}H_{44}FN_5O_6$ $[M+H]^+$: 602.34, found: 602.85.

Synthesis of Structure 37c ((S)-3-(4-(2-(2-(2-(2-azidoethoxy)ethoxy)ethoxy)ethoxy)-3-fluorophenyl)-3-(5-(5,6,7,8-tetrahydro-1,8-naphthyridin-2-yl)pentanamido)propanoic acid)

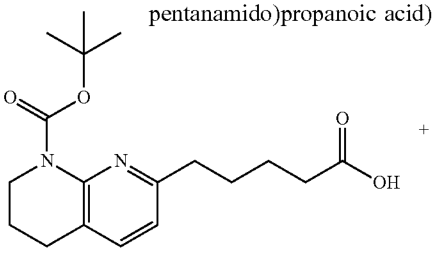

169

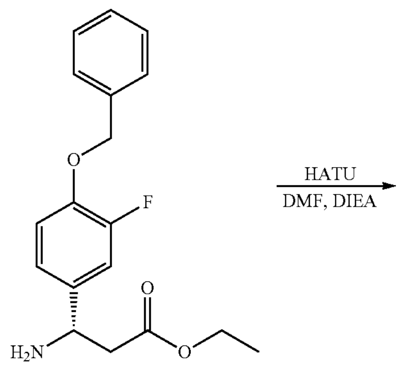

170

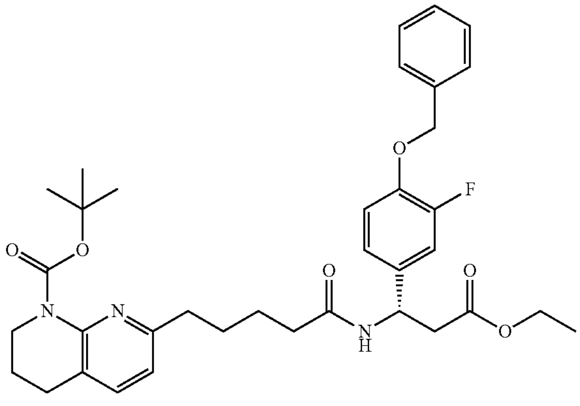

171

Compound 169 (90 mg, 0.268 mmol) in DMF (1.5 mL) was treated with HATU (112 mg, 0.295 mmol) and stirred for 5 minutes. A mixture containing compound 170 (94 mg, 0.295 mmol) and DIEA (0.154 mL, 0.884 mmol) in DMF (0.5) was subsequently added and stirring was continued for 1 hour. Upon completion all volatiles were removed and compound 171 was isolated by separation over silica eluting a gradient of MeOH in DCM yielding 123 mg (72%).

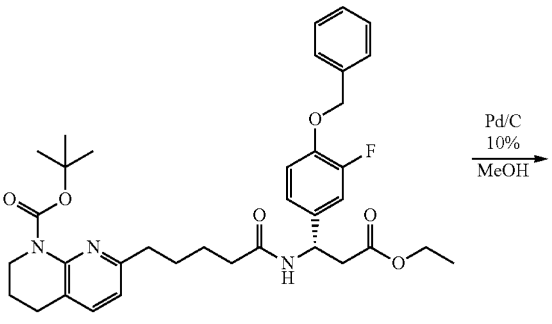

171

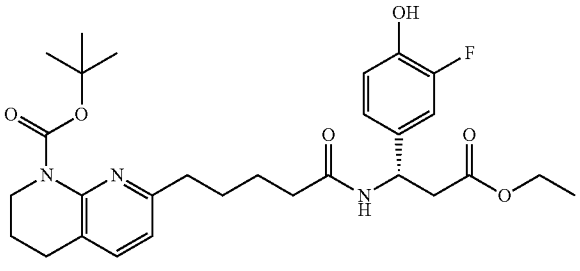

172

A suspension containing 10% palladium on carbon (21 mg, 0.0194 mmol) and compound 171 (123 mg, 0.194 mmol) in MeOH (2 mL) was charged with 60 PSI hydrogen and stirred for 1 hour. Upon completion the suspension was filtered over Celite® and concentrated to yield 88 mg (83%) of crude that was used subsequently without further purification.

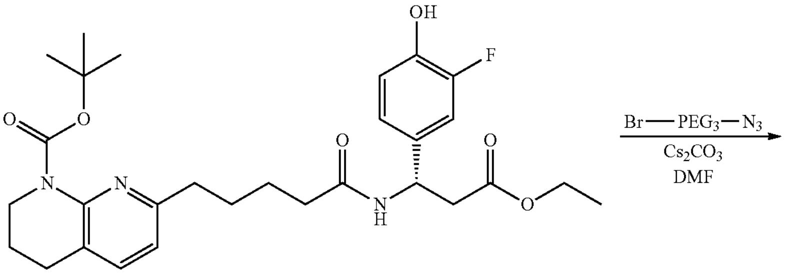

172

-continued

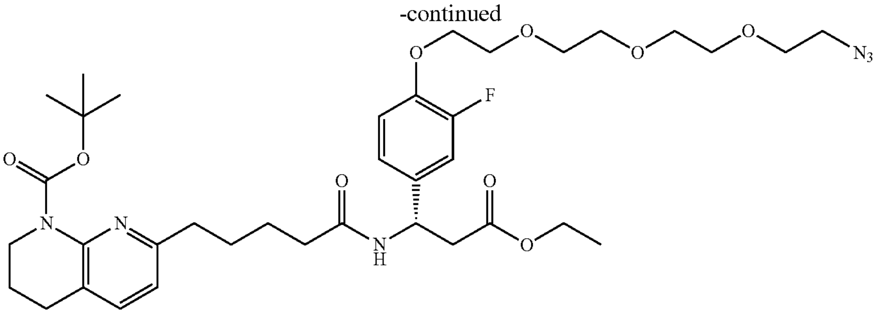

173

A suspension containing compound 172 (87 mg, 0.160 mmol), Br-PEG$_3$-N$_3$ (50 mg, 0.176 mmol) and cesium carbonate (115 mg, 0.352 mmol) in DMF (1 mL) was heated to 60° C. and stirred for 2 hours. Upon completion all volatiles were removed and compound 173 was isolated by separation over silica eluting a gradient of MeOH in DCM yielding 91 mg

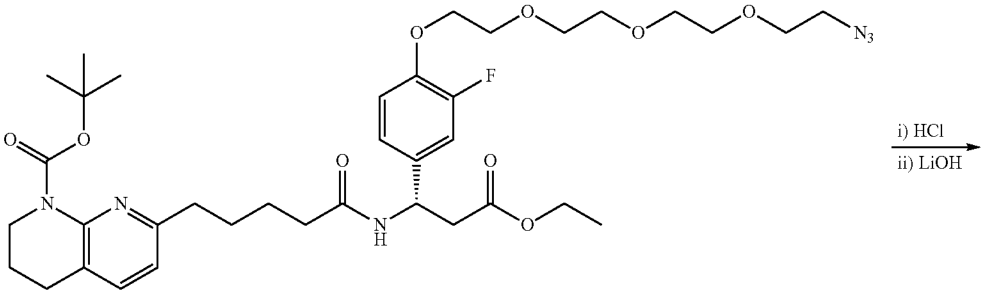

173

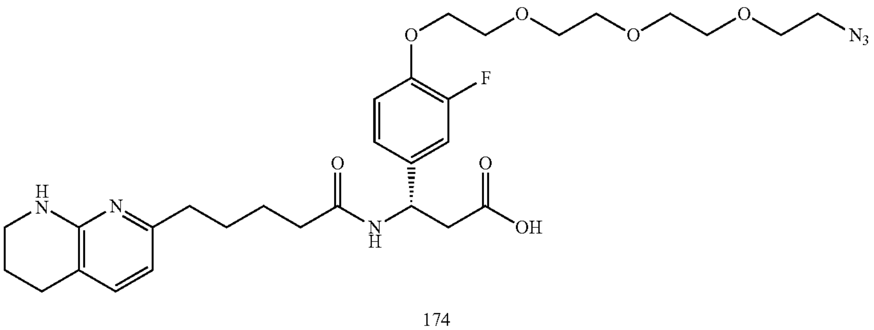

174

Compound 173 (50 mg, 0.067 mmol) in dioxane (0.5 mL) was treated with a 4M HCl (0.671 mmol, 0.168 mL) solution in dioxane and stirred at 40° C. for 3 hours. Upon completion all volatiles were removed. The crude was dissolved in a mixture of $H_2O$ (0.4 mL), THF (0.2 mL) and MeOH (0.4 mL), treated with LiOH (8 mg, 0.356 mmol), and stirred at 40° C. for 16 hours. Upon completion the pH was adjusted to 3 with TFA and the product was isolated by separation over a Phenomenex Gemini C18 column (21.2×250 mm, 5 micron) eluting a gradient of acetonitrile in water containing 0.1% TFA to yield 25 mg (60%, 2-Steps).

Synthesis of Structure 38c ((S)-3-(2-(3-((2-(2-(2-azidoethoxy)ethoxy)ethyl)amino)-3-oxopropyl)pyrimidin-5-yl)-9-(5,6,7,8-tetrahydro-1,8-naphthyridin-2-yl)nonanoic acid) and Structure 39c ((S)-3-(2-(1-azido-12-oxo-3,6,9-trioxa-13-azahexadecan-16-yl)pyrimidin-5-yl)-9-(5,6,7,8-tetrahydro-1,8-naphthyridin-2-yl)nonanoic acid)

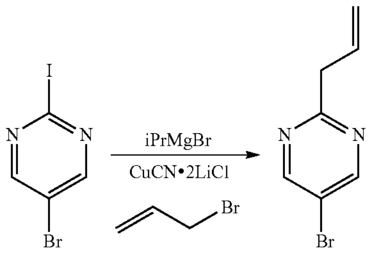

152

To a solution of 5-bromo-2-iodo-pyrimidine (8.00 g, 28.1 mmol) in anhydrous THF (95 mL) was added a solution of i-PrMgBr in THF (0.75 M, 56 mL, 42.0 mmol) at −78° C. while maintaining an internal temperature <−70° C. (ca. 15 m). The resulting solution was then stirred for 15 minutes before adding CuCN·2LiCl solution in THF (1 M, 31 mL, 31.0 mmol) and then allyl bromide (5.10 g, 42 mmol) as a solution in THF (10 mL). The reaction mixture was warmed to room temperature and stirred for 1 h. The reaction mixture was quenched with MeOH (40 mL) and concentrated. The residue was purified by CombiFlash using silica gel as the stationary phase and was eluted with a gradient of EtOAc in hexanes (0-20%). Yield of compound 152: 4.13 g (74%). Mass calculated for $C_7H_7BrN_2$ $[M+H]^+$: 198.99, found: 199.05.

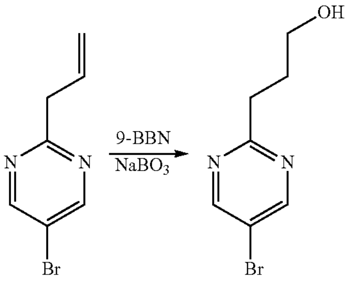

152 153

To a solution of compound 152 (7.70 g, 38.7 mmol) in THF (115 mL) was added a solution of 9-BBN in THF (0.5 M, 131 mL, 65.8 mmol) at 0° C. over 30 m. The reaction mixture was warmed to room temperature and stirred overnight. To the reaction mixture was added a slurry of $NaHCO_3$ (48.7 g, 580 mmol) in water (100 mL) followed by a slurry of $NaBO_3$ monohydrate (46.3 g, 464 mmol) in water (100 mL) at 0° C. The cooling bath was removed, and the mixture was stirred vigorously for 1 h. The reaction mixture was transferred to a separatory funnel and the layers were separated. The aqueous layer was extracted with EtOAc (200 mL). The organic phases were combined and washed with brine (100 mL). The brine layer was back extracted with EtOAc (100 mL). The combined organic phase was dried over $Na_2SO_4$, filtered, and concentrated to yield ~15 g crude, yellow oil. The crude was purified by CombiFlash using silica gel as the stationary phase and was eluted with a gradient of EtOAc in hexanes (50-100%). Yield of compound 153: 3.44 g (41%). Mass calculated for $C_7H_9BrN_2O$ $[M+H]^+$: 217.00, found: 216.97.

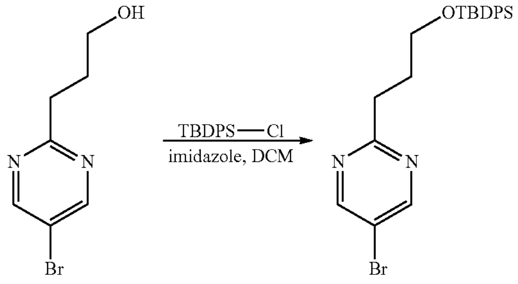

153 154

To a solution of compound 153 (3.44 g, 15.8 mmol) in DCM (40 mL) was added imidazole (1.73 g, 25.4 mmol) and a solution of TBDPSCl (5.23 g, 19.0 mmol) in DCM (12 mL) at 0° C. The reaction was warmed to room temperature and stirred overnight. The reaction mixture was diluted with DCM (75 mL) and washed with water (50 mL) and brine (50 mL). The organic layer was dried over $Na_2SO_4$, filtered, and concentrated. The residue was purified by CombiFlash using silica gel as the stationary phase and was eluted with a gradient of EtOAc (0-8%) in hexanes. Yield of compound 154: 5.56 g (77%). Mass calculated for $C_{23}H_{27}BrN_2OSi$ $[M+H]^+$: 455.12, found: 455.44.

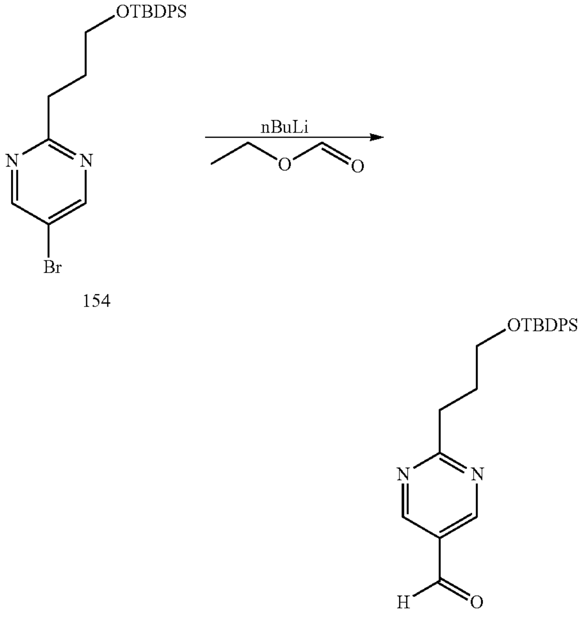

154

155

To a solution of compound 154 (6.07 g, 13.3 mmol) in THF (150 mL) at −75° C. was added a solution of nBuLi in THF (2.5 M, 5.6 mL, 14.0 mmol) dropwise, maintaining an internal temperature <−70° C. (ca. 10 m). After 3 m, a solution of ethyl formate (1.04 g, 1.13 mL, 14.0 mmol) in THF (5 mL) was added dropwise, maintaining an internal temperature <−70° C. The mixture was stirred at −78° C. for 20 m then quenched with HCl in dioxane (4 M, 3.67 mL, 14.7 mmol) that was further diluted with THF (5 mL), maintaining an internal temperature <−65° C. The cooling bath was removed, and the reaction was warmed to ambient temperature and concentrated. The residue was purified by CombiFlash using silica gel as the stationary phase and was eluted with a gradient of EtOAc in hexanes (0-20%). Yield of compound 155: 1.79 g (33%). $^1H$ NMR (400 MHz, $CDCl_3$): δ 10.09 (s, 1H), 9.06 (s, 2H), 7.64 (m, 4H), 7.38 (m, 6H), 3.77 (t, 2H), 3.20 (t, 2H), 2.17 (q, 2H), 1.03 (s, 9H).

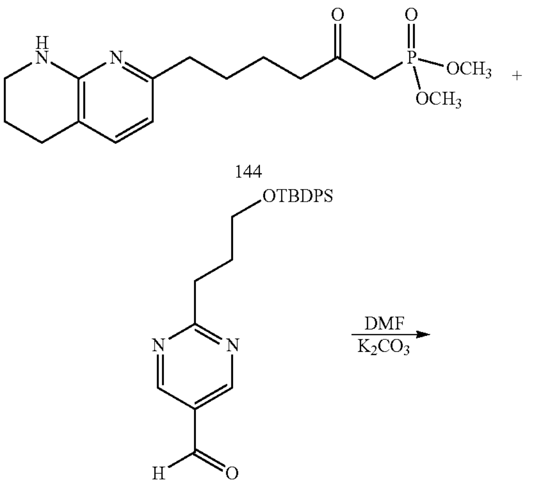

144

155

-continued

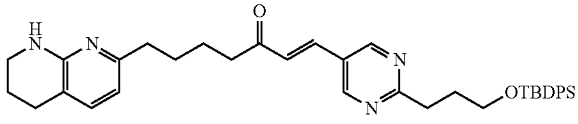

156

To a solution of compound 144 (1.68 g, 4.15 mmol) and compound 155 (1.70 g, 4.98 mmol) in THF (25 mL) was added $K_2CO_3$ (0.861 g, 6.23 mmol). The reaction mixture was heated to 40° C. for 2.5 h then 50° C. for 12 h. The reaction mixture was diluted with EtOAc (100 mL) and washed with water (50 mL) and brine (50 mL). The organic phase was dried over $Na_2SO_4$, filtered, and concentrated. The residue was purified by CombiFlash using silica gel as the stationary phase and was eluted with a gradient of EtOAc (0-100%) in hexanes containing 1% triethylamine. Yield of compound 156: 2.04 g (79%). Mass calculated for $C_{38}H_{46}N_4O_2Si$ $[M+H]^+$: 619.35, found: 619.69.

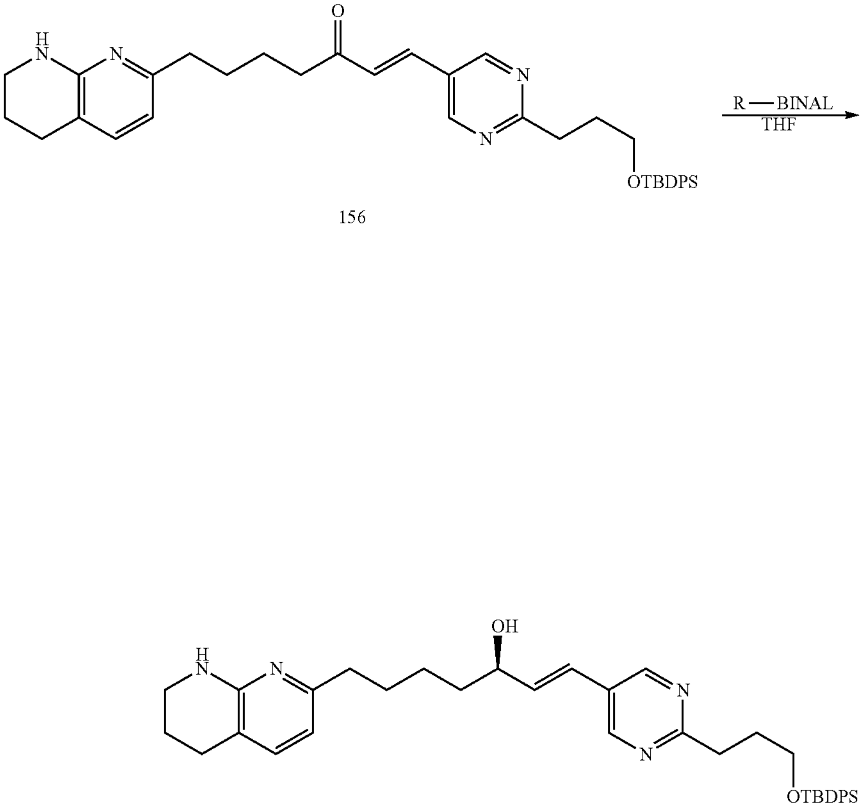

156

157

Preparation of R-BINAL: LAH (1.169 g, 30.8 mmol) was slurried in dry THF (90 mL). To the slurry was added EtOH as a solution in THF (6 M, 5.2 mL, 31.4 mmol) keeping $T_{int}$<40° C. The mixture was aged at 35° C. for 40 m then cooled to 30° C. A solution of R-(BINOL) (9.00 g, 31.4 mmol) in THF (45 mL) was added, keeping $T_{int}$<40° C. The mixture was aged at 50° C. for 1 h, cooled to ambient temperature, then healed to 50° C. and TMEDA (14.1 mL, 11.0 g, 94.3 mmol) was added. The mixture was aged at 50° C. for 1 h, cooled to ambient temperature, and then used with compound 156.

To a solution of R-BINAL (~0.2 M, 110 mL, 22.0 mmol) in THF was added a solution of compound 16 (1.16 g, 1.88 mmol) in THF (12 mL) at −78° C. over 5 m After 30 m, the reaction mixture was quenched with sat. aq. $NH_4Cl$, warmed to rt, and the product was extracted with EtOAc (3×125 mL). The organic layer was dried over $Na_2SO_4$, filtered, and concentrated. The residue was purified by CombiFlash using silica gel as the stationary phase and was eluted with a gradient of MeOH (0-5%) in EtOAc containing 1% triethylamine. Yield of compound 157: 0.96 g (82%). Chiral purity was determined by analytical chiral HPLC, Chiralpak AD-H column 4.6×250 mm, 5 micron, 25% EtOH, 75% hexanes, 0.1% diethylamine isocratic, 2 mL/min). The second eluting R isomer was ~95 area % pure, corresponding to ~90% ee. Mass calculated for $C_{38}H_{48}N_4O_2Si$ $[M+H]^+$. 621.36, found.

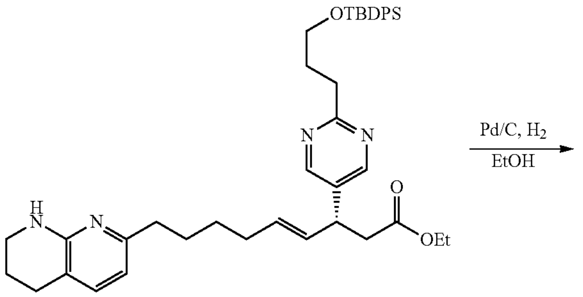

158

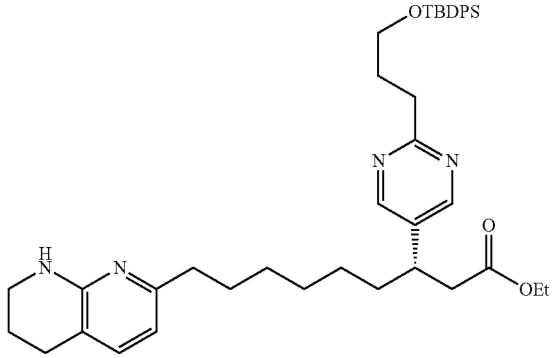

159

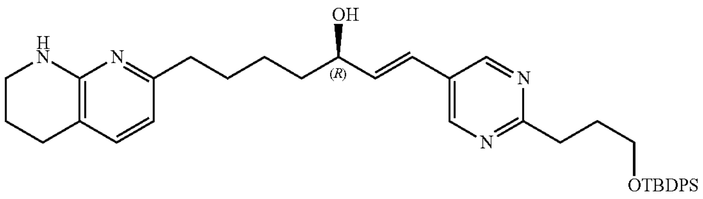

157

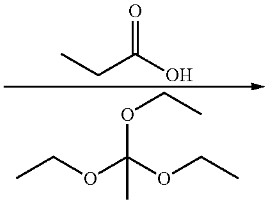

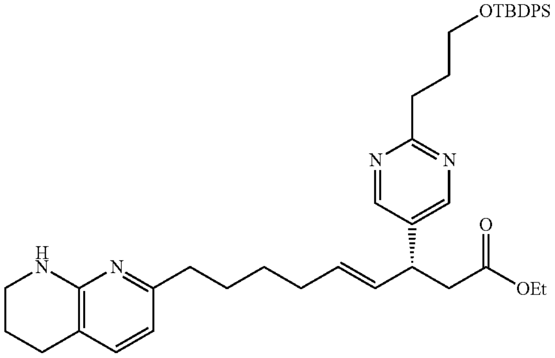

158

To a solution of compound 157 (0.925 g, 1.49 mmol) in triethylorthoacetate (9.25 mL) was added a solution of propionic acid in trimethylorthoacetate (0.15 M, 0.55 mL, 0.08 mmol). The reaction mixture was heated at 140° C. in a sealed vial for 1.5 h. The reaction mixture was concentrated, and the residue was purified by CombiFlash using silica gel as the stationary phase, eluting with a gradient of EtOAc (0-50%) in hexanes containing 1% triethylamine. Yield of compound 158: 0.898 g (87%). Mass calculated for $C_{42}H_{54}N_4O_5Si$ $[M+H]^+$: 691.41, found: 691.93.

To a solution of compound 158 (0.893 g, 1.30 mmol) in EtOH (10 mL) was added a slurry of Pd/C (extent of loading: 10 wt %, 0.138 g, 0.13 mmol) in EtOH (4 mL). The reaction mixture was charged 50 psi $H_2$ and stirred for 4.5 h. The reaction mixture was filtered, concentrated, and used in the next step without further purification. Yield of compound 159: 0.885 g (99%). Mass calculated for $C_{42}H_{56}N_4O_3Si$ $[M+H]^+$: 693.42, found: 693.82.

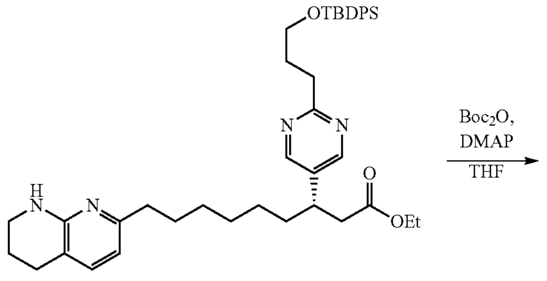

159

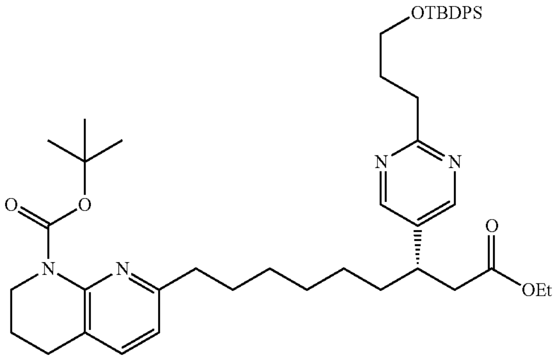

160

A solution of Boc anhydride (0.836 g, 3.83 mmol) in THF (2.5 mL) was added to compound 159 (0.885 g, 1.28 mmol) followed by a solution of DMAP (20 mg/mL in THF, 155 uL, 0.0031 g, 0.026 mmol). The mixture was heated to 60° C. for 6 h. The reaction mixture was concentrated and the residue was purified by CombiFlash using silica gel as the stationary phase, eluting with a gradient of EtOAc (0-50%) in hexanes. Yield of compound 160: 0.721 g (71%). Mass calculated for $C_{47}H_{64}N_4O_5Si$ $[M+H]^+$: 793.47, found: 794.28.

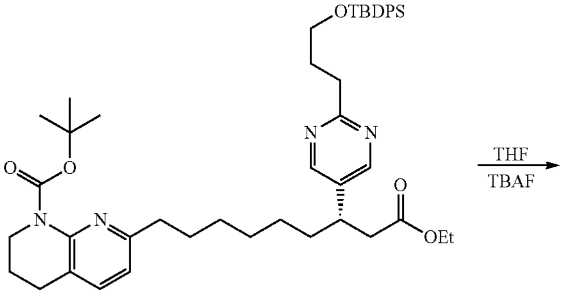

160

-continued

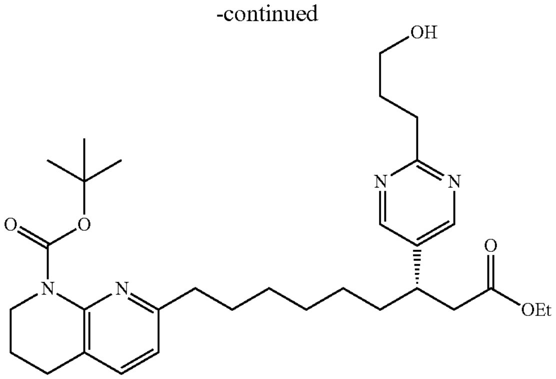

161

To a solution of compound 160 (0.621 g, 0.783 mmol) in THF (6 mL) was added a solution of TBAF in THF (1 M, 1.2 mL, 1.2 mmol) at 0° C. The reaction mixture was warmed to room temperature and stirred for 2 h. The reaction mixture was diluted with EtOAc (30 mL) and washed with sat. aq. $NH_4Cl$ (2×10 mL). The organic layer was concentrated. The residue was purified by CombiFlash using silica gel as the stationary phase and was eluted with a gradient of EtOAc (50-100%) in hexanes. Yield of compound 21: 0.362 g (83%). Chiral purity was determined by analytical chiral HPLC, Chiralpak AD-H column 4.6×250 mm, 5 micron, 20% EtOH, 80% hexanes, 0.1% diethylamine, isocratic, 1.5 mL/min. The second eluting R isomer was 93% pure, corresponding to 86% ee. was Compound 161 was further purified by chiral semi-preparative HPLC (Chiralpak AD-H 21.2×250 mm, 5 micron, 20% EtOH, 80% hexanes, 0.1% diethylamine, 60 mL/min). Final yield of compound 161: 308 mg (99% ee). Mass calculated for $C_{31}H_{46}N_4O_5$ $[M+H]^+$: 555.36, found: 555.72.

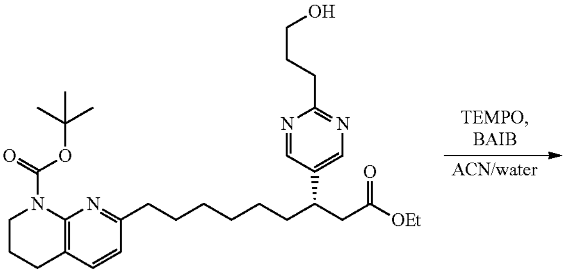

161

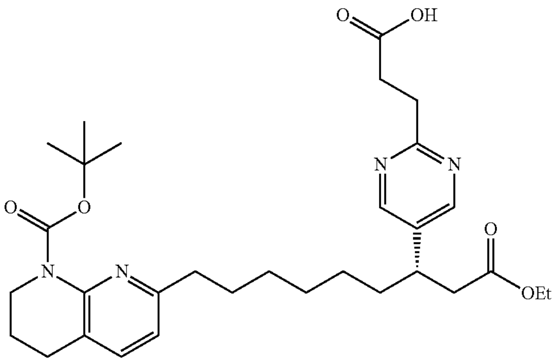

162

To a solution of compound 161 (0.030 g, 0.054 mmol) in ACN (0.30 mL) was added BAIB (0.042 g, 0.130 mmol) and TEMPO (2.5 mg, 0.016 mmol) followed by water (0.30 mL) at room temperature. After 2 hr, the reaction mixture was concentrated. The residue was purified by RP-HPLC (Phenomenex Gemini C18 21.2×250 mm, 5 micron, 0.1% TFA water/ACN, 30-80% ACN gradient). Yield of compound 162: 0.030 g (97%). Mass calculated for $C_{31}H_{44}N_4O_6$ $[M+H]^+$: 569.34, found: 569.68.

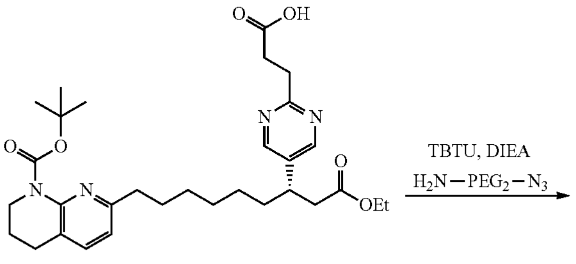

162

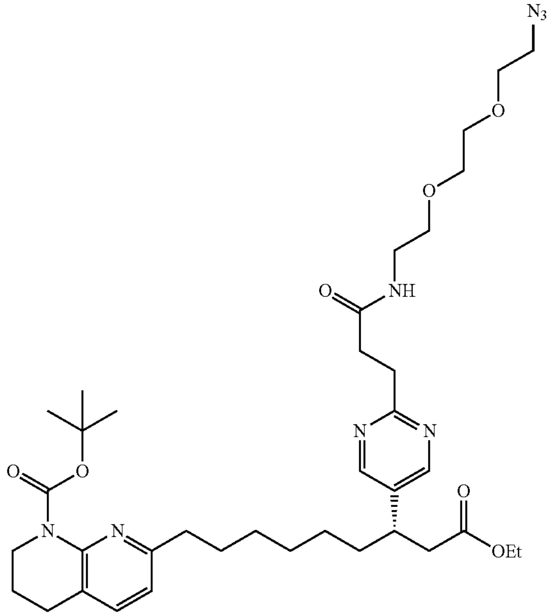

163

To a solution of compound 162 (33 mg, 0.058 mmol) and amino-PEG$_2$-azide (15 mg, 0.087 mmol) in DMF (0.5 mL) was added TBTU (32 mg, 0.099 mmol) then DIEA (35 μL, 26 mg, 0.203 mmol) at 0° C. The reaction mixture was warmed to room temperature and stirred for 30 m. The reaction mixture was concentrated, and the product, compound 163, was used in the next step without purification. Mass calculated for $C_{37}H_{56}N_8O_7$ $[M+H]^+$: 725.44, found: 725.77.

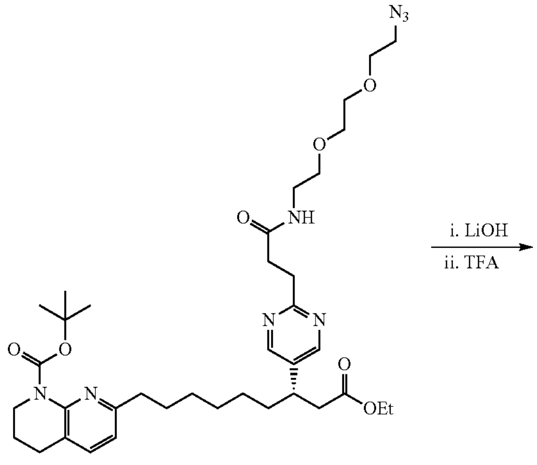

163

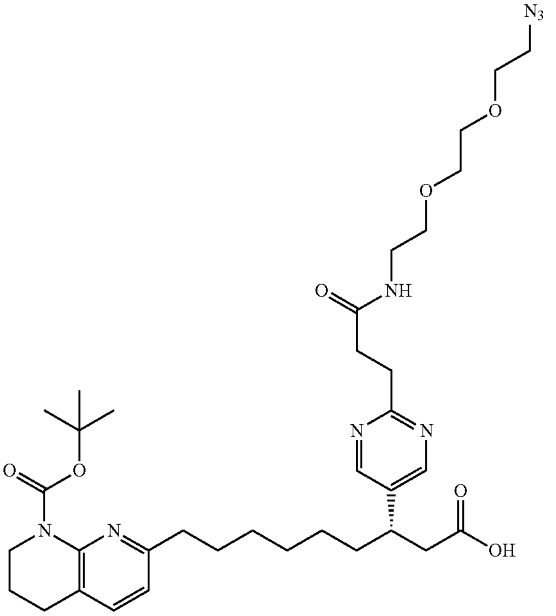

164

To a solution of compound 163 (42 mg, 0.058 mmol) in THF (0.30 mL) was added a 1 M solution of LiOH (0.174 mL, 0.174 mmol). The reaction mixture was heated at 40° C. for 1 hr. An additional portion of LiOH was added (0.174 mL, 0.174 mmol). After 3 h, the reaction stalled, and an additional portion of LiOH was added (0.174 mL, 0.174 mmol). The reaction was stirred for an additional 2 hr (9 eq LiOH, 5 hr total). The reaction mixture was neutralized to pH=5 using 3 N HCl and concentrated. The residue was dissolved in TFA:water [95:5] and stirred for 2 hours at room temperature. The reaction mixture was concentrated and the residue was purified by RP-HPLC (Phenomenex Gemini C18 21.2×250 mm, 5 micron, water/ACN containing 0.1% TFA, 20-50% ACN gradient). Yield of compound 164 (Structure 38c): 23 mg (66%). Mass calculated for $C_{30}H_{44}N_8O_5$ $[M+H]^+$: 597.35, found: 597.85.

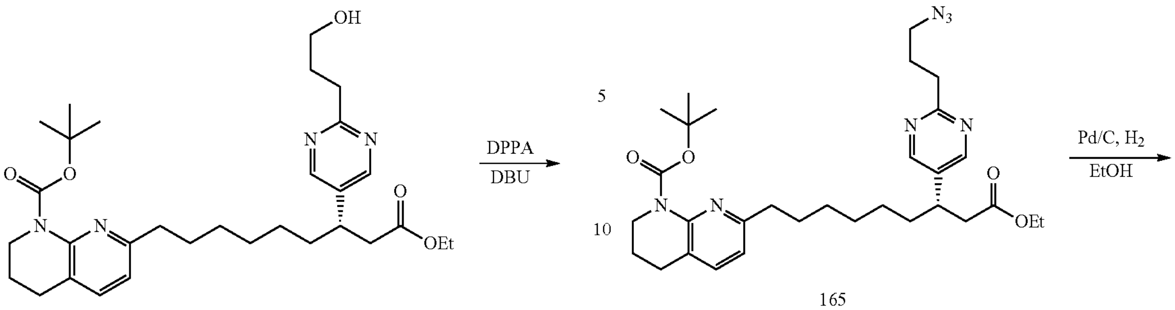

161

165

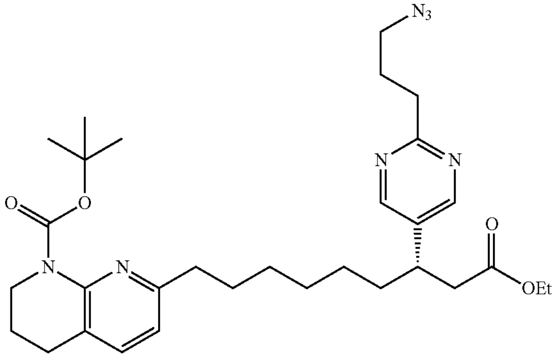

165

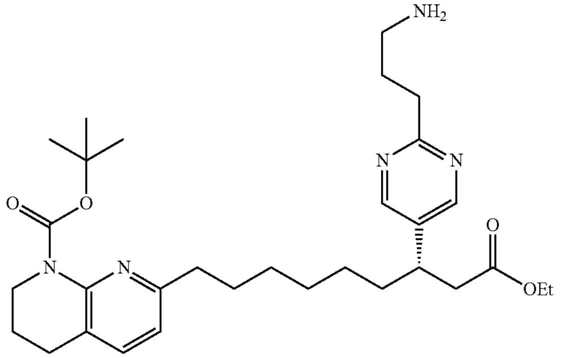

166

To a solution of compound 161 (30 mg, 0.054 mmol) in THF (150 μL) was added diphenyl phosphoryl azide (35 μL, 45 mg, 0.162 mmol) followed by DBU (12 μL, 12 mg, 0.081 mmol) at 0° C. The reaction mixture was warmed to rt and stirred overnight. The next morning, the reaction mixture was heated at 60° C. for 7 h. The reaction mixture was concentrated and purified by RP-HPLC (Phenomenex Gemini C18 21.2x250 mm, 5 micron, 0.1% TFA water/ACN, 32-60% ACN gradient). Yield of compound 165: 14 mg (44%). Mass calculated for $C_{31}H_{45}N_7O_4$ $[M+H]^+$: 580.36, found: 580.66.

To a solution of compound 165 (18 mg, 0.031 mmol) in EtOH (100 μL) was added a slurry of Pd/C (10% loading, 3.3 mg, 0.003 mmol) in EtOH (170 μL). The reaction vessel was charged with $H_2$ then evacuated three times and then charged with $H_2$ (1 atm). After 30 m, the reaction mixture was filtered, concentrated, and used in the next step without further purification. Yield of compound 166: 17 mg (99%). Mass calculated for $C_{31}H_4?N_5O_4$ $[M+H]^+$: 554.37. found: 554.73.

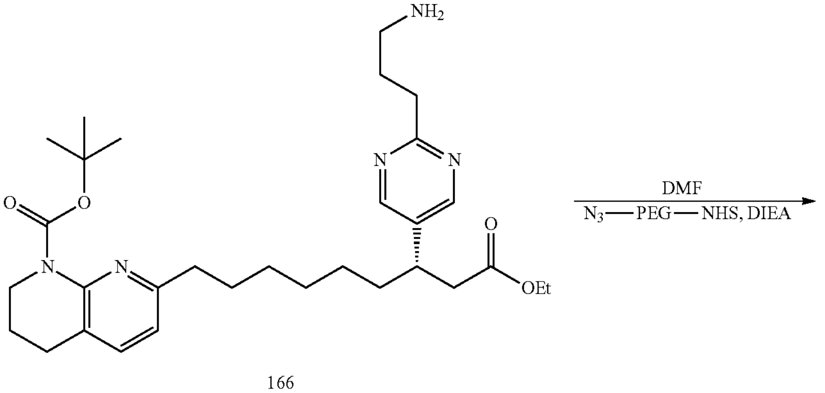

166

-continued

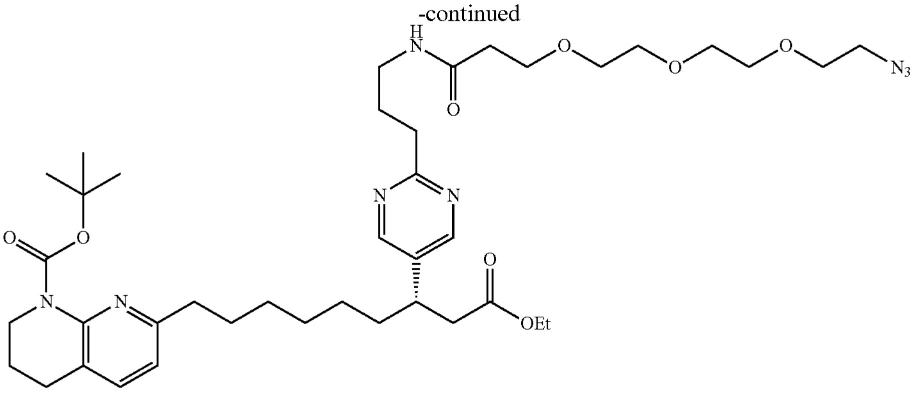

167

To a solution of compound 166 (17 mg, 0.031 mmol) and azido-PEG$_3$-NHS ester (14 mg, 0.040 mmol) in DMF (170 µL) was added DIEA (16 µL, 12 mg, 0.092 mmol) at room temperature. The reaction mixture was stirred for 1 h at room temperature, concentrated, and then used in the next step without purification. Mass calculated for $C_{40}H_{62}N_8O_8$ $[M+H]^+$: 783.48, found: 783.84.

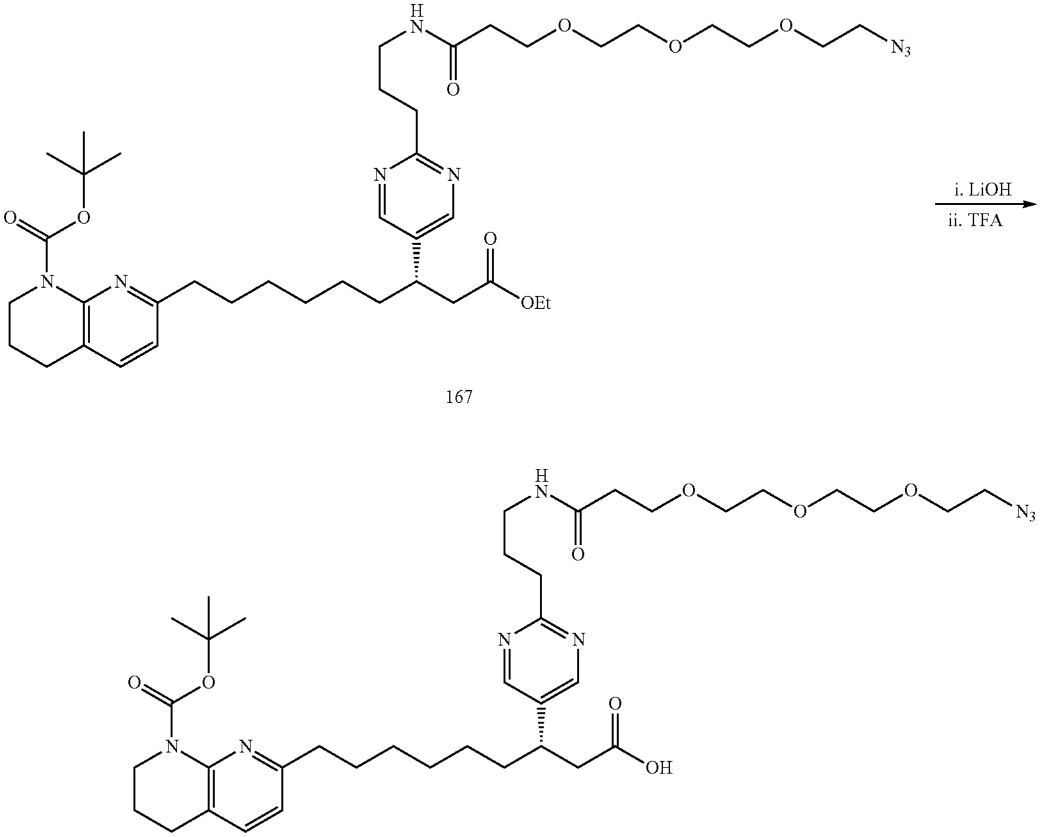

167

168

To a solution of compound 167 (24 mg, 0.031 mmol) in THF (180 µL) was added a 1 M solution of LiOH (153 µL, 0.153 mmol). The reaction mixture was heated at 40° C. After 1 hr, an additional portion of LiOH was added (153 uL, 0.153 mmol, 5 eq). The reaction mixture was stirred for 3 h at 40° C. then room temperature overnight. The reaction mixture was neutralized to pH=5 using 3 N HCl and concentrated. The residue was dissolved in TFA:water [95: 5] and stirred for 3 hours at room temperature. The reaction mixture was concentrated, and the residue was purified by RP-HPLC (Phenomenex Gemini C18 21.2×250 mm, 5 micron, water/ACN containing 0.1% TFA, 15-45% ACN gradient). Yield of compound 168 (Structure 39c): 9.8 mg (49%). Mass calculated for $C_{33}H_{50}N_8O_6$ $[M+H]^+$: 655.40, found: 656.01.

Example 2. Synthesis of Tridentate Integrin Targeting Ligands, RNAi Agents, and Conjugation of Integrin Targeting Ligands to Cargo Molecules (RNAi Agents)

The integrin targeting ligands can be conjugated to one or more RNAi agents useful for inhibiting the expression of one or more targeted genes in cells that express integrins. The integrin targeting ligands disclosed herein facilitate the delivery of the RNAi agents to the targeted cells and/or tissues. Example 1, above, described the synthesis of certain integrin targeting ligands disclosed herein. The following describes the general procedures for the syntheses of certain integrin targeting ligand-RNAi agent conjugates that are illustrated in the non-limiting Examples set forth herein.

A. Synthesis of RNAi Agents. RNAi agents can be synthesized using methods generally known in the art. For the synthesis of the RNAi agents illustrated in the Examples set forth herein, the sense and antisense strands of the RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the following 2'-O-methyl phosphoramidites were used. (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxy trityl-$N^2$-(isobutylyl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxy-ribose-5'-O-(2-cyanoethyl-N,N-diisopropylamino) phosphoramidites were purchased from ChemGenes (Wilmington, MA, USA). The following UNA phosphoramidites were used. 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA aminolink phosphoramidites were also commercially purchased (ThermoFisher).

In some examples, the integrin targeting ligands disclosed herein are conjugated to the RNAi agents by linking the components to a scaffold that includes a tri-alkyne group, or to a modified nucleotide comprising a propargyl group as shown in Table B, above. In some examples, the tri-alky ne group is added by using a tri-alkyne-containing phosphoramidite, which can be added at the 5' terminal end of the sense strand of an RNAi agent. When used in connection with the RNAi agents presented in certain Examples herein, tri-alky ne-containing phosphoramidites were dissolved in anhydrous dichloromethane or anhydrous acetonitrile (50 mM), while all other amidites were dissolved in anhydrous acetonitrile (50 mM), and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

Alternatively, where the integrin targeting ligands are conjugated to the RNAi agents via a tri-alkyne scaffold, instead of using a phosphoramidite approach, tri-alky ne-containing compounds can be introduced post-synthetically (see, for example, section E, below). When used in connection with the RNAi agents presented in certain Examples set forth herein, when attaching a tri-alkyne group post-synthetically to the 5' end of the sense strand the 5' terminal nucleotide of the sense strand was functionalized with a nucleotide that included a primary amine at the 5' end to facilitate attachment to the tri-alkyne-containing scaffold. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster. MA, USA) in anhydrous acetonitrile was employed.

In the examples set forth herein, the following shows the modified nucleotide sequence for the duplexes synthesized:

```
Duplex AD04545:
Modified Antisense Strand
Sequence (5' → 3'):
                                         (SEQ ID NO: 1)
usUfsusCfaUfgAfaAfuCfgUfuAfcGfuUfsg

Modified Sense Strand
Sequence (5' → 3'):
                                         (SEQ ID NO: 2)
(NE12-C6)scsaacguaaCfGtAfuuucaugaasa(invAb)

Duplex AD04546:
Modified Antisense Strand
Sequence (5' → 3'):
                                         (SEQ ID NO: 3)
usUfsusCfaUfgAfaAfuCfgUfuAfcGfuUfsg

Modified Sense Strand
Sequence (5' → 3'):
                                         (SEQ ID NO: 4)
(NH2-C6)scsaacguaaCfGfAfuuucaugaasa(invAb)

(C6-S-Mal-X)

DuplexAD05971:
Modified Antisense Strand
Sequence (5' → 3'):
                                         (SEQ ID NO: 5)
usUfsusCfaUfgAfaAfuCfgUfuAfcGfuUfsg

Modified Sense Strand
Sequence (5' → 3'):
                                         (SEQ ID NO: 6)
(NF12-C6)scsaacguaaCfGfAfuuuAlkcaAlkugAlkaa

Alksa(invAb)(C6-S-Mal-C18 diacid moiety)
```

For the modified nucleotide sequences listed above, a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; aAlk, cAlk, gAlk, and uAlk represent 2'-O-propargyl adenosine, cytidine, guanosine, or uridine, respectively; (invAb) represents an inverted abasic residue (inverted abasic deoxyribonucleotide); s represents a phosphorothioale linkage; (NH2-C6)s represents:

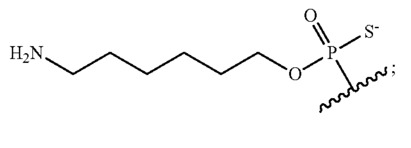

and
(C6-S-Mal-L) represents:

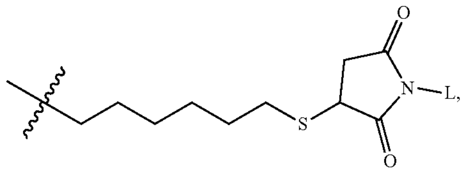

wherein L is a PEG chain, or ethyl, as indicated in the examples below. For the embodiments herein, when viewing the respective strand 5'→3', the inverted abasics are inserted such that the 3' position of the deoxy ribose is linked at the 3' end of the preceding monomer on the respective strand.

B. Cleavage and deprotection of support bound oligomer. After finalization of the solid phase synthesis, the dried solid support was treated with all volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification. Crude oligomers were purified by anionic exchange HPLC using a TSKgel SuperQ-5PW 13 μm column and Shimadzu LC-8 system. Buffer A was 20 mM Tris, 5 mM EDTA. pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water.

D. Annealing. Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.037 mg/(mL·cm), or, alternatively for some experiments, a conversion factor was calculated from an experimentally determined extinction coefficient.

E. Conjugation of Tri-alkyne scaffold. Either prior to or after annealing, the 5' or 3' amine functionalized sense strand of an RNAi agent can be conjugated to a tri-alkyne scaffold. Example tri-alkyne scaffold structures that can be used in forming the constructs disclosed herein include the following.

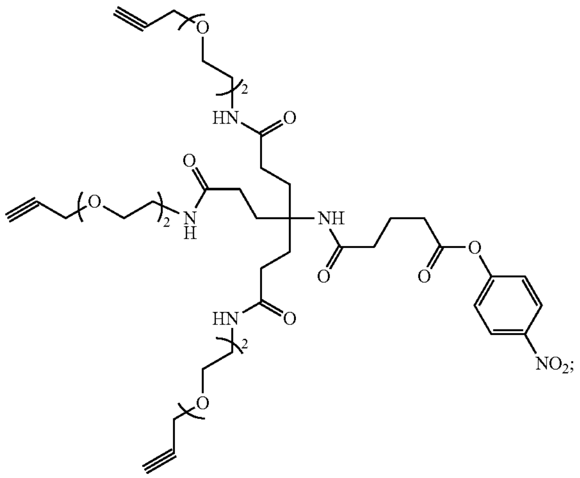

-continued

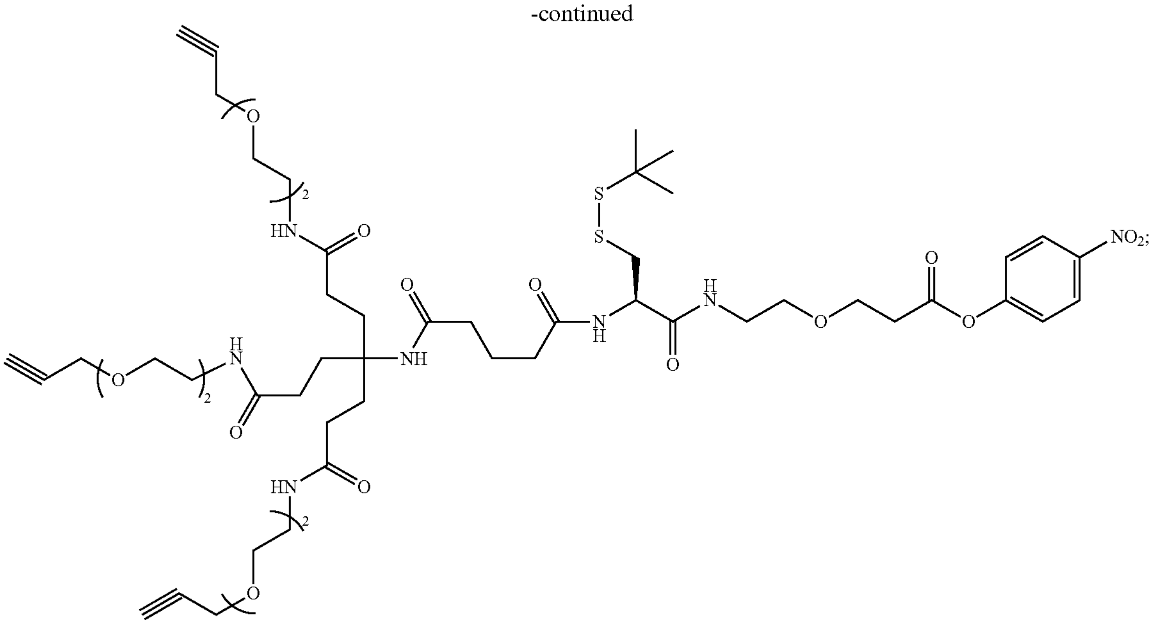

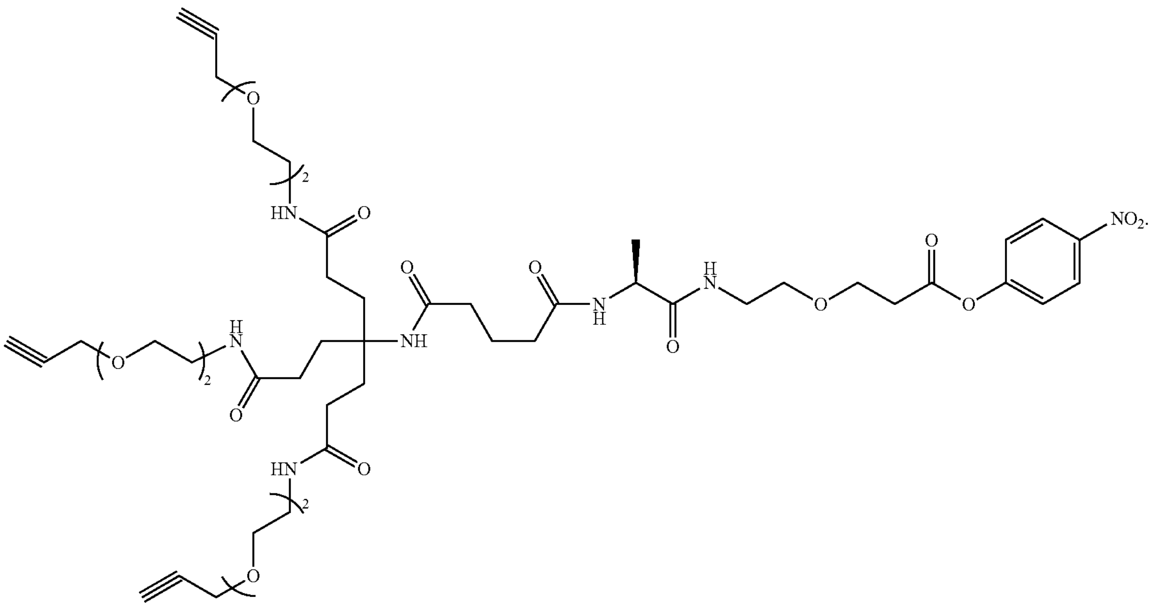

The following describes the conjugation of tri-alkyne scaffold to the annealed duplex: Amine functionalized duplex was dissolved in 90% DMSO/10% $H_2O$, at ~50-70 mg/mL. 40 eq triethylamine was added, followed by 3 eq tri-alkyne-PNP. Once complete, the conjugate was precipitated twice in a solvent system of 1× phosphate buffered saline/acetonitrile (1:14 ratio), and dried.

F. Conjugation of integrin targeting ligands. Either prior to or after annealing, the 5' or 3' tridentate alkyne functionalized sense strand is conjugated to the integrin targeting ligands. The following example describes the conjugation of αvβ3/5 integrin targeting ligands to the annealed duplex: Stock solutions of 0.5M Tris(3-hydroxypropyltriazolylmethyl)amine (THPTA), 0.5M of Cu(II) sulfate pentahydrate (Cu(II)$SO_4$.5$H_2O$) and 2M solution of sodium ascorbate were prepared in deionized water. A 75 mg/mL solution in DMSO of integrin targeting ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed, integrin targeting ligand was added to the reaction (6 eq/duplex, 2 eq/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M $Cu(II)SO_4.5H_2O$, vortexed, and incubated at room temp for 5 min. After 5 min, THPTA/Cu solution (7.2 μL, 6 eq 5:1 THPTA:Cu) was added to the reaction vial, and vortexed. Immediately afterwards, 2M ascorbate (5 μL, 50 eq per duplex, 16.7 per alkyne) was added to the reaction vial and vortexed. Once the reaction was complete (typically complete in 0.5-1 h), the reaction was immediately purified by non-denaturing anion exchange chromatography.

G. Functionalization of Thiol group on Cysteine Linker. In some embodiments, a cysteine linker can be used to facilitate conjugation of the integrin targeting ligands to the RNAi agent. Either prior to or after annealing, the 5' or 3' tridentate alkyne-Cys(Stbu)-$PEG_2$ functionalized sense strand is functionalized with a maleimide-containing moiety, or can be reduced and left as the free thiol, as shown in the following structure:

Example 3. Binding Activity of Integrin Targeting Ligands

As reported in the following Table 1, IC50 binding data was obtained for the integrin targeting ligands of Structures 1c, 2c, and 3c, as w ell as an RGD-mimetic peptide:

TABLE 1

IC50 Binding Activity.

| Group | IC50 (nM) αvβ3 | αvβ5 | αvβ6 |
|---|---|---|---|
| Structure 1c | 0.3 | 0.6 | 5.3 |
| Structure 2c | 0.3 | 5.6 | 8.9 |
| Structure 3c | 0.8 | 1.8 | 81 |
| RGD-mimetic peptide | 1.6 | 2.5 | 81 |

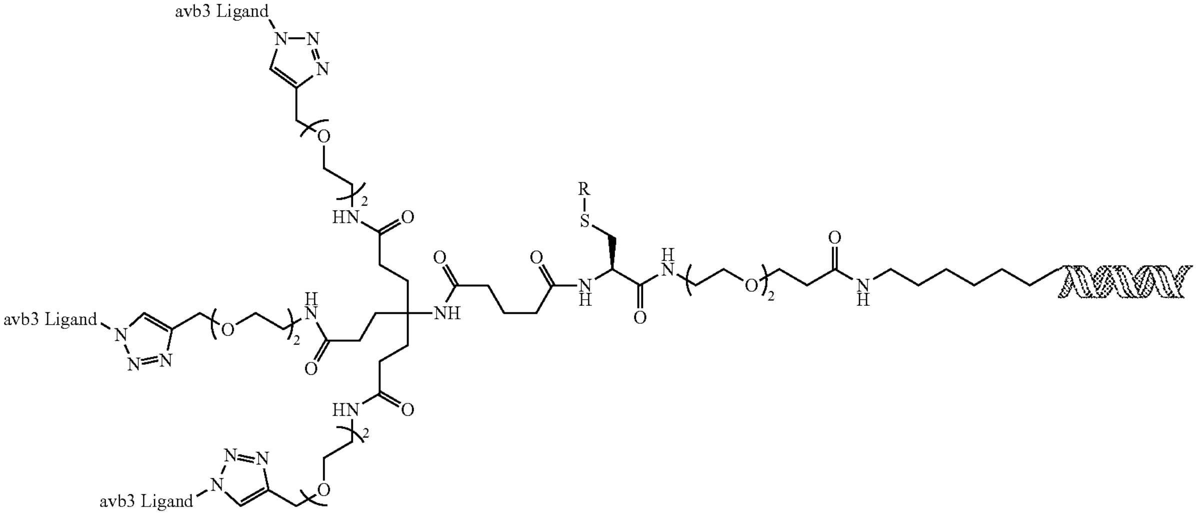

R = H or

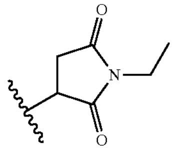

The following example describes the modification of the tri-alkyne-Cys(Stbu)-$PEG_2$-duplex with N-ethyl maleimide: Tri-alky ne-Cys(Stbu)-$PEG_2$-duplex (35 mg) was dissolved in 500 μL deionized $H_2O$. HEPES buffer (1M, pH 8.5, 82 μL), was added to the reaction, and the solution was vortexed. A solution of 1 M Dithiothreitol (DTT, 100 eq, 236 μL) was added and the solution was placed on a vortex shaker for 3 h. After confirmation of reduction of the disulfide by denaturing RP-HPLC, the conjugate was precipitated three times in a solvent system of 1× phosphate buffered saline-acetonitrile (1:14 ratio). The precipitated pellet was reconstituted in 0.5 mL of 0.1 M HEPES, pH 6.5, and N-ethyl maleimide (3 mg, 10 eq) was added to the solution, and placed on a vortex mixer for ~15 min. After completion of the reaction, the conjugate was precipitated three times in a solvent system of 1× phosphate buffered saline acetonitrile (1.14 ratio), desalted, and dried.

As shown in Table 1, above, Structures 1, 2, and 3 each showed potent binding to αvβ3 integrin and αvβ5 integrin, with Structures 2 and 3, for example, showing a particular preference for binding to αvβ3 integrin (IC50=0.3 nM and 0.8 nM, respectively). Further, each of Structure 1, 2, and 3, showed a slightly increased binding activity to αvβ3 integrin compared to an RGD-mimetic peptide (See, e.g., RGD-mimetic ligand structures disclosed in U.S. Pat. No. 9,487,556). Moreover, while the RGD-mimetic ligand is shown to have binding activity, the integrin targeting ligands of the present disclosure have increased stability, both with respect to serum stability in vim and chemical stability ex vim, compared to such peptide-based RGD-mimetic ligands.

Example 4. Kidney Tumor Bearing Mouse Model (Orthotopic Xenograft)

Creation of SEAP-expressing clear cell renal cell carcinoma (ccRCC) A498 cells.

A pCR3.1 expression vector expressing the reporter gene secreted alkaline phosphatase (SEAP) under the CMV promoter was prepared by directional cloning of the SEAP coding sequence PCR amplified from Clontech's pSEAP2-basic vector. Convenient restriction sites were added onto primers used to amplify the SEAP coding sequence for cloning into the pCR3.1 vector (Invitrogen). The resultant construct pCR3-SEAP was used to create a SEAP-expressing A498 ccRCC cell line. Briefly, pCR3-SEAP plasmid was transfected into A498 ccRCC cells by electroporation following manufacturer's recommendation. Stable transfectants were selected by G418 resistance. Selected A498-SEAP clones were evaluated for SEAP expression and integration stability.

Implantation of SEAP-expressing clear cell renal cell carcinoma (ccRCC) A498 cells.

Female athymic nude mice were anesthetized with ~3% isoflorane and placed in the right lateral decubitus position. A small, 0.5-1 cm, longitudinally abdominal incision in the left flank was made. Using a moist cotton swab, the left kidney was lifted out of the peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 μl aliquot of 2:1 (vol:vol) cell/Matrigel® mixture containing about 300,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Serum was collected every 7-14 days after implantation to monitor tumor growth using a commercial SEAP assay kit. For most studies, tumor mice were used 5-6 weeks after implantation, when tumor measurements were typically around 4-8 mm.

Determination of HIF2 mRNA Expression.

For the studies reported in the Examples herein, mice were euthanized the identified day after injection and total RNA was isolated from kidney tumor using Trizol reagent following manufacturer's recommendation. Relative HiF2α mRNA levels were determined by RT-qPCR as described below and compared to mice treated with delivery buffer (isotonic glucose) only.

In preparation for quantitative PCR, total RNA was isolated from tissue samples homogenized in TriReagent (Molecular Research Center, Cincinnati, OH) following the manufacturer's protocol. Approximately 500 ng RNA was reverse-transcribed using the High Capacity cDNA Reverse Transcription Kit (Life Technologies). For human (tumor) Hif2α (EPAS1) expression, pre-manufactured TaqMan gene expression assays for human Hif2α (Catalog #4331182) and CycA (PPIA) Catalog #: 4326316E) were used in biplex reactions in triplicate using TaqMan Gene Expression Master Mix (Life Technologies) or VeriQuest Probe Master Mix (Affymetrix) Quantitative PCR was performed by using a 7500 Fast or StepOnePlus Real-Time PCR system (Life Technologies). The $\Delta\Delta C_T$ method was used to calculate relative gene expression.

Example 5. In Vivo Administration of Integrin Targeting Ligands Conjugated to RNAi Agents Targeting H1F-2 Alpha (EPAS1) in Kidney Tumor Bearing Mice RNAi agents that included a sense strand and an antisense strand were synthesized according to phosphoramidite technology on solid phase in accordance with general procedures known in the art and commonly used in oligonucleotide synthesis, as set forth in Example 2 herein. The RNAi agents included an antisense strand having a nucleobase sequence at least partially complementary to the HIF-2 alpha (Hif2α or EPAS1) gene. EPAS1 is a member of the HIF (hypoxia inducible factor) gene family and encodes half of a transcription factor involved in the induction of genes regulated by oxygen, and which is induced as oxygen levels fall (a condition known as hypoxia), and is known to be frequently overexpressed in clear cell renal carcinoma cells. The Hif2α RNAi agents were designed to be capable of degrading or inhibiting translation of messenger RNA (mRNA) transcripts of Hif2α in a sequence specific manner, thereby inhibiting expression of an EPAS1 gene. The Hif2α RNAi agents were comprised of modified nucleotides and more than one non-phosphodiester linkage.

On study day 1, kidney tumor bearing mice (see Example 4) were dosed via tail vein injection according to the following dosing Groups:

TABLE 2

Dosing Groups of Kidney Tumor Bearing Mice in Example 5.

| Group | RNAi Agent and Dose | Dosing Regimen |
|---|---|---|
| 1 | Isotonic glucose (5% dextrose in water (d5w)) (no RNAi agent) | Single injection on day 1 |
| 2 | 7.5 mg/kg of Hif2α RNAi agent (AD04546) conjugated to a 40 kilodalton (kDa) PEG moiety (with no integrin targeting ligand attached), formulated in isotonic glucose. | Single injection on day 1 |
| 3 | 7.5 mg/kg of Hif2α RNAi agent (AD04546) conjugated to an RGD-mimetic peptide-based ligand, and further including a 40 kDa PEG moiety linked to the construct, formulated in isotonic glucose. | Single injection on day 1 |
| 4 | 7.5 mg/kg of Hif2α RNAi agent (AD04546) conjugated to an integrin targeting ligand of Structure 1a, and further including a 40 kDa PEG moiety linked to the construct, formulated in isotonic glucose. | Single injection on day 1 |

TABLE 2-continued

| Dosing Groups of Kidney Tumor Bearing Mice in Example 5. | | |
|---|---|---|
| Group | RNAi Agent and Dose | Dosing Regimen |
| 5 | 7.5 mg/kg of Hif2α RNAi agent (AD04546) conjugated to an integrin targeting ligand of Structure 2a, and further including a 40 kDa PEG moiety linked to the construct, formulated in isotonic glucose. | Single injection on day 1 |
| 6 | 7.5 mg/kg of Hif2α RNAi agent (AD04546) conjugated to four integrin targeting ligands of Structure 2a (i.e., a tetradentate targeting group), and further including a 40 kDa PEG moiety linked to the construct, formulated in isotonic glucose. | Single injection on day 1 |
| 7 | 7.5 mg/kg of Hif2α RNAi agent (AD04545) conjugated to a cluster containing four integrin targeting ligand of Structure 2a (i.e., a tetradentate targeting group) (without a PEG moiety), formulated in isotonic glucose. | Single injection on day 1 |
| 8 | 7.5 mg/kg of Hif2α RNAi agent (AD04546) conjugated to an integrin targeting ligand of Structure 2a, and further including a 20 kDa PEG moiety linked to the construct, formulated in isotonic glucose. | Single injection on day 1 |

The RNAi agents in Example 5 were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands (or, for Group 3, to the RGD-mimetic peptide-based ligand). The modified sequences of the RNAi agents are shown in Example 2, above. For Groups 4 and 5, a single integrin targeting ligand (referred to herein as a "monodentate" ligand) was conjugated to the RNAi agent via a DBCO-$PEG_5$-NHS ester linker (BroadPharm), which was conjugated to the terminal primary amine on the 5' terminal end of the sense strand. The respective integrin targeting ligands were synthesized having an azide reactive group (see, e.g., Example 1), which was then conjugated to the DBCO component of the linker.

The RNAi agents were synthesized having a PK modulator referred to as "20 kDA PEG moiety" or "40 kDA PEG moiety" having the structure:

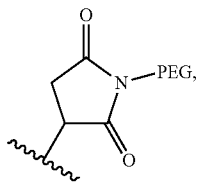

wherein ⌇ indicates the point of attachment to the RNAi agent at the C6-S— group as indicated in AD04546 (see Example 2), and PEG indicates a 20 kDa or 40 kDa PEG chain. The PK modulator was conjugated to the 3' end of the sense strand by reducing the C6-SS-C6 group, as shown in Table A, which then underwent Michael addition with the following compound:

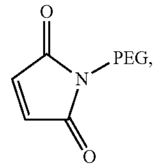

wherein PEG indicates a 20 kDa or 40 kDa PEG chain.

For Groups 6 and 7, four integrin targeting ligands were conjugated via a tetradentate scaffold that included a DBCO functionalized PAMAM-G1 cystamine core having a general structure represented by the following:

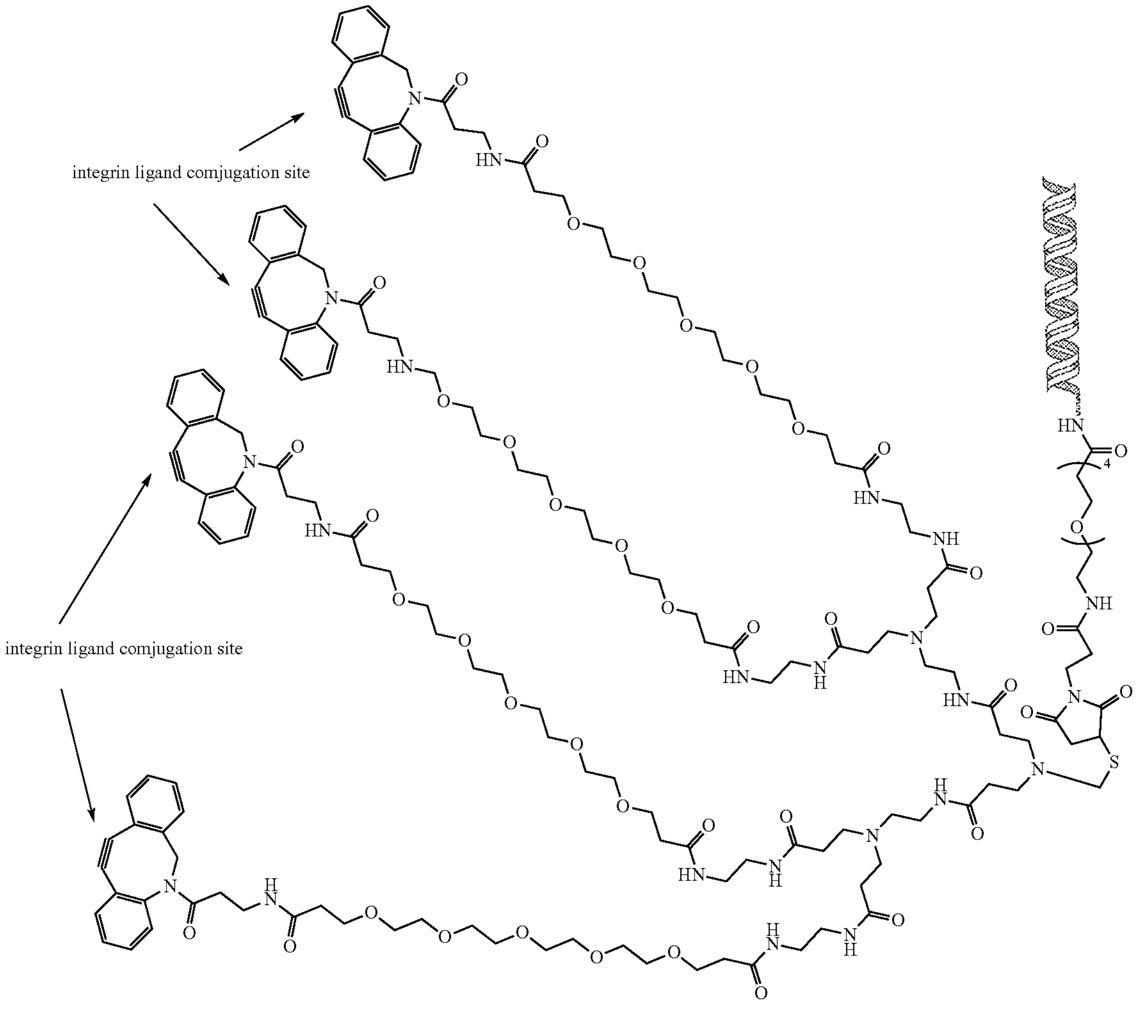

As noted in Table 2 above, in some Groups, a 40 kDa or 20 kDa PEG moiety was attached to serve as a PK enhancer to increase circulation time of the drug product-conjugate. The 40 kDa or 20 kDa PEG moiety was attached using a reagent of the formula:

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 3

Average Relative huHif2α mRNA Expression at Sacrifice in Example 5.

| Group ID | Average Relative huHIF2α mRNA Expression | Low (error) | High (error) |
|---|---|---|---|
| Group 1 (isotonic glucose) | 1.000 | 0.069 | 0.074 |
| Group 2 (7.5 mg/kg RNAi agent) (no ligand, 40 kDa PEG) | 0.563 | 0.016 | 0.017 |
| Group 3 (7.5 mg/kg RNAi agent-RGD mimetic peptide-based ligand, 40 kDa PEG) | 0.400 | 0.087 | 0.112 |
| Group 4 (7.5 mg/kg RNAi agent-integrin targeting ligand of Structure 1a, 40 kDa PEG) | 0.390 | 0.027 | 0.029 |
| Group 5 (7.5 mg/kg RNAi agent-integrin targeting ligand of Structure 2a, 40 kDa PEG) | 0.308 | 0.061 | 0.077 |
| Group 6 (7.5 mg/kg RNAi agent-tetradentate targeting group of integrin targeting ligand Structure 2a, 40 kDa PEG) | 0.289 | 0.069 | 0.091 |
| Group 7 (7.5 mg/kg RNAi agent-tetradentate targeting group of integrin targeting ligand Structure 2a) | 0.589 | 0.050 | 0.054 |
| Group 8 (7.5 mg/kg RNAi agent-integrin targeting ligand Structure 2a, 20 kDa PEG) | 0.647 | 0.098 | 0.115 |

As shown in Table 3 above, each of the Hif2α RNAi agents showed a reduction in mRNA expression in mice compared to control. The inclusion of a 40 kDa PEG moiety as a PK enhancer generally improved inhibition of expression of the targeted gene. Moreover, a comparison of Groups 3, 4, and 5 showed that the integrin targeting ligand of Structure 1a described herein was comparable to an RGD mimetic peptide-based ligand that is known to have affinity to αvβ3, and the ligand of Structure 2a showed a nearly 10% improvement in knockdown over the RGD mimetic ligand. For example. Group 3 (RGD mimetic) had approximately 60% knockdown (0.400); Group 4 (Structure 1a) had approximately 61% knockdown (0.390); and Group 5 (Structure 2a) had approximately 69% knockdown (0.308).

Importantly, the data also showed ligand dependency, as the inclusion of an integrin targeting ligand disclosed herein showed improvement as compared to the same construct without ligand. For example, Group 6 (tridentate integrin targeting ligand Structure 2a) exhibited approximately 72% knockdown (0.289), as compared to Group 2 (no integrin targeting ligand), which exhibited only approximately 44% knockdown (0.563).

Additionally, Group 6 showed a small improvement over Group 5, indicating a slight preference for a multi-dentate ligand over a monodentate ligand; however, both forms were active and delivered the RNAi agent to the kidney (as shown by inhibition of gene expression by the RNAi agent).

Example 6. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 4

Dosing Groups of Kidney Tumor Bearing Mice in Example 6.

| Group | RNAi Agent and Dose | Dosing Regimen |
|---|---|---|
| 1 | Isotonic glucose (d5w) (no RNAi agent) | Single injection on day 1 |
| 2 | 30 mg/kg of Hif2α RNAi agent (AD04546) conjugated to an RGD-mimetic peptide-based ligand, and further including a 40 kDa PEG moiety linked to the construct, formulated in isotonic glucose. | Single injection on day 1 |
| 3 | 15 mg/kg of Hif2α RNAi agent (AD04546) conjugated to an RGD-mimetic peptide-based ligand and further including a 40 kDa PEG moiety linked to the construct, formulated in isotonic glucose. | Single injection on day 1 |

TABLE 4-continued

| Dosing Groups of Kidney Tumor Bearing Mice in Example 6. | | |
|---|---|---|
| Group | RNAi Agent and Dose | Dosing Regimen |
| 4 | 7.5 mg/kg of Hif2α RNAi agent (AD04546) conjugated to an RGD-mimetic peptide-based ligand and further including a 40 kDa PEG moiety linked to the construct, formulated in isotonic glucose. | Single injection on day 1 |
| 5 | 30 mg/kg of Hif2α RNAi agent (AD04546) conjugated to an integrin targeting ligand of Structure 2a and further including a 40 kDa PEG moiety linked to the construct, formulated in isotonic glucose. | Single injection on day 1 |
| 6 | 15 mg/kg of Hif2α RNAi agent (AD04546) conjugated to an integrin targeting ligand of Structure 2a and further including a 40 kDa PEG moiety linked to the construct, formulated in isotonic glucose. | Single injection on day 1 |

The RNAi agents were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands (or, for groups 2, 3 and 4, to the RGD mimetic peptide). For Groups 5 and 6, a single integrin targeting ligand ("monodentate" ligand) was conjugated to the RNAi agent via the following DBCO-$PEG_5$-NHS ester:

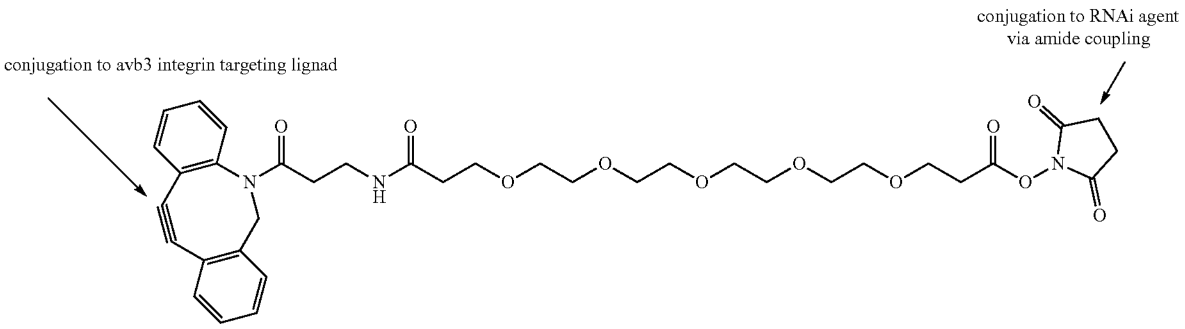 [SMILES: O=C(CCOCCOCCOCCOCCOCCC(=O)ON1C(=O)CCC1=O)NCCC(=O)N1Cc2ccccc2C#Cc2ccccc21]

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 5

| Average Relative Human Hif2α mRNA Expression at Sacrifice in Example 6. | | | |
|---|---|---|---|
| Group ID | Average Relative huHIF2α mRNA Expression | Low (error) | High (error) |
| Group 1 (isotonic glucose) | 1.000 | 0.072 | 0.078 |
| Group 2 (30 mg/kg RNAi agent-RGD peptide-based ligand, 40 kDa PEG) | 0.300 | 0.041 | 0.047 |
| Group 3 (15 mg/kg RNAi agent-RGD peptide-based ligand, 40 kDa PEG) | 0.330 | 0.080 | 0.106 |
| Group 4 (7.5 mg/kg RNAi agent-RGD peptide-based ligand, 40 kDa PEG) | 0.446 | 0.068 | 0.080 |
| Group 5 (30 mg/kg RNAi agent-integrin targeting ligand Structure 2a, 40 kDa PEG) | 0.198 | 0.007 | 0.007 |
| Group 6 (15 mg/kg RNAi agent-integrin targeting ligand Structure 2a, 40 kDa PEG) | 0.271 | 0.012 | 0.012 |

As shown in Table 5 above, each of the Hif2α RNAi agents showed a reduction in mRNA expression compared to control. Moreover, Groups 5 and 6, which contained the integrin targeting ligand of Structure 2a disclosed herein, showed improvement in knockdown of Hif2α mRNA compared to the RGD-mimetic peptide-based ligands of Groups 2 and 3. (e.g., compare Group 6 (approximately 73% knockdown at 15 mg/kg RNAi agent (0.271)) with Group 3 (approximately 67% knockdown at 15 mg/kg RNAi agent (0.330)).

Example 7. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (ERAS1).

On study day 1, kidney tumor bearing mice (see Example 4) were dosed via tail vein injection according to the following dosing Groups:

TABLE 6

Dosing Groups of Kidney Tumor Bearing Mice in Example 7.

| Group | RNAi Agent and Dose | Dosing Regimen |
|---|---|---|
| 1 | Isotonic glucose (d5w (5% dextrose in water)) (no RNAi agent) | Single injection on day 1 |
| 2 | 7.5 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |
| 3 | 30 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |
| 4 | 7.5 mg/kg of Hif2α RNAi agent (AD04546) conjugated to a tridentate integrin targeting ligand of Structure 2.8a, and further including a 40 kDa PEG moiety linked to the construct, formulated in isotonic glucose. | Single injection on day 1 |
| 5 | 7.5 mg/kg of Hif2α RNAi agent (AD04546) conjugated to a tridentate integrin targeting ligand of Structure 2.9a, and further including a 40 kDa PEG moiety linked to the construct, formulated in isotonic glucose. | Single injection on day 1 |
| 6 | 7.5 mg/kg of Hif2α RNAi agent (AD04546) conjugated to a tridentate integrin targeting ligand of Structure 2.10a, and further including a 40 kDa PEG moiety linked to the construct, formulated in isotonic glucose. | Single injection on day 1 |
| 7 | 7.5 mg/kg of Hif2α RNAi agent (AD04546) conjugated to a tridentate integrin targeting ligand of Structure 2.10a, and further including an N-ethyl maleimide attached to a 3' thiol on the sense strand, formulated in isotonic glucose. | Single injection on day 1 |
| 8 | 7.5 mg/kg of Hif2α RNAi agent (AD04546) conjugated to a monodentate integrin targeting ligand of Structure 2a, and further including a 40 kDa PEG moiety linked to the construct, formulated in isotonic glucose. | Single injection on day 1 |

The RNAi agents were synthesized having nucleotide sequences directed to target the human Hif2α gene and included a functionalized amine reactive group ($NH_2$—$C_6$) at the 5' terminal end of the sense strand to facilitate conjugation to the integrin targeting ligands. For Groups 2 through 7, the following compound was used to functionalize the conjugate with tridentate scaffolds:

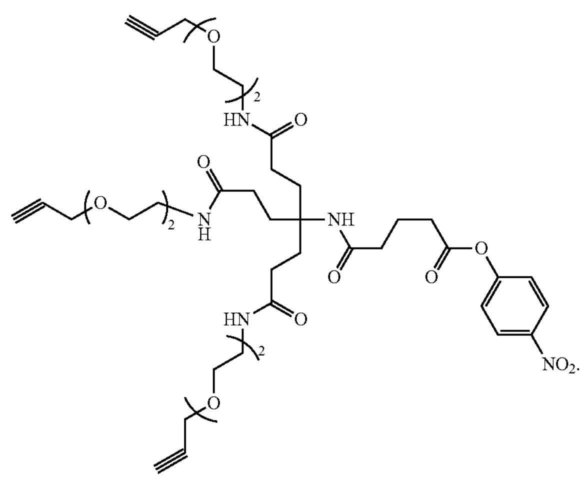

For Group 8, an alkyne-$PEG_4$-NHS ester was used to link the monodentate integrin targeting ligand to the 5' amine on the sense strand. As set forth herein. Groups 4 through 7 used integrin targeting ligands with varied PEG lengths.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 7

| Average Relative Hif2α mRNA Expression at Sacrifice in Example 7. | | | |
|---|---|---|---|
| Group ID | Average Relative huHIF2α mRNA Expression | Low (error) | High (error) |
| Group 1 (isotonic glucose) | 1.000 | 0.078 | 0.085 |
| Group 2 (7.5 mg/kg RNAi agent-tridentate integrin targeting ligand of Structure 2a, 40 kDa PEG) | 0.361 | 0.025 | 0.026 |
| Group 3 (30 mg/kg RNAi agent-tridentate integrin targeting ligand of Structure 2a, 40 kDa PEG) | 0.259 | 0.024 | 0.026 |
| Group 4 (7.5 mg/kg RNAi agent-tridentate integrin targeting ligand of Structure 2.8a, 40 kDa PEG) | 0.428 | 0.062 | 0.073 |
| Group 5 (7.5 mg/kg RNAi agent-tridentate integrin targeting ligand of Structure 2.9a, 40 kDa PEG) | 0.481 | 0.014 | 0.014 |
| Group 6 (7.5 mg/kg RNAi agent-tridentate integrin targeting ligand of Structure 2.10a, 40 kDa PEG) | 0.419 | 0.040 | 0.044 |
| Group 7 (7.5 mg/kg RNAi agent-tridentate integrin targeting ligand of Structure 2.10a, N-ethyl-maleimide) | 0.627 | 0.054 | 0.060 |
| Group 8 (7.5 mg/kg RNAi agent-monodentate integrin targeting ligand of Structure 2a, 40 kDa PEG) | 0.537 | 0.041 | 0.045 |

As shown in Table 7 above, each of the Hif2α RNAi agents showed a reduction in mRNA expression in mice compared to control. For example. Group 2, which included a dose of 7.5 mg/kg RNAi agent conjugated to the tridentate integrin targeting ligand of Structure 2a (which includes a $PEG_4$ group) showed approximately 64% knockdown of Hif2α (0.361). Additionally, while the constructs that increased the length of the PEG group to up to $PEG_{36}$ (e.g., Groups 6 and 7) all showed knockdown, no benefit was seen as compared to the $PEG_4$ group that is present in Structure 2a.

Example 8. Dose Response Study of In Vivo Administration of Integrin Targeting Ligands Conjugated to RNAi Agents Targeting H1F-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 8

| Dosing Groups of Kidney Tumor Bearing Mice in Example 8. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 7.5 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |
| 3 | 10 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |
| 4 | 20 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |

TABLE 8-continued

| Dosing Groups of Kidney Tumor Bearing Mice in Example 8. | | |
|---|---|---|
| Group | RNAi Agent and Dose | Dosing Regimen |
| 5 | 30 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |

The RNAi agents were synthesized having nucleotide sequences directed to target the human Hif2α gene, and included a functionalized amine reactive group ($NH_2—C_6$) at the 5' terminal end of the sense strand to facilitate conjugation to the integrin targeting ligands. Each of the Groups had tridentate integrin ligands of Structure 2a, as depicted by the following structure:

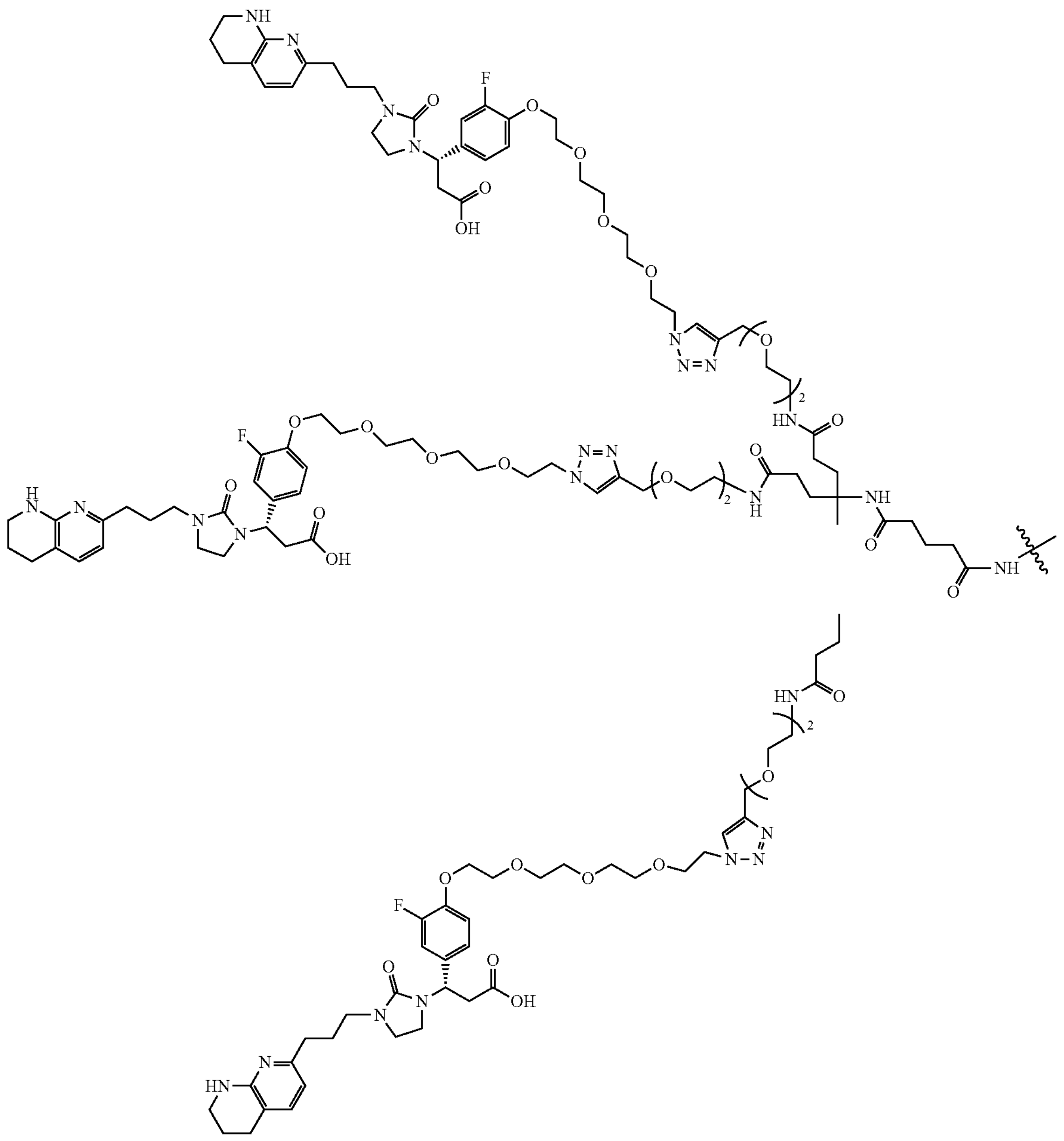

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 9

Average Relative Human Hif2α mRNA Expression at Sacrifice in Example 8.

| Group ID | Average Relative huHIF2α mRNA Expression | Low (error) | High (error) |
|---|---|---|---|
| Group 1 (isotonic glucose) | 1.000 | 0.131 | 0.150 |
| Group 2 (7.5 mg/kg RNAi agent) | 0.313 | 0.027 | 0.030 |
| Group 3 (10 mg/kg RNAi agent) | 0.349 | 0.033 | 0.036 |
| Group 4 (20 mg/kg RNAi agent) | 0.216 | 0.040 | 0.050 |
| Group 5 (30 mg/kg RNAi agent) | 0.203 | 0.035 | 0.042 |

As shown in Table 9 above, the Hi2α RNAi agents conjugated to the integrin targeting ligand of Structure 2a disclosed herein showed a reduction in mRNA expression in mice compared to control across all dosage levels.

Example 9. Duration of Knockdown of RNAi Agents Targeting HIF-2 Alpha Conjugated to Integrin Targeting Ligands in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups.

TABLE 10

Dosing Groups of Mice in Example 9.

| Group | RNAi Agent and Dose | Dosing Regimen |
|---|---|---|
| 1 | Isotonic glucose (d5w (5% dextrose in water)) (no RNAi agent); mice euthanized on day 5 | Single injection on day 1 |
| 1A | Isotonic glucose (d5w (5% dextrose in water)) (no RNAi agent); mice euthanized on day 22 | Single injection on day 1 |
| 2 | 20 mg/kg of Hif2α RNAi agent (AD04546) conjugated to a tridentate integrin targeting ligand of Structure 2a, and further including a 40 kDa PEG moiety linked to the construct, formulated in isotonic glucose; mice euthanized on day 5. | Single injection on day 1 |
| 3 | 20 mg/kg of Hif2α RNAi agent (AD04546) conjugated to a tridentate integrin targeting ligand of Structure 2a, and further including a 40 kDa PEG moiety linked to the construct, formulated in isotonic glucose; mice euthanized on day 8. | Single injection on day 1 |
| 4 | 20 mg/kg of Hif2α RNAi agent (AD04546) conjugated to a tridentate integrin targeting ligand of Structure 2a, and further including a 40 kDa PEG moiety linked to the construct, formulated in isotonic glucose; mice euthanized on day 15. | Single injection on day 1 |
| 5 | 20 mg/kg of Hif2α RNAi agent (AD04546) conjugated to a tridentate integrin targeting ligand of Structure 2a, and further including a 40 kDa PEG moiety linked to the construct, formulated in isotonic glucose; mice euthanized on day 22. | Single injection on day 1 |

Mice in Groups 1 and 2 were euthanized on day 5 after injection; mice in Group 3 were euthanized on day 8 after injection; mice in Group 4 were euthanized on day 15 after injection; and mice in Groups 1A and 5 were euthanized on day 22 after injection.

For the vehicle control groups, two mice were dosed in Group 1 and three mice were dosed in Group 1A. For the RNAi-agent-integrin targeting ligand containing groups (i.e., Groups 2, 3, 4, and 5) four (4) tumor bearing mice were dosed in each group (n=4). Total RNA was isolated from kidney tumor according to the procedures set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 11

Average Relative Human Hif2α mRNA Expression at Sacrifice in Example 9.

| Group ID | Average Relative huHIF2α mRNA Expression | Low (error) | High (error) |
|---|---|---|---|
| Group 1 (isotonic glucose; day 5 sacrifice) | 0.741 | 0.028 | 0.029 |
| Group 1A (isotonic glucose; day 22 sacrifice) | 1.000 | 0.066 | 0.070 |
| Group 2 (7.5 mg/kg RNAi agent-tridentate integrin targeting ligand of Structure 2a, 40 kDa PEG; day 5 sacrifice) | 0.262 | 0.028 | 0.031 |
| Group 3 (7.5 mg/kg RNAi agent-tridentate integrin targeting ligand of Structure 2a, 40 kDa PEG; day 5 sacrifice) | 0.202 | 0.021 | 0.023 |
| Group 4 (7.5 mg/kg RNAi agent-tridentate integrin targeting ligand of Structure 2a, 40 kDa PEG; day 8 sacrifice) | 0.233 | 0.034 | 0.039 |
| Group 5 (7.5 mg/kg RNAi agent-tridentate integrin targeting ligand of Structure 2a, 40 kDa PEG; day 15 sacrifice) | 0.299 | 0.017 | 0.018 |

As shown in Table 11 above, the Hif2α RNAi agents continued to show a reduction in mRNA expression compared to control at day 22 (approximately 70% knockdown at day 22 (0.299)).

Example 10. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 12

Dosing Groups of Mice in Example 10.

| Group | RNAi Agent and Dose | Dosing Regimen |
|---|---|---|
| 1 | Isotonic glucose (d5w (5% dextrose in water)) (no RNAi agent) | Single injection on day 1 |
| 2 | 7.5 mg/kg of Hif2α RNAi agent (AD04546) conjugated to a tridentate integrin targeting ligand of Structure 2a, and further including a 40 kDa PEG moiety linked to the construct, formulated in isotonic glucose. | Single injection on day 1 |
| 3 | 7.5 mg/kg of Hif2α RNAi agent (AD04546) conjugated to a tridentate integrin targeting ligand of Structure 2.6a, and further including a 40 kDa PEG moiety linked to the construct, formulated in isotonic glucose. | Single injection on day 1 |

The RNAi agents were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 13

| Average Relative Hif2α mRNA Expression at Sacrifice in Example 10. | | | |
|---|---|---|---|
| Group ID | Average Relative huHIF2α mRNA Expression | Low (error) | High (error) |
| Group 1 (isotonic glucose) | 1.000 | 0.087 | 0.095 |
| Group 2 (7.5 mg/kg RNAi agent-tridentate integrin targeting ligand of Structure 2a, 40 kDa PEG) | 0.351 | 0.080 | 0.104 |
| Group 3 (7.5 mg/kg RNAi agent-tridentate integrin targeting ligand of Structure 2.6a, 40 kDa PEG) | 0.441 | 0.040 | 0.043 |

As shown in Table 13 above, each of the Hif2α RNAi agent-integrin targeting ligand conjugates showed a reduction in mRNA expression in mice compared to control. For example, Group 2, which included a dose of 7.5 mg/kg RNAi agent conjugated to the tridentate integrin targeting ligand of Structure 2a, showed approximately 65% knockdown of Hif2α mRNA (0.351).

Example 11. In Vivo Administration of Integrin Targeting Ligands Conjugated to RNAi Agents Targeting HIF-2 Alpha in αvβ3 KO A498 Kidney Tumor Bearing Mice Clear cell renal cell carcinoma (ccRCC) A498 tumor cells express both αvβ3 and αvβ5 integrins, with αvβ3 expression about 4-fold higher than αvβ5 by flow-cytometry analysis. To evaluate the contribution of αvβ5 in this model, αvβ3 knockout (KO) A498 cells were synthesized via gene editing technology. Knockout of integrin αvβ3 was confirmed by genomic sequencing and immunohistochemistry staining of αvβ3, which showed that staining was negative in the αvβ3 KO A498 cells. Kidney tumor bearing mice with A498 WT (with both αvβ3 and αvβ5) and αvβ3 KO A498 cells were prepared as described above in Example 4.

On study day 1, kidney tumor bearing mice were dosed via tail vein injection. Three (3) tumor bearing mice were dosed in each Group set forth in Table 13, below (n=3). Mice were sacrificed on study day 8 after injection, and total RNA was isolated from kidney tumor as set forth in Example 4. Relative Human HIF2α mRNA expression was quantitated by probe-based quantitative PCR (RT-qPCR), normalized to human Cyclophilin A (PPIA) expression and expressed as fraction of vehicle control group (isotonic glucose) (geometric mean. +/−95% confidence interval), as set forth in Example 4.

TABLE 14

| Average Relative Hif2α mRNA Expression at Sacrifice in Example 11. | | | | |
|---|---|---|---|---|
| Group ID | Tumor | Average Relative huHIF2α mRNA Expression | Low (error) | High (error) |
| Group 1 (isotonic glucose) | A498 WT | 1.000 | 0.084 | 0.092 |
| Group 2 (7.5 mg/kg RNAi agent-tridentate integrin targeting ligand of Structure 2a, and further including a 40 kDa PEG moiety linked to the construct) | A498 WT | 0.295 | 0.040 | 0.046 |
| Group 3 (isotonic glucose) | A498 αvβ3 KO | 1.000 | 0.232 | 0.302 |
| Group 4 (7.5 mg/kg RNAi agent-tridentate integrin targeting ligand of Structure 2a, and further including a 40 kDa PEG moiety linked to the construct) | A498 αvβ3 KO | 0.621 | 0.068 | 0.077 |

As shown in Table 14 above, the Hif2α RNAi agent-integrin ligand conjugates showed a reduction in Hif2α mRNA expression in A498 WT (wild type) tumors compared control (about 71% (0.295) knockdown). In contrast, as expected the reduction in Hif2α mRNA expression was less efficient in A498 αvβ3 KO tumors; however, the reduction was nevertheless substantial at 38% (0.621) knockdown. This shows that both integrin αvβ3 and integrin αvβ5 contribute to the RNAi agent delivery.

Example 12. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 15

| Dosing Groups of Mice in Example 12. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 7.5 mg/kg of Hif2α RNAi agent (AD04546) conjugated to a tridentate integrin targeting ligand of Structure 2a, and further including a C18-diacid moiety linked to the construct, formulated in isotonic glucose. | Single injection on day 1 |
| 6 | 7.5 mg/kg of Hif2α RNAi agent (AD04546) conjugated to a tridentate integrin targeting ligand of Structure 28a, and further including a Mal-C18-diacid moiety linked to the construct, formulated in isotonic glucose. | Single injection on day 1 |
| 7 | 7.5 mg/kg of Hif2α RNAi agent (AD04546) conjugated to a tridentate integrin targeting ligand of Structure 29a, and further including a Mal-C18-diacid moiety linked to the construct, formulated in isotonic glucose. | Single injection on day 1 |
| 8 | 7.5 mg/kg of Hif2α RNAi agent (AD04546) conjugated to a tridentate integrin targeting ligand of Structure 30a, and further including a Mal-C18-diacid moiety linked to the construct, formulated in isotonic glucose. | Single injection on day 1 |
| 9 | 7.5 mg/kg of Hif2α RNAi agent (AD04546) conjugated to a tridentate integrin targeting ligand of Structure 31a, and further including a Mal-C18-diacid moiety linked to the construct, formulated in isotonic glucose. | Single injection on day 1 |

The RNAi agents were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands.

The RNAi agents were synthesized having a PD modulator referred to as "Mal-C18-diacid moiety" having the structure:

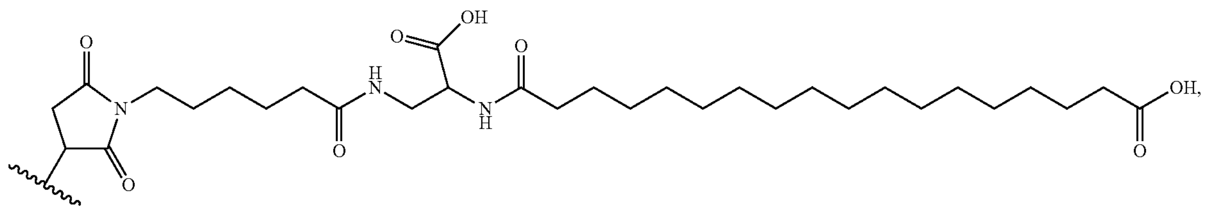 [SMILES: *C1CC(=O)N(CCCCCC(=O)NCC(NC(=O)CCCCCCCCCCCCCCCCC(=O)O)C(=O)O)C1=O]

wherein ⌇ indicates the point of attachment to the RNAi agent at the C6-S— group as indicated in AD05971 (see Example 2). The PD modulator was conjugated to the 3' end of the sense strand by reducing the C6-SS-C6 group, as shown in Table A, which then underwent Michael addition with the following compound:

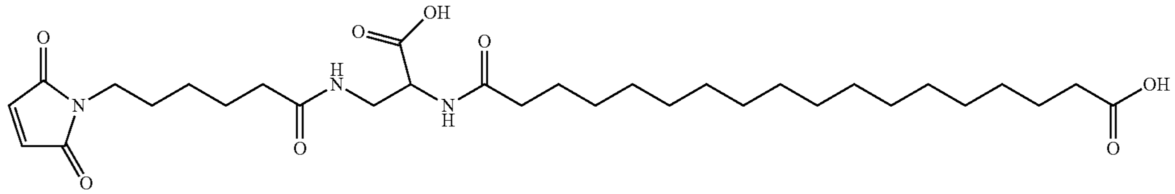 [SMILES: O=C(O)CCCCCCCCCCCCCCCCC(=O)NC(CNC(=O)CCCCCN1C(=O)C=CC1=O)C(=O)O]

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 16

Average Relative Hif2α mRNA Expression at Sacrifice in Example 12.

| Group ID | Average Relative huHIF2α mRNA Expression | Low (error) | High (error) |
|---|---|---|---|
| Group 1 (isotonic glucose) | 1.000 | 0.077 | 0.083 |
| Group 2 (7.5 mg/kg RNAi agent-tridentate integrin targeting ligand of Structure 2a, Mal-C18-diacid) | 0.456 | 0.113 | 0.150 |
| Group 6 (7.5 mg/kg RNAi agent-tridentate integrin targeting ligand of Structure 28a, Mal-C18-diacid) | 0.649 | 0.072 | 0.081 |
| Group 7 (7.5 mg/kg RNAi agent-tridentate integrin targeting ligand of Structure 29a, Mal-C18-diacid) | 0.426 | 0.054 | 0.062 |
| Group 8 (7.5 mg/kg RNAi agent-tri dentate integrin targeting ligand of Structure 30a, Mal-C18-diacid) | 0.699 | 0.064 | 0.070 |
| Group 9 (7.5 mg/kg RNAi agent-tridentate integrin targeting ligand of Structure 31a, Mal-C18-diacid) | 0.580 | 0.069 | 0.079 |

As shown in Table 16 above, each of the Hif2α RNAi agent-integrin targeting ligand conjugates showed a reduction in mRNA expression compared to control.

Example 13. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 17

Dosing Groups of Mice in Example 13.

| Group | RNAi Agent and Dose | Dosing Regimen |
|---|---|---|
| 1 | Isotonic glucose (d5w (5% dextrose in water)) (no RNAi agent) | Single injection on day 1 |
| 4 | 5.0 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 5 | 5.0 mg/kg of HIF-2 alpha RNAi agent AD05971, linked at the 5' terminal end of the sense strand to a tridentate targeting group having three integrin targeting ligands of Structure 32a, with an integrin targeting ligand of Structure 32a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 6 | 5.0 mg/kg of HIF-2 alpha RNAi agent AD05971, linked at the 5' terminal end of the sense strand to a tridentate targeting group having three integrin targeting ligands of Structure 33a, with an integrin targeting ligand of Structure 33a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |

TABLE 17-continued

| Dosing Groups of Mice in Example 13. | | |
|---|---|---|
| Group | RNAi Agent and Dose | Dosing Regimen |
| 7 | 5.0 mg/kg of HIF-2 alpha RNAi agent AD05971, linked at the 5' terminal end of the sense strand to a tridentate targeting group having three integrin targeting ligands of Structure 34a, with an integrin targeting ligand of Structure 34a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |

[(i)]The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 on the sense strand.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 18

| Average Relative Hif2α mRNA Expression at Sacrifice in Example 13. | | | |
|---|---|---|---|
| Group ID | Average Relative huHIF2α mRNA Expression | Low (error) | High (error) |
| Group 1 (isotonic glucose) | 1.000 | 0.083 | 0.090 |
| Group 4 (5.0 mg/kg RNAi agent-tridentate integrin targeting ligand of Structure 2a, three internal ligands of Structure 2a, and C-18-diacid PD modulator) | 0.245 | 0.048 | 0.059 |
| Group 5 (5.0 mg/kg RNAi agent-tridentate integrin targeting ligand of Structure 32a, three internal ligands of Structure 32a, and C-18-diacid PD modulator) | 0.213 | 0.065 | 0.094 |
| Group 6 (5.0 mg/kg RNAi agent-tridentate integrin targeting ligand of Structure 33a, three internal ligands of Structure 33a, and C-18-diacid) | 0.603 | 0.117 | 0.146 |
| Group 7 (5.0 mg/kg RNAi agent-tridentate integrin targeting ligand of Structure 34a, three internal ligands of Structure 34a, and C-18-diacid) | 0.528 | 0.067 | 0.077 |

As shown in Table 18 above, each of the Hif2α RNAi agent-integrin targeting ligand conjugates showed a reduction in mRNA expression in mice compared to control, with the constructs that included the integrin targeting ligands of Structure 2a and Structure 32a showing the greatest inhibitory activity.

Example 14. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 19

| Dosing Groups of Mice in Example 14. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 2.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→ | Single injection on day 1 |

TABLE 19-continued

| Dosing Groups of Mice in Example 14. | | |
|---|---|---|
| Group | RNAi Agent and Dose | Dosing Regimen |
| | 5') from the first nucleotide that forms a base pair with the antisense strand[(i)], and further linked at the 3' terminal end of the sense strand to PD modulator Mal-C18-diacid, formulated in isotonic glucose. | |
| 5 | 2.0 mg/kg of HIF-2 alpha RNAi agent AD05971, linked at the 5' terminal end of the sense strand to a tridentate targeting group having three integrin targeting ligands of Structure 36a, with an integrin targeting ligand of Structure 36a linked internally at the 2' position of each of nucleotides 2, 4, 6, and 8 (3'→ 5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 6 | 2.0 mg/kg of HIF-2 alpha RNAi agent AD05971, linked at the 5' terminal end of the sense strand to a tridentate targeting group having the structure of integrin targeting ligand SM37-avb3, having a SM37-avb3 targeting ligand linked internally at the 2' position of each of nucleotides 2, 4, 6, and 8 (3'→ 5') from the first nucleotide that forms a base pair with the antisense strand[(i)], and further linked at the 3' terminal end of the sense strand to PD modulator Mal-C18-diacid, formulated in isotonic glucose. | Single injection on day 1 |

[(i)]The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 on the sense strand.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 20

| Average Relative Hif2α mRNA Expression at Sacrifice in Example 14. | | | |
|---|---|---|---|
| Group ID | Average Relative huHIF2α mRNA Expression | Low (error) | High (error) |
| Group 1 (isotonic glucose) | 1.000 | 0.090 | 0.099 |
| Group 2 (2.0 mg/kg RNAi agent-tridentate integrin targeting ligand of Structure 2.11a, three internal ligands of Structure 2.11a, and C-18-diacid) | 0.362 | 0.021 | 0.022 |
| Group 5 (2.0 mg/kg RNAi agent-tridentate integrin targeting ligand of Structure 36a, three internal ligands of Structure 36a, and C-18-diacid) | 0.617 | 0.028 | 0.029 |

TABLE 20-continued

| Average Relative Hif2α mRNA Expression at Sacrifice in Example 14. | | | |
|---|---|---|---|
| Group ID | Average Relative huHIF2α mRNA Expression | Low (error) | High (error) |
| Group 6 (2.0 mg/kg RNAi agent-tridentate integrin targeting ligand of Structure 37a, three internal ligands of Structure 37a, and C-18-diacid) | 0.375 | 0.081 | 0.103 |

As shown in Table 20 above, each of the Hif2α RNAi agent-integrin targeting ligand conjugates showed a reduction in mRNA expression compared to control.

Example 15. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 21

| Dosing Groups of Mice in Example 15. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 2.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 3 | 4.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 6 | 2.0 mg/kg of HIF-2 alpha RNAi agent AD05971, linked at the 5' terminal end of the sense strand to a tridentate targeting group having three integrin targeting ligands of Structure 38a, with an integrin targeting ligand of Structure 38a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 7 | 4.0 mg/kg of HIF-2 alpha RNAi agent AD05971, linked at the 5' terminal end of the sense strand to a tridentate targeting group having three integrin targeting ligands of Structure 38a, with an integrin targeting ligand of Structure 38a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 8 | 2.0 mg/kg of HIF-2 alpha RNAi agent AD05971, linked at the 5' terminal end of the sense strand to a tridentate targeting group having three integrin targeting ligands of Structure 39a, with an integrin targeting ligand of Structure 39a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 9 | 4.0 mg/kg of HIF-2 alpha RNAi agent AD05971, linked at the 5' terminal end of the sense strand to a tridentate targeting group having three integrin targeting ligands of Structure 39a, with an integrin targeting ligand of Structure 39a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 10 | 2.0 mg/kg of HIF-2 alpha RNAi agent AD05971, linked at the 5' terminal end of the sense strand to a tridentate targeting group having three integrin targeting ligands of Structure 40a, with an integrin targeting ligand of Structure 40a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 11 | 4.0 mg/kg of HIF-2 alpha RNAi agent AD05971, linked at the 5' terminal end of the sense strand to a tridentate targeting group having three integrin targeting ligands of Structure 40a, with an integrin | Single injection on day 1 |

TABLE 21-continued

| Dosing Groups of Mice in Example 15. | | |
|---|---|---|
| Group | RNAi Agent and Dose | Dosing Regimen |
| | targeting ligand of Structure 40a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | |
| 12 | 2.0 mg/kg of HIF-2 alpha RNAi agent AD05971, linked at the 5' terminal end of the sense strand to a tridentate targeting group having three integrin targeting ligands of Structure 41a, with an integrin targeting ligand of Structure 41a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 13 | 4.0 mg/kg of HIF-2 alpha RNAi agent AD05971, linked at the 5' terminal end of the sense strand to a tridentate targeting group having three integrin targeting ligands of Structure 41a, with an integrin targeting ligand of Structure 41a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |

[(i)]The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 on the sense strand.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 22

| Average Relative Hif2α mRNA Expression at Sacrifice in Example 15. | | | |
|---|---|---|---|
| Group ID | Average Relative huHIF2α mRNA Expression | Low (error) | High (error) |
| Group 1 (isotonic glucose) | 1.000 | 0.247 | 0.327 |
| Group 2 (2.0 mg/kg RNAi agent-tridentate integrin targeting ligand of Structure 2.11a, three internal ligands of Structure 2.11a, and C-18-diacid) | 0.286 | 0.037 | 0.043 |
| Group 3 (4.0 mg/kg RNAi agent-tridentate integrin targeting ligand of Structure 2.11a, three internal ligands of Structure 2.11a, and C-18-diacid) | 0.263 | 0.035 | 0.040 |
| Group 6 (2.0 mg/kg RNAi agent-tridentate integrin targeting ligand of Structure 38a, three internal ligands of Structure 38a, and C-18-diacid) | 0.655 | 0.050 | 0.054 |
| Group 7 (4.0 mg/kg RNAi agent-tridentate integrin targeting ligand of Structure 38a, three internal ligands of Structure 38a, and C-18-diacid) | 0.488 | 0.042 | 0.046 |
| Group 8 (2.0 mg/kg RNAi agent-tridentate integrin targeting ligand of Structure 39a, three internal ligands of Structure 39a, and C-18-diacid) | 0.609 | 0.065 | 0.073 |

TABLE 22-continued

| Average Relative Hif2α mRNA Expression at Sacrifice in Example 15. | | | |
|---|---|---|---|
| Group ID | Average Relative huHIF2α mRNA Expression | Low (error) | High (error) |
| Group 9 (4.0 mg/kg RNAi agent-tridentate integrin targeting ligand of Structure 39a, three internal ligands of Structure 39a, and C-18-diacid) | 0.518 | 0.050 | 0.055 |
| Group 10 (2.0 mg/kg RNAi agent-tridentate integrin targeting ligand of Structure 40a, three internal ligands of Structure 40a, and C-18-diacid) | 0.805 | 0.113 | 0.132 |
| Group 11 (4.0 mg/kg RNAi agent-tridentate integrin targeting ligand of Structure 40a, three internal ligands of Structure 40a, and C-18-diacid) | 0.738 | 0.091 | 0.104 |
| Group 12 (2.0 mg/kg RNAi agent-tridentate integrin targeting ligand of Structure 41a, three internal ligands of Structure 41a, and C-18-diacid) | 0.978 | 0.082 | 0.090 |
| Group 13 (4.0 mg/kg RNAi agent-tridentate integrin targeting ligand of Structure 41a, three internal ligands of Structure 41a, and C-18-diacid) | 0.779 | 0.106 | 0.123 |

As shown in Table 22 above, each of the Hif2α RNAi agent-integrin targeting ligand conjugates showed a reduction in mRNA expression in mice compared to control.

Example 16. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 4) were dosed via tail vein injection according to the following dosing Groups:

TABLE 23

Dosing Groups of Mice in Example 16.

| Group | RNAi Agent and Dose | Dosing Regimen |
|---|---|---|
| 1 | Saline (0.9%) (no RNAi agent) | Single injection on day 1 |
| 2 | 2.5 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 3 | 5.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 4 | 10.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 5 | 2.5 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 6 | 5.0 mg/kg of HIF-2 alpha RNAi agent ADOS971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |
| 7 | 10.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose. | Single injection on day 1 |

TABLE 23-continued

| Dosing Groups of Mice in Example 16. | | |
|---|---|---|
| Group | RNAi Agent and Dose | Dosing Regimen |
| 8 | 2.5 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 9 | 5.0 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 10 | 10.0 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→5') from the first nucleotide that forms a base pair with the antisense strand[(i)], and further linked at the 3' terminal end of the sense strand to PD modulator Mal-C18-diacid, formulated in isotonic glucose. | Single injection on day 1 |

[(i)]The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 on the sense strand.

Four (4) tumor bearing mice were dosed in each Group (n=4), except for Group 4 which only had three (3) mice as one mouse was deemed to have a faulty injection. Mice were sacrificed on study day 8 after injection, and total RNA was isolated from kidney tumor according to the procedure set forth in Example 4. Relative Human HIF2a mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 24

| Average Relative Hif2α mRNA Expression at Sacrifice in Example 16. | | | |
|---|---|---|---|
| Group ID | Average Relative huHIF2α mRNA Expression | Low (error) | High (error) |
| Group 1 (isotonic glucose) | 1.000 | 0.180 | 0.220 |
| Group 2 (2.5 mg/kg RNAi agent-tridentate integrin targeting ligand of Structure 2.11a, three internal ligands of Structure 2.11a, and C-18-diacid) | 0.278 | 0.068 | 0.091 |
| Group 3 (5.0 mg/kg RNAi agent-tridentate integrin targeting ligand of Structure 2.11a, three internal ligands of Structure 2.11a, and C-18-diacid) | 0.229 | 0.062 | 0.086 |
| Group 4 (10.0 mg/kg RNAi agent-tridentate integrin targeting ligand of Structure 2.11a, three internal ligands of Structure 2.11a, and C-18-diacid) | 0.202 | 0.014 | 0.015 |

TABLE 24-continued

| Average Relative Hif2α mRNA Expression at Sacrifice in Example 16. | | | |
|---|---|---|---|
| Group ID | Average Relative huHIF2α mRNA Expression | Low (error) | High (error) |
| Group 5 (2.5 mg/kg RNAi agent-tndentate integrin targeting ligand of Structure 2.11a, three internal ligands of Structure 2.11a, and C-18-diacid) | 0.324 | 0.035 | 0.040 |
| Group 6 (5.0 mg/kg RNAi agent-tridentate integrin targeting ligand of Structure 2.11a, three internal ligands of Structure 2.11a, and C-18-diacid) | 0.308 | 0.018 | 0.019 |
| Group 7 (10.0 mg/kg RNAi agent-tridentate integrin targeting ligand of Structure 2.11a, three internal ligands of Structure 2.11a, and C-18-diacid) | 0.197 | 0.041 | 0.052 |
| Group 8 (2.5 mg/kg RNAi agent-tridentate integrin targeting ligand of Structure 2a, three internal ligands of Structure 2a, and C-18-diacid) | 0.218 | 0.048 | 0.062 |
| Group 9 (5.0 mg/kg RNAi agent-tridentate integrin targeting ligand of Structure 2a, three internal ligands of Structure 2a, and C-18-diacid) | 0.160 | 0.065 | 0.109 |
| Group 10 (10.0 mg/kg RNAi agent-tridentate integrin targeting ligand of Structure 2a, three internal ligands of Structure 2a, and C-18-diacid) | 0.276 | 0.053 | 0.066 |

As shown in Table 24 above, each of the Hif2α RNAi agent-integrin targeting ligand conjugates showed a reduction in mRNA expression in mice compared to control.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An integrin targeting group comprising the structure:

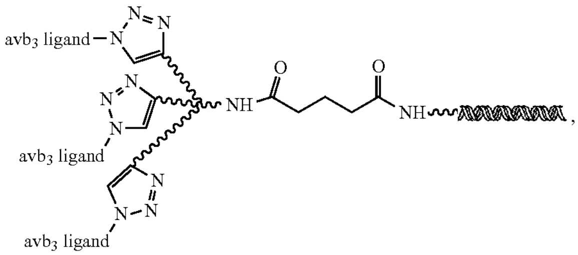

wherein 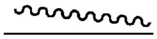 indicates any suitable scaffold or linker that can be used to bind a ligand to an RNAi agent, 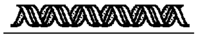 indicates the RNAi agent, and "$avb_3$ ligand" is selected from the group consisting of:

(Structure 1a)

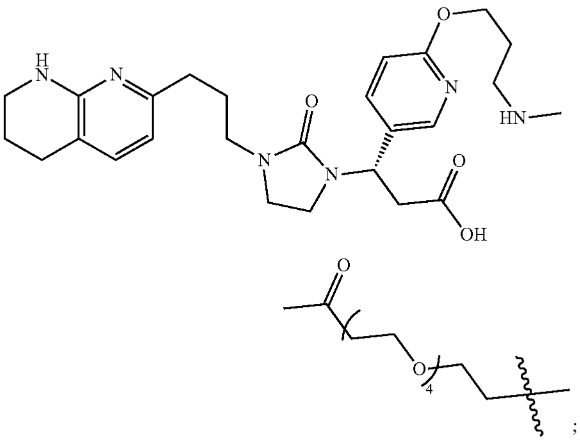

;

(Structure 2a)

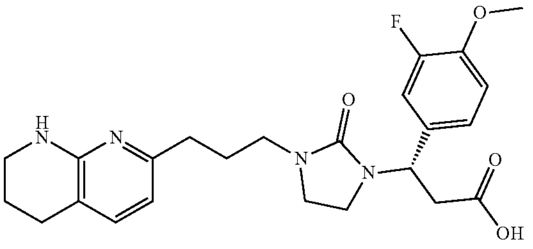

-continued

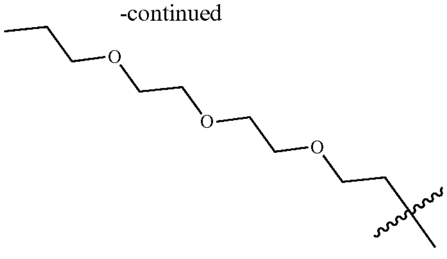

;

(Structure 2.8a)

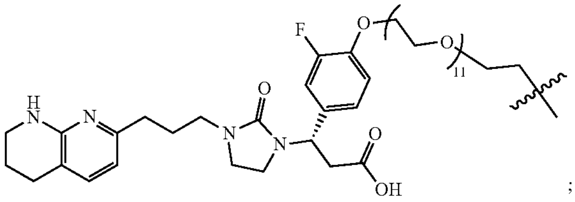

;

(Structure 2.9a)

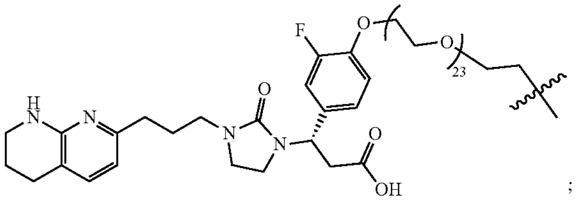

;

(Structure 2.10a)

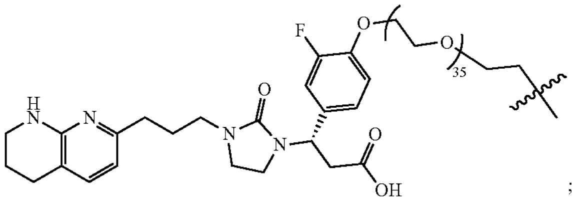

;

(Structure 2.11a)

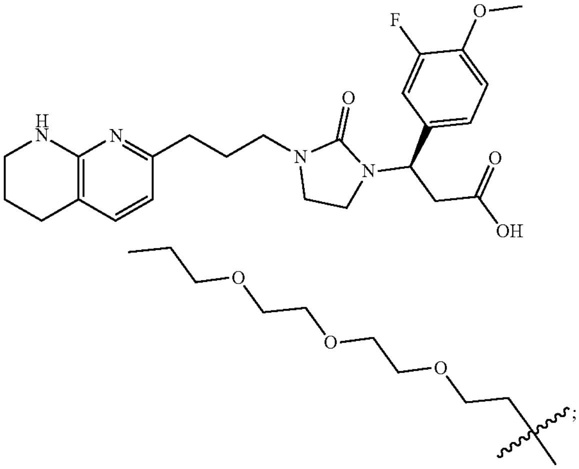

;

-continued
(Structure 28a)
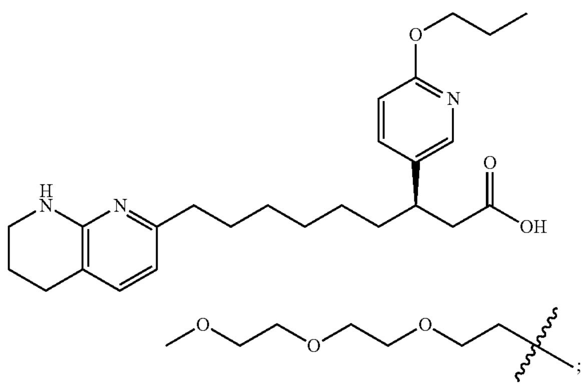
;
(Structure 29a)
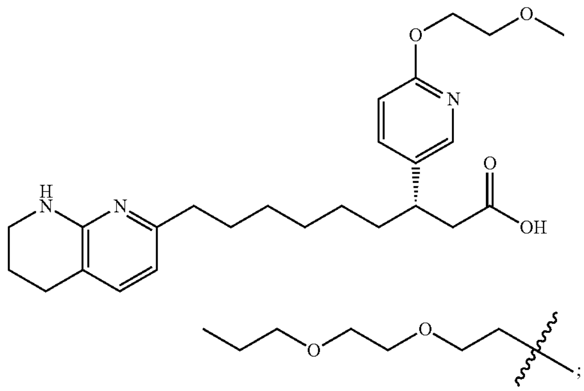
;
(Structure 30a)
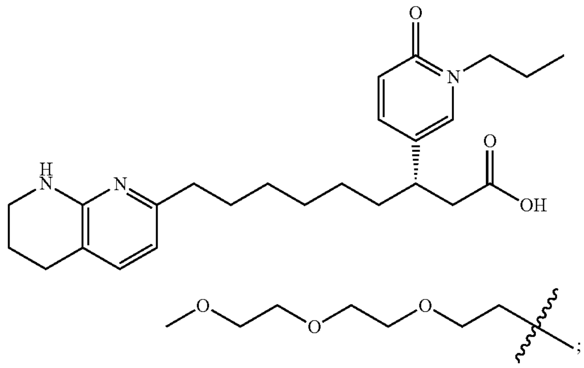
;
(Structure 31a)
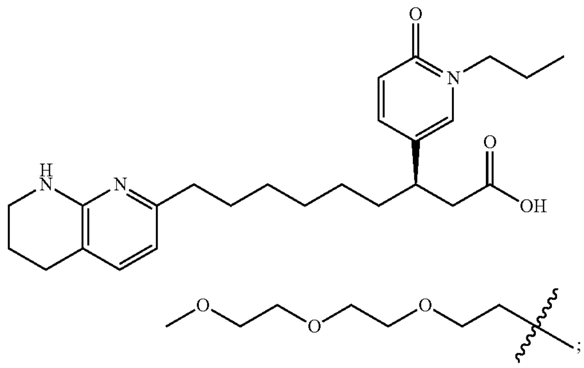
;
-continued
(Structure 32a)
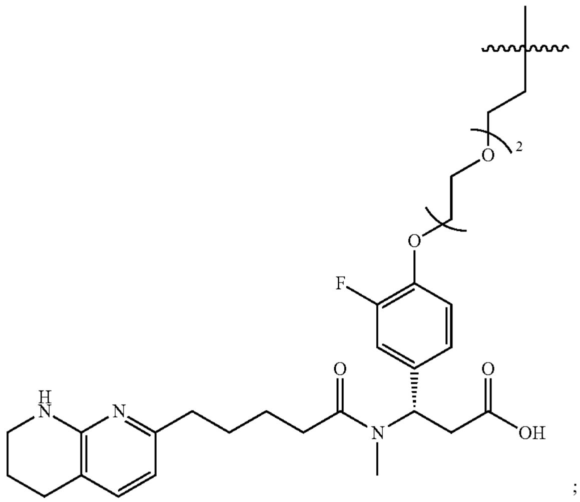
;
(Structure 33a)
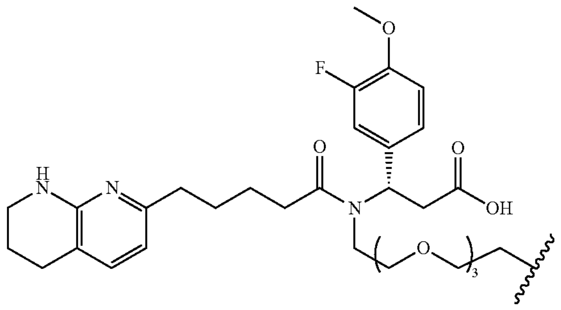
;
(Structure 34a)
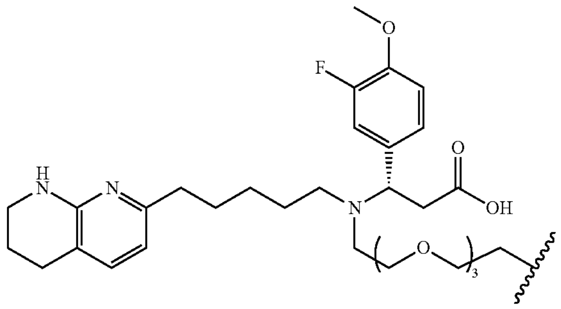
;
(Structure 36a)
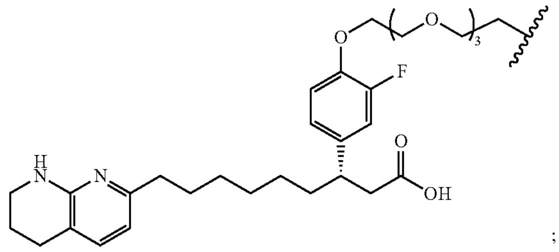
;

-continued (Structure 37a)

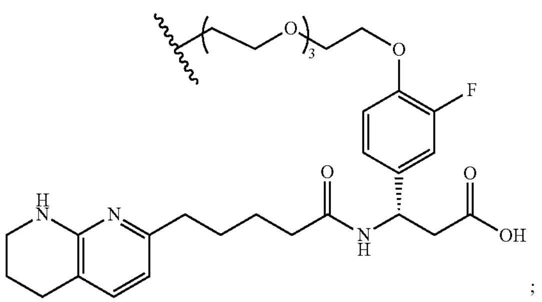

;

(Structure 38a)

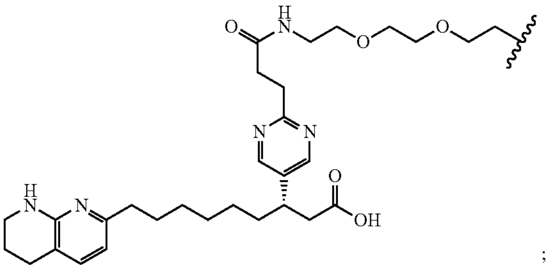

;

(Structure 39a)

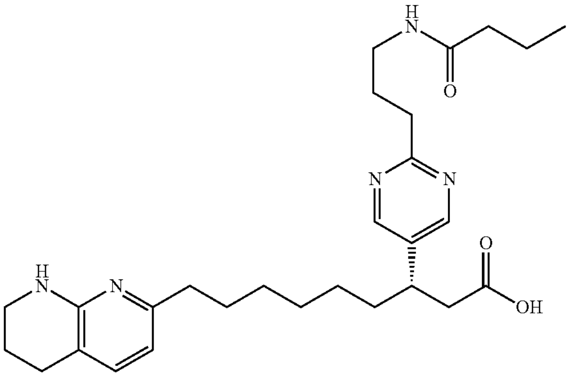

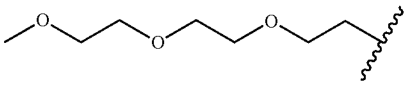

;

-continued (Structure 40a)

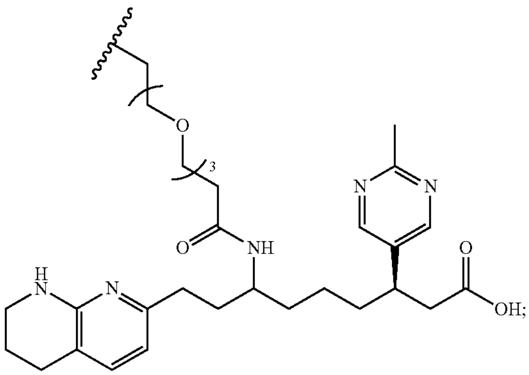

; and (Structure 41a)

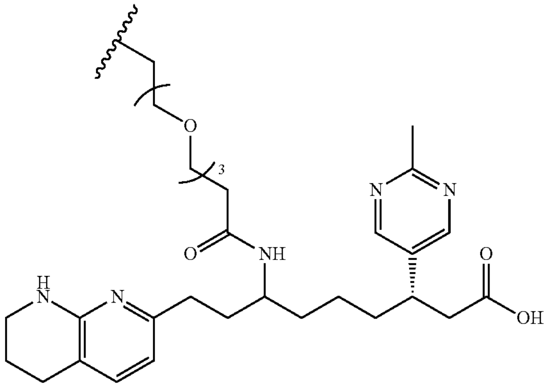

or a pharmaceutically acceptable salt thereof.

2. A composition comprising the integrin targeting group of claim 1, and a pharmaceutically acceptable excipient.

3. A method of delivering one or more RNAi agents to a cell expressing integrin αvβ3, in a subject, the method comprising administering to the subject a composition of claim 2.

4. A method of delivering one or more RNAi agents to a cell or tissue of a subject in vivo, the method comprising administering to the subject a composition of claim 2.

5. A method of inhibiting the expression of a target gene in a cell that expresses integrin αvβ3, in vivo, the method comprising administering to a subject an effective amount of a composition of claim 2.

6. The method of claim 5, wherein the target gene is EPAS1 (HIF2 alpha).

7. The method of claim 5, wherein the cell is a clear cell renal carcinoma tumor cell.

* * * * *